US009598464B2

(12) United States Patent
Scheiflinger et al.

(10) Patent No.: US 9,598,464 B2
(45) Date of Patent: Mar. 21, 2017

(54) BIOLOGICALLY ACTIVE PEPTIDES

(71) Applicants: BAXALTA INCORPORATED, Bannockburn, IL (US); BAXALTA GMBH, Glattpark (Opfikon) (CH)

(72) Inventors: Friedrich Scheiflinger, Vienna (AT); Michael Dockal, Vienna (AT)

(73) Assignees: Baxalta Incorporated, Bannockburn, IL (US); Baxalta GmbH, Glattpark (Opfikon) (CH)

( * ) Notice: Subject to any disclaimer, the term of this patent is extended or adjusted under 35 U.S.C. 154(b) by 0 days.

(21) Appl. No.: 14/941,163

(22) Filed: Nov. 13, 2015

(65) Prior Publication Data

US 2016/0060295 A1 Mar. 3, 2016

Related U.S. Application Data

(62) Division of application No. 14/340,231, filed on Jul. 24, 2014, now Pat. No. 9,206,234, which is a division of application No. 13/238,751, filed on Sep. 21, 2011, now Pat. No. 8,822,638, which is a division of application No. 12/425,277, filed on Apr. 16, 2009, now Pat. No. 8,563,688.

(60) Provisional application No. 61/113,055, filed on Nov. 10, 2008, provisional application No. 61/009,326, filed on Apr. 17, 2008.

(51) Int. Cl.

| | |
|---|---|
| ***C07K 7/06*** | (2006.01) |
| ***C07K 14/755*** | (2006.01) |
| ***C07K 7/08*** | (2006.01) |
| ***C07K 1/04*** | (2006.01) |

(52) U.S. Cl.

CPC .................. *C07K 7/06* (2013.01); *C07K 1/04* (2013.01); *C07K 7/08* (2013.01); *C07K 14/755* (2013.01); *Y02P 20/55* (2015.11)

(58) Field of Classification Search

CPC .................................. C07K 7/06; C07K 1/04
USPC ........................................ 530/328, 327, 334
See application file for complete search history.

(56) References Cited

U.S. PATENT DOCUMENTS

| | | | |
|---|---|---|---|
| 4,447,356 | A | 5/1984 | Olivera et al. |
| 5,093,317 | A | 3/1992 | Lewis et al. |
| 5,171,838 | A | 12/1992 | Chiba |
| 5,439,686 | A | 8/1995 | Desai et al. |
| 5,498,421 | A | 3/1996 | Grinstaff et al. |
| 5,532,153 | A | 7/1996 | Xu et al. |
| 6,005,166 | A | 12/1999 | McMaster et al. |
| 6,037,452 | A | 3/2000 | Minamino et al. |
| 6,624,289 | B1 | 9/2003 | Bajaj |
| 7,033,590 | B1 | 4/2006 | Scheiflinger et al. |
| 7,084,109 | B2 | 8/2006 | Dennis et al. |
| 7,109,170 | B2 | 9/2006 | Bajaj et al. |
| 7,279,548 | B2 | 10/2007 | Pirozzi et al. |
| 2001/0014456 | A1 | 8/2001 | Yu et al. |
| 2002/0018778 | A1 | 2/2002 | Caplan |
| 2002/0182219 | A1 | 12/2002 | Debinski et al. |
| 2003/0013170 | A1 | 1/2003 | Aggarwal et al. |
| 2005/0124544 | A1 | 6/2005 | Granier et al. |
| 2006/0204503 | A1 | 9/2006 | Fitchett et al. |

FOREIGN PATENT DOCUMENTS

| | | | |
|---|---|---|---|
| WO | WO-03/040176 | A2 | 5/2003 |
| WO | WO-2007/065691 | A2 | 6/2007 |
| WO | WO-2007/077561 | A2 | 7/2007 |

OTHER PUBLICATIONS

Blostein et al., Amphipathic helices support function of blood coagulation factor IXa. *Biochemistry,* 39: 12000-6 (2000).
GenBank Accession No. AB102675.1, Rosellinia anti-rot virus gene for hypothecial protein, dated Mar. 30, 2004.
Guichard et al., Antigenic mimicry of natural L-peptides with retro-inverso-peptidomimetics. *Proc. Natl. Acad. Sci. USA*, 91: 9765-9 (1994).
Hamamoto et al., Antimicrobial activity and stability to proteolysis of small linear cationic peptides with D-amino acid substitutions, *Microbiology and Immunology,* 46(11):741-49 (2002).
Harris et al., Effect of pegylation on pharmaceuticals. *Nat. Rev. Drug Discov.,* 2: 214-21 (2003).
Hay, The epidemiology of factor VIII inhibitors. *Haemophilia,* 12(Suppl. 6): 23-9 (2006).
International Preliminary Report on Patentability, PCT/US2009/040857, dated Oct. 19, 2010.
International Search Report and Written Opinion of the International Searching Authority, PCT/US2009/040857, European Patent Office, dated Oct. 2, 2009.
Kasper et al., Proceedings: A more uniform measurement of factor VIII inhibitors. *Thromb Diath Haemorrh.* 34(2): 612 (1975).
Kaufman et al., Can we improve on nature? “Super molecules” of factor VIII. *Haemophilia,* 4: 370-9 (1998).
Landesberg et al., Activation of platelet-rich plasma using thrombin receptor agonist peptide, *J. Oral Maxillof. Surg.* 63(4):529-35 (2005).
Ljung, Prophylactic infusion regimens in the management of hemophilia. *Thromb. Haemost.,* 82: 525-30 (1999).
Meziere et al., In vivo T helper cell response to retro-inverso peptidomimetics. *J. Immunol.,* 159: 3230-7 (1997).
Peerlinck et al., Epidemiology of inhibitor formation with recombinant factor VIII replacement therapy. *Haemophilia,* 12:579-90 (2006).
Roche et al., A virtual screening method for prediction of the HERG potassium channel liability of compound libraries. *Chembiochem.,* 3: 455-9 (2002).
Scharn et al., Sequential nucleophilic substitution on halogenated triazines, pyrimidines, and purines: a novel approach to cyclic peptidomimetics. *J. Org. Chem.* 66(2): 507-13 (2001).

(Continued)

*Primary Examiner* — David Lukton
(74) *Attorney, Agent, or Firm* — Morgan, Lewis & Bockius LLP

(57) ABSTRACT

The invention provides a method of making a peptide or peptide derivative comprising the amino acid sequence comprising imfwydcye or a variant amino acid sequence comprising one, two, three, four, five or six amino acid substitutions in imfwydcye.

5 Claims, 2 Drawing Sheets

(56) References Cited

OTHER PUBLICATIONS

Uniprot Accession No. A2DPM5, Subname: Full-PIKK family atypical protein kinase, Feb. 20, 2007.

Uniprot Accession No. Q0AF26, Subname: Full=Excinuclease ABC, C subunit domain protein, Oct. 17, 2006.

Uniprot Accession No. Q6AKG8, Subname: Full=Putative uncharacterized protein, Sep. 13, 2004.

Wei et al., Complete nucleotide sequences of genome segments 1 and 3 of Rosellinia anti-rot virus in the family, Reoviridae, *Arch. Virol.,* 149: 773-7 (2004).

Uniprot Accession No. Q22C06, Subname: Full=Transmembrane protein, putative, dated Apr. 18, 2006.

Brenneman et al., Protective peptides that are orally active and mechanistically nonchiral. *J. Pharmacol. Exper. Therapeut.* 309(3): 1190-7 (2004).

Wilkemeyer et al., Ethanol antagonist peptides: Structural specificity without stereospecificity. *J. Pharmacol. Exper. Therapeut.* 309(3): 1183-9 (2004).

Animal Disease Model – A01

| | | |
|---|---|---|
| Dose: | 20 mg/kg i.v. | n, 16 |
| Administration: | 5 min before tail clip | |
| Tail clip: | 0.5 cm | |
| Animals: | FVIII ko mice | |

* $p < 0.05$

** $p < 0.01$

BIOLOGICALLY ACTIVE PEPTIDES

CROSS REFERENCE TO RELATED PATENT APPLICATIONS

This application is a divisional of U.S. patent application Ser. No. 14/340,231, filed Jul. 24, 2014, which is a divisional of U.S. application Ser. No. 13/238,751 (now U.S. Pat. No. 8,822,638), filed Sep. 21, 2011, which is a divisional of U.S. application Ser. No. 12/425,277 (now U.S. Pat. No. 8,563, 688), filed Apr. 16, 2009, which claims priority of U.S. Provisional Application No. 61/009,326, filed on Apr. 17, 2008, and U.S. Provisional Application No. 61/113,055, filed on Nov. 10, 2008, each of which is incorporated by reference herein in its entirety.

INCORPORATION BE REFERENCE OF MATERIAL SUBMITTED ELECTRONICALLY

This application incorporates by reference in its entirety a computer-readable nucleotide/amino acid sequence listing identified as follows: One 207693 byte ASCII (text) file name “44907C_SeqListing.txt,” created Nov. 9, 2015.

FIELD OF THE INVENTION

The present invention relates to low molecular weight peptides with procoagulant activity for treatment of patients with a deficiency in FV, FVII, FVIII, FX and/or FXI.

BACKGROUND OF THE INVENTION

The blood coagulation cascade involves a series of serine protease enzymes (zymogens) and protein cofactors. When required, an inactive zymogen precursor is converted into the active form, which consequently converts the next enzyme in the cascade. It is divided into three distinct segments: the intrinsic (contact activation), extrinsic (tissue factor), and common pathways.

In the intrinsic pathway of the cascade, hemophilia is the most pronounced bleeding disorder, which results in insufficient generation of factor Xa by factor FIX (FIXa)/factor VIIIa (FVIIIa) complex (the intrinsic tenase complex) leading to an insufficient clot formation. Bleeding may then occur spontaneously or following injury.

Hemophilia is an inherited bleeding disorder and two forms of hemophilia, hemophilia A and B, are known. Hemophilia A is the consequence of a deficiency of FVIII and is characterized by hemorrhage into the joints and muscles. FVIII circulates in plasma at a very low concentration and is bound non-covalently to von Willebrand factor (vWF). During hemostasis, FVIII is activated by thrombin, separates from vWF and acts as a cofactor for activated FIXa-mediated FX activation by enhancing the rate of activation.

Patients with less than 1% normal FVIII are considered to have severe hemophilia, with 1-5% moderately severe hemophilia, and with more than 5% but less than 40% mild hemophilia.

Nowadays the treatment of choice for the management of hemophilia A is replacement therapy with various plasma derived or recombinant FVIII concentrates. Although specific viral-inactivation steps, including solvent-detergent treatment or liquid-phase heat treatment, are available to inactivate viruses, possible transmission of poorly characterized agents (e.g. prions) in plasma derived concentrates is still an issue discussed in the art.

FVIII is also synthesized as a recombinant protein for therapeutic use in bleeding disorders. Such products have lowered the risk of viral contamination. There are many recombinant products on the market for the treatment of hemophilia A. One of these concentrates is the Advate® FVIII composition, which is produced in CHO-cells and manufactured by Baxter Healthcare Corporation. No human or animal plasma proteins are added in the cell culture process, purification, or final formulation of this product.

Although progress in the production of FVIII to ensure purity, efficacy and viral safety has been made over the past decades, some limitations remain. First of all, severe hemophilia A patients are frequently affected by anti-FVIII inhibitor antibody formation, rendering the therapy ineffective.

Approximately 30% of patients with severe HA develop alloantibody inhibitors that can neutralize FVIII (Hay, *Haemophilia* 2006; 12 Suppl 6:23-9; Peerlinck and Hermans, *Haemophilia* 2006; 12:579-90). These inhibitors are typically immunoglobulin G (IgG), predominantly of the IgG4 subclass, that do not fix complement and do not result in the end-organ damage observed with circulating immune complexes. The inhibitors occur at a young age (about 50% by 10 years), principally in patients with less than 1% FVIII. Furthermore, acquired hemophilia may occur, which is the development of FVIII antibody inhibitors in persons without a history of FVIII deficiency. This condition can be idiopathic (occurring in people>50 years), it can be associated with collagen vascular disease or the peripartum period, or it may represent a drug reaction (e.g., to penicillin). For clinical purposes, the magnitude of the antibody response can be quantified through the performance of a functional inhibitor assay from which the Bethesda unit (BU) inhibitor titer can be obtained. The International Society of Thrombosis and Haemostasis (ISTH) definition of a high titer response is >5 BUs and its definition of a low titer response is between 0.5 and 5 BUs.

Attempts to overwhelm the inhibitors with large doses of human FVIII have been tried. Also porcine FVIII, which has low cross-reactivity with human FVIII antibody, has been administered. More frequently, FVIII-bypassing agents, including activated prothrombin complex concentrates (e.g. FEIBA (Factor Eight Inhibitor Bypassing Agent) and recombinant activated factor FVII (FVIIa) have also been used.

Because therapeutic polypeptide drugs such as FVIII are also rapidly degraded by proteolytic enzymes in addition to the drawback of inhibitor development, FVIII needs to be frequently administered intravenously. Taking into account the average half-lives of the various FVIII products in the circulation, this can usually be achieved by giving FVIII two to three times a week. Thus this treatment is rather complicated for an outpatient population, especially in small children.

Thus currently the aim of many manufacturers of FVIII is to develop a next generation product with enhanced pharmacodynamic and pharmacokinetic properties, while maintaining all other product characteristics. Because improved polypeptide drugs with a longer circulation half-life would decrease the number of necessary administrations, chemical or enzymatic modification of the polypeptide drugs is one of the preferred approaches to achieve this goal.

One such example is PEGylation of polypeptide drugs protecting and improving their pharmacodynamic and pharmacokinetic profiles (Harris and Chess, *Nat Rev Drug Discov.* 2003; 2:214-21). U.S. Pat. No. 6,037,452 describes a poly(alkylene oxide)-FVIII or FIX conjugate, where the protein is covalently bound to a poly(alkylene oxide) through carbonyl groups of said FVIII.

Even if these methods reduce inhibitor development they still would not abrogate the need for intravenous administration. The most elegant option, making most of the drawbacks of hemophilia treatment discussed above obsolete, would be the development of a low molecular weight compound such as a peptide (peptidomimetic) with the capacity to improve coagulation and which can be administered by a non-intravenous route. Though already discussed for many years (for example Kaufman and Pipe, *Haemophilia* 1998; 4.370-9; Llung, *Thromb Haemost.* 1999; 82:525-30) no such agent is currently available or in clinical development.

The current state of the art for the use of small peptides in blood coagulation is documented for example by the following publications:

D K Liles, D M Monroe and H R Roberts (1997) Blood Vol 90 No 10 Supplement 1, 463a is a poster abstract disclosing a peptide 698-712 from FVIII which can promote FIXa mediated activation of FX on a phospholipid surface. However, in the presence of FVIIIa, the peptide inhibits FIXa mediated activation of FX on a phospholipid surface. To date, there has been no peer-reviewed publication by these authors confirming results disclosed in this poster abstract.

Blostein et al (2000) *Biochemistry* 39:12000-12006 discloses that amphipathic alpha helices can interact with FIXa Gla domains and increases activation of FX in the absence of phospholipid. The peptides appeared to work independently of amino acid sequence by mimicking phospholipids. There is no suggestion to use such peptides in therapy. Under normal conditions, activated platelets provide the lipid [0]surface supporting coagulation. Since platelets are activated by thrombin, which is formed at sites of vascular injury, coagulation processes are restricted to the sites of injuries. It is highly undesirable to provide the body with peptides that are general substitutes for procoagulant lipids as this would cause systemic coagulation and ultimately lead to disseminated intravascular coagulation (DIC). Therefore, the peptides described by Blostein would not be useful in therapy.

U.S. Pat. Nos. 7,109,170 and 6,624,289 disclose regions of the FIXa protease domain that interact with FVIIIa. The peptides comprise the FVIIIa binding site of FIXa and inhibit binding of FIXa to FVIIIa. However, they are only useful as anticoagulants for preventing or treating thrombosis.

US20010014456A1 discloses binding molecules for human FVIII and FVIII-like proteins. These polypeptides bind FVIII and/or FVIII-like polypeptides and are useful for the detection and purification of human FVIII and/or FVIII-like polypeptides from solutions such as blood or conditioned media.

In U.S. Pat. No. 7,033,590 FIX/FIXa activating antibodies and antibody derivatives are used for increasing the amidolytic activity of FIXa, and for treating blood coagulation disorders such as hemophilia A and hemorrhagic diathesis.

In U.S. Pat. No. 7,084,109 FVIIa antagonists are disclosed. These antagonists are peptides that inhibit FVIIa activity and are said to be useful for prevention of arterial thrombosis in combination with thrombolytic therapy.

The listing or discussion of a prior-published document in this specification should not necessarily be taken as an acknowledgement that the document is part of the state of the art or is common general knowledge.

There remains a great need in the art for a low molecular weight peptide with procoagulant activity for treatment of patients with hemophilia A (FVIII deficiency). The present invention provides novel low molecular weight peptides with procoagulant activity which can be used for the non-intravenous treatment of hemophilia A. The present prevention also provides these novel peptides for the treatment of a deficiency in FV, FVII, FX and/or FXI.

SUMMARY OF THE INVENTION

A first aspect of the invention provides a peptide or peptide derivative comprising:

(i) WDLYFEIVW (SEQ ID NO: 1); or (ii) a variant amino acid sequence comprising one, two, three or four L-amino acid substitutions in WDLYFEIVW (SEQ ID NO: 1); or (iii) the retro-inverso variant of the peptide or peptide derivative of either one of parts (i) and (ii), wherein said peptide or peptide derivative has procoagulant activity.

For the avoidance of doubt, the sequence WDLYFEIVW (SEQ ID NO: 1) may be represented as the L-amino acids Trp-Asp-Leu-Tyr-Phe-Glu-Ile-Val-Trp using the three letter code for amino acids. The retro-inverso variant of WDLYFEIVW (SEQ ID NO: 1) is wviefyldw and comprises D-amino acids.

A second aspect of the invention provides a peptide or peptide derivative comprising:

(i) an amino acid sequence comprising imfwydcye; or (ii) a variant amino acid sequence comprising one, two, three, four, five or six amino acid substitutions in imfwydcye, wherein said peptide or peptide derivative has procoagulant activity.

For the avoidance of doubt, the sequence cimfwydcye may be represented as D-amino acids ile-met-phe-trp-tyr-asp-cys-tyr-glu using the three letter code for amino acids.

A third aspect of the invention provides a dual peptide comprising a peptide or peptide derivative of the first or second aspects of the invention conjugated to a further peptide or peptide derivative of the first or second aspects of the invention, wherein the two peptides/derivatives may be the same as or different from each other and wherein the dual peptide has procoagulant activity.

A fourth aspect of the invention provides a pharmaceutical composition comprising the peptide or peptide derivative of the first or second aspects of the invention or the dual peptide of the third aspect of the invention.

A fifth aspect of the invention provides a peptide or peptide derivative of the first or second aspects or a dual peptide of the third aspect of the invention for treating a patient having a deficiency in FV, FVII, FVIII, FX and/or FXI.

A sixth aspect of the invention provides a use of a peptide or peptide derivative of the first or second aspects or a dual peptide of the third aspect of the invention in the manufacture of a medicament for the treatment of a deficiency in FV, FVII, FVIII, FX and/or FXI in a patient.

A seventh aspect of the invention provides a method of treating a patient having a deficiency in FV, FVII, FVIII, FX and/or FXI comprising administering a therapeutically effective amount of the pharmaceutical composition of the fourth aspect.

An eighth aspect of the invention provides a peptide or peptide derivative which has procoagulant activity, wherein the peptide or peptide derivative is not FVIII or a fragment thereof and, wherein the procoagulant activity is a thrombin generation time of 25, 50 or 100 μM of peptide, peptide derivative or dual peptide equivalent to that of at least 100 mU/mL Factor Eight Inhibitor Bypassing Activity (FEIBA), preferably at least 300 mU/mL FEIBA, more preferably at least 900 mU/mL FEIBA, most preferably at least 1200 mU/mL FEIBA in the Defined Intrinsic Thrombin Generation Assay.

A ninth aspect of the invention provides a peptide or peptide derivative which has procoagulant activity, wherein the peptide or peptide derivative is not FVIII or a fragment thereof and, wherein the procoagulant activity is a thrombin generation time of 25, 50 or 100 μM of peptide, peptide derivative or dual peptide in a Defined Intrinsic Thrombin Generation Assay peaking within 30 minutes, preferably within 15 minutes and most preferably within 10 minutes.

A tenth aspect of the invention provides a peptide or peptide derivative which has procoagulant activity, wherein the peptide or peptide derivative is not FVIII or a fragment thereof and, wherein the peptide or peptide derivative can at least partially compensate for the absence of biologically active FVIII when administered in an animal model of severe human hemophilia A.

DETAILED DESCRIPTION OF PREFERRED EMBODIMENTS OF THE INVENTION

Figure 1:
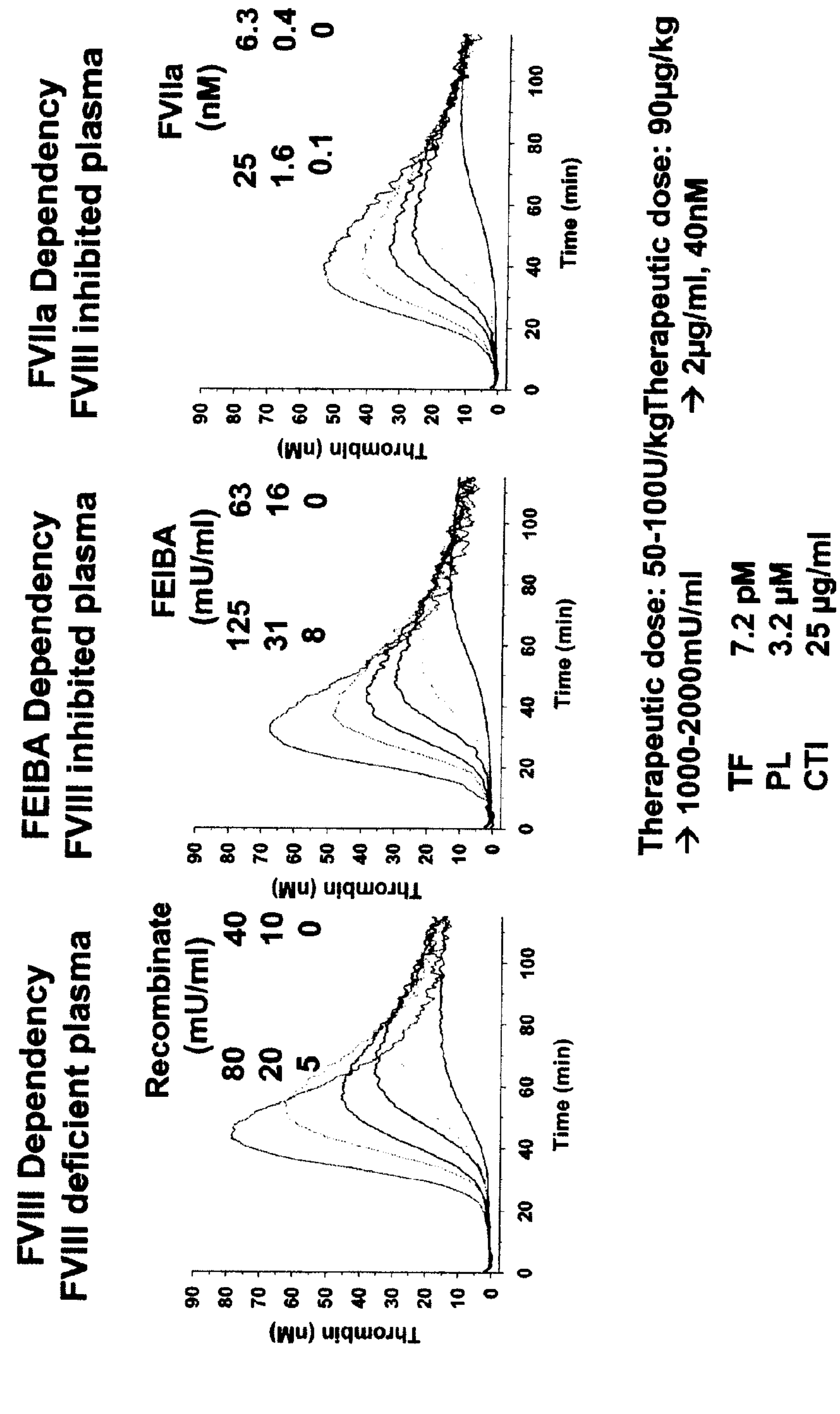
FIG. 1: Effect of therapeutics approved for treatment of hemophilia on peak thrombin generation and thrombin peak time in a defined Dual-pathway thrombin generation assay

The term "amino acid" within the scope of the present invention is intended to include all naturally occurring L α-amino acids. The one and three letter abbreviations for naturally occurring amino acids are used herein (Lehninger, Biochemistry, 2d ed., Worth Publishers, New York, 1995: 71-92). The term "amino acid" also includes stereoisomers (for example D-amino acids) and modifications of naturally occurring amino acids, non-proteinogenic amino acids, and structures designed to mimic amino acids.

Modified and non-proteinogenic amino acids are described generally in Grant, Synthetic Peptides: A User's Guide, Oxford University Press, 1992.

It is possible to provide, for example, improved stability and solubility, resistance to protease degradation, and activity of the peptide by the introduction of various amino acids that do not naturally occur, or by modification of the amino acid as discussed herein.

Non-proteinogenic amino acids may include but are not limited to β-alanine (β-Ala), norvaline (Nva), norleucine (Nle), 4-aminobutyric acid (γ-Abu), 2-aminoisobutyric acid (Aib), 6-aminohexanoic acid (ϵ-Ahx), ornithine (om), hydroxyproline (Hyp), sarcosine, citrulline, cysteic acid (Coh), and cyclohexylalanine, methioninesulfoxide (Meo), methioninesulfone (Moo), homoserinemethylester (Hsm), propargylglycine (Eag), 5-fluorotryptophan (5Fw), 6-fluorotryptophan (6Fw), 3',4'-dimethoxyphenyl-alanine (Ear), 3',4'-difluorophenylalanine (Dff), 4'-fluorophenyl-alanine (Pff), 1-naphthyl-alanine (1Ni), 1-methyltryptophan (1Mw), penicillamine (Pen), homoserine (HSe). Further, such amino acids may include but are not limited to, α-amino isobutyric acid, t-butylglycine, t-butylalanine, phenylglycine (Phg), benzothienylalanine (Bta), L-homo-cysteine (L-Hcys), N-methyl-phenylalanine (NM F), 2-thienylalanine (Thi), 3,3-diphenylalanine (Ebw), homophenylalanine (Hfe), s-benzyl-L-cysteine (Ece) or cyclohexylalanine (Cha). These and other non-proteinogenic amino acids may exist as D- or L-isomers. Where no indication of the isomer is given, the L-isomer is intended.

Structures which are designed to mimic amino acids are compounds in which the amino and/or carboxyl group of an amino acid is replaced by another group. Non-limiting examples are the incorporation of thioamides, ureas, thioureas, acylhydrazides, esters, olefines, sulfonamides, phosphoric acid amides, ketones, alcohols, boronic acid amides, benzodiazepines and other aromatic or non-aromatic heterocycles (for a review see M. A. Estiarte, D. H. Rich in Burgers Medicinal Chemistry, 6th edition, volume 1, part 4, John Wiley & Sons, New York, 2002). If these structures are included in a peptide derivative they are usually connected to the rest of the peptide derivative with at least one of the above mentioned functional groups instead of an amide bond.

By "peptide" we include not only molecules in which amino acid residues are joined by peptide (—CO—NH—) linkages but also molecules in which the peptide bond is reversed. A "retro modified" peptide is a peptide that is made up of amino acids in which the amino acid residues are assembled in opposite direction to the native peptide with respect to which it is retro modified. Where the native peptide comprises L-amino acids, the "retro modified" peptide will also comprise L-amino acids. However, where the native peptide comprises D-amino acids, the "retro modified" peptide will comprise D-amino acids. Retro peptides contain NH—CO bonds instead of CO—NH peptide bonds. An "inverso modified" peptide is a peptide in which the amino acid residues are assembled in the same direction as the native peptide with respect to which it is inverso modified, but the chirality of the amino acids is inverted. Thus, where the native peptide comprises L-amino acids, the "inverso modified" peptide will comprise D-amino acids. Where the native peptide comprises D-amino acids, the "inverso modified" peptide will comprise L-amino acids. Inverso peptides still have CO—NH peptide bonds. A "retro-inverso modified" peptide refers to a peptide that is made up of amino acid residues which are assembled in the opposite direction and which have inverted chirality with respect to the native peptide to which it is retro-inverso modified. A retro-inverso analogue has reversed termini and reversed direction of peptide bonds (i.e. NH—CO) while approximately maintaining the topology of the side chains as in the native peptide sequence. Guichard et al (1994) *Proc. Natl. Acad. Sci USA* 91:9765-9769 described that a retro-inverso peptide mimicked the structure and antigenic activity of the natural L-peptide IRGERA, but not of the D- and retro peptides. Such retro-inverso peptidomimetics may be made using methods known in the art, for example such as those described in Meziere et al (1997) *J. Immunol.* 159, 3230-3237, incorporated herein by reference. Partial retro-inverso peptide analogues are polypeptides in which only part of the sequence is reversed and replaced with enantiomeric amino acid residues. Processes for making such analogues are described in Pessi, A., Pinori, M., Verdini, A. S. & Viscomi, G. C. (1987) "Totally solid phase synthesis of peptide(s)-containing retro-inverted peptide bond, using crosslinked sarcosinyl copolymer as support", European Patent 97994-B.

Conventionally, L-amino acids are designated using upper case, and D-amino acids are designated in lower case. The peptides and peptide derivatives of the invention are designated in their preferred form, but without limiting them to the preferred form. The peptide of the first aspect of the invention is designated as comprising WDLYFEIVW (SEQ ID NO: 1) or a variant thereof. The peptide of the first aspect of the invention may also be the retro-inverso variant of WDLYFEIVW (SEQ ID NO: 1) or a variant thereof, namely wviefyldw or a variant thereof. The peptide of the second aspect of the invention is designated as comprising cimfwydcye or a variant thereof.

Conventionally, where the amino acids are joined by peptide bonds, a peptide is represented such that the amino group at the N-terminus appears to the left and the carboxyl group at the C-terminus to the right. Peptides and peptide derivatives according to the present invention are represented in this manner.

A "peptide derivative" contains a modification of one or more amino acid residues or a linker group or other covalently linked group.

Examples of derivatives include N-acyl derivatives of the amino terminal or of another free amino group, esters of the carboxyl terminal or of another free carboxyl or hydroxy group, amides of the carboxyl terminal or of another free carboxyl group produced by reaction with ammonia or with a suitable amine, glycosylated derivatives, hydroxylated derivatives, nucleotidylated derivatives, ADP-ribosylated derivatives, pegylated derivatives, phosphorylated derivatives, derivatives conjugated to lipophilic moieties, and derivatives conjugated to an antibody or other biological ligand. Also included among the chemical derivatives are those obtained by modification of the peptide bond —CO—NH—, for example by reduction to —$CH_2$—NH— or alkylation to —CO—N(alkyl)-.

A preferred derivatisation is C-terminal amidation. C-terminal amidation of a peptide removes the negative charge of the C terminus. Peptide derivatives having a C-terminal amide are represented with "$NH_2$" at the C-terminus, for example Ac-WDLYFEIVW-$NH_2$ (SEQ ID NO: 1). Another preferred derivatisation is N-terminal acetylation. This removes the positive charge at the N-terminus. Blocking of the C- or N-terminus, such as by C-terminal amidation or N-terminal acetylation, may improve proteolytic stability due to reduced susceptibility to exoproteolytic digestion.

Suitable linkers include the flexible linker 4,7,10-trioxa-1,13-tridecanediamine (Ttds), glycine, 6-aminohexanoic acid, beta-alanine, or combinations of Ttds, glycine, 6-aminohexanoic acid and beta-alanine.

The peptides of this invention can be produced by chemical synthesis, recombinant DNA technology, biochemical or enzymatic fragmentation of larger molecules, combinations of the foregoing or by any other method.

Peptides (at least those containing peptide linkages between amino acid residues) may be synthesised by the Fmoc strategy of solid-phase peptide synthesis as described in "Fmoc Solid Phase Peptide Synthesis—A Practical Approach", edited by W. C. Chan, P. D. White, Oxford University Press, New York 2000 and references therein. Temporary N-amino group protection is afforded by the 9-fluorenylmethyloxycarbonyl (Fmoc) group. Repetitive cleavage of this highly base-labile protecting group is effected using 20% piperidine in N,N-dimethylformamide. Side-chain functionalities may be protected as their butyl ethers (in the case of serine, threonine and tyrosine), butyl esters (in the case of glutamic acid and aspartic acid), butyloxycarbonyl derivative (in the case of lysine and histidine), trityl derivative (in the case of cysteine, asparagine and glutamine) and 4-methoxy-2,3,6-trimethylbenzenesulphonyl derivative (in the case of arginine). The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalising agent). The peptide-to-resin cleavable linked agent used is the acid-labile 4-hydroxymethyl-phenoxyacetic acid derivative, or in case of C-terminal amides, the Rink-amide linker. All amino acid derivatives are added as their preformed symmetrical anhydride derivatives with the exception of asparagine and glutamine, which are added using a reversed N,N-dicyclohexyl-carbodiimide/1-hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used are ethanedithiol, phenol, anisole and water, the exact choice depending on the constituent amino acids of the peptide being synthesised. Trifluoroacetic acid is removed by evaporation in vacuo, with subsequent trituration with diethyl ether affording the crude peptide. Any scavengers present are removed by a simple extraction procedure which on lyophilisation of the aqueous phase affords the crude peptide free of scavengers. Reagents for peptide synthesis are generally available from Calbiochem-Novabiochem (UK) Ltd, Nottingham NG7 2QJ, UK. Purification may be effected by any one, or a combination of, techniques such as size exclusion chromatography, ion-exchange chromatography, affinity chromatography, differential solubility and (principally) reverse-phase high performance liquid chromatography. Analysis of peptides may be carried out using thin layer chromatography, reverse-phase high performance liquid chromatography, amino-acid analysis after acid hydrolysis and by fast atom bombardment (FAB) mass spectrometric analysis.

SPOT-synthesis, which allows the positional addressable, chemical synthesis of peptides on continuous cellulose membranes may be also used (R Frank *Tetrahedron* (1992) 48, 9217).

As an alternative to solid phase peptide synthesis techniques, peptides may also be produced by recombinant protein expression or in vitro translation systems (Sambrook et al, "Molecular cloning: A laboratory manual", 2001, 3$^{rd}$ edition, Cold Spring Harbor Laboratory Press, Cold Spring Harbor, N.Y.). Of course, it is only peptides which contain naturally occurring amino acid residues joined by naturally-occurring peptide bonds which are encodable by a polynucleotide. Such methods are preferred over solid phase peptide synthesis techniques where the peptide is particularly large, such as larger than 50 amino acids, or larger than 100 amino acids.

A "variant" amino acid sequence as defined in relation to the first aspect of the invention may comprise one, two, three or four L-amino acid substitutions in WDLYFEIVW (SEQ ID NO: 1).

Preferably, the variant amino acid sequence comprises an amino acid sequence comprising $X_1X_2X_3YX_4EX_5X_6X_7$ wherein $X_1$ is W, L or P, $X_2$ is D or S, $X_3$ is L or F, $X_4$ is F, Phg, L, Ebw, Pff, Thi, 1Ni, Hfe, Ece or Cha, $X_5$ is I or F, $X_6$ is S, V or G and $X_7$ is W or L (SEQ ID NO: 1).

More preferably, the variant amino acid sequence comprises an amino acid sequence comprising $X_1X_2X_3YX_4EX_5X_6X_7$ wherein $X_1$ is W or L, $X_2$ is D or S, $X_3$ is L or F, $X_4$ is F, Phg or L, $X_5$ is I or F, $X_6$ is S, V or G and $X_7$ is W or L (SEQ ID NO: 1).

A "variant" amino acid sequence as defined in relation to the second aspect of the invention may comprise one, two, three, four, five or six amino acid substitutions in imfwydcye.

Preferably, at least one, two, three, four, five or six of said substitutions in imfwydcye are D-amino acids.

Any substitution within the variant may be non-conservative or conservative.

By "conservative substitutions" we mean substitutions within the following groups: Val, Ile, Leu, Ala, Met; Asp, Glu; Asn, Gln; Ser, Thr, Gly, Ala; Lys, Arg, His; and Phe, Tyr, Trp.

Preferably, the peptide or peptide derivative of the first aspect of the invention comprises RMEFDVWDLYFEIVW (SEQ ID NO: 2) or RMKFDVWDLYFEIVW (SEQ ID NO: 2); or a variant amino acid sequence comprising one, two, three, four, five or six amino acid substitutions in RMEFDVWDLYFEIVW (SEQ ID NO: 2) or RMKFDVWDLYFEIVW (SEQ ID NO: 2).

For the avoidance of doubt, the sequence RMEFDVWDLYFEIVW (SEQ ID NO: 2) may be represented as Arg-Met-Glu-Phe-Asp-Val-Trp-Asp-Leu-Tyr-Phe-Glu-Ile-Val-Trp using the three letter code for amino acids. RMKFDVWDLYFEIVW (SEQ ID NO: 2) may be represented as Arg-Met-Lys-Phe-Asp-Val-Trp-Asp-Leu-Tyr-Phe-Glu-Ile-Val-Trp using the three letter code for amino acids.

More preferably, the variant amino acid sequence comprises an amino acid sequence comprising $X_8X_9X_{10}FDVX_1X_2X_3YX_4EX_5X_6X_7$ wherein $X_8$ is R or P, $X_9$ is M, Nva, Moo, N, Nle, Meo, Q, Eag, $X_{10}$ is E, K or D, $X_1$ is W, L or P, $X_2$ is D or S, $X_3$ is L or F, $X_4$ is F, Phg, L, Ebw, Pff, Thi, 1Ni, Hfe, Ece, Cha, $X_5$ is I or F, $X_6$ is 5, V or G and $X_7$ is W or L (SEQ ID NO: 2).

More preferably, the variant amino acid sequence comprises an amino acid sequence comprising $X_8X_9X_{10}FDVX_1X_2X_3YX_4EX_5X_6X_7$ wherein $X_8$ is R or P, $X_9$ is M or Nva, $X_{10}$ is E, K or D, $X_1$ is W or L, $X_2$ is D or S, $X_3$ is L or F, $X_4$ is F, Phg or L, $X_5$ is I or F, $X_6$ is S, V or G and $X_7$ is W or L (SEQ ID NO: 2).

Suitably, the peptide or peptide derivative of the first aspect of the invention is a peptide or peptide derivative as represented in the table below, or comprises or consists of the amino acid sequence of a peptide or peptide derivative as represented in tables 1 to 3 below:

TABLE 1

| Most preferred peptides | | |
|---|---|---|
| | Peptide | Sequence |
| SEQ ID NO: 2 | A01 | Ac-RMKFDVWDLYFEIVW-$NH_2$ |
| SEQ ID NO: 2 | A02 | Ac-PMKFDVWDLYFEIVW-$NH_2$ |
| SEQ ID NO: 2 | A03 | Ac-RMDFDVWDLYFEIVW-$NH_2$ |
| SEQ ID NO: 2 | A04 | Ac-RMEFDVWDLYFEIVW-$NH_2$ |
| SEQ ID NO: 1 | A05 | Ac-WDLYFEIVW-$NH_2$ |
| SEQ ID NO: 3 | A06 | Ac-WDLYFEIVWE |
| SEQ ID NO: 1 | A07 | Ac-WDLYFEIVW-ttds-E |
| SEQ ID NO: 2 | A08 | ttds-RMEFDVWDLYFEIVW-ttds-$NH_2$ |
| SEQ ID NO: 4 | A09 | ERMEFDVWDLYFEIVW-$NH_2$ |
| SEQ ID NO: 5 | A12 | ERXEFDVWDLYFEIVW-$NH_2$ X is Nva |
| | A13 | ttds-RMEFDVWDLYXEIVW-ttds-$NH_2$ X is Phg |
| SEQ ID NO: 6 | A14 | Ac-WSLYFEIVWE |
| SEQ ID NO: 1 | A15 | Ac-WDLYFEISW-ttds-E |
| SEQ ID NO: 2 | A16 | PEG5000-RMKFDVWDLYFEIVW-$NH_2$ |
| SEQ ID NO: 6 | A17 | PEG5000-WSLYFEIVWE |
| SEQ ID NO: 4 | A18 | PEG5000-ERMEFDVWDLYFEIVW-$NH_2$ |
| SEQ ID NO: 7 | A19 | Ac-VWDLYFEIVW-$NH_2$ |
| SEQ ID NO: 8 | A21 | Ac-FDVWDLYFEIVW-$NH_2$ |
| SEQ ID NO: 9 | A24 | EWDLYFEIVW-$NH_2$ |
| SEQ ID NO: 1 | A25 | E-ttds-WDLYFEIVW-$NH_2$ |
| SEQ ID NO: 1 | A26 | Ac-WDLYFEIVW-ttds-E-$NH_2$ |
| SEQ ID NO: 2 | A27 | Ac-RMEFDVWDLYFEIVW |
| SEQ ID NO: 2 | A28 | RMEFDVWDLYFEIVW |
| SEQ ID NO: 2 | A29 | Ac-K-ttds-RMEFDVWDLYFEIVW-$NH_2$ |
| SEQ ID NO: 10 | A30 | Ac-RMEFDVWDLYFEIVWK |

TABLE 1-continued

| Most preferred peptides | | |
|---|---|---|
| | Peptide | Sequence |
| SEQ ID NO: 10 | A31 | Ac-RMEFDVWDLYFEIVWK-$NH_2$ |
| SEQ ID NO: 2 | A32 | Ac-RMEFDVWDLYFEIVW-ttds-K-$NH_2$ |
| SEQ ID NO: 11 | A33 | Ac-WDLYFEISWE |
| SEQ ID NO: 12 | A34 | Ac-WDLYLEIVWE |
| SEQ ID NO: 13 | A35 | Ac-WDLYFEIVLE |
| SEQ ID NO: 1 | A38 | WDLYFEIVW |
| SEQ ID NO: 2 | A49 | RMEFDVWDLYFEIVW-$NH_2$ |
| SEQ ID NO: 2 | A50 | Ac-RMEFDVWDLYFEIVW-ttds-$NH_2$ |
| SEQ ID NO: 14 | A52 | Ac-KRMEFDVWDLYFEIVW-$NH_2$ |
| SEQ ID NO: 2 | A53 | K-ttds-RMEFDVWDLYFEIVW-$NH_2$ |
| SEQ ID NO: 2 | A54 | Ac-RMEFDVWDLYFEIVW-ttds-K |
| SEQ ID NO: 1 | A55 | Ac-LDLYFEIVW-ttds-E |
| SEQ ID NO: 1 | A56 | Ac-WDLYFEIVL-ttds-E |
| SEQ ID NO: 15 | A57 | E-RMEFDVLDLYFEIVW-$NH_2$ |
| SEQ ID NO: 16 | A58 | E-RMEFDVWDLYFEIVL-$NH_2$ |
| SEQ ID NO: 17 | A84 | Ac-WDFYFEIVWE |
| SEQ ID NO: 18 | A85 | Ac-WDLYFEFVWE |
| SEQ ID NO: 19 | A86 | Ac-LDLYFEIVWE |
| SEQ ID NO: 20 | A87 | Ac-WDLYFEIGWE |
| SEQ ID NO: 21 | A89 | Ac-WDLYLEISLE |
| | A90 | Ac-WDLYXEIVLE X is Phg |
| | A91 | Ac-WSLYXEIVWE X is Phg |
| SEQ ID NO: 22 | A92 | Ac-LDLYFEIVLE |
| SEQ ID NO: 23 | A93 | Ac-LDLYFEISLE |
| | A94 | Ac-LDLYXEISWE X is Phg |
| SEQ ID NO: 24 | A95 | Ac-LSLYFEIVWE |
| SEQ ID NO: 25 | A96 | Ac-LSLYFEIVLE |
| SEQ ID NO: 26 | A97 | Ac-LSLYFEISLE |

TABLE 2

| Preferred peptides | | |
|---|---|---|
| | Peptide | Sequence |
| SEQ ID NO: 1 | A20 | Ac-WDLYFEIVW-ttds-K |
| SEQ ID NO: 27 | A22 | Ac-DVWDLYFEIVW-$NH_2$ |
| | A23 | Ac-wviefyldwvdfkmr-$NH_2$ |
| SEQ ID NO: 1 | A37 | Ac-WDLYFEIVW |
| SEQ ID NO: 1 | A39 | Ac-ttds-WDLYFEIVW-$NH_2$ |
| SEQ ID NO: 1 | A40 | ttds-WDLYFEIVW-$NH_2$ |
| SEQ ID NO: 1 | A41 | Ac-WDLYFEIVW-ttds-$NH_2$ |

TABLE 2-continued

| Preferred peptides | | |
|---|---|---|
| | Peptide | Sequence |
| SEQ ID NO: 1 | A42 | Ac-ttds-WDLYFEIVW-ttds-$NH_2$ |
| SEQ ID NO: 1 | A43 | ttds-WDLYFEIVW-ttds |
| SEQ ID NO: 1 | A44 | ttds-WDLYFEIVW-ttds-$NH_2$ |
| SEQ ID NO: 28 | A45 | Ac-KWDLYFEIVW-$NH_2$ |
| SEQ ID NO: 1 | A46 | Ac-K-ttds-WDLYFEIVW-$NH_2$ |
| SEQ ID NO: 29 | A47 | Ac-WDLYFEIVWK |

TABLE 2-continued

| Preferred peptides | | |
|---|---|---|
| Peptide Sequence | | |
| SEQ ID NO: 29 | A48 | Ac-WDLYFEIVWK-$NH_2$ |
| | A71 | E-R(Moo)EFDVWDLYFEIVW-$NH_2$ |
| SEQ ID NO: 30 | A73 | E-RNEFDVWDLYFEIVW-$NH_2$ |
| | A78 | ttds-RM EFDVWDLY(Ebw)EIVW-ttds-$NH_2$ |
| | A83 | ttds-RMEFDVWDLY(Pff)EIVW-ttds-$NH_2$ |
| SEQ ID NO: 31 | A88 | Ac-PDLYFEIVWE |
| SEQ ID NO: 32 | A98 | Ac-LSLYLEIVLE |
| SEQ ID NO: 33 | A99 | Ac-LSLYLEISLE |
| | A100 | Ac-LSLYXEIVLE X is Phg |
| SEQ ID NO: 1 | A101 | Ac-WDLYFEIVW-ttds-K-$NH_2$ |

TABLE 3

| Active peptides | | |
|---|---|---|
| Peptide Sequence | | |
| SEQ ID NO: 34 | A10 | E-PMKFDVWDLYFEIVW-$NH_2$ |
| SEQ ID NO: 2 | A11 | ttds-RMDFDVWDLYFEIVW-ttds-$NH_2$ |
| SEQ ID NO: 2 | A16 | PEG5000-RMKFDVWDLYFEIVW-$NH_2$ |
| SEQ ID NO: 1 | A36 | WDLYFEIVW-$NH_2$ |
| SEQ ID NO: 14 | A51 | KRMEFDVWDLYFEIVW-$NH_2$ |
| SEQ ID NO: 2 | A59 | ttds-PMKFDVWDLYFEIVW-ttds-$NH_2$ |
| SEQ ID NO: 35 | A60 | E-RMDFDVWDLYFEIVW-$NH_2$ |
| SEQ ID NO: 2 | A61 | (Coh)-ttds-RMEFDVWDLYFEIVW-ttds-$NH_2$ |
| SEQ ID NO: 2 | A62 | Glucosyl-aminooxyacetyl-ttds-RMEFDVWDLYFEIVW-ttds-$NH_2$ |
| | A63 | Ac-P(Moo)KFDVWDLYFEIVW-$NH_2$ |
| SEQ ID NO: 2 | A64 | Ac-P(Nle)KFDVVVDLYFEIVW-$NH_2$ |
| SEQ ID NO: 2 | A65 | Ac-PNKFDVWDLYFEIVW-$NH_2$ |
| | A66 | Ac-R(Moo)DFDVWDLYFEIVW-$NH_2$ |
| SEQ ID NO: 2 | A67 | Ac-R(Nle)DFDVWDLYFEIVW-$NH_2$ |
| SEQ ID NO: 2 | A68 | Ac-RNDFDVWDLYFEIVW-$NH_2$ |
| SEQ ID NO: 2 | A69 | ttds-R(Nle)EFDVWDLYFEIVW-ttds-$NH_2$ |
| SEQ ID NO: 2 | A70 | ttds-RNEFDVWDLYFEIVW-ttds-$NH_2$ |
| SEQ ID NO: 321 | A72 | E-R(Nle)EFDVWDLYFEIVW-$NH_2$ |
| | A74 | E-R(Meo)EFDVWDLYFEIVW-$NH_2$ |
| SEQ ID NO: 36 | A75 | E-R(Gln)EFDVWDLYFEIVW-$NH_2$ |
| | A76 | E-R(Eag)EFDVWDLYFEIVW-$NH_2$ |
| | A77 | ttds-RM EFDVWDLY(Thi)EIVW-ttds-$NH_2$ |
| | A79 | ttds-RMEFDVWDLY(1Ni)EIVW-ttds-$NH_2$ |
| | A80 | ttds-RM EFDVWDLY(Hfe)EIVW-ttds-$NH_2$ |
| | A81 | ttds-RMEFDVWDLY(Ece)EIVW-ttds-$NH_2$ |
| | A82 | ttds-RMEFDVWDLY(Cha)EIVW-ttds-$NH_2$ |
| SEQ ID NO: 28 | A102 | KWDLYFEIVW-$NH_2$ |
| SEQ ID NO: 1 | A103 | K-ttds-WDLYFEIVW-$NH_2$ |

In the above tables, -ttds- is 4,7,10-trioxa-1,13-tridecane-diamine. “N” is asparagine. “$NH_2$” is a C-terminal amide group.

Preferably, the peptide or peptide derivative of the first aspect of the invention does not comprise or consist of a peptide represented in the list below:

AMKFDVWDLYFEIVW, (SEQ ID NO: 37)

CMKFDVWDLYFEIVW, (SEQ ID NO: 38)

DMKFDVWDLYFEIVW, (SEQ ID NO: 39)

EMKFDVWDLYFEIVW, (SEQ ID NO: 40)

FMKFDVWDLYFEIVW, (SEQ ID NO: 41)

GMKFDVWDLYFEIVW, (SEQ ID NO: 42)

HMKFDVWDLYFEIVW, (SEQ ID NO: 43)

IMKFDVWDLYFEIVW, (SEQ ID NO: 44)

KMKFDVWDLYFEIVW, (SEQ ID NO: 45)

LMKFDVWDLYFEIVW, (SEQ ID NO: 46)

MMKFDVWDLYFEIVW, (SEQ ID NO: 47)

NMKFDVWDLYFEIVW, (SEQ ID NO: 48)

QMKFDVWDLYFEIVW, (SEQ ID NO: 49)

SMKFDVWDLYFEIVW, (SEQ ID NO: 50)

TMKFDVWDLYFEIVW, (SEQ ID NO: 51)

VMKFDVWDLYFEIVW, (SEQ ID NO: 52)

WMKFDVWDLYFEIVW, (SEQ ID NO: 53)

YMKFDVWDLYFEIVW, (SEQ ID NO: 54)

RAKFDVWDLYFEIVW, (SEQ ID NO: 55)

RCKFDVWDLYFEIVW, (SEQ ID NO: 56)

RDKFDVWDLYFEIVW, (SEQ ID NO: 57)

REKFDVWDLYFEIVW, (SEQ ID NO: 58)

RFKFDVWDLYFEIVW, (SEQ ID NO: 59)

RGKFDVWDLYFEIVW, (SEQ ID NO: 60)

-continued

RHKFDVWDLYFEIVW, (SEQ ID NO: 61)

RIKFDVWDLYFEIVW, (SEQ ID NO: 62)

RKKFDVWDLYFEIVW, (SEQ ID NO: 63)

RLKFDVWDLYFEIVW, (SEQ ID NO: 64)

RNKFDVWDLYFEIVW, (SEQ ID NO: 65)

RPKFDVWDLYFEIVW, (SEQ ID NO: 66)

RQKFDVWDLYFEIVW, (SEQ ID NO: 67)

RRKFDVWDLYFEIVW, (SEQ ID NO: 68)

RSKFDVWDLYFEIVW, (SEQ ID NO: 69)

RTKFDVWDLYFEIVW, (SEQ ID NO: 70)

RVKFDVWDLYFEIVW, (SEQ ID NO: 71)

RWKFDVWDLYFEIVW, (SEQ ID NO: 72)

RYKFDVWDLYFEIVW, (SEQ ID NO: 73)

RMAFDVWDLYFEIVW, (SEQ ID NO: 74)

RMCFDVWDLYFEIVW, (SEQ ID NO: 75)

RMFFDVWDLYFEIVW, (SEQ ID NO: 76)

RMGFDVWDLYFEIVW, (SEQ ID NO: 77)

RMHFDVWDLYFEIVW, (SEQ ID NO: 78)

RMIFDVWDLYFEIVW, (SEQ ID NO: 79)

RMLFDVWDLYFEIVW, (SEQ ID NO: 80)

RMMFDVWDLYFEIVW, (SEQ ID NO: 81)

RMNFDVWDLYFEIVW, (SEQ ID NO: 82)

RMPFDVWDLYFEIVW, (SEQ ID NO: 83)

RMQFDVWDLYFEIVW, (SEQ ID NO: 84)

RMRFDVWDLYFEIVW, (SEQ ID NO: 85)

RMSFDVWDLYFEIVW, (SEQ ID NO: 86)

RMTFDVWDLYFEIVW, (SEQ ID NO: 87)

-continued (SEQ ID NO: 88)
RMVFDVWDLYFEIVW, (SEQ ID NO: 89)
RMWFDVWDLYFEIVW, (SEQ ID NO: 90)
RMYFDVWDLYFEIVW, (SEQ ID NO: 91)
RMKADVWDLYFEIVW, (SEQ ID NO: 92)
RMKCDVWDLYFEIVW, (SEQ ID NO: 93)
RMKADVWDLYFEIVW, (SEQ ID NO: 94)
RMKEDVWDLYFEIVW, (SEQ ID NO: 95)
RMKGDVWDLYFEIVW, (SEQ ID NO: 96)
RMKHDVWDLYFEIVW, (SEQ ID NO: 97)
RMKIDVWDLYFEIVW, (SEQ ID NO: 98)
RMKKDVWDLYFEIVW, (SEQ ID NO: 99)
RMKLDVWDLYFEIVW, (SEQ ID NO: 100)
RMKMDVWDLYFEIVW, (SEQ ID NO: 101)
RMKNDVWDLYFEIVW, (SEQ ID NO: 102)
RMKPDVWDLYFEIVW, (SEQ ID NO: 103)
RMKQDVWDLYFEIVW, (SEQ ID NO: 104)
RMKRDVWDLYFEIVW, (SEQ ID NO: 105)
RMKADVWDLYFEIVW, (SEQ ID NO: 106)
RMKTDVWDLYFEIVW, (SEQ ID NO: 107)
RMKVDVWDLYFEIVW, (SEQ ID NO: 108)
RMKWDVWDLYFEIVW, (SEQ ID NO: 109)
RMKYDVWDLYFEIVW, (SEQ ID NO: 110)
RMKFAVWDLYFEIVW, (SEQ ID NO: 111)
RMKFCVWDLYFEIVW, (SEQ ID NO: 112)
RMKFEVWDLYFEIVW, (SEQ ID NO: 113)
RMKFFVWDLYFEIVW, (SEQ ID NO: 114)
RMKFGVWDLYFEIVW, -continued (SEQ ID NO: 115)
RMKFHVWDLYFEIVW, (SEQ ID NO: 116)
RMKFIVWDLYFEIVW, (SEQ ID NO: 117)
RMKFKVWDLYFEIVW, (SEQ ID NO: 118)
RMKFLVWDLYFEIVW, (SEQ ID NO: 119)
RMKFMVWDLYFEIVW, (SEQ ID NO: 120)
RMKFNVWDLYFEIVW, (SEQ ID NO: 121)
RMKFPVWDLYFEIVW, (SEQ ID NO: 122)
RMKFQVWDLYFEIVW, (SEQ ID NO: 123)
RMKFRVWDLYFEIVW, (SEQ ID NO: 124)
RMKFCVWDLYFEIVW, (SEQ ID NO: 125)
RMKFTVWDLYFEIVW, (SEQ ID NO: 126)
RMKFVVWDLYFEIVW, (SEQ ID NO: 127)
RMKFWVWDLYFEIVW, (SEQ ID NO: 128)
RMKFYVWDLYFEIVW, (SEQ ID NO: 129)
RMKFDAWDLYFEIVW, (SEQ ID NO: 130)
RMKFDCWDLYFEIVW, (SEQ ID NO: 131)
RMKFDDWDLYFEIVW, (SEQ ID NO: 132)
RMKFDEWDLYFEIVW, (SEQ ID NO: 133)
RMKFDFWDLYFEIVW, (SEQ ID NO: 134)
RMKFDGWDLYFEIVW, (SEQ ID NO: 135)
RMKFDHWDLYFEIVW, (SEQ ID NO: 136)
RMKFDIWDLYFEIVW, (SEQ ID NO: 137)
RMKFDKWDLYFEIVW, (SEQ ID NO: 138)
RMKFDLWDLYFEIVW, (SEQ ID NO: 139)
RMKFDMWDLYFEIVW, (SEQ ID NO: 140)
RMKFDNWDLYFEIVW, (SEQ ID NO: 141)
RMKFDPWDLYFEIVW, -continued (SEQ ID NO: 142)
RMKFDQWDLYFEIVW, (SEQ ID NO: 143)
RMKFDRWDLYFEIVW, (SEQ ID NO: 144)
RMKFDSWDLYFEIVW, (SEQ ID NO: 145)
RMKFDTWDLYFEIVW, (SEQ ID NO: 146)
RMKFDWWDLYFEIVW, (SEQ ID NO: 147)
RMKFDYWDLYFEIVW, (SEQ ID NO: 148)
RMKFDVADLYFEIVW, (SEQ ID NO: 149)
RMKFDVCDLYFEIVW, (SEQ ID NO: 150)
RMKFDVDDLYFEIVW, (SEQ ID NO: 151)
RMKFDVEDLYFEIVW, (SEQ ID NO: 152)
RMKFDVFDLYFEIVW, (SEQ ID NO: 153)
RMKFDVGDLYFEIVW, (SEQ ID NO: 154)
RMKFDVHDLYFEIVW, (SEQ ID NO: 155)
RMKFDVIDLYFEIVW, (SEQ ID NO: 156)
RMKFDVKDLYFEIVW, (SEQ ID NO: 157)
RMKFDVLDLYFEIVW, (SEQ ID NO: 158)
RMKFDVMDLYFEIVW, (SEQ ID NO: 159)
RMKFDVNDLYFEIVW, (SEQ ID NO: 160)
RMKFDVPDLYFEIVW, (SEQ ID NO: 161)
RMKFDVQDLYFEIVW, (SEQ ID NO: 162)
RMKFDVRDLYFEIVW, (SEQ ID NO: 163)
RMKFDVSDLYFEIVW, (SEQ ID NO: 164)
RMKFDVTDLYFEIVW, (SEQ ID NO: 165)
RMKFDVVDLYFEIVW, (SEQ ID NO: 166)
RMKFDVYDLYFEIVW, (SEQ ID NO: 167)
RMKFDVWALYFEIVW, (SEQ ID NO: 168)
RMKFDVWCLYFEIVW, -continued (SEQ ID NO: 169)
RMKFDVWELYFEIVW, (SEQ ID NO: 170)
RMKFDVWFLYFEIVW, (SEQ ID NO: 171)
RMKFDVWGLYFEIVW, (SEQ ID NO: 172)
RMKFDVWHLYFEIVW, (SEQ ID NO: 173)
RMKFDVWILYFEIVW, (SEQ ID NO: 174)
RMKFDVWKLYFEIVW, (SEQ ID NO: 175)
RMKFDVWALYFEIVW, (SEQ ID NO: 176)
RMKFDVWMLYFEIVW, (SEQ ID NO: 177)
RMKFDVWNLYFEIVW, (SEQ ID NO: 178)
RMKFDVWPLYFEIVW, (SEQ ID NO: 179)
RMKFDVWQLYFEIVW, (SEQ ID NO: 180)
RMKFDVWRLYFEIVW, (SEQ ID NO: 181)
RMKFDVWSLYFEIVW, (SEQ ID NO: 182)
RMKFDVWTLYFEIVW, (SEQ ID NO: 183)
RMKFDVWVLYFEIVW, (SEQ ID NO: 184)
RMKFDVWWLYFEIVW, (SEQ ID NO: 185)
RMKFDVWYLYFEIVW, (SEQ ID NO: 186)
RMKFDVWDAYFEIVW, (SEQ ID NO: 187)
RMKFDVWDCYFEIVW, (SEQ ID NO: 188)
RMKFDVWDDYFEIVW, (SEQ ID NO: 189)
RMKFDVWDEYFEIVW, (SEQ ID NO: 190)
RMKFDVWDFYFEIVW, (SEQ ID NO: 191)
RMKFDVWDGYFEIVW, (SEQ ID NO: 192)
RMKFDVWDHYFEIVW, (SEQ ID NO: 193)
RMKFDVWDIYFEIVW, (SEQ ID NO: 194)
RMKFDVWDKYFEIVW, (SEQ ID NO: 195)
RMKFDVWDMYFEIVW, -continued (SEQ ID NO: 196)
RMKFDVWDNYFEIVW, (SEQ ID NO: 197)
RMKFDVWDPYFEIVW, (SEQ ID NO: 198)
RMKFDVWDQYFEIVW, (SEQ ID NO: 199)
RMKFDVWDRYFEIVW, (SEQ ID NO: 200)
RMKFDVWDSYFEIVW, (SEQ ID NO: 201)
RMKFDVWDTYFEIVW, (SEQ ID NO: 202)
RMKFDVWDVYFEIVW, (SEQ ID NO: 203)
RMKFDVWDWYFEIVW, (SEQ ID NO: 204)
RMKFDVWDYYFEIVW, (SEQ ID NO: 205)
RMKFDVWDLAFEIVW, (SEQ ID NO: 206)
RMKFDVWDLCFEIVW, (SEQ ID NO: 207)
RMKFDVWDLDFEIVW, (SEQ ID NO: 208)
RMKFDVWDLEFEIVW, (SEQ ID NO: 209)
RMKFDVWDLFFEIVW, (SEQ ID NO: 210)
RMKFDVWDLGFEIVW, (SEQ ID NO: 211)
RMKFDVWDLHFEIVW, (SEQ ID NO: 212)
RMKFDVWDLIFEIVW, (SEQ ID NO: 213)
RMKFDVWDLKFEIVW, (SEQ ID NO: 214)
RMKFDVWDLCFEIVW, (SEQ ID NO: 215)
RMKFDVWDLMFEIVW, (SEQ ID NO: 216)
RMKFDVWDLNFEIVW, (SEQ ID NO: 217)
RMKFDVWDLPFEIVW, (SEQ ID NO: 218)
RMKFDVWDLQFEIVW, (SEQ ID NO: 219)
RMKFDVWDLRFEIVW, (SEQ ID NO: 220)
RMKFDVWDLSFEIVW, (SEQ ID NO: 221)
RMKFDVWDLTFEIVW, (SEQ ID NO: 222)
RMKFDVWDLVFEIVW, -continued (SEQ ID NO: 223)
RMKFDVWDLWFEIVW, (SEQ ID NO: 224)
RMKFDVWDLYAEIVW, (SEQ ID NO: 225)
RMKFDVWDLYCEIVW, (SEQ ID NO: 226)
RMKFDVWDLYDEIVW, (SEQ ID NO: 227)
RMKFDVWDLYEEIVW, (SEQ ID NO: 228)
RMKFDVWDLYGEIVW, (SEQ ID NO: 229)
RMKFDVWDLYHEIVW, (SEQ ID NO: 230)
RMKFDVWDLYIEIVW, (SEQ ID NO: 231)
RMKFDVWDLYKEIVW, (SEQ ID NO: 232)
RMKFDVWDLYLEIVW, (SEQ ID NO: 233)
RMKFDVWDLYMEIVW, (SEQ ID NO: 234)
RMKFDVWDLYNEIVW, (SEQ ID NO: 235)
RMKFDVWDLYPEIVW, (SEQ ID NO: 236)
RMKFDVWDLYQEIVW, (SEQ ID NO: 237)
RMKFDVWDLYREIVW, (SEQ ID NO: 238)
RMKFDVWDLYSEIVW, (SEQ ID NO: 239)
RMKFDVWDLYTEIVW, (SEQ ID NO: 240)
RMKFDVWDLYVEIVW, (SEQ ID NO: 241)
RMKFDVWDLYWEIVW, (SEQ ID NO: 242)
RMKFDVWDLYYEIVW, (SEQ ID NO: 243)
RMKFDVWDLYFAIVW, (SEQ ID NO: 244)
RMKFDVWDLYFCIVW, (SEQ ID NO: 245)
RMKFDVWDLYFDIVW, (SEQ ID NO: 246)
RMKFDVWDLYFFIVW, (SEQ ID NO: 247)
RMKFDVWDLYFGIVW, (SEQ ID NO: 248)
RMKFDVWDLYFHIVW, (SEQ ID NO: 249)
RMKFDVWDLYFIIVW, -continued

RMKFDVWDLYFKIVW, (SEQ ID NO: 250)

RMKFDVWDLYFLIVW, (SEQ ID NO: 251)

RMKFDVWDLYFMIVW, (SEQ ID NO: 252)

RMKFDVWDLYFNIVW, (SEQ ID NO: 253)

RMKFDVWDLYFPIVW, (SEQ ID NO: 254)

RMKFDVWDLYFQIVW, (SEQ ID NO: 255)

RMKFDVWDLYFRIVW, (SEQ ID NO: 256)

RMKFDVWDLYFTIVW, (SEQ ID NO: 257)

RMKFDVWDLYFTIVW, (SEQ ID NO: 258)

RMKFDVWDLYFVIVW, (SEQ ID NO: 259)

RMKFDVWDLYFWIVW, (SEQ ID NO: 260)

RMKFDVWDLYFYIVW, (SEQ ID NO: 261)

RMKFDVWDLYFEAVW, (SEQ ID NO: 262)

RMKFDVWDLYFECVW, (SEQ ID NO: 263)

RMKFDVWDLYFEDVW, (SEQ ID NO: 264)

RMKFDVWDLYFEEVW, (SEQ ID NO: 265)

RMKFDVWDLYFEFVW, (SEQ ID NO: 266)

RMKFDVWDLYFEGVW, (SEQ ID NO: 267)

RMKFDVWDLYFEHVW, (SEQ ID NO: 268)

RMKFDVWDLYFEKVW, (SEQ ID NO: 269)

RMKFDVWDLYFELVW, (SEQ ID NO: 270)

RMKFDVWDLYFEMVW, (SEQ ID NO: 271)

RMKFDVWDLYFENVW, (SEQ ID NO: 272)

RMKFDVWDLYFEPVW, (SEQ ID NO: 273)

RMKFDVWDLYFEQVW, (SEQ ID NO: 274)

RMKFDVWDLYFERVW, (SEQ ID NO: 275)

RMKFDVWDLYFESVW, (SEQ ID NO: 276)

-continued

RMKFDVWDLYFETVW, (SEQ ID NO: 277)

RMKFDVWDLYFEVVW, (SEQ ID NO: 278)

RMKFDVWDLYFEWVW, (SEQ ID NO: 279)

RMKFDVWDLYFEYVW, (SEQ ID NO: 280)

RMKFDVWDLYFEIAW, (SEQ ID NO: 281)

RMKFDVWDLYFEICW, (SEQ ID NO: 282)

RMKFDVWDLYFEIDW, (SEQ ID NO: 283)

RMKFDVWDLYFEIEW, (SEQ ID NO: 284)

RMKFDVWDLYFEIFW, (SEQ ID NO: 285)

RMKFDVWDLYFEIGW, (SEQ ID NO: 286)

RMKFDVWDLYFEIHW, (SEQ ID NO: 287)

RMKFDVWDLYFEIIW, (SEQ ID NO: 288)

RMKFDVWDLYFEIKW, (SEQ ID NO: 289)

RMKFDVWDLYFEILW, (SEQ ID NO: 290)

RMKFDVWDLYFEIMW, (SEQ ID NO: 291)

RMKFDVWDLYFEINW, (SEQ ID NO: 292)

RMKFDVWDLYFEIPW, (SEQ ID NO: 293)

RMKFDVWDLYFEIQW, (SEQ ID NO: 294)

RMKFDVWDLYFEIRW, (SEQ ID NO: 295)

RMKFDVWDLYFEISW, (SEQ ID NO: 296)

RMKFDVWDLYFEITW, (SEQ ID NO: 297)

RMKFDVWDLYFEIWW, (SEQ ID NO: 298)

RMKFDVWDLYFEIYW, (SEQ ID NO: 299)

RMKFDVWDLYFEIVA, (SEQ ID NO: 300)

RMKFDVWDLYFEIVC, (SEQ ID NO: 301)

RMKFDVWDLYFEIVD, (SEQ ID NO: 302)

RMKFDVWDLYFEIVE, (SEQ ID NO: 303)

-continued (SEQ ID NO: 304)
RMKFDVWDLYFEIVF, (SEQ ID NO: 305)
RMKFDVWDLYFEIVG, (SEQ ID NO: 306)
RMKFDVWDLYFEIVH, (SEQ ID NO: 307)
RMKFDVWDLYFEIVI, (SEQ ID NO: 308)
RMKFDVWDLYFEIVK, (SEQ ID NO: 309)
RMKFDVWDLYFEIVL, (SEQ ID NO: 310)
RMKFDVWDLYFEIVM, (SEQ ID NO: 311)
RMKFDVWDLYFEIVN, (SEQ ID NO: 312)
RMKFDVWDLYFEIVP, (SEQ ID NO: 313)
RMKFDVWDLYFEIVQ, (SEQ ID NO: 314)
RMKFDVWDLYFEIVR, (SEQ ID NO: 315)
RMKFDVWDLYFEIVS, (SEQ ID NO: 316)
RMKFDVWDLYFEIVT, (SEQ ID NO: 317)
RMKFDVWDLYFEIVV, (SEQ ID NO: 318)
RMKFDVWDLYFEIVY, (SEQ ID NO: 319)
MKFDVWDLYFEIVW, (SEQ ID NO: 320)
KFDVWDLYFEIVW.

Preferably, the peptide or peptide derivative of the second aspect of the invention comprises:

(i) an amino acid sequence comprising cimfwydcye; or (ii) a variant amino acid sequence comprising one, two, three, four, five, six or seven amino acid substitutions in cimfwydcye.

Preferably, at least one, two, three, four, five, six or seven of said substitutions in cimfwydcye are D-amino acids.

Preferably, the peptide or peptide derivative of the second aspect of the invention comprises: an amino acid sequence comprising $X_1X_2X_3X_4X_5X_6X_7X_8X_9X_{10}$, wherein $X_1$, where present, is c, s, y, i, D-Pen, C, t, D-Nva, D-Nle or k, $X_2$ is i, y, w or d, $X_3$ is c or m, $X_4$ is f, t, v or c, $X_5$ is w or c, $X_6$ is y or c, $X_7$ is d, e or f, $X_8$ is c, e, f, y or d, $X_9$ is y or w and $X_{10}$ is e or i, with no more than seven amino acids substitutions compared to cimfwydcye.

Preferably, the peptide or peptide derivative comprises an amino acid sequence comprising $X_1X_2X_3X_4$wyd$X_8$ye, wherein $X_1$ is c, C, D-Pen or s, $X_2$ is I, y or w, $X_3$ is c or m, $X_4$ is f, t, or v and $X_8$ is c or e.

Preferably, the peptide or peptide derivative comprises an amino acid sequence comprising $X_1X_2$m$X_4$wyd$X_8$ye, wherein $X_1$ is c, C or D-Pen, $X_2$ is i or y, $X_4$ is f, t, or v and $X_8$ is c or e.

Suitably, the peptide or peptide derivative of the second aspect of the invention is a peptide or peptide derivative as represented in the table below, or comprises or consists of the amino acid sequence of a peptide or peptide derivative as represented in tables 4 to 6 below:

TABLE 4

| Most preferred peptides | |
|---|---|
| Peptide | Sequence |
| B03 | Ac-cimfwydeye-$NH_2$ |
| B04 | Disulphide-Dimer(Ac-cimfwydeye-$NH_2$)$_2$ |
| B05 | Ac-TTDS-(cymfwydc)-ye-$NH_2$ |
| B06 | K-TTDS-(cymfwydc)-ye-$NH_2$ |
| B14 | Ac-(cimtwydc)-ye-$NH_2$ |
| B15 | Ac-(cimvwydc)-ye-$NH_2$ |
| B17 | (cymfwydc)-ye |
| B18 | Ac-(cymfwydc)-yeG-$NH_2$ |
| B19 | Ac-(D-Pen)imfwydeye-$NH_2$ |
| B23 | $O(CH_2$—$CH_2$—O—$CH_2$—CO-imfwydeye-$NH_2)_2$ |
| B24 | Pyridine-3 (SEQ ID NO: 1), 5-(CO-imfwydeye-$NH_2)_2$ |
| B34 | $H_2N$-E-TTDS-(cymfwydc)-ye-$NH_2$ |
| B35 | Ac-(cymfwydc)-yeK |
| B37 | Ac-(cymfwydc)-ye-TTDS-K |

In a preferred embodiment, peptides B05, B06, B14, B15, B17, B18, B34, B35 and B37 are cyclic.

TABLE 5

| Preferred peptides | |
|---|---|
| Peptide | Sequence |
| B07 | Ac-simfwydeye-$NH_2$ |
| B07 | Ac-simfwydeye-$NH_2$ |
| B09 | Ac-ydmcwcefyi-$NH_2$ |
| B10 | Ac-idmccyfywe-$NH_2$ |
| B16 | Ac-cimfwyddye-$NH_2$ |
| B26 | Ac-(cymfwydc)-ye |
| B27 | Ac-(cymfwydc)-ye-TTDS-$NH_2$ |
| B28 | Ac-TTDS-(cymfwydc)-ye-TTDS-$NH_2$ |
| B30 | K-(cymfwydc)-ye-$NH_2$ |
| B31 | Ac—K-(cymfwydc)-ye-$NH_2$ |
| B32 | E-(cymfwydc)-ye-$NH_2$ |
| B33 | Ac—K-TTDS-(cymfwydc)-ye-$NH_2$ |
| B36 | Ac-(cymfwydc)-yeK-$NH_2$ |
| B38 | Ac-(cymfwydc)-ye-TTDS-K-$NH_2$ |
| B39 | Ac-(cymfwydc)-ye-TTDS-E-$NH_2$ |
| B41 | Ac-timfwydeye-$NH_2$ |

In a preferred embodiment, peptides B26, B27, B28, B30, B31, B32, B33, B36, B38 and B39 are cyclic.

TABLE 6

| Active peptides | |
|---|---|
| Peptide | Sequence |
| B01 | Ac-(cimfwydc)-ye-$NH_2$ |
| B02 | Ac-(cymfwydc)-ye-$NH_2$ |
| B11 | Ac-(cwmfwydc)-ye-$NH_2$ |
| B13 | Ac-cicfwydcye-$NH_2$ |
| B20 | Ac-(D-Nva)imfwydeye-$NH_2$ |
| B21 | Ac-(D-Nle)imfwydeye-$NH_2$ |
| B22 | Ac-(Cys)imfwydeye-$NH_2$ |
| B25 | (cymfwydc)-ye-$NH_2$ |
| B29 | TTDS-(cymfwydc)-ye-TTDS-$NH_2$ |
| B40 | Ac-kimfwydeye-$NH_2$ |

In a preferred embodiment, peptides B01, B02, B11, B25 and B29 are cyclic.

In the above tables, -TTDS- is 4,7,10-trioxa-1,13-tridecanediamine. "$NH_2$" is a C-terminal amide group.

B08 is deleted in the above tables, as being identical to B01. B12 is deleted in the above tables, as being identical to B02.

Preferably, the peptide or peptide derivative of the first aspect of the invention does not comprise or consist of a peptide represented in the list below:

feiycwdcym, ywcfiymced, dmwceyfcyi,
ceicwyfdym, ccwfiemdyy, cemdwycyfi,
aimfwydcye, dimfwydcye, eimfwydcye,
fimfwydcye, himfwydcye, iimfwydcye,
kimfwydcye, limfwydcye, mimfwydcye,
nimfwydcye, pimfwydcye, qimfwydcye,
rimfwydcye, simfwydcye, timfwydcye,
vimfwydcye, wimfwydcye, yimfwydcye,
camfwydcye, ccmfwydsye, cdmfwydcye,
cemfwydcye, cfmfwydcye, chmfwydcye,
ckmfwydcye, clmfwydcye, cmmfwydcye,
cnmfwydcye, cpmfwydcye, cqmfwydcye,
crmfwydcye, csmfwydcye, ctmfwydcye,
cvmfwydcye, ciafwydcye, cidfwydcye,
ciefwydcye, ciffwydcye, cihfwydcye,
ciifwydcye, cikfwydcye, cilfwydcye,
cinfwydcye, cipfwydcye, ciqfwydcye,
cirfwydcye, cisfwydcye, citfwydcye,
civfwydcye, ciwfwydcye, ciyfwydcye,
cimawydcye, cimcwydsye, cimdwydcye,
cimewydcye, cimhwydcye, cimiwydcye,
cimkwydcye, cimwwydcye, cimmwydcye,
cimnwydcye, cimpwydcye, cimqwydcye,
cimrwydcye, cimswydcye, cimwwydcye,
cimywydcye, cimfaydcye, cimfcydsye,
cimfdydcye, cimfeydcye, cimffydcye,
cimfhydcye, cimfiydcye, cimfkydcye,
cimflydcye, cimfmydcye, cimfnydcye,
cimfpydcye, cimfqydcye, cimfrydcye,
cimfsydcye, cimftydcye, cimfvydcye,
cimfyydcye, cimfwadcye, cimfwcdsye,
cimfwddcye, cimfwedcye, cimfwfdcye,
cimfwhdcye, cimfwidcye, cimfwkdcye,
cimfwldcye, cimfwmdcye, cimfwndcye,
cimfwpdcye, cimfwqdcye, cimfwrdcye,
cimfwsdcye, cimfwtdcye, cimfwvdcye, -continued cimfwwdcye, cimfwyacye, cimfwycsye,
cimfwyecye, cimfwyfcye, cimfwyhcye,
cimfwyicye, cimfwykcye, cimfwylcye,
cimfwymcye, cimfwyncye, cimfwypcye,
cimfwyqcye, cimfwyrcye, cimfwyscye,
cimfwytcye, cimfwyvcye, cimfwywcye,
cimfwyycye, cimfwydaye, cimfwydfye,
cimfwydhye, cimfwydiye, cimfwydkye,
cimfwydlye, cimfwydmye, cimfwydnye,
cimfwydpye, cimfwydqye, cimfwydnye,
cimfwydsye, cimfwydtye, cimfwydvye,
cimfwydwye, cimfwydyye, cimfwydcae,
cimfwydsce, cimfwydcde, cimfwydcee,
cimfwydcfe, cimfwydche, cimfwydcie,
cimfwydcke, cimfwydcle, cimfwydcme,
cimfwydcne, cimfwydcpe, cimfwydcqe,
cimfwydcre, cimfwydcse, cimfwydcte,
cimfwydcve, cimfwydcwe, cimfwydcya,
cimfwydsyc, cimfwydcyd, cimfwydcyf,
cimfwydcyh, cimfwydcyi, cimfwydcyk,
cimfwydcyl, cimfwydcym, cimfwydcyn,
cimfwydcyp, cimfwydcyq, cimfwydcyr,
cimfwydcys, cimfwydcyt, cimfwydcyv,
cimfwydcyw, cimfwydcyy.

Preferably, the peptide or peptide derivative of the second aspect of the invention is a cyclic peptide. The peptide or peptide derivatives of the first aspect may also be cyclic.

The term "cyclic peptide" as used herein refers to a cyclic derivative of a peptide to which, for example, two or more additional groups suitable for cyclization have been added, often at the carboxyl terminus and at the amino terminus. Suitable groups include amino acid residues. A cyclic peptide may contain either an intramolecular disulfide bond, i.e. —S—S—, an intramolecular amide bond between the two added residues, i.e. —CONH— or —NHCO—, or intramolecular S-alkyl bonds, i.e. —S—$(CH_2)$n-CONH— or —NH—$CO(CH_2)$n-S—, wherein n is 1, 2 or more and preferably no more than 6. Cyclization may be also carried out by triazine chemistry as exemplified in Scham, D. et al. (2001) *J. Org. Chem* 66; 507. Cyclic peptide sequences are denoted with the prefix "cyclo" in front of the peptide sequence and the cyclic part of the sequence is incorporated in parenthesis and additionally separated from the rest of the sequence by hyphens.

A peptide or peptide derivative of the first or second aspect of the invention may be modified by conjugation to polyethylene glycol (PEG). Suitable methods of PEGylation are disclosed in U.S. Pat. No. 5,122,614 (Zalipsky; Enzon, Inc.) and U.S. Pat. No. 5,539,063 (Hakimi et al; Hoffmann-La Roche Inc.), all of which PEGylation methods are incorporated herein by reference. Various molecular weights of PEG may be used, suitably from 5000 to 40000 kD. A preferred molecular weight is 5000 kD. Preferably, the PEG is monodisperse, meaning that there is little variation in molecular weight between PEG molecules. PEGylation may improve the solubility and plasma half-life of a peptide.

A third aspect of the invention provides a dual peptide comprising a peptide or peptide derivative of the first or second aspects of the invention conjugated to a further peptide or peptide derivative of the first or second aspects of the invention, wherein the peptide or peptide derivative may be the same as or different from the further peptide or peptide derivative, and wherein the dual peptide has procoagulant activity.

The dual peptide may comprise two of the same, or two different, peptides or peptide derivatives of the first or second aspects of the invention covalently linked to one another, either by a flexible linker which can be peptidic, peptidomimetic or non-peptidic, or by a conformationally constrained linker that can comprise conformationally constrained peptidic, peptidomimetic or non-peptidic building blocks e.g. triazine moieties, or by any other possible method known in the art.

Preferably, the peptide or peptide derivative of the first and second aspects of the invention and the dual peptide of the third aspect of the invention has a molecular weight of between 0.5 and 3.5 kD. By "molecular weight" we mean the theoretical mass of a monomer of the peptide or peptide derivative exclusive of any counter ions or adducts. For PEGylated peptides the molecular weight is defined as the mass of the monomeric molecule exclusive of any counter ions or adducts and exclusive of the PEG moiety or moieties. Peptides, peptide derivatives and dual peptides of between 0.5 kD and 3.5 kD are more readily synthesised than larger peptides, have a reduced risk being immunogenic, and are generally easily administered to a patient. Peptides of less than 0.5 kD may be readily synthesised and administered and are less likely to be immunogenic, but may not possess the required procoagulant activity. Nevertheless, peptides, peptide derivatives and dual peptides of less than 0.5 kD and greater than 3.5 kD are encompassed by the invention if they possess the appropriate activity.

The peptides and peptide derivatives of the first and second aspects of the invention and the dual peptide of the third aspect of the invention possess procoagulant activity.

By "procoagulant activity" we mean the ability to promote thrombin generation and/or fibrin deposition in a suitable test system.

It will be appreciated that different assays are available to determine procoagulant activity. Indeed, there are different types of procoagulant activity. Peptides and peptide derivatives may promote coagulation in plasma depleted of FV, FVII, FVIII, FX or FXI. In a preferred embodiment, a peptide or peptide derivative of the invention promotes thrombin generation and/or fibrin deposition in plasma in which FVIII is depleted or absent. This type of activity is referred to as coagulation FVIII activity. Where the plasma is from an individual lacking FVIII, the activity is typically referred to as FVIII equivalent activity. Where the plasma contains inhibitors against FVIII, the activity is typically referred to as FVIII inhibitor bypassing equivalent activity. Other procoagulant activities include FV activity, FVII activity, FX activity and FXI activity.

Individual peptides and peptide derivatives may vary in their relative efficacy between different types of assay. Therefore, even if a peptide or peptide derivative appears to have a low efficacy in a particular assay, it may nevertheless possess a suitably high level of procoagulant activity in another assay.

A suitable assay to determine procoagulant activity is the Defined Intrinsic Thrombin Generation Assay described below. In this assay, a compound is considered to have procoagulant activity if, at a concentration of 25, 50 or 100 μM it can stimulate the generation of 5 nM thrombin in 60 minutes, and preferably in 50, 40, 30, 20 or 10 minutes. Preferably, it can stimulate generation of 10 nM thrombin in 60 minutes, and more preferably in 50, 40, 30, 20 or 10 minutes. An alternative assay is the Defined Dual-Pathway Thrombin Generation Assay described below. In this assay, a compound is considered to have procoagulant activity if, at a concentration of 25, 50 or 100 μM it can stimulate the generation of 5 nM thrombin in 70 minutes, and preferably 60, 50, 40, 30 or 20 minutes. Preferably, it can stimulate generation of 10 nM thrombin in 70 minutes, and more preferably 60, 50, 40, 30 or 20 minutes. The above assays are particularly useful for determining coagulation FVIII activity because they are conducted in the presence of FVIII-depleted or inhibited plasma. However, they can be readily adapted to test for other types of procoagulant activity by substituting a suitable depleted or inhibited plasma for FVIII-depleted or inhibited plasma.

Suitably, the procoagulant activity is a thrombin generation time of 25, 50 or 100 μM of compound in a Defined Intrinsic Thrombin Generation Assay equivalent to that of at least 100 mU/mL Factor Eight Inhibitor Bypassing Activity (FEIBA), preferably at least 300 mU/mL FEIBA, more preferably at least 600 mU/mL FEIBA and most preferably at least 1200 mU/mL FEIBA. Thrombin generation time or peak time is the time interval from the addition of the pre-warmed plasma to the other components in the assay described below, to the time of the thrombin peak maximum.

Alternatively, the procoagulant activity is a thrombin peak maximum of 25, 50 or 100 μM of compound in a Defined Dual-Pathway Thrombin Generation Assay (DDPTGA) equivalent to at least 1 mU/mL Factor Eight Inhibitor Bypassing Activity (FEIBA), preferably at least 5 mU/mL FEIBA, most preferably at least 10 mU/mL FEIBA. Thrombin peak maximum, also referred to as Peak Ha is the maximal thrombin concentration generated during the assay. The Defined Dual-Pathway Thrombin Generation Assay can be used to determine coagulation activities other than FVIII activity if suitable factor depleted plasma is substituted for FVIII deficient or inhibited plasma. A peptide, peptide derivative or dual peptide of the invention is considered to have FV, FVII, FX or FXI activity if, at a concentration of 25, 50 or 100 μM, it can stimulate the generation of more thrombin in a DDPTGA using FV, FVII, FX or FXI deficient plasma respectively over 120 minutes than is stimulated in the absence of peptide.

Suitably, the procoagulant activity is a thrombin generation time of 25, 50 or 100 μM of compound in a Defined Intrinsic Thrombin Generation Assay peaking within 30 minutes, preferably within 15 minutes and most preferably within 10 minutes. [0]Alternatively, the procoagulant activity is a thrombin generation time of 25, 50 or 100 μM of compound in a Defined Dual-Pathway Thrombin Generation Assay peaking within 50 minutes, preferably within 45 minutes and most preferably within 30 minutes.

The effect of a peptide or peptide derivative or dual peptide on thrombin generation may be determined in FVIII immuno inhibited, FVIII immuno depleted, FVIII inhibitor patient or hemophilia A patient plasma or other types of coagulation factor deficient plasmas, for example by continuously monitoring the slow cleavage of the thrombin-specific fluorogenic substrate I-1140 (Bachem) in a black 96-well micro plate (Cliniplate, Thermo Labsystems) as described below. Parameters that can usefully be measured in thrombin generation assays to determine the effect of the peptide or peptide derivative are thrombin concentration at peak time; thrombin generation time at peak thrombin; slope of propagation phase of thrombin generation curve and lag time of thrombin generation (initiation phase).

The intrinsic pathway of thrombin generation may be assayed in a thrombin generation assay by including FXIa and phospholipids. In such an assay, which is similar to an activated partial thromboplastin time (aPTT) test, thrombin generation is solely directed through the intrinsic pathway, and is FVIII dependent. A suitable assay is the Defined Intrinsic Thrombin Generation Assay described below. Alternatively, by employing low concentrations of TF and phospholipids instead of FXIa and phospholipids, thrombin is generated by both the extrinsic (tissue factor) and the intrinsic pathways. This form of the thrombin generation assay is the more physiologic one, as both thrombin generation pathways are involved; it is partially FVIII dependent. A suitable assay is the Defined Dual-Pathway Thrombin Generation Assay.

The Defined Intrinsic Thrombin Generation Assay is performed as follows. FVIII activity of human plasma is inhibited by incubating (2 hours, 37° C.) 40 µl of human normal plasma with 10 µl heat inactivated anti-human FVIII plasma raised in goat (600 BU/ml, 6 hours incubated at 56° C.). A 15 µl mix of FXIa (16.67 nM) (Enzyme Research Laboratories) and phospholipids (Phosphatidylcholine/Phosphatidylserine 60%/40%, 120 µM) (Avanti Polar Lipids), 15 µl mix of 3.33 mM 1-1140 and 50 mM $CaCl_2$ and 10 µl peptide solution (different concentrations) are added to 10 µl 2×HNa/HSA5 (50 mM Hepes, 350 mM NaCl, pH7.35, 10 mg/ml HSA). After six minutes incubation at 37° C., thrombin generation is started by the addition of 50 µl pre-warmed (37° C.) FVIII-inhibited plasma. Instead of FVIII-inhibited plasma, FVIII inhibitor patient plasma or several depleted plasmas can be used. The micro-plate is immediately put into a GENios Plus (Tecan) or Safire 2 (Tecan) fluorescence reader and the fluorescence signal (ex 340 nm/em 440 nM) is followed kinetically by reading the plate every 21 seconds. By deviating the original fluorescence data the amount of generated thrombin is calculated from a standard curve constructed using a concentration range of thrombin.

For calculation of activity equivalent units experiments are performed with dilutions of Factor Eight Inhibitor Bypassing Agent (FEIBA, Baxter AG), Immunate (human FVIII, purified plasma derived) reference standard (Baxter AG) or Recombinate standard (human FVIII, purified recombinant, Baxter AG). A linear fit of the logarithm of FEIBA (FVIII) concentration plotted against thrombin generation time at peak thrombin results in a standard curve. With this curve FEIBA (FVIII) equivalent activity is calculated for a defined peptide concentration.

Where a peptide concentration is given herein, it is to be understood that it is not the concentration of peptide in the final assay volume, but a concentration as corrected for plasma volume. The concentration in the final assay volume is the corrected concentration divided by 2.5. Thus, where a concentration of 100 µM is given, the actual concentration in the final assay volume in 40 µM. Similarly, the FEIBA equivalent activity is also corrected for plasma volume. Thus, if it is stated that at 100 µM a peptide has an activity equivalent to 100 mU/ml FEIBA in the DITGA, the concentration of peptide in the final assay volume is 40 µM and the equivalent concentration of FEIBA in the control assay is 40 mU/ml FEIBA.

The Defined Dual-Pathway Thrombin Generation Assay is performed as described below, using a commercial test kit (Technothrombin TGA, Technoclone GmbH, Vienna, Austria). Briefly, a mix of 40 µl 1.25 mM fluorogenic substrate (Z-GGR-AMC) 18.75 mM $CaCl_2$, 10 µl TGA reagent B (phospholipid vesicles Phosphatidylcholine/Phosphatidylserine 80%/20% (3.2 µM) containing 17.9 µM recombinant human tissue factor; Technoclone GmbH) or 10 µl TGA reagent C high (phospholipid vesicles Phosphatidylcholine/Phosphatidylserine 80%/20% (32 µM) containing 71.6 µM recombinant human tissue factor; Technoclone GmbH) and 10 µl peptide dilution, FEIBA reference standard or FVIIa standard dilutions (Enzyme Research Laboratories, South Bend, Ind. USA) are incubated four minutes at 37° C. Preferably, Reagent C high is used. Thrombin generation is started by the addition of 40 µl of one of several types of human plasma (37° C.). Conversion of the fluorogenic substrate by thrombin is followed by immediately putting the plate into a preheated (37° C.) microplate fluorescence reader (Tecan Safire 2, ex 360 nm/em 460 nm) and kinetically reading the plate every 30 seconds. By deviating the original fluorescence data the amount of generated thrombin is calculated from a standard curve constructed using a concentration range of thrombin. Non linear regression analysis of factor VIIa or FEIBA concentrations plotted against the thrombin at peak of the thrombin generation curve or time to peak thrombin results in standard curves. With these curves, factor VIIa or FEIBA equivalent activity can be calculated for a defined peptide concentration. As described in relation to DITGA, where a peptide concentration is given herein in relation to the DDPTGA, it is to be understood that it is not the concentration of peptide in the final assay volume, but a concentration as corrected for plasma volume. The concentration in the final assay volume is the corrected concentration divided by 2.5. FEIBA equivalent activity is also corrected for plasma volume by applying the same correction factor.

Another suitable assay to determine procoagulant activity, and particularly FVIII equivalent activity or FVIII inhibitor bypassing activity, is the Defined Fibrin Deposition Assay as described below. Suitably, the procoagulant activity of a sample of 25 µM test compound in the Defined Fibrin Deposition Assay is equivalent to at least 30 mU/mL Factor Eight Inhibitor Bypassing Activity (FEIBA), preferably at least 80 mU/mL FEIBA, most preferably at least 200 mU/mL FEIBA. This assay is particularly useful for determining coagulation FVIII activity because it is conducted in the presence of FVIII-depleted or inhibited plasma.

The Defined Fibrin Deposition Assay is performed as follows. FVIII activity of human citrated plasma (Baxter AG) is first inhibited by incubating (2 hours, 37° C.) 100 µl of human normal plasma with 25 µl heat inactivated anti-human FVIII plasma (300 BU/ml, 6 hours incubated at 56° C.) raised in goat. For each sample to be tested, 125 µl of this FVIII-inhibited human normal plasma is transferred to a pre-warmed cuvette and a 75 µl dilution of a test compound or FEIBA reference standard (Baxter AG) is added. The dilutions of test compound or FEIBA reference standard contain 50 mM imidazole, 100 mM NaCl and 10 mg/ml human serum albumin (Sigma) pH 7.4. As a trigger and for providing procoagulant surfaces 100 µl of a mix of human factor XIa (3.13 nM, Enzyme Research Laboratories) and phospholipid (PL) vesicles (Phosphatidylcholine/Phosphatidylserine 60%/40%, 30 µM; Avanti Polar Lipids) in 50 mM Imidazole, 100 mM NaCl, 10 mg/ml human serum albumin (Sigma) pH 7.4 is included. After incubating for three minutes at 37° C. the coagulation reaction is started by adding 100 μl of 25 mM $CaCl_2$. Clot formation is monitored by a coagulometer (KC10A, Amelung, Germany). In brief, each cuvette rotates slowly above the magnetic detection device and contains a small magnetic metallic ball. Whilst the plasma components remain in solution, the ball sits at the bottom of the cuvette. Over time, a clot begins to form, such that the ball starts to rotate with the developing clot in the rotating cuvette. The "clotting time" is recorded and is defined as the time from addition of the $CaCl_2$ to the time that the developing clot begins to rotate the metallic ball. A standard curve for FEIBA reference standard dilutions is calculated by linear regression of logarithmic FEIBA concentrations (x-axis) against the clotting time (y-axis). Based on the clotting time of each compound concentration FEIBA equivalent activities are calculated according to this standard curve.

Where a peptide concentration is given herein in relation to the Defined Fibrin Deposition Assay, it is to be understood that it is not the concentration of peptide in the final assay volume, but a concentration as corrected for plasma volume. The concentration in the final assay volume is the corrected concentration divided by 4. Thus, where a concentration of 100 μM is given, the actual concentration in the final assay volume in 25 μM. Similarly, the FEIBA equivalent activity is also corrected for plasma volume. Thus, if it is stated that at 100 μM a peptide has an activity equivalent to 100 mU/ml FEIBA in the Defined Fibrin Deposition Assay, the concentration of peptide in the final assay volume is 25 μM and the equivalent concentration of FEIBA in the control assay is 25 mU/ml FEIBA.

Preferably, the peptides and peptide derivatives of the first and second aspects of the invention and the dual peptide of the third aspect of the invention can at least partially compensate for the absence of biologically active FVIII when administered in an animal model of severe human hemophilia A. For example, they may be active in controlling bleeding in FVIII deficient mice, such as the strains described in detail by Bi et al (Nat Genet. 1995; 10:119-21), in which exon 17 or exon 16 of FVIII is disrupted. The exon 16 FVIII−/− mice are available from Jackson Laboratory, 600 Main Street, Bar Harbor, Me. 04609 USA (strain name: B6;129S4-F8$^{tmfKaz}$/J).

A suitable assay to test the ability of a compound to control bleeding is the tail clip assay. Peptides, peptide derivatives or dual peptides are administered to mice in a suitable vehicle, typically i.v., i.p. or s.c. Different doses of each peptide or peptide derivative may be administered to different groups of mice to determine dose-dependency. Groups of mice, typically 8-16 male and female exon 17 FVIII knockout mice with severe hemorrhagic diathesis, receive a single i.v. (tail vein), i.p. or s.c. bolus injection (10 ml/kg body weight). Two minutes before tail clip, animals are anesthetized by an i.p. application of 100 mg/kg ketamine and 5 mg/kg xylazine. Five minutes after i.v. and 60 minutes after i.p. or s.c. peptide or peptide derivative administration 0.5 cm of the tail tip is ablated. Blood dropping from the wound is collected in tubes containing 5.0 ml 0.04% $NH_3$ for defined time periods, such as 0-2 minutes, 2-4 minutes, 4-6 minutes, 6-8, 8-10, 10-12, 12-14, 14-16, 16-20, 20-24, 24-28, 28-32, 32-42, 42-52 and 52-62 minutes. Blood cells in each tube are disrupted and hemoglobin is extracted by a three hour incubation period at room temperature followed by ultrasound treatment. The absorbance at 414 nm and 620 nm of the extracts is determined in micro titre plates. 620 nm is a reference wavelength and the $A_{620}$ reading is subtracted from the $A_{414}$ reading. The amount of blood in the extract corresponding to the subtracted reading is calculated from a standard curve created by known amounts of blood from wild type control mice, such as C57/Bl6 mice. Parameters of the bleeding characteristics of the mice to be recorded are total blood loss, bleeding rate, bleeding time, 1 h, 2 h, 3 h, 4 h, 24 h and 48 h survival. Cumulative blood loss is calculated by summing up the amounts of blood for each time period. Data for the animals of a group are averaged and plotted against bleeding time. At each time point data sets for treatment and vehicle control groups are analysed by Student's t-test for statistical significance.

Preferably, mice administered the peptide, peptide derivative or dual peptide have a blood loss in the tail clip assay at 62 minutes from tail clip of no more than 70% of the blood loss of mice administered the vehicle alone, more preferably no more than 60% and most preferably no more than 50% of the blood loss of mice administered the vehicle alone.

Preferably, survival of mice administered the peptide, peptide derivative or dual peptide in the above assay is at least 40%, more preferably at least 60% and most preferably at least 80% at 2 hours after tail clip. Preferably, survival of mice administered the peptide or peptide derivative in the tail clip assay is at least 20%, more preferably at least 30% and most preferably at least 40% at 24 hours after tail clip.

Preferably, the peptide or peptide derivative of the first and second aspects of the invention or the dual peptide of the third aspect of the invention has a stability in human plasma at 30 minutes of at least 50%, preferably at least 70%, more preferably at least 80% and most preferably at least 90%. A suitable assay to determine stability in human plasma is described in the Examples.

Preferably, the peptide or peptide derivative of the first and second aspects of the invention or the dual peptide of the third aspect of the invention has an aqueous solubility in phosphate buffered saline pH 7.4 at 25° C. of at least 25 μM, preferably at least 60 μM and most preferably at least 100 μM. A suitable assay to determine aqueous solubility in phosphate buffered saline pH 7.4 at 25° C. is described in the Examples.

Herein, the term "Factor VIII" or "FVIII" refers to any FVIII moiety which exhibits biological activity that is associated with native FVIII. The sequence of FVIII can be found as NCBI Accession Number NP_000123 or UniProtKB/Swiss-Prot entry P00451.

As used herein, "plasma-derived FVIII" includes all forms of the protein found in blood obtained from a mammal having the property of activating the coagulation pathway.

As used herein, "rFVIII" denotes FVIII obtained via recombinant DNA technology.

A fourth aspect of the invention provides a pharmaceutical composition comprising the peptide or peptide derivative of the first or second aspects of the invention or the dual peptide of the third aspect of the invention. Peptides, peptide derivatives and dual peptides may be in the form of pharmaceutically acceptable salts, solvates or hydrates. Suitably, the pharmaceutical composition comprises a pharmaceutically acceptable carrier. The carrier may be preferably a liquid formulation, and is preferably a buffered, isotonic, aqueous solution. Suitably, the pharmaceutical composition has a pH that is physiologic, or close to physiologic. Suitably it is of physiologic or close to physiologic osmolarity and salinity. It may contain sodium chloride and/or sodium acetate. The peptides, peptide derivatives and dual peptides of the invention can be made without significant pyrogenicity that might occur in production of biological treatments. This can be important, especially for intravenous formulations where only low levels of endotoxin can be tolerated. It is preferred that subcutaneous, intraperitoneal, buccal, intravenous and other parenteral formulations are sterile and endotoxin free.

Pharmaceutically acceptable carriers may also include excipients, such as diluents, and the like, and additives, such as stabilizing agents, preservatives, solubilizing agents, and the like. The peptides of this invention may be also in the form of any pharmaceutically acceptable salt.

As used herein, the term "pharmaceutically acceptable" means approved by a regulatory agency of US or EU or other government or listed in the U.S. Pharmacopeia or other generally recognized pharmacopeia for use in humans.

The composition can be also for example a suspension, emulsion, sustained release formulation, cream, gel or powder. The composition can be formulated as a suppository, with traditional binders and carriers such as triglycerides.

Though intravenous delivery of the peptides, peptide derivatives and dual peptides of the present invention may be possible a non-intravenous route is preferred, particularly subcutaneous, nasal, buccal, oral or pulmonary delivery. Intraperitoneal (i.p.) delivery may also be used.

Pharmaceutical compositions may additionally comprise, for example, one or more of water, buffers (e.g., neutral buffered saline or phosphate buffered saline), ethanol, mineral oil, vegetable oil, dimethylsulfoxide, carbohydrates (e.g., glucose, mannose, sucrose or dextrans), mannitol, proteins, adjuvants, polypeptides or amino acids such as glycine, antioxidants, chelating agents such as EDTA or glutathione and/or preservatives. Furthermore, one or more other active ingredients may (but need not) be included in the pharmaceutical compositions provided herein.

Pharmaceutical compositions may be formulated for any appropriate manner of administration, including, for example, topical (e.g., transdermal or ocular), oral, buccal, nasal, vaginal, rectal or parenteral administration. The term parenteral as used herein includes subcutaneous, intradermal, intravascular (e.g., intravenous), intramuscular, spinal, intracranial, intrathecal, intraocular, periocular, intraorbital, intrasynovial and intraperitoneal injection, as well as any similar injection or infusion technique. Forms suitable for oral use include, for example, tablets, troches, lozenges, aqueous or oily suspensions, dispersible powders or granules, emulsion, hard or soft capsules, or syrups or elixirs. Compositions provided herein may be formulated as a lyophilizate.

Aqueous suspensions contain the active ingredient(s) in admixture with excipients suitable for the manufacture of aqueous suspensions. Such excipients include suspending agents (e.g., sodium carboxymethylcellulose, methylcellulose, hydropropylmethylcellulose, sodium alginate, polyvinyl-pyrrolidone, gum tragacanth and gum acacia); and dispersing or wetting agents (e.g., naturally-occurring phosphatides such as lecithin, condensation products of an alkylene oxide with fatty acids such as polyoxyethylene stearate, condensation products of ethylene oxide with long chain aliphatic alcohols such as heptadecaethyleneoxycetanol, condensation products of ethylene oxide with partial esters derived from fatty acids and a hexitol such as polyoxyethylene sorbitol monooleate, or condensation products of ethylene oxide with partial esters derived from fatty acids and hexitol anhydrides such as polyethylene sorbitan monooleate). Aqueous suspensions may also comprise one or more preservatives, for example ethyl, or n-propyl p-hydroxybenzoate, one or more coloring agents, one or more flavoring agents, and one or more sweetening agents, such as sucrose or saccharin.

Peptides or peptide derivatives may be formulated for local or topical administration, such as for topical application to the skin, wounds or mucous membranes, such as in the eye. Formulations for topical administration typically comprise a topical vehicle combined with active agent(s), with or without additional optional components. Suitable topical vehicles and additional components are well known in the art, and it will be apparent that the choice of a vehicle will depend on the particular physical form and mode of delivery. Topical vehicles include water; organic solvents such as alcohols (e.g., ethanol or isopropyl alcohol) or glycerin; glycols (e.g., butylene, isoprene or propylene glycol); aliphatic alcohols (e.g., lanolin); mixtures of water and organic solvents and mixtures of organic solvents such as alcohol and glycerin; lipid-based materials such as fatty acids, acylglycerols (including oils, such as mineral oil, and fats of natural or synthetic origin), phosphoglycerides, sphingolipids and waxes; protein-based materials such as collagen and gelatin; silicone-based materials (both non-volatile and volatile); and hydrocarbon-based materials such as microsponges and polymer matrices. A composition may further include one or more components adapted to improve the stability or effectiveness of the applied formulation, such as stabilizing agents, suspending agents, emulsifying agents, viscosity adjusters, gelling agents, preservatives, antioxidants, skin penetration enhancers, moisturizers and sustained release materials. Examples of such components are described in Martindale—The Extra Pharmacopoeia (Pharmaceutical Press, London 1993) and Martin (ed.), Remington's Pharmaceutical Sciences. Formulations may comprise microcapsules, such as hydroxymethylcellulose or gelatin-microcapsules, liposomes, albumin microspheres, microemulsions, nanoparticles or nanocapsules.

A pharmaceutical composition may be formulated as inhaled formulations, including sprays, mists, or aerosols. For inhalation formulations, the compounds provided herein may be delivered via any inhalation methods known to those skilled in the art. Such inhalation methods and devices include, but are not limited to, metered dose inhalers with propellants such as CFC or HFA or propellants that are physiologically and environmentally acceptable. Other suitable devices are breath operated inhalers, multidose dry powder inhalers and aerosol nebulizers. Aerosol formulations for use in the subject method typically include propellants, surfactants and co-solvents and may be filled into conventional aerosol containers that are closed by a suitable metering valve.

Inhalant compositions may comprise liquid or powdered compositions containing the active ingredient that are suitable for nebulization and intrabronchial use, or aerosol compositions administered via an aerosol unit dispensing metered doses. Suitable liquid compositions comprise the active ingredient in an aqueous, pharmaceutically acceptable inhalant solvent, e.g., isotonic saline or bacteriostatic water. The solutions are administered by means of a pump or squeeze-actuated nebulized spray dispenser, or by any other conventional means for causing or enabling the requisite dosage amount of the liquid composition to be inhaled into the patient's lungs. Suitable formulations, wherein the carrier is a liquid, for administration, as for example, a nasal spray or as nasal drops, include aqueous or oily solutions of the active ingredient.

Formulations or compositions suitable for nasal administration, wherein the carrier is a solid, include a coarse powder having a particle size, for example, in the range of 20 to 500 microns which is administered in the manner in which snuff is administered (i.e., by rapid inhalation through the nasal passage from a container of the powder held close up to the nose). Suitable powder compositions include, by way of illustration, powdered preparations of the active ingredient thoroughly intermixed with lactose or other inert powders acceptable for intrabronchial administration. The powder compositions can be administered via an aerosol dispenser or encased in a breakable capsule which may be inserted by the patient into a device that punctures the capsule and blows the powder out in a steady stream suitable for inhalation.

Pharmaceutical compositions may be formulated as sustained release formulations (i.e., a formulation such as a capsule that effects a slow release of modulator following administration). Such formulations may generally be prepared using well known technology and administered by, for example, oral, rectal or subcutaneous implantation, or by implantation at the desired target site. Carriers for use within such formulations are biocompatible, and may also be biodegradable; preferably the formulation provides a relatively constant level of modulator release. The amount of modulator contained within a sustained release formulation depends upon, for example, the site of implantation, the rate and expected duration of release and the nature of the condition to be treated or prevented.

Pharmaceutical compositions may be formulated with an agent to improve bioavailability, such an as organic solvent. For example, Cremophor EL® (Product No. 00647/1/63; BASF Aktiengesellschaft, Germany) is a polyethoxylated castor oil which is prepared by reacting 35 moles of ethylene oxide with each mole of castor oil. It may be used to stabilise emulsions of non-polar materials in aqueous systems. Alternatively, peptide, peptide derivative or dual peptide may be incorporated within or bound to a proteinaceous micro or nano-particle for improved bioavailability. Suitable micro- and nano-particles are described in U.S. Pat. No. 5,439,686 (Desai et al; Vivorx Pharmaceuticals, Inc., CA) and U.S. Pat. No. 5,498,421 (Grinstaff et al; Vivorx Pharmaceuticals, Inc., CA). Suitably, the proteinaceous nano-particle comprises human serum albumin, particularly human serum albumin or a recombinant form thereof. WO 2007/077561 (Gabbai; Do-Coop Technologies Ltd., Israel) describe another suitable carrier comprising nanostructures and a liquid, referred to therein as Neowater™.

For oral and parenteral administration to patients, including human patients, the daily dosage level of the peptide, peptide derivative or dual peptide of the invention will usually be from 2 to 2000 mg per adult (i.e. from about 0.03 to 30 mg/kg), administered in single or divided doses.

Thus, for example, the tablets or capsules of the peptide, peptide derivative or dual peptide of the invention may contain from 2 mg to 2000 mg of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

For veterinary use, a peptide, peptide derivative or dual peptide of the invention is administered as a suitably acceptable formulation in accordance with normal veterinary practice and the veterinary surgeon will determine the dosing regimen and route of administration which will be most appropriate for a particular animal.

The peptides, peptide derivatives and dual peptides disclosed herein can be used for medical applications and animal husbandry or veterinary applications. Typically, the product is used in humans. The term "patient" is intended to denote a mammalian individual, and is so used throughout the specification and in the claims.

A fifth aspect of the invention provides a peptide or peptide derivative of the first or second aspects or a dual peptide of the third aspect of the invention for treating a patient having a deficiency in FV, FVII, FVIII, FX and/or FXI.

A sixth aspect of the invention provides a use of a peptide or peptide derivative of the first or second aspects or a dual peptide of the third aspect of the invention in the manufacture of a medicament for the treatment of a deficiency in FV, FVII, FVIII, FX and/or FXI in a patient.

An seventh aspect of the invention provides a method of treating a patient having a deficiency in FV, FVII, FVIII, FX and/or FXI comprising administering a therapeutically effective amount of the pharmaceutical composition of the fourth aspect.

The peptides, peptide derivatives and dual peptides of the present invention can be used for the treatment of a deficiency in FV, FVII, FVIII, FX and/or FXI for both the prophylaxis and for treatment of acute bleeds. Patients with FVIII deficiency (hemophilia A) often develop inhibitor antibodies to FVIII. Inhibitor development (to FIX) is also known in FIX deficiency (hemophilia B). Since FV, FVII, FXI and FX deficiencies are very rare congenital disorders little is known about inhibitor development, although it is feasible that patients having such disorders might develop inhibitors. Treatment of inhibitor patients is a preferred embodiment of the fifth, sixth and seventh aspects. Such inhibitor patients may have either a high titer response of greater than 5 BU or a low titer response of between 0.5 and 5 BU. Typically, the inhibitors are directed against FVIII and the patients have hemophilia A.

The magnitude of the antibody response to FVIII can be quantified using a functional inhibitor assay, such as that described in [0]Kasper C K et at (1975) Proceedings: A more uniform measurement of factor VIII inhibitors. Thromb Diath Haemorrh. 34(2):612. FXI inhibitors could be quantified by an aPTT assay as described by Kasper. Inhibitors of FV, FVII and FX could be quantified by a PT based assay following the procedure of Kasper.

A peptide or peptide derivative according to the eighth, ninth or tenth aspects of the invention is not FVIII or a fragment thereof. Typically, it does not consist of or comprise the amino acid sequence of any FVIII protein, whether of human, mammalian or vertebrate origin. Neither does it consist of a fragment of a FVIII protein. Typically, it comprises fewer than 50, fewer than 20, fewer than 10, fewer than 5 contiguous amino acids of a FVIII protein, such as a human FVIII protein. Preferred peptides and peptide derivatives are the peptides and peptide derivatives of the first and second aspects of the invention, or the dual peptides of the third aspect of the invention. Alternative peptides and peptide derivative may be synthesised and tested for procoagulant activity as described in relation to the exemplified peptides and peptide derivatives.

Peptides and peptide derivatives of the eighth, ninth or tenth aspects of the invention may be formulated as pharmaceutical compositions, as described above, and may be used in medicine as described above.

The present invention will be further illustrated in the following examples, without any limitation thereto.

Example 1

Synthesis and Identification of Compounds with Thrombin Generating Activity

Compounds were screened using the "Defined intrinsic thrombin generation assay" in which thrombin generation was quantified in vitro in FVIII-inhibited human plasma in the presence of Factor XIa and phospholipid vesicles. Further compounds were screened in the above assay, and in the "Defined dual-pathway thrombin generation assay" using tissue factor and phospholipids instead of Factor XIa and phospholipids, as described in the specific description.

The compounds, which are peptides and peptide derivatives, were synthesised by classical solid phase peptide synthesis or SPOT-Synthesis at 50-100 nmol peptide per spot, which allows positionally addressable, chemical synthesis of peptides on continuous cellulose membranes. Peptides were dissolved in either 10% or 50% DMSO in water.

PEGylation of peptides and peptide derivatives was carried out as follows. PEG5000 NHS-ester was coupled to the N-terminus of the HPLC-purified peptides in solution. If lysine was present in the peptide sequence, this amino acid was protected with the ivDde protecting group in order to avoid PEGylation at the ε-amino group. After coupling of the PEG5000 to the N-terminus, the ivDde protecting group was cleaved off by 3% hydrazine hydrate in dimethyl formamide followed by repurification of the final product by HPLC.

Compounds deemed to promote thrombin generation were identified, as indicated in Tables 7 and 8 below.

TABLE 7

| Compounds based on A01 | | |
|---|---|---|
| | Peptide | Sequence |
| SEQ ID NO: 2 | A01 | Ac-RMKFDVWDLYFEIVW-$NH_2$ |
| SEQ ID NO: 2 | A02 | Ac-PMKFDVWDLYFEIVW-$NH_2$ |
| SEQ ID NO: 2 | A03 | Ac-RMDFDVWDLYFEIVW-$NH_2$ |
| SEQ ID NO: 2 | A04 | Ac-RMEFDVWDLYFEIVW-$NH_2$ |
| SEQ ID NO: 1 | A05 | Ac-WDLYFEIVW-$NH_2$ |
| SEQ ID NO: 3 | A06 | Ac-WDLYFEIVWE |
| SEQ ID NO: 1 | A07 | Ac-WDLYFEIVW-O-E |
| SEQ ID NO: 2 | A08 | O-RMEFDVWDLYFEIVW-O-$NH_2$ |
| SEQ ID NO: 4 | A09 | ERMEFDVWDLYFEIVW-$NH_2$ |
| SEQ ID NO: 34 | A10 | EPMKFDVWDLYFEIVW-$NH_2$ |
| SEQ ID NO: 2 | A11 | O-RMDFDVWDLYFEIVW-O-$NH_2$ |
| SEQ ID NO: 5 | A12 | ERXEFDVWDLYFEIVW-$NH_2$ X is Nva |
| | A13 | O-RMEFDVWDLYXEIVW-O-$NH_2$ X is Phg |
| SEQ ID NO: 6 | A14 | Ac-WSLYFEIVWE |
| SEQ ID NO: 1 | A15 | Ac-WDLYFEISW-O-E |
| SEQ ID NO: 2 | A16 | PEG5000-RMKFDVWDLYFEIVW-$NH_2$ |

TABLE 7-continued

| Compounds based on A01 | | |
|---|---|---|
| | Peptide | Sequence |
| SEQ ID NO: 6 | A17 | PEG5000-WSLYFEIVWE |
| SEQ ID NO: 4 | A18 | PEG5000-ERMEFDVWDLYFEIVW-$NH_2$ |
| SEQ ID NO: 7 | A19 | Ac-VWDLYFEIVW-$NH_2$ |
| SEQ ID NO: 1 | A20 | Ac-WDLYFEIVW-O-K |

In the above table O- is 4,7,10-trioxa-1,13-tridecanediamine (ttds)

TABLE 8

| Compounds based on B01 | |
|---|---|
| Peptide | Sequence |
| B01 | Ac-(cimfwydc)-ye-$NH_2$ |
| B02 | Ac-(cymfwydc)-ye-$NH_2$ |
| B03 | Ac-cimfwydeye-$NH_2$ |
| B04 | Disulphide-Dimer(Ac-cimfwydeye-$NH_2$)$_2$ |
| B05 | Ac-O-(cymfwydc)-ye-$NH_2$ |
| B06 | K-O-(cymfwydc)-ye-$NH_2$ |
| B07 | Ac-simfwydeye-$NH_2$ |

In the above table, -O- is 4,7,10-trioxa-1,13-tridecanediamine (ttds). The actual peptides used in this study, designated B01, B02, B05 and B06, were cyclic.

Example 2

Testing of Compounds in Intrinsic and Dual-Pathway Thrombin Generation Assays

Various concentrations of each peptide were tested in the defined intrinsic thrombin generation assay using human FVIII inhibited plasma. Results are given in the table below.

TABLE 9

Activity of peptide compounds in the defined intrinsic thrombin generation assay (triggered by FXIa). Thrombin peak time is given as FEIBA equivalent activity (mU/ml) calculated based on a FEIBA standard calibration curve.

| | Concentration (μM) | | | | | |
|---|---|---|---|---|---|---|
| Compound | 200 | 100 | 50 | 25 | 12.5 | 6.25 |
| A01 | | 338 | 227 | 160 | 138 | 97 |
| A03 | | 1396 | 1069 | 762 | 639 | 477 |
| A05 | | 816 | 631 | 562 | 487 | 390 |
| A19 | | 826 | 663 | 525 | 495 | 383 |
| B01 | | 103 | 89 | 62 | 35 | |
| A02 | | 1305 | 1018 | 780 | 674 | 577 |
| B03 | | 1394 | 1030 | 738 | 602 | 454 |
| B05 | 1089 | 649 | 270 | 152 | 126 | |
| B06 | 902 | 378 | 172 | 157 | 95 | |
| A06 | | 879 | 919 | 843 | 750 | 571 |
| A20 | | 1101 | 873 | 597 | 501 | 391 |
| A07 | | 1129 | 965 | 750 | 585 | 415 |
| A08 | | 1213 | 958 | 764 | 656 | 563 |
| A09 | | 1365 | 1170 | 896 | 742 | 600 |

An in vitro thrombin generation assay based on the cleavage of Z-GGR-AMC to release the fluorophore AMC was developed using normal human plasma, i.e. the Defined Dual-Pathway Thrombin Generation Assay. Tissue factor dependency of peak thrombin generation and thrombin peak time was characterised in a composition containing a fixed concentration of phospholipid (namely 3.2 μM). Phospholipid dependency was characterised in a composition containing a fixed concentration of tissue factor (namely 7.2 pM). Peak time (time to peak thrombin generation) was dependent on the concentration of phospholipid or tissue factor. The final version of this assay is as described in the specific description, in which 10 μl reagent C high containing (32 μM phospholipid and 71.6 μM tissue factor) is used in a total volume of 100 μl.

Further studies were conducted using 3.2 μM phospholipid and 7.2 μM tissue factor in FVIII deficient or inhibited plasma, to characterise the effect on peak thrombin generation and thrombin peak time of various coagulation factor preparations. These studies provided a basis from which to compare the efficacy of the compounds in the assay. Briefly, rFVIII (Recombinate® FVIII from Baxter) was tested at 0, 5, 10, 20, 40 and 80 m U/ml in FVIII deficient plasma. FEIBA was tested at 0, 8, 16, 31, 63 and 125 mU/ml in FVIII inhibited plasma. FVIIa was tested at 0, 0.1, 0.4, 1.6, 6.3 and 25 nM in FVIII inhibited plasma. Results are shown in FIG. 1. For recombinant FVIII (Recombinate®) in FVIII deficient plasma and for both FEIBA and FVIIa in FVIII-immuno inhibited plasma a concentration dependent improvement of thrombin generation parameters is observed. Peak thrombin increased and both the lag time and the thrombin peak time decrease.

The compounds were tested in this Defined Dual-Pathway Thrombin Generation Assay (DDPTGA) using reagent C high (Technoclone) for triggering thrombin generation. Results are given in the table below. Even though this assay is less sensitive for FVIII-like activity than the Defined Intrinsic Thrombin Generation Assay (DITGA), several compounds possessed detectable activity.

TABLE 10

Summary results

| | | DDPTGA FVIII inhibited plasma | | | | DDPTGA FVIII deficient plasma | |
|---|---|---|---|---|---|---|---|
| Peptide | Conc [μM] | Peak Time FEIBA EU (mU/ml) | Peak IIa FEIBA EU (mU/ml) | Peak Time FVIIa EU (nM) | Peak IIa FVIIa EU (nM) | Peak Time FVIII EU (mU/ml) | Peak IIa FVIII EU (mU/ml) |
| A02 | 50 | 10.2 | BLS | 0.4 | BLS | BLS | BLS |
| A03 | 100 | BLS | BLS | BLS | BLS | BLS | BLS |
| A03 | 50 | BLS | BLS | BLS | BLS | BLS | BLS |
| A05 | 100 | BLS | BLS | BLS | BLS | BLS | BLS |
| A05 | 50 | BLS | BLS | BLS | BLS | BLS | BLS |
| A08 | 50 | 9.1 | BLS | 0.4 | BLS | BLS | BLS |
| A09 | 50 | BLS | 8.6 | BLS | BLS | 27.2 | BLS |
| A09 | 25 | 7.9 | BLS | 0.2 | BLS | 15.6 | BLS |
| A18 | 100 | BLS | BLS | BLS | BLS | 17.1 | BLS |
| A18 | 50 | BLS | BLS | BLS | BLS | BLS | BLS |
| A01 | 90 | BLS | BLS | BLS | BLS | BLS | BLS |
| A01 | 50 | BLS | BLS | BLS | BLS | BLS | BLS |
| A16 | 100 | BLS | BLS | BLS | BLS | BLS | BLS |
| A16 | 50 | BLS | BLS | BLS | BLS | BLS | BLS |
| B03 | 100 | BLS | 12.3 | BLS | 0.6 | 7.5 | 5.3 |
| B03 | 40 | BLS | 7.2 | BLS | 0.2 | 8.7 | 4.8 |
| B04 | 100 | BLS | 13.3 | BLS | 0.7 | 1.6 | 5.0 |
| B04 | 40 | BLS | 12.8 | BLS | 0.6 | 7.3 | 4.8 |
| B04 | 16 | BLS | BLS | BLS | 0.1 | 4.1 | 4.4 |
| A07 | 100 | BLS | BLS | BLS | 0.1 | BLS | BLS |
| A07 | 50 | BLS | BLS | BLS | BLS | BLS | BLS |
| A15 | 100 | BLS | 13.6 | BLS | 0.7 | 12.7 | 5.0 |
| A15 | 50 | BLS | BLS | BLS | BLS | 14.4 | 4.3 |
| A06 | 100 | BLS | BLS | 0.4 | BLS | BLS | BLS |
| A06 | 50 | BLS | BLS | BLS | BLS | BLS | BLS |
| A14 | 100 | BLS | BLS | BLS | BLS | BLS | BLS |
| A14 | 50 | BLS | BLS | BLS | BLS | BLS | BLS |
| A17 | 100 | BLS | BLS | 0.1 | BLS | 5.9 | BLS |
| A17 | 50 | BLS | BLS | BLS | BLS | 5.1 | BLS |

"Peak IIa" is the amount of thrombin generated at the peak of the thrombin generation curve.
"Peak time" is the time from start of the thrombin generation reaction to when the maximum amount is generated.
BLS = below lowest standard.

Thrombin is still generated in this assay even in the absence of added peptide. Thus, where Peak IIa is "BLS" at a particular peptide concentration, there is still a thrombin peak, but it is lower than that achieved by the lowest concentration of standard, which is 5 mU/ml FVIII, 8 mU/ml FEIBA or 0.1 nM FVII. Similarly, when peak time is "BLS", the time to peak thrombin generation is greater than the peak time achieved by the lowest concentration of standard. A peptide can have a significant effect on peak time but not peak IIa, or vice versa. However, it is preferred that a peptide has an effect on both peak time and peak IIa. B03, B04 and A15 positively affected both aspects of thrombin generation. In the case of some peptides, concentration dependency of an effect on thrombin generation was not seen at high peptide concentration, which might be explained by non-specific interactions.

Example 3

Testing of Compounds in Thrombin Generation Assays with Several Depleted Plasmas The in vitro thrombin generation assay based on the cleavage of Z-GGR-AMC to release the fluorophore AMC, described in the specific description, i.e. the Defined Dual-Pathway Thrombin Generation Assay was used to characterise the effect of the compounds in several depleted human plasmas. In these experiments, each 100 µl reaction contained 10 µl reagent B, which comprises phospholipid vesicles Phosphatidylcholine/Phosphatidylserine 80%/20% (3.2 µM) and 17.9 µM recombinant human tissue factor. 10 µl peptide dilution, 40 µl TGA substrate and 40 µl plasma were used as described in the specific description.

The plasmas used in the experiments were fresh frozen and were deficient in Factor V, Factor VII/VIIa, Factor VIII, Factor X or Factor XI (George King Bio-Medical, Inc.). Residual coagulation factor levels of deficient plasmas were specified as less than 1%.

For each depleted plasma used in the experiments, compounds were tested at two concentrations, namely 50 µM and 80, 90 or 100 µM. A negative control was used, in which no test compound was included. Results are summarised in the table below.

TABLE 11

Summary results of effect of compounds on thrombin generation in various depleted plasmas

| Depleted | Compounds | | | | | | | | |
|---|---|---|---|---|---|---|---|---|---|
| plasma | Control | A01 | A02 | A05 | B03 | A06 | A07 | A08 | A09 |
| FV | − | − | − | − | − | + | − | | − |
| FVII | − | + | + | + | + | + | + | | + |
| FVIII | − | + | + | + | + | + | + | + | + |
| FX | − | − | + | + | + | + | + | | + |
| FXI | − | + | + | + | + | + | + | | + |

Stimulation of thrombin generation: "+" means stimulates; "−" means does not stimulate. In control experiments, no peptide was included.

All depleted plasmas tested showed no or very low thrombin generation in the absence of peptides, indicating that at the tissue factor concentration used the interplay of all coagulation factors is important for thrombin generation. Several peptides stimulated thrombin generation in all zymogen depleted plasmas (FVII, FX or FXI) whereas thrombin generation in FV depleted plasmas is low, indicating that the common pathway is important for peptide stimulated thrombin generation.

Example 4

Activity of Compounds in Defined Fibrin Deposition Assay

Various peptides were tested for the ability to stimulate fibrin deposition in the Defined Fibrin Deposition Assay as described in the specific description. Results are shown in the table below.

TABLE 12

Compound characterization in the Defined Fibrin Deposition Assay

| Compound | Concentration (µM) | FEIBA EU (mU/ml) |
|---|---|---|
| A01 | 100 | 145 |
| A01 | 50 | 127 |
| A01 | 25 | 80 |
| B01 | 100 | 94 |
| B01 | 50 | 47 |
| B01 | 25 | 31 |
| A05 | 50 | 219 |
| A05 | 25 | 193 |
| A05 | 10 | 119 |
| B03 | 25 | 325 |
| B03 | 12.5 | 291 |
| B03 | 6.3 | 264 |
| A06 | 25 | 168 |
| A06 | 12.5 | 232 |
| A06 | 6.3 | 251 |
| A07 | 50 | 199 |
| A07 | 25 | 246 |
| A07 | 12.5 | 268 |

All test compounds shortened the clotting time and fibrin formation of FVIII inhibited plasma. In combination with the thrombin generation experiments this confirms the procoagulant activities of the test compounds. Most compounds acted in a concentration dependent manner, although a small number had reduced activity at higher concentrations, which may be due to non-specific interactions.

Example 5

In Vitro Assays for the Characterisation of Compounds

Compounds are characterised not only for activity in the thrombin generation assays but also for pharmacokinetics, solubility, HERG inhibition and molecular weight.

Pharmacokinetic (PK) Studies

PK studies are required for the design and interpretation of in vivo efficacy studies. Plasma protein binding, plasma stability and microsomal stability are all included in this category.

1. Plasma Protein Binding

The extent of compound binding to human plasma (Bioreclamation, Hicksville, N.Y.), mouse plasma (Lampire Laboratory, Pipersville, Pa.) or mouse serum albumin (Sigma, St. Louis, Mo.), referred to as matrices, was determined in a 96-well micro-equilibrium dialysis block system (HDT-96; HTDialysis, LLC, Gales Ferry, Conn.). Briefly, each unit of the system comprises a donor chamber and a receiver chamber separated by a semi-permeable membrane.

The principle of the experiment is that proteins (and compound bound to the proteins) are retained in the donor chamber and cannot cross the membrane. Free compound can diffuse between both chambers via the membrane and reaches equilibrium during the experiment. In these experiments, the semi-permeable membrane was made of regenerated cellulose and had a molecular weight cut-off of 12-14 kD (cat. no 1101, HTDialysis, LLC).

A protease inhibitor cocktail (P2714-1BTL), purchased from Sigma, was included in the assay to inhibit proteolysis of test compounds. It was freshly prepared at 50× stock solution in distilled water. Mouse serum albumin was freshly prepared in phosphate buffered saline (PBS) at 40 g/L. The PBS was purchased from Invitrogen (Carlsbad, Calif.), and it was adjusted to a pH of 7.4 prior to use. Plasmas were used without dilution. The protease inhibitor stock solution was added to each matrix (i.e. mouse serum albumin in PBS) at a final 1× concentration. Stock solutions of each test compound were prepared in DMSO with the control compound, warfarin. Warfarin, which is a high protein-binding compound, was included in each stock solution to ensure the integrity of the membrane during the experiment. An aliquot of the stock solution was added to each matrix to yield a final concentration of 5 μM of the test compound and 10 μM of warfarin. The final concentration of DMSO was 0.72% (v/v). The dilution of the matrices by the addition of the other components was negligible (less than 4%). The membrane strips were hydrated in distilled water for 1 hour; the membrane was soaked in 30% ethanol aqueous solution for 20 minutes, and then the membrane was rinsed twice with distilled water. After the rinse, the membrane was placed in PBS and was ready for use. The assembly of the dialysis block followed the manufacturer's protocol. After the assembly, an aliquot of 150 μl of each matrix/test compound was added to a separate donor chamber and 150 μl of PBS was added to the corresponding receiver chamber on the other side of the membrane. The remainder of each matrix/test compound was stored at −80° C. for further analysis. The concentrations of the test compounds and warfarin in these matrices were measured and the values were used in the recovery calculations. The 96-well dialysis block was then placed in an enclosed, heated rocker, which was pre-warmed to 37° C., and allowed to incubate for 6 hours. After the incubation, both sides were sampled. The concentrations of the test compounds, as well as warfarin, were measured by LC/MS/MS analysis.

The recovery and protein binding values were calculated as follows:

$$\%\ \text{Recovery}=[(\text{Conc. in Donor}+\text{Conc. in Receiver})/(\text{Measured Conc. in Matrix})]\times 100\% \quad (1)$$

$$\%\ \text{Bound}=[(\text{Conc. in Donor}-\text{Conc. in Receiver})/(\text{Conc. in Donor})]\times 100\% \quad (2)$$

"% Recovery" is a measure of how much of the compound added to the matrix is recoverable from the donor and receiver chambers. Where recovery is less than 100%, a proportion of the compound may have bound to the membrane or the plastic surfaces of the chambers or it may have degraded. "% Bound" is a measure of how much of the compound has bound to the matrix and is therefore unable to equilibrate between donor and receiver chambers.

Results are shown for A01 and warfarin (control) in the tables below.

TABLE 13

Protein Binding of A01 In Tested Matrices

| Matrix | A01 Conc. In Matrix (μM) | Receiver Concentrations (μM) Rep 1 | Rep 2 | Rep 3 | Donor Concentrations (μM) Rep 1 | Rep 2 | Rep 3 | Average % Bound | Average % Recovery |
|---|---|---|---|---|---|---|---|---|---|
| Human plasma | 1.69 | <0.025 | <0.025 | <0.025 | 1.47 | 1.57 | 1.45 | >98.3 | >88.6 |
| Mouse plasma | 4.48 | <0.025 | <0.025 | <0.025 | 3.18 | 3.43 | 3.24 | >99.2 | >73.3 |
| Mouse serum albumin | 1.42 | <0.005 | <0.005 | <0.005 | 1.50 | 1.43 | 1.47 | >99.7 | >103 |

TABLE 14

Protein Binding of warfarin in Tested Matrices

| Matrix | Warfarin Conc. in Matrix (μM) | Receiver Concentrations (μM) Rep 1 | Rep 2 | Rep 3 | Donor Concentrations (μM) Rep 1 | Rep 2 | Rep 3 | Average % Bound (StDev) | Average % Recovery (StDev) |
|---|---|---|---|---|---|---|---|---|---|
| Human plasma | 9.88 | 0.0749 | 0.0765 | 0.0791 | 9.86 | 9.43 | 9.91 | 99.2 (0.03) | 99.3 (2.68) |
| Mouse plasma | 10.1 | 0.457 | 0.403 | 0.400 | 8.37 | 8.72 | 8.50 | 95.1 (0.462) | 88.6 (1.53) |
| Mouse serum albumin | 9.61 | 0.365 | 0.354 | 0.347 | 9.78 | 9.14 | 8.34 | 96.1 (0.218) | 98.3 (7.60) |

2. Plasma Stability

Half-life of compounds in human or mouse plasma, or percentage of compound remaining after an incubation in human or mouse plasma, is determined as follows. In the experimental procedure, test compound concentrations are 5 μM, prepared from test compound stock solutions of 10 mM in DMSO. Propantheline is used as a standard. To prepare tests samples, a 1/20 dilution of the test compound stock solution in DMSO is prepared in 50% acetonitrile/50% $H_2O$, and this is then diluted 1/100 in pre-warmed (37° C.) plasma (5 μl compound [1/20 dilution]+495 μl plasma) in a 1.5 ml Eppendorf-tube. The standard compound 2 mM propantheline is diluted 1/4 in DMSO and subsequently 1/100 in pre-warmed plasma (5 μl compound [1/4 dilution]+495 μl plasma) in a 1.5 ml Eppendorf-tube. All of the samples are incubated in a water bath at 37° C. 500 μl acetonitrile is added immediately after compounds, or propantheline standard, have been mixed with plasma (designated as t=0 min). After a chosen duration of incubation (generally at t=60 min) each sample is mixed with a further 500 μl acetonitrile. The samples are mixed on a vortex mixer for 30 s and placed on ice for 10 min and collected for centrifugation. Samples are centrifuged at 20 000 g for 10 min at 4° C. 500 μl supernatant is transferred into a new 1.5 ml Eppendorf tube and an equal volume of acetonitrile is added. The sample is mixed again for 30 s using a vortex mixer. After a second centrifugation step (20 000 g, 10 min, 4° C.) 250 μl of the supernatant is transferred into HPLC glass vials for HPLC-MS analysis. Conditions for performing HPLC are as follows: Injection-volume is set to 20 μl. Temperature is set to 25° C. A linear gradient from 95:5 to 5:95 water:acetonitrile both containing 0.05% trifluoroacetic acid (TFA) (v/v) is applied at a flow rate of 0.3 ml/min for 10 min. The PDA-detector is scanning from 210-400 nm. The ion-trap is equipped with an ESI-source with temperature at 280° C., mass-scanning is done in full scan-mode from 50-2000 amu followed by dynamic exclusion $MS^2$-experiment with 1.5 V collision energy (105 as min. count of parent ion). Percent-stability is calculated from area-under-curve (AUC) ratio monitoring the protonated molecular-mass ion of the target compound in the total-ion-current (tic) in full-scan mode at 60 min incubation time (or time of choice) vs. 0 min incubation time.

Results are shown in the table below. Decreases in compound concentration over time might be due to proteolytic degradation and/or chemical modification.

TABLE 15

| Plasma stability of compounds | |
|---|---|
| Peptide | % remaining in human plasma (30 min) |
| A01 | 58 |
| A19 | 99 |
| A07 | 117 |
| A20 | 95 |
| A06 | 98 |
| A02 | 84 |
| A03 | 92 |
| A08 | 70 |
| A09 | 67 |
| B07 | 89 |
| B06 | 93 |
| B05 | 112 |
| A05 | 93 |

3. Microsomal Stability

Tests were used to determine the stability of compounds in microsomal preparations of human or animal origin. The microsomal stability is measured either in assays provided by Cerep (France, Catalog ref. 900-8h) or by the protocol described below. Compound solutions of 10 mM/5 mM (test compound, standards verapamil, imipramine, and terfenadine) are prepared in 100% DMSO. They are diluted by distilled $H_2O$/MeOH resulting in a final concentration of 1 μM in the assay, with less then 0.4% DMSO (v/v) in the final mixture. The mastermix for the stability assay is prepared in a 10 ml Falcontube (total volume 4.4 ml): 3414 μl distilled water, 440 μl 500 mM $NaPO_4$-buffer pH 7.4, 440 μl NADP (10 mM), 22 μl Glc-6-P (1 M), 17.6 μl Glc-6-P-DH of a 1 U/ml solution, 66 μl liver microsomes (rat or mouse, final concentration in the assay 300 μg/ml). The mastermix is preincubated at 37° C. for 10 minutes in the water bath. 5 μl of 60 μM compound solution is added per well in a 96-well-U-Plate (PP-Nunc) together with 300 μl of reaction mixture (pre-incubated mastermix). All wells must be carefully mixed to ensure a homogenous suspension before the next steps. 75 μl samples (duplicates) at t=0 minutes are taken for each compound. The plate is sealed and returned to the water bath/thermomixer for 30 minutes. The test compounds/standards are extracted by addition of 200 μl methanol, also including an internal standard. The internal standard is "Pep770" (Jerini A G, Berlin, Germany) and is used at a final concentration of 6.25 ng/ml. The samples are centrifuged at 1300 g for 10 min at 4° C. 200 μl of the supernatant is transferred into a 96-well plate with 10 μl DMSO per well. Compound stability is measured by HPLC-MS analysis (triplicates). The same procedure is repeated after 30 min. The ratio of the mean "AUC t=0 min" and "AUC t=30 min" is calculated and the percentage of the amount of remaining compound after 30 min is determined. The signal to noise ratio for all peaks must be 5:1 or better. The ratio $AUC_{analyte}$: $AUC_{standard}$ at the different timepoints must be used. The calculated stability for the control compound must fall in a certain range to validate the assay.

Results are shown in the table below.

TABLE 16

| Stability of compounds in mouse microsomes | |
|---|---|
| Peptide | Stability after 30 min [%], duplicates |
| A01 | 27/32 |
| A02 | 44/45 |
| A06 | 51/47 |
| A07 | 39/28 |
| A09 | 22/23 |
| Terfenadine | 63/68 |

Solubility

Aqueous solubility is measured in PBS at pH 7.4 either in an assay provided by Cerep (France, Catalog ref. 900-11a) or according to the following protocol. The aim of this procedure is to determine the solubility of a drug candidate (analyte) in a buffer, by estimating the saturation concentration of the candidate in the buffer using HPLC. A known concentration of the candidate in an organic solvent is used as a standard. A stock solution of the test compound in DMSO must be prepared as the initial step. Depending on the maximum solubility of the compound, a concentration of 50 mM in DMSO should be reached. DMSO stock-solutions are diluted to a final concentration of 50 μM with DMSO (100% reference-solution) and buffer (test-solution) to provide a minimum volume of 500 μL of each. Both solutions are shaken at 25° C. at 950 rpm in an Eppendorf "thermomixer comfort" for at least 60 min. The suspension is centrifuged at 22 330 g for at least two min and 100 μL of the supernatant is transferred into polypropylene-inserts placed in glass vials and closed by snap-ring caps. Alternatively the solutions can be prepared in microtiter plates with half of the previously described starting solvent volume. For the determination of the solubility all samples are analyzed by HPLC in triplicate. Injection volume is at least 10 μL. The obtained data are analyzed by "Chemstation-software" (Agilent, Waldbronn, Germany). The peaks from the analyses of the organic solutions are integrated and the arithmetic mean is reported as "AUC 1" (reference area of known amount injected at the HPLC). The same procedure is applied to the spectra obtained from the analyses of the buffer solution to give "AUC 2" (area of the unknown amount of compound dissolved in buffer). In general the AUC must be greater then 20 area units and signal to noise (height of the peak) must be better than 3. The ratio of the mean "AUC 2" and "AUC 1" is calculated and thus the percentage of the dissolved amount of compound in buffer is obtained and solubility can be reported in μM.

Results are shown in the table below.

TABLE 17

| Solubility of compounds in PBS | |
|---|---|
| Compound | Solubility in PBS [μM] |
| A09 | 63 |
| B03 | 114 |
| B07 | 195 |
| B06 | 48 |
| B05 | 174 |
| A01 | 9 |
| A08 | 11 |
| A05 | 6 |
| A19 | 14 |
| A07 | 165 |
| A20 | 166 |
| A06 | 164 |
| A02 | 35 |
| A03 | 110 |
| A16 | >200 |

HERG Inhibition

QT prolongation is assessed by HERG inhibition measured by patch-clamp techniques or $Rb^+$ efflux.

The Rb+ efflux method (Cerep, France, Catalog. Ref. 900-36rb) is used for initial screening. For the Rb+ efflux assay, the reference compound (Astemizole) was tested concurrently with the test compounds in order to assess the assay suitability. It was tested at 10 μM and the data were compared with historical values determined at Cerep.

For rigorous characterization of HERG inhibition the patch clamp assay is applied (Cerep, France, Catalog ref. 900-36). The general potency ranking system is adopted from Roche et al., 2002, *Chem Bio Chem* 3:455-459. To ensure that no change in the sensitivity of the assay has occurred, separate experiments conducted on the same (clone) batch of cells using 10 nM E-4031 (Wako, cat. no. 052-06523) yielded results (56.7±1.8% inhibition, Mean±SEM, n=3) comparable to historically obtained data (58.4±2.0% inhibition, Mean±SEM, n=3) at Cerep. The test compounds (10 mM stock solutions) were dissolved in dimethylsulfoxide (DMSO). The solutions at 1 μM contained 0.01 DMSO. Bath solutions containing up to 1% DMSO have no significant effect on the H ERG-encoded tail currents.

Screening of several compounds by the Rb+ efflux method at 10 μM indicated no inhibition of HERG channel activity. In the more sensitive patch clamp assay compounds A01, A05 and A16 can be classified as low-potency HERG-channel blockers whereas B03 was identified as a high potency HERG-channel blocker. Results are provided in the table below.

TABLE 18

| HERG inhibition results | | |
|---|---|---|
| Compound | HERG inhibition patch-clamp (% Inhibition of Tail Current at 1 μM) | HERG inhibition Rb+ efflux (% Inhibition at 10 μM) |
| A01 | 16.5 | |
| A02 | | −3.3 |
| A05 | 14.5 | |
| B03 | 84.5 | −2.1 |
| A06 | | −6.4 |

TABLE 18-continued

| HERG inhibition results | | |
|---|---|---|
| Compound | HERG inhibition patch-clamp (% Inhibition of Tail Current at 1 μM) | HERG inhibition Rb+ efflux (% Inhibition at 10 μM) |
| A07 | | −3.4 |
| A09 | | −1.6 |
| A16 | 22.2 | |
| Astemizole | | 73.5 |

Molecular Weight

The molecular weight is defined as the theoretical mass of the monomeric molecule exclusive of any counter ions or adducts. The molecular weights of the compounds are indicated in the table below.

TABLE 19

| Molecular weights of compounds | |
|---|---|
| Compound | Molecular weight (g/mol) |
| A09 | 2175 |
| B03 | 1439 |
| B07 | 1423 |
| B06 | 1849 |
| B05 | 1763 |
| A01 | 2087 |
| A08 | 2175 |
| A05 | 1311 |
| A19 | 1410 |
| A07 | 1743 |
| A20 | 1742 |
| A06 | 1741 |
| A02 | 2028 |
| A03 | 2074 |
| A16 | 2087 |

Example 6

ADME-Tox

ADME-Tox analyses of various compounds were performed as described in Example 5. Summary results are shown in the table below.

TABLE 20

| Summary ADME-Tox data | | | | | | | | | |
|---|---|---|---|---|---|---|---|---|---|
| | A01 | A02 | A05 | B03 | A06 | A07 | A09 | A16 | A17 |
| Aqueous solubility | 9 | 35 | 6 | 114 | 164 | 165 | 63 | 220 | 2000 |
| Proteolytic stability (human) | 58 | 84 | 94 | | 98 | 117 | 67 | | |
| Microsomal stability | 30 | 45 | | | 49 | 34 | 23 | | |
| HERG channel | 17 | | 15 | 85 | | | | 22 | |

Briefly, aqueous solubility was tested in PBS pH 7.4. Results are given in μM. Proteolytic stability was tested in human plasma for 30 minutes. Results for each are given as % stability. Microsomal stability was tested in a mouse microsomal preparation for 30 minutes. Results are given as % stability. HERG channel inhibition was tested using the patch clamp method in which the peptide or peptide derivative at 1 μM and are given as % inhibition.

Example 7

Animal Models

The following assays are performed in animals.

1. Acute Toxicology

Toxicology studies involved monitoring of attitude changes due to toxic effects immediately after application and twice daily; monitoring of body weight; histopathology of brain, heart, kidney, liver, lung. Experiments were performed in C57Bl/6 mice.

2. Pharmacokinetics

Pharmacokinetics of compounds were tested in C57Bl/6 mice or Wistar rats at 1-30 mg/kg. Compound concentrations in the blood stream were monitored at appropriate intervals using LC-MS.

3. Circulation Analysis

Blood pressure and heart rate were monitored and electrocardiogram taken in C57Bl/6 mice.

4. Animal Disease Model

A tail clip model was used in FVIII −/− (E17) mice, FIX −/− mice and C57Bl/6 control mice. Parameters quantified were total blood loss, bleeding time, bleeding rate and survival.

Example 8

Acute Toxicology

C57Bl/6 mice weighing 18-20 g were administered with compounds in a suitable vehicle i.v. in the tail vein or i.p. or s.c at 10 ml/kg. Quantities of the compounds administered were in the range of 0.075 to 125 mg/kg (i.v.), 15-125 mg/kg (i.p.) and 125 mg/kg (s.c.). There were four mice per group. Attitude changes due to toxic effects were monitored immediately after administration of the compound and for 60 minutes thereafter. Body weight was monitored for five days after administration. At day 5 after administration, mice were culled and autopsy performed. Brain, heart, kidney, liver, lung and spleen were biopsied. Results are described below.

TABLE 21

| Attitude changes due to toxic effects at different compound doses | | | | |
|---|---|---|---|---|
| | | Max dose (mg/kg) within toxicity category | | |
| Compound | route | No detected toxicity | Some toxicity | Severe toxicity |
| A01 | i.v. | 20 | | |
| | i.p. | 20 | | |
| A02 | i.v. | 25 | | |
| | i.p. | 25 | | |
| A05 | i.v. | | 1.5 | 15 |
| | i.p. | 15 | | |
| B03 | i.v. | 1.5 | | 15 |
| | i.p. | 15 | | |
| A06 | i.v. | 1 | 5 | 25 |
| | i.p. | 25 | | |
| A07 | i.v. | 1 | 5 | 25 |
| | i.p. | 25 | | |
| A09 | i.v. | 15 | | |
| | i.p. | 15 | | |
| A16 | i.v. | 82 | | |
| | i.p. | 82 | | |
| A17 | i.v.. | 125 | | |
| | i.p. | 125 | | |
| | s.c. | 125 | | |

In the above table, the maximum dose tested giving rise to no detected toxicity, some toxicity or severe toxicity over the period of 60 minutes following administration is reported. "No detected toxicity" indicates no acute toxic observations. "Some toxicity" indicates that ataxy or catalepsy were recorded, but no animals died. "Severe toxicity" indicates that one of the animals died within one hour of compound application.

In summary, most of the compounds were tolerated well. Doses of compounds which resulted in severe toxicity when administered by a particular route were not tested in pharmacokinetics, circulation analysis or animal disease models by that route.

For most of the compounds, even at the highest dose, no macroscopic pathological findings were observed in biopsy samples collected at five days from surviving mice, indicating that the compounds were tolerated well. The only pathological changes identified in any animal were minor abnormalities in the liver, kidney, lung or heart. These were spontaneous observations in single animals probably due to non compound-related minor infections or due to culling.

For each compound tested, no effect on average body weight of surviving mice, indicative of a negative response, was noted.

Example 9

Pharmacokinetics of Compounds

Pharmacokinetic studies were performed to monitor compound concentrations in plasma following i.v., i.p. or s.c. administration. Studies were conducted in C57Bl/6 mice weighing approximately 20 g.

For each peptide, the same formulations were used for all administration routes and were as follows: A01 was formulated in 5% DMSO, 5% Cremophor EL (Sigma-Aldrich), 0.5% Tween 80; A02 and A09 were each formulated in 5% DMSO, 30% PEG 400 (polyethylene glycol) 50 mM sodium phosphate pH 7.4; A05 was formulated in 5% DMSO, 20 mM glycine pH 9.0; A06 and A07 were each formulated in 5% DMSO, 0.9% NaCl, 50 mM sodium phosphate pH 7.4.

Peptide concentrations in the plasma were analysed by HPLC-MS on a Surveyor HPLC combined with mass spectrometer LCQ classic or Advantage (all Thermo Electron, US) equipped with an ESI-source. All HPLC experiments were carried out on a Phenomenex C-18 Luna column (50 mm×2.0 mm, 5 μl injection volume) using a linear gradient: eluent A 0.05% trifluoracetic acid (TFA) in water; eluent B 0.05% TFA in acetonitrile; flow rate 0.3 mL/min in 10 min. UV spectra were recorded by the PDA from 220 to 400 nm. The internal standard is prepared as a 0.1 μg/ml solution in 100% methanol. 50 μl plasma and 50 μl internal standard are mixed. 100 μl methanol is added and mixed thoroughly. After 30 min incubation on ice the vial is centrifuged for 15 min at 4° C. (20820 g). 150 μl of the supernatant are transferred into the HPLC vial Results following i.v. or i.p. administration are shown in the table below. In brief, peptide clearance from plasma following i.v. administration followed a roughly logarithmic course. Following i.p. administration, Cmax was reached at between 40 and 60 minutes. There then followed a decrease in compound concentration. This profile is typical for i.p. or s.c. administration.

TABLE 22

| Data obtained in pharmacokinetics analyses | | | | | | |
|---|---|---|---|---|---|---|
| | Peptide concentration in plasma (μg/ml) at time intervals after admin. | | | | | |
| [min] i.v. | 5 | 10 | 15 | 20 | 25 | 30 |
| A01 | 0.673 | 0.352 | 0.454 | 0.145 | 0.282 | 0.115 |
| A02 | 11.625 | 7.260 | 3.182 | 2.738 | 1.436 | 1.308 |
| A05 | 2.605 | 2.039 | 0.173 | 0.101 | 0.023 | — |
| A06 | 49.963 | 32.610 | 20.981 | 15.593 | 11.267 | 7.787 |
| A07 | 12.512 | 7.796 | 5.482 | 2.132 | 3.309 | 2.218 |
| A09 | 0.350 | 0.184 | 0.109 | 0.119 | 0.064 | 0.080 |

TABLE 22-continued

| Data obtained in pharmacokinetics analyses | | | | | | |
|---|---|---|---|---|---|---|
| [min] i.p. | 5 | 20 | 40 | 60 | 80 | 100 |
| A02 | 0.273 | 0.315 | 0.289 | 0.612 | 0.099 | 0.176 |
| A05 | 0.119 | 0.165 | 0.185 | 0.130 | 0.049 | 0.050 |
| A06 | 6.442 | 7.773 | 0.547 | 5.800 | 4.057 | 3.024 |
| A07 | 2.444 | 2.627 | 3.180 | 3.869 | 2.202 | 1.678 |
| A09 | 0.034 | 0.067 | 0.060 | 0.129 | 0.074 | 0.068 |

Example 10

Circulation Analysis Following Administration of A01

Mean arterial blood pressure and heart rate were monitored and electrocardiogram taken in three groups of three male and three female C57Bl/6 mice, each weighing about 20 g. The groups were assigned to "control" receiving 10 ml/kg NaCl i.v.; "vehicle" receiving 10 ml/kg i.v.; or "compound" receiving A01 in vehicle at 20 mg/kg i.v. "Vehicle" was DMSO 5%, Cremophor EL (Sigma-Aldrich) 5%, Tween 80 0.05% in water for injection.

For each mouse, a catheter filled with saline/heparin was fixed to the aorta carotis. The catheter was linked via a transducer to a blood pressure Plugsys-module (Hugo Sachs Electronik-Harvard Apparatus GmbH, Germany (HSE)). ECG electrodes were implanted s.c. and were linked via a ECG Plugsys-module (HSE) to a PC. Heart rate was calculated from the ECG. After a period of at least ten minutes to stabilize circulation parameters, saline, vehicle or compound was administered as appropriate via a catheter connected to the vena jugularis. Circulation parameters were monitored and recorded for 60 minutes after administration. For each animal, the time course in mean arterial blood pressure and heart rate within the observation period after study drug administration was estimated using the area under the curve (AUC) using the linear trapezoidal rule. The individual AUCs (A01 20 mg/kg i.v.) were compared with those of vehicle (10 mL/kg i.v.) and saline (10 mL/kg i.v.). The null hypothesis (no differences between compound and vehicle or saline) were assessed using the exact Wilcoxon rank sum test. Unadjusted and adjusted two-sided p-values for multiple comparisons were calculated. Adjustment for multiplicity was performed by using the Bonferroni-Holm method. The level of significance was set to 5%. All statistical analyses were performed with R Version 2.4.0. The null hypothesis of no difference was tested against the two-sided alternative. Results are shown in the table below.

TABLE 23

| Statistical results of circulation analysis | | | |
|---|---|---|---|
| Parameter | Comparison | Unadjusted two-sided p-value | Adjusted two-sided p-value |
| Mean arterial BP | A01 vs. saline | 0.5887 | 1.0000 |
| | A01 vs. vehicle | 1.0000 | 1.0000 |

TABLE 23-continued

| Statistical results of circulation analysis | | | |
|---|---|---|---|
| Parameter | Comparison | Unadjusted two-sided p-value | Adjusted two-sided p-value |
| Heart rate | A01 vs. saline | 0.6991 | 0.6991 |
| | A01 vs. vehicle | 0.2403 | 0.4805 |

There were no statistically significant (at the 5% level) differences in AUC of mean arterial blood pressure within 60 min after study drug administration between A01 20 mg/kg i.v. and saline 10 ml/kg i.v. as well as between A01 20 mg/kg i.v. and vehicle 10 ml/kg i.v. There were no statistically significant (at the 5% level) differences in AUC in heart rate within 60 min after study drug administration between A01 20 mg/kg i.v. and saline 10 ml/kg i.v. as well as between A01 20 mg/kg i.v. and vehicle 10 ml/kg i.v.

Example 11

Animal Disease Model—Control Experiments

Experiments were performed to develop a mouse tail clip assay to characterise bleeding parameters in FVIII (E17)−/−, FIX−/− (Lin H F Blood 1997; 90: 3962-6) and wild-type C57Bl/6 mice and their response to coagulation factor preparations.

Coagulation factor preparations tested were Advate® and Immunine®. Advate® is a rFVIII preparation (Baxter AG, Austria). Immunine® is a purified plasma FIX preparation (Baxter AG, Austria).

Blood loss was monitored in the tail clip assay as described in the specific description for 62 minutes after tail clip. FVIII −/− mice were administered with rFVIII (Advate®) at 25, 50 or 100 U/kg i.v. or with vehicle alone. The vehicle was Advate formulation buffer which is 38 mg/ml mannitol, 10 mg/ml trehalose, 108 mEq/l sodium, 12 mM histidine, 12 mM Tris, 1.9 mM calcium, 0.17 mg/ml Polysorbate-80, 0.1 mg/ml glutathione. As a control, C57Bl/6 mice were administered vehicle alone. Administration of rFVIII resulted in a dose-dependent reduction of blood loss over the 62 minutes. Survival data for the experiment are shown in the table below.

TABLE 24

Survival of FVIII −/− mice treated with Advate ® FVIII in tail clip experiment

| | Dose (U/kg) | Animals (n) | Survival (%) 2 hours | Survival (%) 4 hours | Survival (%) 24 hours | Survival (%) 48 hours |
|---|---|---|---|---|---|---|
| Advate | 100 | 10 | 100 | 90 | 90 | 90 |
| Advate | 50 | 10 | 100 | 100 | 90 | 90 |
| Advate | 25 | 10 | 100 | 100 | 90 | 90 |
| Vehicle | — | 10 | 70 | 50 | 50 | 50 |
| C57Bl/6 | — | 16 | 100 | 100 | 100 | 100 |

Blood loss was monitored for 62 minutes after tail clip of FIX −/− mice administered with Immunine® FIX at 50, 100 or 200 U/kg i.v. or with vehicle alone. As a control, C57Bl/6 mice were administered vehicle alone. Administration of FIX resulted in a dose-dependent reduction of blood loss over the 62 minutes. Survival data for the experiment are shown in the table below.

TABLE 25

Survival of FIX −/− mice treated with Immunine ® FIX in tail clip experiment

| | Dose (U/kg) | Animals (n) | Survival (%) 2 hours | Survival (%) 4 hours | Survival (%) 24 hours | Survival (%) 48 hours |
|---|---|---|---|---|---|---|
| Immunine | 200 | 16 | 100 | 100 | 100 | 100 |
| Immunine | 100 | 16 | 100 | 100 | 94 | 94 |
| Immunine | 50 | 16 | 94 | 69 | 63 | 63 |
| Vehicle | — | 16 | 44 | 19 | 6 | 0 |
| C57Bl/6 | — | 16 | 100 | 100 | 100 | 100 |

The data show that in the FVIII −/− model, Advate® FVIII at 25-100 U/kg dose dependently improves bleeding parameters and survival. In the FIX −/− model, Immunine® FIX at 50-200 U/kg dose dependently improves bleeding parameters and survival. Thus, the FVIII −/− model is an appropriate model to test coagulation FVIII activity of the lead compounds. The FIX −/− model is an appropriate model to test coagulation FIX activity of the compounds.

Example 12

Animal Disease Models—Efficacy of A01

The effect of administered A01 on bleeding parameters and survival of FVIII −/− mice was tested in the tail clip model described in the specific description. Similar experiments were performed in FIX −/− mice.

Figure 2:
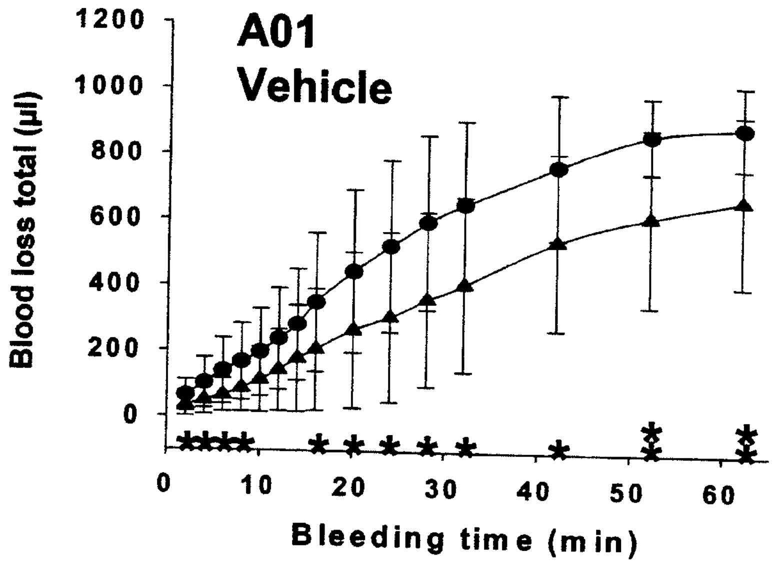
FIG. 2: Effect of A01 on FVIII −/− mouse bleeding model—blood loss

Mean volume of blood loss following tail clip in a group of 8 male and 8 female FVIII −/− mice administered 20 mg/kg of A01 i.v. five minutes before tail clip was significantly different ($p<0.05$) at most time points compared to mean volume of blood loss by a control group of mice administered vehicle alone. Vehicle was 5% DMSO, 5% Cremophor EL, 0.05% Tween 80 in water for injection. At 52 and 62 minutes after tail clip, the difference was significant at $p<0.01$. Data are shown in FIG. 2 and the table below. A log-rank test used to compare the survival curves of mice in this experiment shows a statistically significant longer survival with A01 20 mg/kg i.v. than with vehicle control (p-value=0.0028).

TABLE 26

Survival of FVIII −/− mice treated with A01 in tail clip experiment

| Treatment | Animals (n) | Survival (%) 2 hours | Survival (%) 4 hours | Survival (%) 24 hours | Survival (%) 48 hours |
|---|---|---|---|---|---|
| A01 | 16 | 56 | 25 | 6 | 0 |
| Vehicle | 16 | 6 | 6 | 0 | 0 |

The above experiment was repeated to provide an indication of its reproducibility. Results are shown in the table below. Although variability is observed within these two independently performed experiments animals treated with A01 bleed less and survive longer.

TABLE 27

Survival of FVIII −/− mice treated with A01 in tail clip experiments

| | Exp | Animals (n) | Survival (%) 2 hours | Survival (%) 3 hours | Survival (%) 4 hours | Survival (%) 24 hours |
|---|---|---|---|---|---|---|
| A01 | 1 | 16 | 56 | 44 | 25 | 6 |
| Vehicle | 1 | 16 | 6 | 6 | 6 | 0 |
| A01 | 2 | 16 | 63 | 38 | 31 | 13 |
| Vehicle | 2 | 16 | 44 | 25 | 25 | 0 |

Further data were obtained using the same model, although the tail clip was 1 cm rather than 0.5 cm, and mice were grouped according to gender. Agents were administered i.v. In this experiment, it appeared that A01 was more effective in female than male mice. Results are shown in the table below.

TABLE 28

Gender effects of A01 in FVIII −/− mouse tail snip experiment

| Compound | No. of animals (n) | Survival 2 hours (%) | Survival 24 hours (%) |
|---|---|---|---|
| A01 formulation buffer | 20 | 30 | 0 |
| A01 formulation buffer | 10 female | 50 | 0 |
| A01 formulation buffer | 10 male | 10 | 0 |
| A01 20 mg/kg | 10 female | 80 | 10 |
| A01 20 mg/kg | 10 male | 20 | 0 |
| Advate formulation buffer | 10 | 10 | 0 |
| Advate 200 IU/kg | 10 | 90 | 90 |
| Advate 100 IU/kg | 10 | 70 | 50 |

Groups contained equal numbers of male and female mice, unless otherwise stated.

Mean volume of blood loss following tail clip in a group of 16 FIX −/− mice administered 20 mg/kg of A01 i.v. five minutes before tail clip was not significantly different ($p<0.05$) at any time points compared to mean volume of blood loss by a control group of mice administered vehicle alone. There was no significant difference in survival of mice administered A01 and mice administered vehicle alone.

These results demonstrate that A01 can at least partially compensate for the lack of FVIII in FVIII−/− mice by reducing blood loss and increasing survival following tail clip, but has no effect in FIX−/− mice. A01 is regarded as the most preferred peptide because it has demonstrated efficacy in a hemophilia model.

Example 13

Results of Compound Testing in FVIII−/− Mouse Tail Clip Model

A01 was further tested by i.p. administration in the FVIII −/− tail clip model using a 0.5 cm tail clip. Data are summarised in the table below.

TABLE 29

Survival of FVIII −/− mice treated with A01 in tail clip experiment

| Compound | Treatment dose | Animals (n) | Total blood loss (% of Vehicle) | Survival 2 hours (%) | Survival 4 hours (%) | Survival 24 hours (%) |
|---|---|---|---|---|---|---|
| A01 | 20 mg/kg i.p. female | 8 | 72 | 75 | 25 | 25 |
| A01 | 20 mg/kg i.p. male | 8 | 83 | 38 | 25 | 25 |
| Vehicle control | 10 ml/kg i.p. female | 8 | | 13 | 0 | 0 |
| Vehicle control | 10 ml/kg i.p. male | 8 | | 13 | 13 | 13 |

Female mice administered with A01 20 mg/kg had a statistically significant (at the 5% level) longer survival than female mice administered with vehicle 10 ml/kg i.p. (two-sided p-value $p=0.0073$; log-rank test). There was no statistically significant difference (at the 5% level) in survival curves between male mice administered with A01 20 mg/kg i.p. and male mice administered with vehicle 10 ml/kg i.p. In this experiment, the males in the control group seemed to survive better than the females in the control group.

Example 14

Summary of Experiments for Characterising Lead Compounds

The following compounds possess activity in the Defined Intrinsic Thrombin Generation Assay: A01, A03, A05, A19, B01, A02, B03, B05, B06, A06, A20, A07, A08, A09 and B07. Of these, A03, A02, B03, A08 and A09 have a thrombin generation activity at 100 μM of at least 1200 mU/mL FEIBA.

The following compounds possess activity in the Defined Dual-Pathway Thrombin Generation Assay: A02, A03, A08, A09, A18, B03, B04, A07, A15, A06 and A17. Of these, A09 had a peak IIa activity at 50 μM of at least 10 mU/mL FEIBA. B03, B04 and A15 had a peak IIa activity at 50 or 100 μM of at least 10 mU/mL FEIBA.

The following compounds possess activity in the Defined Fibrin Deposition Assay: A01, B01, A05, B03, A06 and A07.

The following compounds have a stability of at least 50% following incubation for 30 minutes in human plasma: A01, A19, A07, A20, A06, A02, A03, A08, A09, B07, B06, B05 and A05.

The following compounds have solubility in PBS pH 7.4 of at least 25 μM: A09, B03, B07, B06, B05, A07, A20, A06, A02, A03 and A16. Of these, B03, B07, B05, A07, A20, A06, A03 and A16 have a solubility in PBS pH 7.4 of at least 100 μM.

A01, A05 and A16 were identified as low-potency HERG-channel blockers.

A01 was identified as possessing activity in the tail clip assay in FVIII−/− mice.

Example 15

Treatment of Hemophilia A in an Adult Human Subject

It is typical for hemophilia A patients to develop alloantibody inhibitors to FVIII following high dose FVIII therapy. In a typical scenario, the presence of such antibodies in serum prepared from the patient's blood plasma is monitored by a clinician. When the titre of the antibody response becomes unacceptably high, such as about 5 BU, the clinician may decide to stop infusing the patient with FVIII, and start administering a peptide of the invention, such as peptide A01.

The peptide may be formulated as a microparticle of about 10 μm diameter in an albumin shell, suspended in an aqueous medium, as described in U.S. Pat. No. 5,439,686. The patient may self administer the formulation by inhalation using a nebulizer. A daily or twice daily dose of 5 or 10 mg may be inhaled. The clinician may test the partial thromboplastin time shortly after commencement of the peptide therapy, to confirm efficacy. Depending on the result, the dose could be varied accordingly. If it is necessary to substantially increase the dose, smaller microparticles could be used, typically of about 5 μm diameter, and they could be administered intravenously.

The invention claimed is:

1. A method of making a peptide or peptide derivative comprising an amino acid sequence comprising imfwydcye (SEQ ID NO: 431) or a variant amino acid sequence comprising one, two, three, four, five or six amino acid substitutions in imfwydcye (SEQ ID NO: 431), said variant amino acid sequence comprising X1X2X3X4X5X6X7X8X9X10, wherein X1, when present, is c, s, y, i, D-Pen, C, t, D-Nva, D-Nle or k; X2 is i, y, w or d; X3 is c or m; X4 is f, t, v or c; X5 is w or c; X6 is y or c; X7 is d, e or f; X8 is c, e, f, y or d; X9 is y or w; and X10 is e or i (SEQ ID NO: 433), the method comprising (a) coupling the C-terminal amino acid of the peptide to a cleavable linking moiety that is bonded to a solid phase support material, wherein the alpha-amino group of the C-terminal amino acid that is to be coupled bears an Fmoc protecting group;

(b) removing the Fmoc protecting group from the C-terminal amino acid that is coupled to the linking moiety;

(c) successively coupling Fmoc-protecting amino acids to the C-terminal amino acid, with attendant cleavage of the Fmoc protecting group prior to each successive amino acid addition, thereby producing an amino acid sequence bearing side chain protecting groups; and (d) removing the side chain protecting groups and cleaving the peptide from the solid phase support material.

2. The method of claim 1, wherein the peptide or peptide derivative comprises an amino acid sequence comprising cimfwydcye (SEQ ID NO: 432).

3. The method of claim 1, wherein the variant amino acid sequence comprises an amino acid sequence comprising X1X2X3X4wydX8ye, wherein X1, when present, is c, C, D-Pen or s; X2 is i, y or w; X3 is c or m; X4 is f, t, or v; and X8 is c or e (SEQ ID NO: 434).

4. The method of claim 1, wherein the variant amino acid sequence comprises an amino acid sequence comprising X1X2mX4wydX8ye, wherein X1, when present, is c, C or D-Pen; X2 is i or y; X4 is f, t, or v; and X8 is c or e (SEQ ID NO: 435).

5. The method of claim 1, wherein peptide or peptide derivative comprises or consists of an amino acid sequence selected from the group consisting of Ac-cimfwydeye-$NH_2$ (SEQ ID NO: 436), Disulphide-Dimer(Ac-cimfwydeye-$NH_2$)$_2$ (SEQ ID NO: 437), Ac-TTDS-(cymfwydc)-ye-$NH_2$ (SEQ ID NO: 438), K-TTDS-(cymfwydc)-ye-$NH_2$ (SEQ ID NO: 439), Ac-cimtwydcye-$NH_2$ (SEQ ID NO: 440), Ac-cimvwydcye-$NH_2$ (SEQ ID NO: 441), cymfwydcye (SEQ ID NO: 442), Ac-(cymfwydc)-yeG-$NH_2$ (SEQ ID NO: 443), Ac-(D-Pen)imfwydeye-$NH_2$ (SEQ ID NO: 444), O($CH_2$—$CH_2$—O—$CH_2$—CO-imfwydeye-$NH_2$)$_2$ (SEQ ID NO: 445), Pyridine-3,5-(CO-imfwydeye-$NH_2$)$_2$ (SEQ ID NO: 446), $H_2$N-E-TTDS-(cymfwydc)-ye-$NH_2$ (SEQ ID NO: 447), Ac-(cymfwydc)-yeK (SEQ ID NO: 448), Ac-(cymfwydc)-ye-TTDS-K (SEQ ID NO: 449), Ac-simfwydeye-$NH_2$(SEQ ID NO: 450), Ac-simfwydeye-$NH_2$(SEQ ID NO: 451), Ac-ydmcwcefyi-$NH_2$ (SEQ ID NO: 452), Ac-idmccyfywe-$NH_2$ (SEQ ID NO: 453), Ac-cimfwyddye-$NH_2$ (SEQ ID NO: 454), Ac-(cymfwydc)-ye (SEQ ID NO: 455), Ac-(cymfwydc)-ye-TTDS-$NH_2$ (SEQ ID NO: 456), Ac-TTDS-(cymfwydc)-ye-TTDS-$NH_2$ (SEQ ID NO: 457), K-(cymfwydc)-ye-$NH_2$ (SEQ ID NO: 458), Ac—K-(cymfwydc)-ye-$NH_2$ (SEQ ID NO: 459), E-(cymfwydc)-ye-$NH_2$ (SEQ ID NO: 460), Ac—K-TTDS-(cymfwydc)-ye-$NH_2$ (SEQ ID NO: 461), Ac-(cymfwydc)-yeK-$NH_2$(SEQ ID NO: 462), Ac-(cymfwydc)-ye-TTDS-K—$NH_2$ (SEQ ID NO: 463), Ac-(cymfwydc)-ye-TTDS-E-$NH_2$ (SEQ ID NO: 464), Ac-timfwydeye-$NH_2$ (SEQ ID NO: 465), Ac-(cimfwydc)-ye-$NH_2$ (SEQ ID NO: 466), Ac-(cymfwydc)-ye-$NH_2$ (SEQ ID NO: 467), Ac-(cwmfwydc)-ye-$NH_2$ (SEQ ID NO: 468), Ac-cicfwydcye-$NH_2$ (SEQ ID NO: 469), Ac-(D-Nva)imfwydeye-$NH_2$ (SEQ ID NO: 470), Ac-(D-Nle)imfwydeye-$NH_2$ (SEQ ID NO: 471), Ac-(Cys)imfwydeye-$NH_2$ (SEQ ID NO: 472), (cymfwydc)-ye-$NH_2$ (SEQ ID NO: 473), TTDS-(cymfwydc)-ye-TTDS-$NH_2$ (SEQ ID NO: 474), and Ac-kimfwydeye-$NH_2$(SEQ ID NO: 475), wherein TTDS is 4,7,10-trioxa-1,13-tridecanediamine, (D-Pen) is D-penicillamine, (D-Nva) is D-norvaline, (D-Nle) is D-norleucine.

* * * * *

SEQUENCE LISTING

```
<160> NUMBER OF SEQ ID NOS: 658

<210> SEQ ID NO 1
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (1)..(1)
<223> OTHER INFORMATION: Xaa is Trp, Leu or Pro
<220> FEATURE:
<221> NAME/KEY: VARIANT
<222> LOCATION: (2)..(2)
<223> OTHER INFORMATION: Xaa is Asp or Ser
<220> FEATURE:
<221> NAME/KEY: VARIANT
<222> LOCATION: (3)..(3)
<223> OTHER INFORMATION: Xaa is Leu or Phe
<220> FEATURE:
<221> NAME/KEY: VARIANT
<222> LOCATION: (5)..(5)
<223> OTHER INFORMATION: Xaa is Phe, Phg, Leu, Ebw, Pff, Thi, 1Ni, Hfe,
      Ece or Cha
<220> FEATURE:
<221> NAME/KEY: VARIANT
<222> LOCATION: (7)..(7)
<223> OTHER INFORMATION: Xaa is Ile or Phe
<220> FEATURE:
<221> NAME/KEY: VARIANT
<222> LOCATION: (8)..(8)
<223> OTHER INFORMATION: Xaa is Val, Ser or Gly
<220> FEATURE:
<221> NAME/KEY: VARIANT
<222> LOCATION: (9)..(9)
<223> OTHER INFORMATION: Xaa is Trp or Leu

<400> SEQUENCE: 1

Xaa Xaa Xaa Tyr Xaa Glu Xaa Xaa Xaa
1               5


<210> SEQ ID NO 2
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (1)..(1)
<223> OTHER INFORMATION: Xaa is Arg or Pro
<220> FEATURE:
<221> NAME/KEY: VARIANT
<222> LOCATION: (2)..(2)
<223> OTHER INFORMATION: Xaa is Met, Nva, Moo, Asn, Nle, Meo, Gln or Eag
<220> FEATURE:
<221> NAME/KEY: VARIANT
<222> LOCATION: (3)..(3)
<223> OTHER INFORMATION: Xaa is Glu, Lys or Asp
<220> FEATURE:
<221> NAME/KEY: VARIANT
<222> LOCATION: (7)..(7)
<223> OTHER INFORMATION: Xaa is Trp, Leu or Pro
```

```
<220> FEATURE:
<221> NAME/KEY: VARIANT
<222> LOCATION: (8)..(8)
<223> OTHER INFORMATION: Xaa is Asp or Ser
<220> FEATURE:
<221> NAME/KEY: VARIANT
<222> LOCATION: (9)..(9)
<223> OTHER INFORMATION: Xaa is Leu or Phe
<220> FEATURE:
<221> NAME/KEY: VARIANT
<222> LOCATION: (11)..(11)
<223> OTHER INFORMATION: Xaa is Phe, Phg, Leu, Ebw, Pff, Thi, 1Ni, Hfe,
      Ece or Cha
<220> FEATURE:
<221> NAME/KEY: VARIANT
<222> LOCATION: (13)..(13)
<223> OTHER INFORMATION: Xaa is Ile or Phe
<220> FEATURE:
<221> NAME/KEY: VARIANT
<222> LOCATION: (14)..(14)
<223> OTHER INFORMATION: Xaa is Val, Ser or Gly
<220> FEATURE:
<221> NAME/KEY: VARIANT
<222> LOCATION: (15)..(15)
<223> OTHER INFORMATION: Xaa is Trp or Leu

<400> SEQUENCE: 2

Xaa Xaa Xaa Phe Asp Val Xaa Xaa Xaa Tyr Xaa Glu Xaa Xaa Xaa
1               5                   10                  15


<210> SEQ ID NO 3
<211> LENGTH: 10
<212> TYPE: PRT
<213> ORGANISM: Artificial Sequence
<220> FEATURE:
<223> OTHER INFORMATION: Synthetic Peptide A06

<400> SEQUENCE: 3

Trp Asp Leu Tyr Phe Glu Ile Val Trp Glu
1               5                   10


<210> SEQ ID NO 4
<211> LENGTH: 16
<212> TYPE: PRT
<213> ORGANISM: Artificial Sequence
<220> FEATURE:
<223> OTHER INFORMATION: Synthetic Peptide A09

<400> SEQUENCE: 4

Glu Arg Met Glu Phe Asp Val Trp Asp Leu Tyr Phe Glu Ile Val Trp
1               5                   10                  15


<210> SEQ ID NO 5
<211> LENGTH: 16
<212> TYPE: PRT
<213> ORGANISM: Artificial Sequence
<220> FEATURE:
<223> OTHER INFORMATION: Synthetic Peptide A12
<220> FEATURE:
<221> NAME/KEY: MISC_FEATURE
<222> LOCATION: (3)..(3)
<223> OTHER INFORMATION: Xaa is Nva

<400> SEQUENCE: 5

Glu Arg Xaa Glu Phe Asp Val Trp Asp Leu Tyr Phe Glu Ile Val Trp
1               5                   10                  15


<210> SEQ ID NO 6
<211> LENGTH: 10
<212> TYPE: PRT
<213> ORGANISM: Artificial Sequence
```

-continued

<220> FEATURE:
<223> OTHER INFORMATION: Synthetic Peptide A14

<400> SEQUENCE: 6

Trp Ser Leu Tyr Phe Glu Ile Val Trp Glu
1 5 10

<210> SEQ ID NO 7
<211> LENGTH: 10
<212> TYPE: PRT
<213> ORGANISM: Artificial Sequence
<220> FEATURE:
<223> OTHER INFORMATION: Synthetic Peptide A19

<400> SEQUENCE: 7

Val Trp Asp Leu Tyr Phe Glu Ile Val Trp
1 5 10

<210> SEQ ID NO 8
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 8

Phe Asp Val Trp Asp Leu Tyr Phe Glu Ile Val Trp
1 5 10

<210> SEQ ID NO 9
<211> LENGTH: 10
<212> TYPE: PRT
<213> ORGANISM: Artificial Sequence
<220> FEATURE:
<223> OTHER INFORMATION: Synthetic Peptide A24

<400> SEQUENCE: 9

Glu Trp Asp Leu Tyr Phe Glu Ile Val Trp
1 5 10

<210> SEQ ID NO 10
<211> LENGTH: 16
<212> TYPE: PRT
<213> ORGANISM: Artificial Sequence
<220> FEATURE:
<223> OTHER INFORMATION: Synthetic Peptide A30

<400> SEQUENCE: 10

Arg Met Glu Phe Asp Val Trp Asp Leu Tyr Phe Glu Ile Val Trp Lys
1 5 10 15

<210> SEQ ID NO 11
<211> LENGTH: 10
<212> TYPE: PRT
<213> ORGANISM: Artificial Sequence
<220> FEATURE:
<223> OTHER INFORMATION: Synthetic Peptide A33

<400> SEQUENCE: 11

Trp Asp Leu Tyr Phe Glu Ile Ser Trp Glu
1 5 10

<210> SEQ ID NO 12
<211> LENGTH: 10
<212> TYPE: PRT
<213> ORGANISM: Artificial Sequence
<220> FEATURE:

-continued

<223> OTHER INFORMATION: Synthetic Peptide A34

<400> SEQUENCE: 12

Trp Asp Leu Tyr Leu Glu Ile Val Trp Glu
1 5 10

<210> SEQ ID NO 13
<211> LENGTH: 10
<212> TYPE: PRT
<213> ORGANISM: Artificial Sequence
<220> FEATURE:
<223> OTHER INFORMATION: Synthetic Peptide A35

<400> SEQUENCE: 13

Trp Asp Leu Tyr Phe Glu Ile Val Leu Glu
1 5 10

<210> SEQ ID NO 14
<211> LENGTH: 16
<212> TYPE: PRT
<213> ORGANISM: Artificial sequence
<220> FEATURE:
<223> OTHER INFORMATION: Synthetic Peptide A52

<400> SEQUENCE: 14

Lys Arg Met Glu Phe Asp Val Trp Asp Leu Tyr Phe Glu Ile Val Trp
1 5 10 15

<210> SEQ ID NO 15
<211> LENGTH: 16
<212> TYPE: PRT
<213> ORGANISM: Artificial Sequence
<220> FEATURE:
<223> OTHER INFORMATION: Synthetic Peptide A57

<400> SEQUENCE: 15

Glu Arg Met Glu Phe Asp Val Leu Asp Leu Tyr Phe Glu Ile Val Trp
1 5 10 15

<210> SEQ ID NO 16
<211> LENGTH: 16
<212> TYPE: PRT
<213> ORGANISM: Artificial Sequence
<220> FEATURE:
<223> OTHER INFORMATION: Synthetic Peptide A58

<400> SEQUENCE: 16

Glu Arg Met Glu Phe Asp Val Trp Asp Leu Tyr Phe Glu Ile Val Leu
1 5 10 15

<210> SEQ ID NO 17
<211> LENGTH: 10
<212> TYPE: PRT
<213> ORGANISM: Artificial Sequence
<220> FEATURE:
<223> OTHER INFORMATION: Synthetic Peptide A84

<400> SEQUENCE: 17

Trp Asp Phe Tyr Phe Glu Ile Val Trp Glu
1 5 10

<210> SEQ ID NO 18
<211> LENGTH: 10
<212> TYPE: PRT
<213> ORGANISM: Artificial Sequence
<220> FEATURE:
<223> OTHER INFORMATION: Synthetic Peptide A85

-continued

<400> SEQUENCE: 18

Trp Asp Leu Tyr Phe Glu Phe Val Trp Glu
1 5 10

<210> SEQ ID NO 19
<211> LENGTH: 10
<212> TYPE: PRT
<213> ORGANISM: Artificial Sequence
<220> FEATURE:
<223> OTHER INFORMATION: Synthetic Peptide A86

<400> SEQUENCE: 19

Leu Asp Leu Tyr Phe Glu Ile Val Trp Glu
1 5 10

<210> SEQ ID NO 20
<211> LENGTH: 10
<212> TYPE: PRT
<213> ORGANISM: Artificial Sequence
<220> FEATURE:
<223> OTHER INFORMATION: Synthetic Peptide A87

<400> SEQUENCE: 20

Trp Asp Leu Tyr Phe Glu Ile Gly Trp Glu
1 5 10

<210> SEQ ID NO 21
<211> LENGTH: 10
<212> TYPE: PRT
<213> ORGANISM: Artificial Sequence
<220> FEATURE:
<223> OTHER INFORMATION: Synthetic Peptide A89

<400> SEQUENCE: 21

Trp Asp Leu Tyr Leu Glu Ile Ser Leu Glu
1 5 10

<210> SEQ ID NO 22
<211> LENGTH: 10
<212> TYPE: PRT
<213> ORGANISM: Artificial Sequence
<220> FEATURE:
<223> OTHER INFORMATION: Synthetic Peptide A92

<400> SEQUENCE: 22

Leu Asp Leu Tyr Phe Glu Ile Val Leu Glu
1 5 10

<210> SEQ ID NO 23
<211> LENGTH: 10
<212> TYPE: PRT
<213> ORGANISM: Artificial Sequence
<220> FEATURE:
<223> OTHER INFORMATION: Synthetic Peptide A93

<400> SEQUENCE: 23

Leu Asp Leu Tyr Phe Glu Ile Ser Leu Glu
1 5 10

<210> SEQ ID NO 24
<211> LENGTH: 10
<212> TYPE: PRT
<213> ORGANISM: Artificial Sequence
<220> FEATURE:
<223> OTHER INFORMATION: Synthetic Peptide A95

<400> SEQUENCE: 24

Leu Ser Leu Tyr Phe Glu Ile Val Trp Glu
1 5 10

<210> SEQ ID NO 25
<211> LENGTH: 10
<212> TYPE: PRT
<213> ORGANISM: Artificial Sequence
<220> FEATURE:
<223> OTHER INFORMATION: Synthetic Peptide A96

<400> SEQUENCE: 25

Leu Ser Leu Tyr Phe Glu Ile Val Leu Glu
1 5 10

<210> SEQ ID NO 26
<211> LENGTH: 10
<212> TYPE: PRT
<213> ORGANISM: Artificial Sequence
<220> FEATURE:
<223> OTHER INFORMATION: Synthetic Peptide A97

<400> SEQUENCE: 26

Leu Ser Leu Tyr Phe Glu Ile Ser Leu Glu
1 5 10

<210> SEQ ID NO 27
<211> LENGTH: 11
<212> TYPE: PRT
<213> ORGANISM: Artificial Sequence
<220> FEATURE:
<223> OTHER INFORMATION: Synthetic Peptide A22

<400> SEQUENCE: 27

Asp Val Trp Asp Leu Tyr Phe Glu Ile Val Trp
1 5 10

<210> SEQ ID NO 28
<211> LENGTH: 10
<212> TYPE: PRT
<213> ORGANISM: Artificial Sequence
<220> FEATURE:
<223> OTHER INFORMATION: Synthetic Peptide A45

<400> SEQUENCE: 28

Lys Trp Asp Leu Tyr Phe Glu Ile Val Trp
1 5 10

<210> SEQ ID NO 29
<211> LENGTH: 10
<212> TYPE: PRT
<213> ORGANISM: Artificial Sequence
<220> FEATURE:
<223> OTHER INFORMATION: Synthetic Peptide A47

<400> SEQUENCE: 29

Trp Asp Leu Tyr Phe Glu Ile Val Trp Lys
1 5 10

<210> SEQ ID NO 30
<211> LENGTH: 16
<212> TYPE: PRT
<213> ORGANISM: Artificial Sequence
<220> FEATURE:
<223> OTHER INFORMATION: Synthetic Peptide A73

<400> SEQUENCE: 30

Glu Arg Asn Glu Phe Asp Val Trp Asp Leu Tyr Phe Glu Ile Val Trp
1 5 10 15

<210> SEQ ID NO 31
<211> LENGTH: 10
<212> TYPE: PRT
<213> ORGANISM: Artificial Sequence
<220> FEATURE:
<223> OTHER INFORMATION: Synthetic Peptide A88

<400> SEQUENCE: 31

Pro Asp Leu Tyr Phe Glu Ile Val Trp Glu
1 5 10

<210> SEQ ID NO 32
<211> LENGTH: 10
<212> TYPE: PRT
<213> ORGANISM: Artificial Sequence
<220> FEATURE:
<223> OTHER INFORMATION: Synthetic Peptide A98

<400> SEQUENCE: 32

Leu Ser Leu Tyr Leu Glu Ile Val Leu Glu
1 5 10

<210> SEQ ID NO 33
<211> LENGTH: 10
<212> TYPE: PRT
<213> ORGANISM: Artificial Sequence
<220> FEATURE:
<223> OTHER INFORMATION: Synthetic Peptide A99

<400> SEQUENCE: 33

Leu Ser Leu Tyr Leu Glu Ile Ser Leu Glu
1 5 10

<210> SEQ ID NO 34
<211> LENGTH: 16
<212> TYPE: PRT
<213> ORGANISM: Artificial Sequence
<220> FEATURE:
<223> OTHER INFORMATION: Synthetic Peptide A10

<400> SEQUENCE: 34

Glu Pro Met Lys Phe Asp Val Trp Asp Leu Tyr Phe Glu Ile Val Trp
1 5 10 15

<210> SEQ ID NO 35
<211> LENGTH: 16
<212> TYPE: PRT
<213> ORGANISM: Artificial Sequence
<220> FEATURE:
<223> OTHER INFORMATION: Synthetic Peptide A60

<400> SEQUENCE: 35

Glu Arg Met Asp Phe Asp Val Trp Asp Leu Tyr Phe Glu Ile Val Trp
1 5 10 15

<210> SEQ ID NO 36
<211> LENGTH: 16
<212> TYPE: PRT
<213> ORGANISM: Artificial Sequence
<220> FEATURE:
<223> OTHER INFORMATION: Synthetic Peptide A75

<400> SEQUENCE: 36

Glu Arg Gly Glu Phe Asp Val Trp Asp Leu Tyr Phe Glu Ile Val Trp
1 5 10 15

<210> SEQ ID NO 37
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 37

Ala Met Lys Phe Asp Val Trp Asp Leu Tyr Phe Glu Ile Val Trp
1 5 10 15

<210> SEQ ID NO 38
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 38

Cys Met Lys Phe Asp Val Trp Asp Leu Tyr Phe Glu Ile Val Trp
1 5 10 15

<210> SEQ ID NO 39
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 39

Asp Met Lys Phe Asp Val Trp Asp Leu Tyr Phe Glu Ile Val Trp
1 5 10 15

<210> SEQ ID NO 40
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 40

Glu Met Lys Phe Asp Val Trp Asp Leu Tyr Phe Glu Ile Val Trp
1 5 10 15

<210> SEQ ID NO 41
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 41

Phe Met Lys Phe Asp Val Trp Asp Leu Tyr Phe Glu Ile Val Trp
1 5 10 15

<210> SEQ ID NO 42
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 42

Gly Met Lys Phe Asp Val Trp Asp Leu Tyr Phe Glu Ile Val Trp 1 5 10 15

<210> SEQ ID NO 43
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 43

His Met Lys Phe Asp Val Trp Asp Leu Tyr Phe Glu Ile Val Trp
1 5 10 15

<210> SEQ ID NO 44
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 44

Ile Met Lys Phe Asp Val Trp Asp Leu Tyr Phe Glu Ile Val Trp
1 5 10 15

<210> SEQ ID NO 45
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 45

Lys Met Lys Phe Asp Val Trp Asp Leu Tyr Phe Glu Ile Val Trp
1 5 10 15

<210> SEQ ID NO 46
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 46

Leu Met Lys Phe Asp Val Trp Asp Leu Tyr Phe Glu Ile Val Trp
1 5 10 15

<210> SEQ ID NO 47
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 47

Met Met Lys Phe Asp Val Trp Asp Leu Tyr Phe Glu Ile Val Trp
1 5 10 15

<210> SEQ ID NO 48
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 48

Asn Met Lys Phe Asp Val Trp Asp Leu Tyr Phe Glu Ile Val Trp
1 5 10 15

<210> SEQ ID NO 49
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 49

Gln Met Lys Phe Asp Val Trp Asp Leu Tyr Phe Glu Ile Val Trp
1 5 10 15

<210> SEQ ID NO 50
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 50

Ser Met Lys Phe Asp Val Trp Asp Leu Tyr Phe Glu Ile Val Trp
1 5 10 15

<210> SEQ ID NO 51
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 51

Thr Met Lys Phe Asp Val Trp Asp Leu Tyr Phe Glu Ile Val Trp
1 5 10 15

<210> SEQ ID NO 52
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 52

Val Met Lys Phe Asp Val Trp Asp Leu Tyr Phe Glu Ile Val Trp
1 5 10 15

<210> SEQ ID NO 53
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 53

Trp Met Lys Phe Asp Val Trp Asp Leu Tyr Phe Glu Ile Val Trp
1 5 10 15

<210> SEQ ID NO 54
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 54

Tyr Met Lys Phe Asp Val Trp Asp Leu Tyr Phe Glu Ile Val Trp
1 5 10 15

<210> SEQ ID NO 55
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 55

Arg Ala Lys Phe Asp Val Trp Asp Leu Tyr Phe Glu Ile Val Trp
1 5 10 15

<210> SEQ ID NO 56
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 56

Arg Cys Lys Phe Asp Val Trp Asp Leu Tyr Phe Glu Ile Val Trp
1 5 10 15

<210> SEQ ID NO 57
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 57

Arg Asp Lys Phe Asp Val Trp Asp Leu Tyr Phe Glu Ile Val Trp
1 5 10 15

<210> SEQ ID NO 58
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 58

Arg Glu Lys Phe Asp Val Trp Asp Leu Tyr Phe Glu Ile Val Trp
1 5 10 15

<210> SEQ ID NO 59
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 59

Arg Phe Lys Phe Asp Val Trp Asp Leu Tyr Phe Glu Ile Val Trp
1 5 10 15

<210> SEQ ID NO 60
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 60

Arg Gly Lys Phe Asp Val Trp Asp Leu Tyr Phe Glu Ile Val Trp
1 5 10 15

-continued

<210> SEQ ID NO 61
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 61

Arg His Lys Phe Asp Val Trp Asp Leu Tyr Phe Glu Ile Val Trp
1 5 10 15

<210> SEQ ID NO 62
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 62

Arg Ile Lys Phe Asp Val Trp Asp Leu Tyr Phe Glu Ile Val Trp
1 5 10 15

<210> SEQ ID NO 63
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 63

Arg Lys Lys Phe Asp Val Trp Asp Leu Tyr Phe Glu Ile Val Trp
1 5 10 15

<210> SEQ ID NO 64
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 64

Arg Leu Lys Phe Asp Val Trp Asp Leu Tyr Phe Glu Ile Val Trp
1 5 10 15

<210> SEQ ID NO 65
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 65

Arg Asn Lys Phe Asp Val Trp Asp Leu Tyr Phe Glu Ile Val Trp
1 5 10 15

<210> SEQ ID NO 66
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 66

Arg Pro Lys Phe Asp Val Trp Asp Leu Tyr Phe Glu Ile Val Trp
1 5 10 15

<210> SEQ ID NO 67

<211> LENGTH: 15
<212> TYPE: PRT
<213> ORGANISM: Artificial Sequence
<220> FEATURE:
<223> OTHER INFORMATION: Synthetic Peptide

<400> SEQUENCE: 67

Arg Gln Lys Phe Asp Val Trp Asp Leu Tyr Phe Glu Ile Val Trp
1 5 10 15

<210> SEQ ID NO 68
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 68

Arg Arg Lys Phe Asp Val Trp Asp Leu Tyr Phe Glu Ile Val Trp
1 5 10 15

<210> SEQ ID NO 69
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 69

Arg Ser Lys Phe Asp Val Trp Asp Leu Tyr Phe Glu Ile Val Trp
1 5 10 15

<210> SEQ ID NO 70
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 70

Arg Thr Lys Phe Asp Val Trp Asp Leu Tyr Phe Glu Ile Val Trp
1 5 10 15

<210> SEQ ID NO 71
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 71

Arg Val Lys Phe Asp Val Trp Asp Leu Tyr Phe Glu Ile Val Trp
1 5 10 15

<210> SEQ ID NO 72
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 72

Arg Trp Lys Phe Asp Val Trp Asp Leu Tyr Phe Glu Ile Val Trp
1 5 10 15

<210> SEQ ID NO 73
<211> LENGTH: 15

<212> TYPE: PRT
<213> ORGANISM: Artificial Sequence
<220> FEATURE:
<223> OTHER INFORMATION: Synthetic Peptide

<400> SEQUENCE: 73

Arg Tyr Lys Phe Asp Val Trp Asp Leu Tyr Phe Glu Ile Val Trp
1 5 10 15

<210> SEQ ID NO 74
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 74

Arg Met Ala Phe Asp Val Trp Asp Leu Tyr Phe Glu Ile Val Trp
1 5 10 15

<210> SEQ ID NO 75
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 75

Arg Met Cys Phe Asp Val Trp Asp Leu Tyr Phe Glu Ile Val Trp
1 5 10 15

<210> SEQ ID NO 76
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 76

Arg Met Phe Phe Asp Val Trp Asp Leu Tyr Phe Glu Ile Val Trp
1 5 10 15

<210> SEQ ID NO 77
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 77

Arg Met Gly Phe Asp Val Trp Asp Leu Tyr Phe Glu Ile Val Trp
1 5 10 15

<210> SEQ ID NO 78
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 78

Arg Met His Phe Asp Val Trp Asp Leu Tyr Phe Glu Ile Val Trp
1 5 10 15

<210> SEQ ID NO 79
<211> LENGTH: 15
<212> TYPE: PRT

<213> ORGANISM: Artificial Sequence
<220> FEATURE:
<223> OTHER INFORMATION: Synthetic Peptide

<400> SEQUENCE: 79

Arg Met Ile Phe Asp Val Trp Asp Leu Tyr Phe Glu Ile Val Trp
1 5 10 15

<210> SEQ ID NO 80
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 80

Arg Met Leu Phe Asp Val Trp Asp Leu Tyr Phe Glu Ile Val Trp
1 5 10 15

<210> SEQ ID NO 81
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 81

Arg Met Met Phe Asp Val Trp Asp Leu Tyr Phe Glu Ile Val Trp
1 5 10 15

<210> SEQ ID NO 82
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 82

Arg Met Asn Phe Asp Val Trp Asp Leu Tyr Phe Glu Ile Val Trp
1 5 10 15

<210> SEQ ID NO 83
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 83

Arg Met Pro Phe Asp Val Trp Asp Leu Tyr Phe Glu Ile Val Trp
1 5 10 15

<210> SEQ ID NO 84
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 84

Arg Met Gln Phe Asp Val Trp Asp Leu Tyr Phe Glu Ile Val Trp
1 5 10 15

<210> SEQ ID NO 85
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 85

Arg Met Arg Phe Asp Val Trp Asp Leu Tyr Phe Glu Ile Val Trp
1               5                   10                  15

<210> SEQ ID NO 86
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 86

Arg Met Ser Phe Asp Val Trp Asp Leu Tyr Phe Glu Ile Val Trp
1               5                   10                  15

<210> SEQ ID NO 87
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 87

Arg Met Thr Phe Asp Val Trp Asp Leu Tyr Phe Glu Ile Val Trp
1               5                   10                  15

<210> SEQ ID NO 88
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 88

Arg Met Val Phe Asp Val Trp Asp Leu Tyr Phe Glu Ile Val Trp
1               5                   10                  15

<210> SEQ ID NO 89
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 89

Arg Met Trp Phe Asp Val Trp Asp Leu Tyr Phe Glu Ile Val Trp
1               5                   10                  15

<210> SEQ ID NO 90
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 90

Arg Met Tyr Phe Asp Val Trp Asp Leu Tyr Phe Glu Ile Val Trp
1               5                   10                  15

<210> SEQ ID NO 91
<211> LENGTH: 15
<212> TYPE: PRT
<213> ORGANISM: Artificial Sequence
<220> FEATURE:

<223> OTHER INFORMATION: Synthetic Peptide

<400> SEQUENCE: 91

Arg Met Lys Ala Asp Val Trp Asp Leu Tyr Phe Glu Ile Val Trp
1 5 10 15

<210> SEQ ID NO 92
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 92

Arg Met Lys Cys Asp Val Trp Asp Leu Tyr Phe Glu Ile Val Trp
1 5 10 15

<210> SEQ ID NO 93
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 93

Arg Met Lys Asp Asp Val Trp Asp Leu Tyr Phe Glu Ile Val Trp
1 5 10 15

<210> SEQ ID NO 94
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 94

Arg Met Lys Glu Asp Val Trp Asp Leu Tyr Phe Glu Ile Val Trp
1 5 10 15

<210> SEQ ID NO 95
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 95

Arg Met Lys Gly Asp Val Trp Asp Leu Tyr Phe Glu Ile Val Trp
1 5 10 15

<210> SEQ ID NO 96
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 96

Arg Met Lys His Asp Val Trp Asp Leu Tyr Phe Glu Ile Val Trp
1 5 10 15

<210> SEQ ID NO 97
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 97

Arg Met Lys Ile Asp Val Trp Asp Leu Tyr Phe Glu Ile Val Trp
1 5 10 15

<210> SEQ ID NO 98
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 98

Arg Met Lys Lys Asp Val Trp Asp Leu Tyr Phe Glu Ile Val Trp
1 5 10 15

<210> SEQ ID NO 99
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 99

Arg Met Lys Leu Asp Val Trp Asp Leu Tyr Phe Glu Ile Val Trp
1 5 10 15

<210> SEQ ID NO 100
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 100

Arg Met Lys Met Asp Val Trp Asp Leu Tyr Phe Glu Ile Val Trp
1 5 10 15

<210> SEQ ID NO 101
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 101

Arg Met Lys Asn Asp Val Trp Asp Leu Tyr Phe Glu Ile Val Trp
1 5 10 15

<210> SEQ ID NO 102
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 102

Arg Met Lys Pro Asp Val Trp Asp Leu Tyr Phe Glu Ile Val Trp
1 5 10 15

<210> SEQ ID NO 103
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 103

Arg Met Lys Gln Asp Val Trp Asp Leu Tyr Phe Glu Ile Val Trp
1 5 10 15

<210> SEQ ID NO 104
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 104

Arg Met Lys Arg Asp Val Trp Asp Leu Tyr Phe Glu Ile Val Trp
1 5 10 15

<210> SEQ ID NO 105
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 105

Arg Met Lys Ser Asp Val Trp Asp Leu Tyr Phe Glu Ile Val Trp
1 5 10 15

<210> SEQ ID NO 106
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 106

Arg Met Lys Thr Asp Val Trp Asp Leu Tyr Phe Glu Ile Val Trp
1 5 10 15

<210> SEQ ID NO 107
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 107

Arg Met Lys Val Asp Val Trp Asp Leu Tyr Phe Glu Ile Val Trp
1 5 10 15

<210> SEQ ID NO 108
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 108

Arg Met Lys Trp Asp Val Trp Asp Leu Tyr Phe Glu Ile Val Trp
1 5 10 15

<210> SEQ ID NO 109
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 109

Arg Met Lys Tyr Asp Val Trp Asp Leu Tyr Phe Glu Ile Val Trp
1 5 10 15

<210> SEQ ID NO 110
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 110

Arg Met Lys Phe Ala Val Trp Asp Leu Tyr Phe Glu Ile Val Trp
1 5 10 15

<210> SEQ ID NO 111
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 111

Arg Met Lys Phe Cys Val Trp Asp Leu Tyr Phe Glu Ile Val Trp
1 5 10 15

<210> SEQ ID NO 112
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 112

Arg Met Lys Phe Glu Val Trp Asp Leu Tyr Phe Glu Ile Val Trp
1 5 10 15

<210> SEQ ID NO 113
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 113

Arg Met Lys Phe Phe Val Trp Asp Leu Tyr Phe Glu Ile Val Trp
1 5 10 15

<210> SEQ ID NO 114
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 114

Arg Met Lys Phe Gly Val Trp Asp Leu Tyr Phe Glu Ile Val Trp
1 5 10 15

<210> SEQ ID NO 115
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 115

Arg Met Lys Phe His Val Trp Asp Leu Tyr Phe Glu Ile Val Trp
1 5 10 15

<210> SEQ ID NO 116
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 116

Arg Met Lys Phe Ile Val Trp Asp Leu Tyr Phe Glu Ile Val Trp
1 5 10 15

<210> SEQ ID NO 117
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 117

Arg Met Lys Phe Lys Val Trp Asp Leu Tyr Phe Glu Ile Val Trp
1 5 10 15

<210> SEQ ID NO 118
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 118

Arg Met Lys Phe Leu Val Trp Asp Leu Tyr Phe Glu Ile Val Trp
1 5 10 15

<210> SEQ ID NO 119
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 119

Arg Met Lys Phe Met Val Trp Asp Leu Tyr Phe Glu Ile Val Trp
1 5 10 15

<210> SEQ ID NO 120
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 120

Arg Met Lys Phe Asn Val Trp Asp Leu Tyr Phe Glu Ile Val Trp
1 5 10 15

<210> SEQ ID NO 121
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 121

Arg Met Lys Phe Pro Val Trp Asp Leu Tyr Phe Glu Ile Val Trp

-continued 1 5 10 15

<210> SEQ ID NO 122
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 122

Arg Met Lys Phe Gln Val Trp Asp Leu Tyr Phe Glu Ile Val Trp
1 5 10 15

<210> SEQ ID NO 123
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 123

Arg Met Lys Phe Arg Val Trp Asp Leu Tyr Phe Glu Ile Val Trp
1 5 10 15

<210> SEQ ID NO 124
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 124

Arg Met Lys Phe Ser Val Trp Asp Leu Tyr Phe Glu Ile Val Trp
1 5 10 15

<210> SEQ ID NO 125
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 125

Arg Met Lys Phe Thr Val Trp Asp Leu Tyr Phe Glu Ile Val Trp
1 5 10 15

<210> SEQ ID NO 126
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 126

Arg Met Lys Phe Val Val Trp Asp Leu Tyr Phe Glu Ile Val Trp
1 5 10 15

<210> SEQ ID NO 127
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 127

Arg Met Lys Phe Trp Val Trp Asp Leu Tyr Phe Glu Ile Val Trp
1 5 10 15

<210> SEQ ID NO 128
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 128

Arg Met Lys Phe Tyr Val Trp Asp Leu Tyr Phe Glu Ile Val Trp
1 5 10 15

<210> SEQ ID NO 129
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 129

Arg Met Lys Phe Asp Ala Trp Asp Leu Tyr Phe Glu Ile Val Trp
1 5 10 15

<210> SEQ ID NO 130
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 130

Arg Met Lys Phe Asp Cys Trp Asp Leu Tyr Phe Glu Ile Val Trp
1 5 10 15

<210> SEQ ID NO 131
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 131

Arg Met Lys Phe Asp Asp Trp Asp Leu Tyr Phe Glu Ile Val Trp
1 5 10 15

<210> SEQ ID NO 132
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 132

Arg Met Lys Phe Asp Glu Trp Asp Leu Tyr Phe Glu Ile Val Trp
1 5 10 15

<210> SEQ ID NO 133
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 133

Arg Met Lys Phe Asp Phe Trp Asp Leu Tyr Phe Glu Ile Val Trp
1 5 10 15

<210> SEQ ID NO 134
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 134

```
Arg Met Lys Phe Asp Gly Trp Asp Leu Tyr Phe Glu Ile Val Trp
1               5                   10                  15
```

<210> SEQ ID NO 135
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 135

```
Arg Met Lys Phe Asp His Trp Asp Leu Tyr Phe Glu Ile Val Trp
1               5                   10                  15
```

<210> SEQ ID NO 136
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 136

```
Arg Met Lys Phe Asp Ile Trp Asp Leu Tyr Phe Glu Ile Val Trp
1               5                   10                  15
```

<210> SEQ ID NO 137
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 137

```
Arg Met Lys Phe Asp Lys Trp Asp Leu Tyr Phe Glu Ile Val Trp
1               5                   10                  15
```

<210> SEQ ID NO 138
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 138

```
Arg Met Lys Phe Asp Leu Trp Asp Leu Tyr Phe Glu Ile Val Trp
1               5                   10                  15
```

<210> SEQ ID NO 139
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 139

```
Arg Met Lys Phe Asp Met Trp Asp Leu Tyr Phe Glu Ile Val Trp
1               5                   10                  15
```

<210> SEQ ID NO 140
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 140

Arg Met Lys Phe Asp Asn Trp Asp Leu Tyr Phe Glu Ile Val Trp
1               5                   10                  15

<210> SEQ ID NO 141
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 141

Arg Met Lys Phe Asp Pro Trp Asp Leu Tyr Phe Glu Ile Val Trp
1               5                   10                  15

<210> SEQ ID NO 142
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 142

Arg Met Lys Phe Asp Gln Trp Asp Leu Tyr Phe Glu Ile Val Trp
1               5                   10                  15

<210> SEQ ID NO 143
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 143

Arg Met Lys Phe Asp Arg Trp Asp Leu Tyr Phe Glu Ile Val Trp
1               5                   10                  15

<210> SEQ ID NO 144
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 144

Arg Met Lys Phe Asp Ser Trp Asp Leu Tyr Phe Glu Ile Val Trp
1               5                   10                  15

<210> SEQ ID NO 145
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 145

Arg Met Lys Phe Asp Thr Trp Asp Leu Tyr Phe Glu Ile Val Trp
1               5                   10                  15

<210> SEQ ID NO 146

<211> LENGTH: 15
<212> TYPE: PRT
<213> ORGANISM: Artificial Sequence
<220> FEATURE:
<223> OTHER INFORMATION: Synthetic Peptide

<400> SEQUENCE: 146

Arg Met Lys Phe Asp Trp Trp Asp Leu Tyr Phe Glu Ile Val Trp
1 5 10 15

<210> SEQ ID NO 147
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 147

Arg Met Lys Phe Asp Tyr Trp Asp Leu Tyr Phe Glu Ile Val Trp
1 5 10 15

<210> SEQ ID NO 148
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 148

Arg Met Lys Phe Asp Val Ala Asp Leu Tyr Phe Glu Ile Val Trp
1 5 10 15

<210> SEQ ID NO 149
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 149

Arg Met Lys Phe Asp Val Cys Asp Leu Tyr Phe Glu Ile Val Trp
1 5 10 15

<210> SEQ ID NO 150
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 150

Arg Met Lys Phe Asp Val Asp Asp Leu Tyr Phe Glu Ile Val Trp
1 5 10 15

<210> SEQ ID NO 151
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 151

Arg Met Lys Phe Asp Val Glu Asp Leu Tyr Phe Glu Ile Val Trp
1 5 10 15

<210> SEQ ID NO 152
<211> LENGTH: 15

<212> TYPE: PRT
<213> ORGANISM: Artificial Sequence
<220> FEATURE:
<223> OTHER INFORMATION: Synthetic Peptide

<400> SEQUENCE: 152

Arg Met Lys Phe Asp Val Phe Asp Leu Tyr Phe Glu Ile Val Trp
1 5 10 15

<210> SEQ ID NO 153
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 153

Arg Met Lys Phe Asp Val Gly Asp Leu Tyr Phe Glu Ile Val Trp
1 5 10 15

<210> SEQ ID NO 154
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 154

Arg Met Lys Phe Asp Val His Asp Leu Tyr Phe Glu Ile Val Trp
1 5 10 15

<210> SEQ ID NO 155
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 155

Arg Met Lys Phe Asp Val Ile Asp Leu Tyr Phe Glu Ile Val Trp
1 5 10 15

<210> SEQ ID NO 156
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 156

Arg Met Lys Phe Asp Val Lys Asp Leu Tyr Phe Glu Ile Val Trp
1 5 10 15

<210> SEQ ID NO 157
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 157

Arg Met Lys Phe Asp Val Leu Asp Leu Tyr Phe Glu Ile Val Trp
1 5 10 15

<210> SEQ ID NO 158
<211> LENGTH: 15
<212> TYPE: PRT

<213> ORGANISM: Artificial Sequence
<220> FEATURE:
<223> OTHER INFORMATION: Synthetic Peptide

<400> SEQUENCE: 158

Arg Met Lys Phe Asp Val Met Asp Leu Tyr Phe Glu Ile Val Trp
1 5 10 15

<210> SEQ ID NO 159
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 159

Arg Met Lys Phe Asp Val Asn Asp Leu Tyr Phe Glu Ile Val Trp
1 5 10 15

<210> SEQ ID NO 160
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 160

Arg Met Lys Phe Asp Val Pro Asp Leu Tyr Phe Glu Ile Val Trp
1 5 10 15

<210> SEQ ID NO 161
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 161

Arg Met Lys Phe Asp Val Gln Asp Leu Tyr Phe Glu Ile Val Trp
1 5 10 15

<210> SEQ ID NO 162
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 162

Arg Met Lys Phe Asp Val Arg Asp Leu Tyr Phe Glu Ile Val Trp
1 5 10 15

<210> SEQ ID NO 163
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 163

Arg Met Lys Phe Asp Val Ser Asp Leu Tyr Phe Glu Ile Val Trp
1 5 10 15

<210> SEQ ID NO 164
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 164

Arg Met Lys Phe Asp Val Thr Asp Leu Tyr Phe Glu Ile Val Trp
1 5 10 15

<210> SEQ ID NO 165
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 165

Arg Met Lys Phe Asp Val Val Asp Leu Tyr Phe Glu Ile Val Trp
1 5 10 15

<210> SEQ ID NO 166
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 166

Arg Met Lys Phe Asp Val Tyr Asp Leu Tyr Phe Glu Ile Val Trp
1 5 10 15

<210> SEQ ID NO 167
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 167

Arg Met Lys Phe Asp Val Trp Ala Leu Tyr Phe Glu Ile Val Trp
1 5 10 15

<210> SEQ ID NO 168
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 168

Arg Met Lys Phe Asp Val Trp Cys Leu Tyr Phe Glu Ile Val Trp
1 5 10 15

<210> SEQ ID NO 169
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 169

Arg Met Lys Phe Asp Val Trp Glu Leu Tyr Phe Glu Ile Val Trp
1 5 10 15

<210> SEQ ID NO 170
<211> LENGTH: 15
<212> TYPE: PRT
<213> ORGANISM: Artificial Sequence
<220> FEATURE:

<223> OTHER INFORMATION: Synthetic Peptide

<400> SEQUENCE: 170

Arg Met Lys Phe Asp Val Trp Phe Leu Tyr Phe Glu Ile Val Trp
1 5 10 15

<210> SEQ ID NO 171
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 171

Arg Met Lys Phe Asp Val Trp Gly Leu Tyr Phe Glu Ile Val Trp
1 5 10 15

<210> SEQ ID NO 172
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 172

Arg Met Lys Phe Asp Val Trp His Leu Tyr Phe Glu Ile Val Trp
1 5 10 15

<210> SEQ ID NO 173
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 173

Arg Met Lys Phe Asp Val Trp Ile Leu Tyr Phe Glu Ile Val Trp
1 5 10 15

<210> SEQ ID NO 174
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 174

Arg Met Lys Phe Asp Val Trp Lys Leu Tyr Phe Glu Ile Val Trp
1 5 10 15

<210> SEQ ID NO 175
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 175

Arg Met Lys Phe Asp Val Trp Leu Leu Tyr Phe Glu Ile Val Trp
1 5 10 15

<210> SEQ ID NO 176
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 176

Arg Met Lys Phe Asp Val Trp Met Leu Tyr Phe Glu Ile Val Trp
1 5 10 15

<210> SEQ ID NO 177
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 177

Arg Met Lys Phe Asp Val Trp Asn Leu Tyr Phe Glu Ile Val Trp
1 5 10 15

<210> SEQ ID NO 178
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 178

Arg Met Lys Phe Asp Val Trp Pro Leu Tyr Phe Glu Ile Val Trp
1 5 10 15

<210> SEQ ID NO 179
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 179

Arg Met Lys Phe Asp Val Trp Gln Leu Tyr Phe Glu Ile Val Trp
1 5 10 15

<210> SEQ ID NO 180
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 180

Arg Met Lys Phe Asp Val Trp Arg Leu Tyr Phe Glu Ile Val Trp
1 5 10 15

<210> SEQ ID NO 181
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 181

Arg Met Lys Phe Asp Val Trp Ser Leu Tyr Phe Glu Ile Val Trp
1 5 10 15

<210> SEQ ID NO 182
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 182

Arg Met Lys Phe Asp Val Trp Thr Leu Tyr Phe Glu Ile Val Trp
1 5 10 15

<210> SEQ ID NO 183
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 183

Arg Met Lys Phe Asp Val Trp Val Leu Tyr Phe Glu Ile Val Trp
1 5 10 15

<210> SEQ ID NO 184
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 184

Arg Met Lys Phe Asp Val Trp Trp Leu Tyr Phe Glu Ile Val Trp
1 5 10 15

<210> SEQ ID NO 185
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 185

Arg Met Lys Phe Asp Val Trp Tyr Leu Tyr Phe Glu Ile Val Trp
1 5 10 15

<210> SEQ ID NO 186
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 186

Arg Met Lys Phe Asp Val Trp Asp Ala Tyr Phe Glu Ile Val Trp
1 5 10 15

<210> SEQ ID NO 187
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 187

Arg Met Lys Phe Asp Val Trp Asp Cys Tyr Phe Glu Ile Val Trp
1 5 10 15

<210> SEQ ID NO 188
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 188

Arg Met Lys Phe Asp Val Trp Asp Asp Tyr Phe Glu Ile Val Trp
1 5 10 15

<210> SEQ ID NO 189
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 189

Arg Met Lys Phe Asp Val Trp Asp Glu Tyr Phe Glu Ile Val Trp
1 5 10 15

<210> SEQ ID NO 190
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 190

Arg Met Lys Phe Asp Val Trp Asp Phe Tyr Phe Glu Ile Val Trp
1 5 10 15

<210> SEQ ID NO 191
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 191

Arg Met Lys Phe Asp Val Trp Asp Gly Tyr Phe Glu Ile Val Trp
1 5 10 15

<210> SEQ ID NO 192
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 192

Arg Met Lys Phe Asp Val Trp Asp His Tyr Phe Glu Ile Val Trp
1 5 10 15

<210> SEQ ID NO 193
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 193

Arg Met Lys Phe Asp Val Trp Asp Ile Tyr Phe Glu Ile Val Trp
1 5 10 15

<210> SEQ ID NO 194
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 194

Arg Met Lys Phe Asp Val Trp Asp Lys Tyr Phe Glu Ile Val Trp
1 5 10 15

<210> SEQ ID NO 195
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 195

Arg Met Lys Phe Asp Val Trp Asp Met Tyr Phe Glu Ile Val Trp
1 5 10 15

<210> SEQ ID NO 196
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 196

Arg Met Lys Phe Asp Val Trp Asp Asn Tyr Phe Glu Ile Val Trp
1 5 10 15

<210> SEQ ID NO 197
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 197

Arg Met Lys Phe Asp Val Trp Asp Pro Tyr Phe Glu Ile Val Trp
1 5 10 15

<210> SEQ ID NO 198
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 198

Arg Met Lys Phe Asp Val Trp Asp Gln Tyr Phe Glu Ile Val Trp
1 5 10 15

<210> SEQ ID NO 199
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 199

Arg Met Lys Phe Asp Val Trp Asp Arg Tyr Phe Glu Ile Val Trp
1 5 10 15

<210> SEQ ID NO 200
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 200

Arg Met Lys Phe Asp Val Trp Asp Ser Tyr Phe Glu Ile Val Trp

-continued 1 5 10 15

<210> SEQ ID NO 201
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 201

Arg Met Lys Phe Asp Val Trp Asp Thr Tyr Phe Glu Ile Val Trp
1 5 10 15

<210> SEQ ID NO 202
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 202

Arg Met Lys Phe Asp Val Trp Asp Val Tyr Phe Glu Ile Val Trp
1 5 10 15

<210> SEQ ID NO 203
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 203

Arg Met Lys Phe Asp Val Trp Asp Trp Tyr Phe Glu Ile Val Trp
1 5 10 15

<210> SEQ ID NO 204
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 204

Arg Met Lys Phe Asp Val Trp Asp Tyr Tyr Phe Glu Ile Val Trp
1 5 10 15

<210> SEQ ID NO 205
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 205

Arg Met Lys Phe Asp Val Trp Asp Leu Ala Phe Glu Ile Val Trp
1 5 10 15

<210> SEQ ID NO 206
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 206

Arg Met Lys Phe Asp Val Trp Asp Leu Cys Phe Glu Ile Val Trp
1 5 10 15

<210> SEQ ID NO 207
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 207

Arg Met Lys Phe Asp Val Trp Asp Leu Asp Phe Glu Ile Val Trp
1 5 10 15

<210> SEQ ID NO 208
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 208

Arg Met Lys Phe Asp Val Trp Asp Leu Glu Phe Glu Ile Val Trp
1 5 10 15

<210> SEQ ID NO 209
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 209

Arg Met Lys Phe Asp Val Trp Asp Leu Phe Phe Glu Ile Val Trp
1 5 10 15

<210> SEQ ID NO 210
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 210

Arg Met Lys Phe Asp Val Trp Asp Leu Gly Phe Glu Ile Val Trp
1 5 10 15

<210> SEQ ID NO 211
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 211

Arg Met Lys Phe Asp Val Trp Asp Leu His Phe Glu Ile Val Trp
1 5 10 15

<210> SEQ ID NO 212
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 212

Arg Met Lys Phe Asp Val Trp Asp Leu Ile Phe Glu Ile Val Trp
1 5 10 15

-continued

<210> SEQ ID NO 213
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 213

Arg Met Lys Phe Asp Val Trp Asp Leu Lys Phe Glu Ile Val Trp
1               5                   10                  15

<210> SEQ ID NO 214
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 214

Arg Met Lys Phe Asp Val Trp Asp Leu Leu Phe Glu Ile Val Trp
1               5                   10                  15

<210> SEQ ID NO 215
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 215

Arg Met Lys Phe Asp Val Trp Asp Leu Met Phe Glu Ile Val Trp
1               5                   10                  15

<210> SEQ ID NO 216
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 216

Arg Met Lys Phe Asp Val Trp Asp Leu Asn Phe Glu Ile Val Trp
1               5                   10                  15

<210> SEQ ID NO 217
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 217

Arg Met Lys Phe Asp Val Trp Asp Leu Pro Phe Glu Ile Val Trp
1               5                   10                  15

<210> SEQ ID NO 218
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 218

Arg Met Lys Phe Asp Val Trp Asp Leu Gln Phe Glu Ile Val Trp
1               5                   10                  15

<210> SEQ ID NO 219
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 219

Arg Met Lys Phe Asp Val Trp Asp Leu Arg Phe Glu Ile Val Trp
1 5 10 15

<210> SEQ ID NO 220
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 220

Arg Met Lys Phe Asp Val Trp Asp Leu Ser Phe Glu Ile Val Trp
1 5 10 15

<210> SEQ ID NO 221
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 221

Arg Met Lys Phe Asp Val Trp Asp Leu Thr Phe Glu Ile Val Trp
1 5 10 15

<210> SEQ ID NO 222
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 222

Arg Met Lys Phe Asp Val Trp Asp Leu Val Phe Glu Ile Val Trp
1 5 10 15

<210> SEQ ID NO 223
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 223

Arg Met Lys Phe Asp Val Trp Asp Leu Trp Phe Glu Ile Val Trp
1 5 10 15

<210> SEQ ID NO 224
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 224

Arg Met Lys Phe Asp Val Trp Asp Leu Tyr Ala Glu Ile Val Trp
1 5 10 15

<210> SEQ ID NO 225

<211> LENGTH: 15
<212> TYPE: PRT
<213> ORGANISM: Artificial Sequence
<220> FEATURE:
<223> OTHER INFORMATION: Synthetic Peptide

<400> SEQUENCE: 225

Arg Met Lys Phe Asp Val Trp Asp Leu Tyr Cys Glu Ile Val Trp
1 5 10 15

<210> SEQ ID NO 226
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 226

Arg Met Lys Phe Asp Val Trp Asp Leu Tyr Asp Glu Ile Val Trp
1 5 10 15

<210> SEQ ID NO 227
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 227

Arg Met Lys Phe Asp Val Trp Asp Leu Tyr Glu Glu Ile Val Trp
1 5 10 15

<210> SEQ ID NO 228
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 228

Arg Met Lys Phe Asp Val Trp Asp Leu Tyr Gly Glu Ile Val Trp
1 5 10 15

<210> SEQ ID NO 229
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 229

Arg Met Lys Phe Asp Val Trp Asp Leu Tyr His Glu Ile Val Trp
1 5 10 15

<210> SEQ ID NO 230
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 230

Arg Met Lys Phe Asp Val Trp Asp Leu Tyr Ile Glu Ile Val Trp
1 5 10 15

<210> SEQ ID NO 231
<211> LENGTH: 15

<212> TYPE: PRT
<213> ORGANISM: Artificial Sequence
<220> FEATURE:
<223> OTHER INFORMATION: Synthetic Peptide

<400> SEQUENCE: 231

Arg Met Lys Phe Asp Val Trp Asp Leu Tyr Lys Glu Ile Val Trp
1 5 10 15

<210> SEQ ID NO 232
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 232

Arg Met Lys Phe Asp Val Trp Asp Leu Tyr Leu Glu Ile Val Trp
1 5 10 15

<210> SEQ ID NO 233
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 233

Arg Met Lys Phe Asp Val Trp Asp Leu Tyr Met Glu Ile Val Trp
1 5 10 15

<210> SEQ ID NO 234
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 234

Arg Met Lys Phe Asp Val Trp Asp Leu Tyr Asn Glu Ile Val Trp
1 5 10 15

<210> SEQ ID NO 235
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 235

Arg Met Lys Phe Asp Val Trp Asp Leu Tyr Pro Glu Ile Val Trp
1 5 10 15

<210> SEQ ID NO 236
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 236

Arg Met Lys Phe Asp Val Trp Asp Leu Tyr Gln Glu Ile Val Trp
1 5 10 15

<210> SEQ ID NO 237
<211> LENGTH: 15
<212> TYPE: PRT

<213> ORGANISM: Artificial Sequence
<220> FEATURE:
<223> OTHER INFORMATION: Synthetic Peptide

<400> SEQUENCE: 237

Arg Met Lys Phe Asp Val Trp Asp Leu Tyr Arg Glu Ile Val Trp
1 5 10 15

<210> SEQ ID NO 238
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 238

Arg Met Lys Phe Asp Val Trp Asp Leu Tyr Ser Glu Ile Val Trp
1 5 10 15

<210> SEQ ID NO 239
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 239

Arg Met Lys Phe Asp Val Trp Asp Leu Tyr Thr Glu Ile Val Trp
1 5 10 15

<210> SEQ ID NO 240
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 240

Arg Met Lys Phe Asp Val Trp Asp Leu Tyr Val Glu Ile Val Trp
1 5 10 15

<210> SEQ ID NO 241
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 241

Arg Met Lys Phe Asp Val Trp Asp Leu Tyr Trp Glu Ile Val Trp
1 5 10 15

<210> SEQ ID NO 242
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 242

Arg Met Lys Phe Asp Val Trp Asp Leu Tyr Tyr Glu Ile Val Trp
1 5 10 15

<210> SEQ ID NO 243
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 243

Arg Met Lys Phe Asp Val Trp Asp Leu Tyr Phe Ala Ile Val Trp
1 5 10 15

<210> SEQ ID NO 244
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 244

Arg Met Lys Phe Asp Val Trp Asp Leu Tyr Phe Cys Ile Val Trp
1 5 10 15

<210> SEQ ID NO 245
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 245

Arg Met Lys Phe Asp Val Trp Asp Leu Tyr Phe Asp Ile Val Trp
1 5 10 15

<210> SEQ ID NO 246
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 246

Arg Met Lys Phe Asp Val Trp Asp Leu Tyr Phe Phe Ile Val Trp
1 5 10 15

<210> SEQ ID NO 247
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 247

Arg Met Lys Phe Asp Val Trp Asp Leu Tyr Phe Gly Ile Val Trp
1 5 10 15

<210> SEQ ID NO 248
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 248

Arg Met Lys Phe Asp Val Trp Asp Leu Tyr Phe His Ile Val Trp
1 5 10 15

<210> SEQ ID NO 249
<211> LENGTH: 15
<212> TYPE: PRT
<213> ORGANISM: Artificial Sequence
<220> FEATURE:

<223> OTHER INFORMATION: Synthetic Peptide

<400> SEQUENCE: 249

Arg Met Lys Phe Asp Val Trp Asp Leu Tyr Phe Ile Ile Val Trp
1 5 10 15

<210> SEQ ID NO 250
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 250

Arg Met Lys Phe Asp Val Trp Asp Leu Tyr Phe Lys Ile Val Trp
1 5 10 15

<210> SEQ ID NO 251
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 251

Arg Met Lys Phe Asp Val Trp Asp Leu Tyr Phe Leu Ile Val Trp
1 5 10 15

<210> SEQ ID NO 252
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 252

Arg Met Lys Phe Asp Val Trp Asp Leu Tyr Phe Met Ile Val Trp
1 5 10 15

<210> SEQ ID NO 253
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 253

Arg Met Lys Phe Asp Val Trp Asp Leu Tyr Phe Asn Ile Val Trp
1 5 10 15

<210> SEQ ID NO 254
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 254

Arg Met Lys Phe Asp Val Trp Asp Leu Tyr Phe Pro Ile Val Trp
1 5 10 15

<210> SEQ ID NO 255
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 255

Arg Met Lys Phe Asp Val Trp Asp Leu Tyr Phe Gln Ile Val Trp
1 5 10 15

<210> SEQ ID NO 256
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 256

Arg Met Lys Phe Asp Val Trp Asp Leu Tyr Phe Arg Ile Val Trp
1 5 10 15

<210> SEQ ID NO 257
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 257

Arg Met Lys Phe Asp Val Trp Asp Leu Tyr Phe Ser Ile Val Trp
1 5 10 15

<210> SEQ ID NO 258
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 258

Arg Met Lys Phe Asp Val Trp Asp Leu Tyr Phe Thr Ile Val Trp
1 5 10 15

<210> SEQ ID NO 259
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 259

Arg Met Lys Phe Asp Val Trp Asp Leu Tyr Phe Val Ile Val Trp
1 5 10 15

<210> SEQ ID NO 260
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 260

Arg Met Lys Phe Asp Val Trp Asp Leu Tyr Phe Trp Ile Val Trp
1 5 10 15

<210> SEQ ID NO 261
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 261

Arg Met Lys Phe Asp Val Trp Asp Leu Tyr Phe Tyr Ile Val Trp
1 5 10 15

<210> SEQ ID NO 262
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 262

Arg Met Lys Phe Asp Val Trp Asp Leu Tyr Phe Glu Ala Val Trp
1 5 10 15

<210> SEQ ID NO 263
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 263

Arg Met Lys Phe Asp Val Trp Asp Leu Tyr Phe Glu Cys Val Trp
1 5 10 15

<210> SEQ ID NO 264
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 264

Arg Met Lys Phe Asp Val Trp Asp Leu Tyr Phe Glu Asp Val Trp
1 5 10 15

<210> SEQ ID NO 265
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 265

Arg Met Lys Phe Asp Val Trp Asp Leu Tyr Phe Glu Glu Val Trp
1 5 10 15

<210> SEQ ID NO 266
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 266

Arg Met Lys Phe Asp Val Trp Asp Leu Tyr Phe Glu Phe Val Trp
1 5 10 15

<210> SEQ ID NO 267
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 267

```
Arg Met Lys Phe Asp Val Trp Asp Leu Tyr Phe Glu Gly Val Trp
1               5                   10                  15


<210> SEQ ID NO 268
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 268

Arg Met Lys Phe Asp Val Trp Asp Leu Tyr Phe Glu His Val Trp
1               5                   10                  15


<210> SEQ ID NO 269
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 269

Arg Met Lys Phe Asp Val Trp Asp Leu Tyr Phe Glu Lys Val Trp
1               5                   10                  15


<210> SEQ ID NO 270
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 270

Arg Met Lys Phe Asp Val Trp Asp Leu Tyr Phe Glu Leu Val Trp
1               5                   10                  15


<210> SEQ ID NO 271
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 271

Arg Met Lys Phe Asp Val Trp Asp Leu Tyr Phe Glu Met Val Trp
1               5                   10                  15


<210> SEQ ID NO 272
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 272

Arg Met Lys Phe Asp Val Trp Asp Leu Tyr Phe Glu Asn Val Trp
1               5                   10                  15


<210> SEQ ID NO 273
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 273
```

-continued

Arg Met Lys Phe Asp Val Trp Asp Leu Tyr Phe Glu Pro Val Trp
1 5 10 15

<210> SEQ ID NO 274
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 274

Arg Met Lys Phe Asp Val Trp Asp Leu Tyr Phe Glu Gln Val Trp
1 5 10 15

<210> SEQ ID NO 275
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 275

Arg Met Lys Phe Asp Val Trp Asp Leu Tyr Phe Glu Arg Val Trp
1 5 10 15

<210> SEQ ID NO 276
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 276

Arg Met Lys Phe Asp Val Trp Asp Leu Tyr Phe Glu Ser Val Trp
1 5 10 15

<210> SEQ ID NO 277
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 277

Arg Met Lys Phe Asp Val Trp Asp Leu Tyr Phe Glu Thr Val Trp
1 5 10 15

<210> SEQ ID NO 278
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 278

Arg Met Lys Phe Asp Val Trp Asp Leu Tyr Phe Glu Val Val Trp
1 5 10 15

<210> SEQ ID NO 279
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 279

Arg Met Lys Phe Asp Val Trp Asp Leu Tyr Phe Glu Trp Val Trp

-continued 1 5 10 15

<210> SEQ ID NO 280
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 280

Arg Met Lys Phe Asp Val Trp Asp Leu Tyr Phe Glu Tyr Val Trp
1 5 10 15

<210> SEQ ID NO 281
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 281

Arg Met Lys Phe Asp Val Trp Asp Leu Tyr Phe Glu Ile Ala Trp
1 5 10 15

<210> SEQ ID NO 282
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 282

Arg Met Lys Phe Asp Val Trp Asp Leu Tyr Phe Glu Ile Cys Trp
1 5 10 15

<210> SEQ ID NO 283
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 283

Arg Met Lys Phe Asp Val Trp Asp Leu Tyr Phe Glu Ile Asp Trp
1 5 10 15

<210> SEQ ID NO 284
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 284

Arg Met Lys Phe Asp Val Trp Asp Leu Tyr Phe Glu Ile Glu Trp
1 5 10 15

<210> SEQ ID NO 285
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 285

Arg Met Lys Phe Asp Val Trp Asp Leu Tyr Phe Glu Ile Phe Trp
1 5 10 15

<210> SEQ ID NO 286
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 286

Arg Met Lys Phe Asp Val Trp Asp Leu Tyr Phe Glu Ile Gly Trp
1 5 10 15

<210> SEQ ID NO 287
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 287

Arg Met Lys Phe Asp Val Trp Asp Leu Tyr Phe Glu Ile His Trp
1 5 10 15

<210> SEQ ID NO 288
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 288

Arg Met Lys Phe Asp Val Trp Asp Leu Tyr Phe Glu Ile Ile Trp
1 5 10 15

<210> SEQ ID NO 289
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 289

Arg Met Lys Phe Asp Val Trp Asp Leu Tyr Phe Glu Ile Lys Trp
1 5 10 15

<210> SEQ ID NO 290
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 290

Arg Met Lys Phe Asp Val Trp Asp Leu Tyr Phe Glu Ile Leu Trp
1 5 10 15

<210> SEQ ID NO 291
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 291

Arg Met Lys Phe Asp Val Trp Asp Leu Tyr Phe Glu Ile Met Trp
1 5 10 15

<210> SEQ ID NO 292
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 292

Arg Met Lys Phe Asp Val Trp Asp Leu Tyr Phe Glu Ile Asn Trp
1 5 10 15

<210> SEQ ID NO 293
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 293

Arg Met Lys Phe Asp Val Trp Asp Leu Tyr Phe Glu Ile Pro Trp
1 5 10 15

<210> SEQ ID NO 294
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 294

Arg Met Lys Phe Asp Val Trp Asp Leu Tyr Phe Glu Ile Gln Trp
1 5 10 15

<210> SEQ ID NO 295
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 295

Arg Met Lys Phe Asp Val Trp Asp Leu Tyr Phe Glu Ile Arg Trp
1 5 10 15

<210> SEQ ID NO 296
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 296

Arg Met Lys Phe Asp Val Trp Asp Leu Tyr Phe Glu Ile Ser Trp
1 5 10 15

<210> SEQ ID NO 297
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 297

Arg Met Lys Phe Asp Val Trp Asp Leu Tyr Phe Glu Ile Thr Trp
1 5 10 15

<210> SEQ ID NO 298
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 298

Arg Met Lys Phe Asp Val Trp Asp Leu Tyr Phe Glu Ile Trp Trp
1 5 10 15

<210> SEQ ID NO 299
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 299

Arg Met Lys Phe Asp Val Trp Asp Leu Tyr Phe Glu Ile Tyr Trp
1 5 10 15

<210> SEQ ID NO 300
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 300

Arg Met Lys Phe Asp Val Trp Asp Leu Tyr Phe Glu Ile Val Ala
1 5 10 15

<210> SEQ ID NO 301
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 301

Arg Met Lys Phe Asp Val Trp Asp Leu Tyr Phe Glu Ile Val Cys
1 5 10 15

<210> SEQ ID NO 302
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 302

Arg Met Lys Phe Asp Val Trp Asp Leu Tyr Phe Glu Ile Val Asp
1 5 10 15

<210> SEQ ID NO 303
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 303

Arg Met Lys Phe Asp Val Trp Asp Leu Tyr Phe Glu Ile Val Glu
1 5 10 15

<210> SEQ ID NO 304

-continued

<211> LENGTH: 15
<212> TYPE: PRT
<213> ORGANISM: Artificial Sequence
<220> FEATURE:
<223> OTHER INFORMATION: Synthetic Peptide

<400> SEQUENCE: 304

Arg Met Lys Phe Asp Val Trp Asp Leu Tyr Phe Glu Ile Val Phe
1 5 10 15

<210> SEQ ID NO 305
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 305

Arg Met Lys Phe Asp Val Trp Asp Leu Tyr Phe Glu Ile Val Gly
1 5 10 15

<210> SEQ ID NO 306
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 306

Arg Met Lys Phe Asp Val Trp Asp Leu Tyr Phe Glu Ile Val His
1 5 10 15

<210> SEQ ID NO 307
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 307

Arg Met Lys Phe Asp Val Trp Asp Leu Tyr Phe Glu Ile Val Ile
1 5 10 15

<210> SEQ ID NO 308
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 308

Arg Met Lys Phe Asp Val Trp Asp Leu Tyr Phe Glu Ile Val Lys
1 5 10 15

<210> SEQ ID NO 309
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 309

Arg Met Lys Phe Asp Val Trp Asp Leu Tyr Phe Glu Ile Val Leu
1 5 10 15

<210> SEQ ID NO 310
<211> LENGTH: 15

<212> TYPE: PRT
<213> ORGANISM: Artificial Sequence
<220> FEATURE:
<223> OTHER INFORMATION: Synthetic Peptide

<400> SEQUENCE: 310

Arg Met Lys Phe Asp Val Trp Asp Leu Tyr Phe Glu Ile Val Met
1 5 10 15

<210> SEQ ID NO 311
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 311

Arg Met Lys Phe Asp Val Trp Asp Leu Tyr Phe Glu Ile Val Asn
1 5 10 15

<210> SEQ ID NO 312
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 312

Arg Met Lys Phe Asp Val Trp Asp Leu Tyr Phe Glu Ile Val Pro
1 5 10 15

<210> SEQ ID NO 313
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 313

Arg Met Lys Phe Asp Val Trp Asp Leu Tyr Phe Glu Ile Val Gln
1 5 10 15

<210> SEQ ID NO 314
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 314

Arg Met Lys Phe Asp Val Trp Asp Leu Tyr Phe Glu Ile Val Arg
1 5 10 15

<210> SEQ ID NO 315
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 315

Arg Met Lys Phe Asp Val Trp Asp Leu Tyr Phe Glu Ile Val Ser
1 5 10 15

<210> SEQ ID NO 316
<211> LENGTH: 15
<212> TYPE: PRT

<213> ORGANISM: Artificial Sequence
<220> FEATURE:
<223> OTHER INFORMATION: Synthetic Peptide

<400> SEQUENCE: 316

Arg Met Lys Phe Asp Val Trp Asp Leu Tyr Phe Glu Ile Val Thr
1 5 10 15

<210> SEQ ID NO 317
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 317

Arg Met Lys Phe Asp Val Trp Asp Leu Tyr Phe Glu Ile Val Val
1 5 10 15

<210> SEQ ID NO 318
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 318

Arg Met Lys Phe Asp Val Trp Asp Leu Tyr Phe Glu Ile Val Tyr
1 5 10 15

<210> SEQ ID NO 319
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 319

Met Lys Phe Asp Val Trp Asp Leu Tyr Phe Glu Ile Val Trp
1 5 10

<210> SEQ ID NO 320
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 320

Lys Phe Asp Val Trp Asp Leu Tyr Phe Glu Ile Val Trp
1 5 10

<210> SEQ ID NO 321
<211> LENGTH: 16
<212> TYPE: PRT
<213> ORGANISM: Artificial Sequence
<220> FEATURE:
<223> OTHER INFORMATION: Synthetic Peptide A72
<220> FEATURE:
<221> NAME/KEY: misc_feature
<222> LOCATION: (3)..(3)
<223> OTHER INFORMATION: Xaa is Nle

<400> SEQUENCE: 321

Glu Arg Xaa Glu Phe Asp Val Trp Asp Leu Tyr Phe Glu Ile Val Trp
1 5 10 15

```
<210> SEQ ID NO 322
<211> LENGTH: 9
<212> TYPE: PRT
<213> ORGANISM: Artificial Sequence
<220> FEATURE:
<223> OTHER INFORMATION: Synthetic peptide

<400> SEQUENCE: 322

Trp Asp Leu Tyr Phe Glu Ile Val Trp
1               5


<210> SEQ ID NO 323
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa is Trp, Leu or Pro
<220> FEATURE:
<221> NAME/KEY: VARIANT
<222> LOCATION: (2)..(2)
<223> OTHER INFORMATION: Xaa is Asp or Ser
<220> FEATURE:
<221> NAME/KEY: VARIANT
<222> LOCATION: (3)..(3)
<223> OTHER INFORMATION: Xaa is Leu or Phe
<220> FEATURE:
<221> NAME/KEY: VARIANT
<222> LOCATION: (5)..(5)
<223> OTHER INFORMATION: Xaa is Phe, Phg, Leu, Ebw, Pff, Thi, 1Ni, Hfe,
      Ece or Cha
<220> FEATURE:
<221> NAME/KEY: VARIANT
<222> LOCATION: (7)..(7)
<223> OTHER INFORMATION: Xaa is Ile or Phe
<220> FEATURE:
<221> NAME/KEY: VARIANT
<222> LOCATION: (8)..(8)
<223> OTHER INFORMATION: Xaa is Ser, Val or Gly
<220> FEATURE:
<221> NAME/KEY: VARIANT
<222> LOCATION: (9)..(9)
<223> OTHER INFORMATION: Xaa is Trp or Leu

<400> SEQUENCE: 323

Xaa Xaa Xaa Tyr Xaa Glu Xaa Xaa Xaa
1               5


<210> SEQ ID NO 324
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa is Trp or Leu
<220> FEATURE:
<221> NAME/KEY: VARIANT
<222> LOCATION: (2)..(2)
<223> OTHER INFORMATION: Xaa is Asp or Ser
<220> FEATURE:
<221> NAME/KEY: VARIANT
<222> LOCATION: (3)..(3)
<223> OTHER INFORMATION: Xaa is Leu or Phe
<220> FEATURE:
<221> NAME/KEY: VARIANT
<222> LOCATION: (5)..(5)
<223> OTHER INFORMATION: Xaa is Phe, Phg or Leu
<220> FEATURE:
<221> NAME/KEY: VARIANT
```

<222> LOCATION: (7)..(7)
<223> OTHER INFORMATION: Xaa is Ile or Phe
<220> FEATURE:
<221> NAME/KEY: VARIANT
<222> LOCATION: (8)..(8)
<223> OTHER INFORMATION: Xaa is Ser, Val or Gly
<220> FEATURE:
<221> NAME/KEY: VARIANT
<222> LOCATION: (9)..(9)
<223> OTHER INFORMATION: Xaa is Trp or Leu

<400> SEQUENCE: 324

Xaa Xaa Xaa Tyr Xaa Glu Xaa Xaa Xaa
1 5

<210> SEQ ID NO 325
<211> LENGTH: 15
<212> TYPE: PRT
<213> ORGANISM: Artificial Sequence
<220> FEATURE:
<223> OTHER INFORMATION: Synthetic peptide

<400> SEQUENCE: 325

Arg Met Glu Phe Asp Val Trp Asp Leu Tyr Phe Glu Ile Val Trp
1 5 10 15

<210> SEQ ID NO 326
<211> LENGTH: 15
<212> TYPE: PRT
<213> ORGANISM: Artificial Sequence
<220> FEATURE:
<223> OTHER INFORMATION: Synthetic peptide

<400> SEQUENCE: 326

Arg Met Lys Phe Asp Val Trp Asp Leu Tyr Phe Glu Ile Val Trp
1 5 10 15

<210> SEQ ID NO 327
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa is Arg or Pro
<220> FEATURE:
<221> NAME/KEY: VARIANT
<222> LOCATION: (2)..(2)
<223> OTHER INFORMATION: Xaa is Met, Nva, Moo, Asn, Nle, Meo, Gln or Eag
<220> FEATURE:
<221> NAME/KEY: VARIANT
<222> LOCATION: (3)..(3)
<223> OTHER INFORMATION: Xaa is Glu, Lys or Asp
<220> FEATURE:
<221> NAME/KEY: VARIANT
<222> LOCATION: (7)..(7)
<223> OTHER INFORMATION: Xaa is Trp, Leu or Pro
<220> FEATURE:
<221> NAME/KEY: VARIANT
<222> LOCATION: (8)..(8)
<223> OTHER INFORMATION: Xaa is Asp or Ser
<220> FEATURE:
<221> NAME/KEY: VARIANT
<222> LOCATION: (9)..(9)
<223> OTHER INFORMATION: Xaa is Leu or Phe
<220> FEATURE:
<221> NAME/KEY: VARIANT
<222> LOCATION: (11)..(11)
<223> OTHER INFORMATION: Xaa is Phe, Phg, Leu, Ebw, Pff, Thi, 1Ni, Hfe,
Ece, Cha
<220> FEATURE:

<221> NAME/KEY: VARIANT
<222> LOCATION: (13)..(13)
<223> OTHER INFORMATION: Xaa is Ile or Phe
<220> FEATURE:
<221> NAME/KEY: VARIANT
<222> LOCATION: (14)..(14)
<223> OTHER INFORMATION: Xaa is Ser, Val or Gly
<220> FEATURE:
<221> NAME/KEY: VARIANT
<222> LOCATION: (15)..(15)
<223> OTHER INFORMATION: Xaa is Trp or Leu

<400> SEQUENCE: 327

Xaa Xaa Xaa Phe Asp Val Xaa Xaa Xaa Tyr Xaa Glu Xaa Xaa Xaa
1 5 10 15

<210> SEQ ID NO 328
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa is Arg or Pro
<220> FEATURE:
<221> NAME/KEY: VARIANT
<222> LOCATION: (2)..(2)
<223> OTHER INFORMATION: Xaa is Met or Nva
<220> FEATURE:
<221> NAME/KEY: VARIANT
<222> LOCATION: (3)..(3)
<223> OTHER INFORMATION: Xaa is Glu, Lys or Asp
<220> FEATURE:
<221> NAME/KEY: VARIANT
<222> LOCATION: (7)..(7)
<223> OTHER INFORMATION: Xaa is Trp or Leu
<220> FEATURE:
<221> NAME/KEY: VARIANT
<222> LOCATION: (8)..(8)
<223> OTHER INFORMATION: Xaa is Asp or Ser
<220> FEATURE:
<221> NAME/KEY: VARIANT
<222> LOCATION: (9)..(9)
<223> OTHER INFORMATION: Xaa is Leu or Phe
<220> FEATURE:
<221> NAME/KEY: VARIANT
<222> LOCATION: (11)..(11)
<223> OTHER INFORMATION: Xaa is Phe, Phg or Leu
<220> FEATURE:
<221> NAME/KEY: VARIANT
<222> LOCATION: (13)..(13)
<223> OTHER INFORMATION: Xaa is Ile or Phe
<220> FEATURE:
<221> NAME/KEY: VARIANT
<222> LOCATION: (14)..(14)
<223> OTHER INFORMATION: Xaa is Ser, Val or Gly
<220> FEATURE:
<221> NAME/KEY: VARIANT
<222> LOCATION: (15)..(15)
<223> OTHER INFORMATION: Xaa is Trp or Leu

<400> SEQUENCE: 328

Xaa Xaa Xaa Phe Asp Val Xaa Xaa Xaa Tyr Xaa Glu Xaa Xaa Xaa
1 5 10 15

<210> SEQ ID NO 329
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (15)..(15)
<223> OTHER INFORMATION: C-terminal amidation

<400> SEQUENCE: 329

Arg Met Lys Phe Asp Val Trp Asp Leu Tyr Phe Glu Ile Val Trp
1 5 10 15

<210> SEQ ID NO 330
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (15)..(15)
<223> OTHER INFORMATION: C-terminal amidation

<400> SEQUENCE: 330

Pro Met Lys Phe Asp Val Trp Asp Leu Tyr Phe Glu Ile Val Trp
1 5 10 15

<210> SEQ ID NO 331
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (15)..(15)
<223> OTHER INFORMATION: C-terminal amidation

<400> SEQUENCE: 331

Arg Met Asp Phe Asp Val Trp Asp Leu Tyr Phe Glu Ile Val Trp
1 5 10 15

<210> SEQ ID NO 332
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (15)..(15)
<223> OTHER INFORMATION: C-terminal amidation

<400> SEQUENCE: 332

Arg Met Glu Phe Asp Val Trp Asp Leu Tyr Phe Glu Ile Val Trp
1 5 10 15

<210> SEQ ID NO 333
<211> LENGTH: 9
<212> TYPE: PRT

<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (9)..(9)
<223> OTHER INFORMATION: C-terminal amidation

<400> SEQUENCE: 333

Trp Asp Leu Tyr Phe Glu Ile Val Trp
1 5

<210> SEQ ID NO 334
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation

<400> SEQUENCE: 334

Trp Asp Leu Tyr Phe Glu Ile Val Trp Glu
1 5 10

<210> SEQ ID NO 335
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (9)..(10)
<223> OTHER INFORMATION: Trp linked to Glu via ttds linker

<400> SEQUENCE: 335

Trp Asp Leu Tyr Phe Glu Ile Val Trp Glu
1 5 10

<210> SEQ ID NO 336
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Linked to ttds
<220> FEATURE:
<221> NAME/KEY: MISC_FEATURE
<222> LOCATION: (15)..(15)
<223> OTHER INFORMATION: Linked to ttds, which terminates in an amide

<400> SEQUENCE: 336

Arg Met Glu Phe Asp Val Trp Asp Leu Tyr Phe Glu Ile Val Trp
1 5 10 15

<210> SEQ ID NO 337
<211> LENGTH: 16

<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (16)..(16)
<223> OTHER INFORMATION: C-terminal amidation

<400> SEQUENCE: 337

Glu Arg Met Glu Phe Asp Val Trp Asp Leu Tyr Phe Glu Ile Val Trp
1               5                   10                  15

<210> SEQ ID NO 338
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa is norvaline
<220> FEATURE:
<221> NAME/KEY: MISC_FEATURE
<222> LOCATION: (16)..(16)
<223> OTHER INFORMATION: C-terminal amidation

<400> SEQUENCE: 338

Glu Arg Xaa Glu Phe Asp Val Trp Asp Leu Tyr Phe Glu Ile Val Trp
1               5                   10                  15

<210> SEQ ID NO 339
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Linked to ttds
<220> FEATURE:
<221> NAME/KEY: MISC_FEATURE
<222> LOCATION: (11)..(11)
<223> OTHER INFORMATION: Xaa is phenylglycine
<220> FEATURE:
<221> NAME/KEY: MISC_FEATURE
<222> LOCATION: (15)..(15)
<223> OTHER INFORMATION: Linked to ttds, which terminates in an amide

<400> SEQUENCE: 339

Arg Met Glu Phe Asp Val Trp Asp Leu Tyr Xaa Glu Ile Val Trp
1               5                   10                  15

<210> SEQ ID NO 340
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: N-terminal acetylation

<400> SEQUENCE: 340

Trp Ser Leu Tyr Phe Glu Ile Val Trp Glu
1               5                   10

<210> SEQ ID NO 341
<211> LENGTH: 10

```
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (9)..(10)
<223> OTHER INFORMATION: Trp linked to Glu via ttds linker

<400> SEQUENCE: 341

Trp Asp Leu Tyr Phe Glu Ile Ser Trp Glu
1               5                   10


<210> SEQ ID NO 342
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to PEG5000
<220> FEATURE:
<221> NAME/KEY: MISC_FEATURE
<222> LOCATION: (15)..(15)
<223> OTHER INFORMATION: C-terminal amidation

<400> SEQUENCE: 342

Arg Met Lys Phe Asp Val Trp Asp Leu Tyr Phe Glu Ile Val Trp
1               5                   10                  15


<210> SEQ ID NO 343
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to PEG5000

<400> SEQUENCE: 343

Trp Ser Leu Tyr Phe Glu Ile Val Trp Glu
1               5                   10


<210> SEQ ID NO 344
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to PEG5000
<220> FEATURE:
<221> NAME/KEY: MISC_FEATURE
<222> LOCATION: (16)..(16)
<223> OTHER INFORMATION: C-terminal amidation

<400> SEQUENCE: 344

Glu Arg Met Glu Phe Asp Val Trp Asp Leu Tyr Phe Glu Ile Val Trp
1               5                   10                  15


<210> SEQ ID NO 345
```

```
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (10)..(10)
<223> OTHER INFORMATION: C-terminal amidation

<400> SEQUENCE: 345

Val Trp Asp Leu Tyr Phe Glu Ile Val Trp
1               5                   10


<210> SEQ ID NO 346
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal amidation
<220> FEATURE:
<221> NAME/KEY: MISC_FEATURE
<222> LOCATION: (12)..(12)
<223> OTHER INFORMATION: C-terminal amidation

<400> SEQUENCE: 346

Phe Asp Val Trp Asp Leu Tyr Phe Glu Ile Val Trp
1               5                   10


<210> SEQ ID NO 347
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (10)..(10)
<223> OTHER INFORMATION: C-terminal amidation

<400> SEQUENCE: 347

Glu Trp Asp Leu Tyr Phe Glu Ile Val Trp
1               5                   10


<210> SEQ ID NO 348
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(2)
<223> OTHER INFORMATION: Glu linked to Trp via ttds linker
<220> FEATURE:
<221> NAME/KEY: MISC_FEATURE
<222> LOCATION: (10)..(10)
<223> OTHER INFORMATION: C-terminal amidation

<400> SEQUENCE: 348

Glu Trp Asp Leu Tyr Phe Glu Ile Val Trp
1               5                   10
```

-continued

```
<210> SEQ ID NO 349
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (9)..(10)
<223> OTHER INFORMATION: Trp linked to Glu via ttds linker
<220> FEATURE:
<221> NAME/KEY: MISC_FEATURE
<222> LOCATION: (10)..(10)
<223> OTHER INFORMATION: C-terminal amidation

<400> SEQUENCE: 349

Trp Asp Leu Tyr Phe Glu Ile Val Trp Glu
1               5                   10


<210> SEQ ID NO 350
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation

<400> SEQUENCE: 350

Arg Met Glu Phe Asp Val Trp Asp Leu Tyr Phe Glu Ile Val Trp
1               5                   10                  15


<210> SEQ ID NO 351
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (1)..(2)
<223> OTHER INFORMATION: Lys linked to Arg via ttds linker
<220> FEATURE:
<221> NAME/KEY: MISC_FEATURE
<222> LOCATION: (16)..(16)
<223> OTHER INFORMATION: C-terminal amidation

<400> SEQUENCE: 351

Lys Arg Met Glu Phe Asp Val Trp Asp Leu Tyr Phe Glu Ile Val Trp
1               5                   10                  15


<210> SEQ ID NO 352
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: N-terminal acetylation

<400> SEQUENCE: 352
```

-continued

Arg Met Glu Phe Asp Val Trp Asp Leu Tyr Phe Glu Ile Val Trp Lys
1 5 10 15

<210> SEQ ID NO 353
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 353

Arg Met Glu Phe Asp Val Trp Asp Leu Tyr Phe Glu Ile Val Trp Lys
1 5 10 15

<210> SEQ ID NO 354
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (15)..(16)
<223> OTHER INFORMATION: Trp linked to Lys via ttds linker
<220> FEATURE:
<221> NAME/KEY: MISC_FEATURE
<222> LOCATION: (16)..(16)
<223> OTHER INFORMATION: C-terminal amidation

<400> SEQUENCE: 354

Arg Met Glu Phe Asp Val Trp Asp Leu Tyr Phe Glu Ile Val Trp Lys
1 5 10 15

<210> SEQ ID NO 355
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation

<400> SEQUENCE: 355

Trp Asp Leu Tyr Phe Glu Ile Ser Trp Glu
1 5 10

<210> SEQ ID NO 356
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation

<400> SEQUENCE: 356

Trp Asp Leu Tyr Leu Glu Ile Val Trp Glu
1 5 10

<210> SEQ ID NO 357
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation

<400> SEQUENCE: 357

Trp Asp Leu Tyr Phe Glu Ile Val Leu Glu
1 5 10

<210> SEQ ID NO 358
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (15)..(15)
<223> OTHER INFORMATION: C-terminal amidation

<400> SEQUENCE: 358

Arg Met Glu Phe Asp Val Trp Asp Leu Tyr Phe Glu Ile Val Trp
1 5 10 15

<210> SEQ ID NO 359
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (15)..(15)
<223> OTHER INFORMATION: Linked to ttds, which terminates in an amide

<400> SEQUENCE: 359

Arg Met Glu Phe Asp Val Trp Asp Leu Tyr Phe Glu Ile Val Trp
1 5 10 15

<210> SEQ ID NO 360
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 360

Lys Arg Met Glu Phe Asp Val Trp Asp Leu Tyr Phe Glu Ile Val Trp
1 5 10 15

<210> SEQ ID NO 361
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(2)
<223> OTHER INFORMATION: Lys linked to Arg via ttds linker
<220> FEATURE:
<221> NAME/KEY: MISC_FEATURE
<222> LOCATION: (16)..(16)
<223> OTHER INFORMATION: C-terminal amidation

<400> SEQUENCE: 361

Lys Arg Met Glu Phe Asp Val Trp Asp Leu Tyr Phe Glu Ile Val Trp
1 5 10 15

<210> SEQ ID NO 362
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (15)..(16)
<223> OTHER INFORMATION: Trp linked to Lys via ttds linker

<400> SEQUENCE: 362

Arg Met Glu Phe Asp Val Trp Asp Leu Tyr Phe Glu Ile Val Trp Lys
1 5 10 15

<210> SEQ ID NO 363
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (9)..(10)
<223> OTHER INFORMATION: Trp linked to Glu via ttds linker

<400> SEQUENCE: 363

Leu Asp Leu Tyr Phe Glu Ile Val Trp Glu
1 5 10

<210> SEQ ID NO 364
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation

<400> SEQUENCE: 364

Trp Asp Leu Tyr Phe Glu Ile Val Leu Glu 1 5 10

<210> SEQ ID NO 365
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (16)..(16)
<223> OTHER INFORMATION: C-terminal amidation

<400> SEQUENCE: 365

Glu Arg Met Glu Phe Asp Val Leu Asp Leu Tyr Phe Glu Ile Val Trp
1 5 10 15

<210> SEQ ID NO 366
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (16)..(16)
<223> OTHER INFORMATION: C-terminal amidation

<400> SEQUENCE: 366

Glu Arg Met Glu Phe Asp Val Trp Asp Leu Tyr Phe Glu Ile Val Leu
1 5 10 15

<210> SEQ ID NO 367
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation

<400> SEQUENCE: 367

Trp Asp Phe Tyr Phe Glu Ile Val Trp Glu
1 5 10

<210> SEQ ID NO 368
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation

<400> SEQUENCE: 368

Trp Asp Leu Tyr Phe Glu Phe Val Trp Glu
1 5 10

<210> SEQ ID NO 369
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation

<400> SEQUENCE: 369

Leu Asp Leu Tyr Phe Glu Ile Val Trp Glu
1 5 10

<210> SEQ ID NO 370
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation

<400> SEQUENCE: 370

Trp Asp Leu Tyr Phe Glu Ile Gly Trp Glu
1 5 10

<210> SEQ ID NO 371
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation

<400> SEQUENCE: 371

Trp Asp Leu Tyr Leu Glu Ile Ser Leu Glu
1 5 10

<210> SEQ ID NO 372
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (5)..(5)
<223> OTHER INFORMATION: Xaa is Phg

<400> SEQUENCE: 372

Trp Asp Leu Tyr Xaa Glu Ile Val Leu Glu
1 5 10

<210> SEQ ID NO 373
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (5)..(5)
<223> OTHER INFORMATION: Xaa is Phg

<400> SEQUENCE: 373

Trp Ser Leu Tyr Xaa Glu Ile Val Trp Glu
1 5 10

<210> SEQ ID NO 374
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation

<400> SEQUENCE: 374

Leu Asp Leu Tyr Phe Glu Ile Val Leu Glu
1 5 10

<210> SEQ ID NO 375
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation

<400> SEQUENCE: 375

Leu Asp Leu Tyr Phe Glu Ile Ser Leu Glu
1 5 10

<210> SEQ ID NO 376
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (5)..(5)
<223> OTHER INFORMATION: Xaa is Phg

<400> SEQUENCE: 376

Leu Asp Leu Tyr Xaa Glu Ile Ser Trp Glu
1 5 10

<210> SEQ ID NO 377
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation

<400> SEQUENCE: 377

Leu Ser Leu Tyr Phe Glu Ile Val Trp Glu
1 5 10

<210> SEQ ID NO 378

<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation

<400> SEQUENCE: 378

Leu Ser Leu Tyr Phe Glu Ile Val Leu Glu
1               5                   10

<210> SEQ ID NO 379
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation

<400> SEQUENCE: 379

Leu Ser Leu Tyr Phe Glu Ile Ser Leu Glu
1               5                   10

<210> SEQ ID NO 380
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (9)..(10)
<223> OTHER INFORMATION: Trp linked to Lys via ttds linker

<400> SEQUENCE: 380

Trp Asp Leu Tyr Phe Glu Ile Val Trp Lys
1               5                   10

<210> SEQ ID NO 381
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (11)..(11)
<223> OTHER INFORMATION: C-terminal amidation

<400> SEQUENCE: 381

Asp Val Trp Asp Leu Tyr Phe Glu Ile Val Trp
1               5                   10

<210> SEQ ID NO 382
<211> LENGTH: 15
<212> TYPE: PRT
<213> ORGANISM: Artificial Sequence -continued
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MOD_RES
<222> LOCATION: (1)..(1)
<223> OTHER INFORMATION: D-Trp
<220> FEATURE:
<221> NAME/KEY: MOD_RES
<222> LOCATION: (2)..(2)
<223> OTHER INFORMATION: D-Val
<220> FEATURE:
<221> NAME/KEY: MOD_RES
<222> LOCATION: (3)..(3)
<223> OTHER INFORMATION: D-Ile
<220> FEATURE:
<221> NAME/KEY: MOD_RES
<222> LOCATION: (4)..(4)
<223> OTHER INFORMATION: D-Glu
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (6)..(6)
<223> OTHER INFORMATION: D-Tyr
<220> FEATURE:
<221> NAME/KEY: MOD_RES
<222> LOCATION: (7)..(7)
<223> OTHER INFORMATION: D-Leu
<220> FEATURE:
<221> NAME/KEY: MOD_RES
<222> LOCATION: (8)..(8)
<223> OTHER INFORMATION: D-Asp
<220> FEATURE:
<221> NAME/KEY: MOD_RES
<222> LOCATION: (9)..(9)
<223> OTHER INFORMATION: D-Trp
<220> FEATURE:
<221> NAME/KEY: MOD_RES
<222> LOCATION: (10)..(10)
<223> OTHER INFORMATION: D-Val
<220> FEATURE:
<221> NAME/KEY: MOD_RES
<222> LOCATION: (11)..(11)
<223> OTHER INFORMATION: D-Asp
<220> FEATURE:
<221> NAME/KEY: MOD_RES
<222> LOCATION: (12)..(12)
<223> OTHER INFORMATION: D-Phe
<220> FEATURE:
<221> NAME/KEY: MOD_RES
<222> LOCATION: (13)..(13)
<223> OTHER INFORMATION: D-Lys
<220> FEATURE:
<221> NAME/KEY: MOD_RES
<222> LOCATION: (14)..(14)
<223> OTHER INFORMATION: D-Met
<220> FEATURE:
<221> NAME/KEY: MOD_RES
<222> LOCATION: (15)..(15)
<223> OTHER INFORMATION: D-Arg
<220> FEATURE:
<221> NAME/KEY: MISC_FEATURE
<222> LOCATION: (15)..(15)
<223> OTHER INFORMATION: C-terminal amidation

<400> SEQUENCE: 382

Trp Val Ile Glu Phe Tyr Leu Asp Trp Val Asp Phe Lys Met Arg
1               5                   10                  15

<210> SEQ ID NO 383
<211> LENGTH: 9

<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation

<400> SEQUENCE: 383

Trp Asp Leu Tyr Phe Glu Ile Val Trp
1               5

<210> SEQ ID NO 384
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetyl group linked to Trp via ttds
      linker
<220> FEATURE:
<221> NAME/KEY: MISC_FEATURE
<222> LOCATION: (9)..(9)
<223> OTHER INFORMATION: C-terminal amidation

<400> SEQUENCE: 384

Trp Asp Leu Tyr Phe Glu Ile Val Trp
1               5

<210> SEQ ID NO 385
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal ttds
<220> FEATURE:
<221> NAME/KEY: MISC_FEATURE
<222> LOCATION: (9)..(9)
<223> OTHER INFORMATION: C-terminal amidation

<400> SEQUENCE: 385

Trp Asp Leu Tyr Phe Glu Ile Val Trp
1               5

<210> SEQ ID NO 386
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (9)..(9)
<223> OTHER INFORMATION: Linked to ttds, which terminates in an amide

<400> SEQUENCE: 386

Trp Asp Leu Tyr Phe Glu Ile Val Trp
1               5

<210> SEQ ID NO 387
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetyl group linked to Trp via ttds linker
<220> FEATURE:
<221> NAME/KEY: MISC_FEATURE
<222> LOCATION: (9)..(9)
<223> OTHER INFORMATION: Linked to ttds, which terminates in an amide

<400> SEQUENCE: 387

Trp Asp Leu Tyr Phe Glu Ile Val Trp
1 5

<210> SEQ ID NO 388
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal ttds
<220> FEATURE:
<221> NAME/KEY: MISC_FEATURE
<222> LOCATION: (9)..(9)
<223> OTHER INFORMATION: C-terminal ttds

<400> SEQUENCE: 388

Trp Asp Leu Tyr Phe Glu Ile Val Trp
1 5

<210> SEQ ID NO 389
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal ttds
<220> FEATURE:
<221> NAME/KEY: MISC_FEATURE
<222> LOCATION: (9)..(9)
<223> OTHER INFORMATION: Linked to ttds, which terminates in an amide

<400> SEQUENCE: 389

Trp Asp Leu Tyr Phe Glu Ile Val Trp
1 5

<210> SEQ ID NO 390
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (10)..(10)
<223> OTHER INFORMATION: C-terminal amidation

<400> SEQUENCE: 390

Lys Trp Asp Leu Tyr Phe Glu Ile Val Trp
1               5                   10

<210> SEQ ID NO 391
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (1)..(2)
<223> OTHER INFORMATION: Lys linked to Trp via ttds linker
<220> FEATURE:
<221> NAME/KEY: MISC_FEATURE
<222> LOCATION: (10)..(10)
<223> OTHER INFORMATION: C-terminal amidation

<400> SEQUENCE: 391

Lys Trp Asp Leu Tyr Phe Glu Ile Val Trp
1               5                   10

<210> SEQ ID NO 392
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation

<400> SEQUENCE: 392

Trp Asp Leu Tyr Phe Glu Ile Val Trp Lys
1               5                   10

<210> SEQ ID NO 393
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (10)..(10)
<223> OTHER INFORMATION: C-terminal amidation

<400> SEQUENCE: 393

Trp Asp Leu Tyr Phe Glu Ile Val Trp Lys
1               5                   10

<210> SEQ ID NO 394
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa is methioninesulfone
<220> FEATURE:
<221> NAME/KEY: MISC_FEATURE
<222> LOCATION: (16)..(16)
<223> OTHER INFORMATION: C-terminal amidation

<400> SEQUENCE: 394

Glu Arg Xaa Glu Phe Asp Val Trp Asp Leu Tyr Phe Glu Ile Val Trp
1 5 10 15

<210> SEQ ID NO 395
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (16)..(16)
<223> OTHER INFORMATION: C-terminal amidation

<400> SEQUENCE: 395

Glu Arg Asn Glu Phe Asp Val Trp Asp Leu Tyr Phe Glu Ile Val Trp
1 5 10 15

<210> SEQ ID NO 396
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal ttds
<220> FEATURE:
<221> NAME/KEY: MISC_FEATURE
<222> LOCATION: (11)..(11)
<223> OTHER INFORMATION: Xaa is 3,3-diphenylalanine
<220> FEATURE:
<221> NAME/KEY: MISC_FEATURE
<222> LOCATION: (15)..(15)
<223> OTHER INFORMATION: Linked to ttds, which terminates in an amide

<400> SEQUENCE: 396

Arg Met Glu Phe Asp Val Trp Asp Leu Tyr Xaa Glu Ile Val Trp
1 5 10 15

<210> SEQ ID NO 397
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal ttds
<220> FEATURE:
<221> NAME/KEY: MISC_FEATURE
<222> LOCATION: (11)..(11)
<223> OTHER INFORMATION: Xaa is 4-fluorophenyl-alanine
<220> FEATURE:
<221> NAME/KEY: MISC_FEATURE
<222> LOCATION: (15)..(15)
<223> OTHER INFORMATION: Linked to ttds, which terminates in an amide

<400> SEQUENCE: 397

Arg Met Glu Phe Asp Val Trp Asp Leu Tyr Xaa Glu Ile Val Trp
1 5 10 15

<210> SEQ ID NO 398

```
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation

<400> SEQUENCE: 398

Pro Asp Leu Tyr Phe Glu Ile Val Trp Glu
1               5                   10


<210> SEQ ID NO 399
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation

<400> SEQUENCE: 399

Leu Ser Leu Tyr Leu Glu Ile Val Leu Glu
1               5                   10


<210> SEQ ID NO 400
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation

<400> SEQUENCE: 400

Leu Ser Leu Tyr Leu Glu Ile Ser Leu Glu
1               5                   10


<210> SEQ ID NO 401
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (5)..(5)
<223> OTHER INFORMATION: Xaa is Phg

<400> SEQUENCE: 401

Leu Ser Leu Tyr Xaa Glu Ile Val Leu Glu
1               5                   10


<210> SEQ ID NO 402
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
```

<222> LOCATION: (1)..(1)
<223> OTHER INFORMATION: N-terminal acetylation
<220> FEATURE:
<221> NAME/KEY: MISC_FEATURE
<222> LOCATION: (9)..(10)
<223> OTHER INFORMATION: Trp linked to Lys via ttds linker
<220> FEATURE:
<221> NAME/KEY: MISC_FEATURE
<222> LOCATION: (10)..(10)
<223> OTHER INFORMATION: C-terminal amidation

<400> SEQUENCE: 402

Trp Asp Leu Tyr Phe Glu Ile Val Trp Lys
1 5 10

<210> SEQ ID NO 403
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (16)..(16)
<223> OTHER INFORMATION: C-terminal amidation

<400> SEQUENCE: 403

Glu Pro Met Lys Phe Asp Val Trp Asp Leu Tyr Phe Glu Ile Val Trp
1 5 10 15

<210> SEQ ID NO 404
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal ttds
<220> FEATURE:
<221> NAME/KEY: MISC_FEATURE
<222> LOCATION: (15)..(15)
<223> OTHER INFORMATION: Linked to ttds, which terminates in an amide

<400> SEQUENCE: 404

Arg Met Asp Phe Asp Val Trp Asp Leu Tyr Phe Glu Ile Val Trp
1 5 10 15

<210> SEQ ID NO 405
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to PEG5000
<220> FEATURE:
<221> NAME/KEY: MISC_FEATURE
<222> LOCATION: (15)..(15)
<223> OTHER INFORMATION: C-terminal amidation

<400> SEQUENCE: 405

Arg Met Lys Phe Asp Val Trp Asp Leu Tyr Phe Glu Ile Val Trp
1 5 10 15

<210> SEQ ID NO 406
<211> LENGTH: 9
<212> TYPE: PRT

<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: N-terminal amidation

<400> SEQUENCE: 406

Trp Asp Leu Tyr Phe Glu Ile Val Trp
1               5

<210> SEQ ID NO 407
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (16)..(16)
<223> OTHER INFORMATION: C-terminal amidation

<400> SEQUENCE: 407

Lys Arg Met Glu Phe Asp Val Trp Asp Leu Tyr Phe Glu Ile Val Trp
1               5                   10                  15

<210> SEQ ID NO 408
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal ttds
<220> FEATURE:
<221> NAME/KEY: MISC_FEATURE
<222> LOCATION: (15)..(15)
<223> OTHER INFORMATION: Linked to ttds, which terminates in an amide

<400> SEQUENCE: 408

Pro Met Lys Phe Asp Val Trp Asp Leu Tyr Phe Glu Ile Val Trp
1               5                   10                  15

<210> SEQ ID NO 409
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (16)..(16)
<223> OTHER INFORMATION: C-terminal amidation

<400> SEQUENCE: 409

Glu Arg Met Asp Phe Asp Val Trp Asp Leu Tyr Phe Glu Ile Val Trp
1               5                   10                  15

<210> SEQ ID NO 410
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is Cysteic Acid
<220> FEATURE:
<221> NAME/KEY: MISC_FEATURE
<222> LOCATION: (1)..(2)
<223> OTHER INFORMATION: Cystic Acid linked to Arg via ttds linker
<220> FEATURE:
<221> NAME/KEY: MISC_FEATURE
<222> LOCATION: (16)..(16)
<223> OTHER INFORMATION: Linked to ttds, which terminates in an amide

<400> SEQUENCE: 410

Xaa Arg Met Glu Phe Asp Val Trp Asp Leu Tyr Phe Glu Ile Val Trp
1               5                   10                  15

<210> SEQ ID NO 411
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is Glucosyl-aminooxyacetyl
<220> FEATURE:
<221> NAME/KEY: MISC_FEATURE
<222> LOCATION: (1)..(2)
<223> OTHER INFORMATION: Glucosyl-aminooxyacetyl linked to Arg via ttds
      linker
<220> FEATURE:
<221> NAME/KEY: MISC_FEATURE
<222> LOCATION: (16)..(16)
<223> OTHER INFORMATION: Linked to ttds, which terminates in an amide

<400> SEQUENCE: 411

Xaa Arg Met Glu Phe Asp Val Trp Asp Leu Tyr Phe Glu Ile Val Trp
1               5                   10                  15

<210> SEQ ID NO 412
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (2)..(2)
<223> OTHER INFORMATION: Xaa is methioninesulfone
<220> FEATURE:
<221> NAME/KEY: MISC_FEATURE
<222> LOCATION: (15)..(15)
<223> OTHER INFORMATION: C-terminal amidation

<400> SEQUENCE: 412

Pro Xaa Lys Phe Asp Val Trp Asp Leu Tyr Phe Glu Ile Val Trp
1               5                   10                  15

<210> SEQ ID NO 413
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (2)..(2)

<223> OTHER INFORMATION: Xaa is norleucine
<220> FEATURE:
<221> NAME/KEY: MISC_FEATURE
<222> LOCATION: (15)..(15)
<223> OTHER INFORMATION: C-terminal amidation

<400> SEQUENCE: 413

Pro Xaa Lys Phe Asp Val Trp Asp Leu Tyr Phe Glu Ile Val Trp
1 5 10 15

<210> SEQ ID NO 414
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (15)..(15)
<223> OTHER INFORMATION: C-terminal amidation

<400> SEQUENCE: 414

Pro Asn Lys Phe Asp Val Trp Asp Leu Tyr Phe Glu Ile Val Trp
1 5 10 15

<210> SEQ ID NO 415
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (2)..(2)
<223> OTHER INFORMATION: Xaa is methioninesulfone
<220> FEATURE:
<221> NAME/KEY: MISC_FEATURE
<222> LOCATION: (15)..(15)
<223> OTHER INFORMATION: C-terminal amidation

<400> SEQUENCE: 415

Arg Xaa Asp Phe Asp Val Trp Asp Leu Tyr Phe Glu Ile Val Trp
1 5 10 15

<210> SEQ ID NO 416
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (15)..(15)
<223> OTHER INFORMATION: C-terminal amidation

<400> SEQUENCE: 416

```
Arg Xaa Asp Phe Asp Val Trp Asp Leu Tyr Phe Glu Ile Val Trp
1               5                   10                  15


<210> SEQ ID NO 417
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (15)..(15)
<223> OTHER INFORMATION: C-terminal amidation

<400> SEQUENCE: 417

Arg Asn Asp Phe Asp Val Trp Asp Leu Tyr Phe Glu Ile Val Trp
1               5                   10                  15


<210> SEQ ID NO 418
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal ttds
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (15)..(15)
<223> OTHER INFORMATION: Linked to ttds, which terminates in an amide

<400> SEQUENCE: 418

Arg Xaa Glu Phe Asp Val Trp Asp Leu Tyr Phe Glu Ile Val Trp
1               5                   10                  15


<210> SEQ ID NO 419
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal ttds
<220> FEATURE:
<221> NAME/KEY: MISC_FEATURE
<222> LOCATION: (15)..(15)
<223> OTHER INFORMATION: Linked to ttds, which terminates in an amide

<400> SEQUENCE: 419

Arg Asn Glu Phe Asp Val Trp Asp Leu Tyr Phe Glu Ile Val Trp
1               5                   10                  15


<210> SEQ ID NO 420
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
```

<222> LOCATION: (3)..(3)
<223> OTHER INFORMATION: Xaa is Norleucine
<220> FEATURE:
<221> NAME/KEY: MISC_FEATURE
<222> LOCATION: (16)..(16)
<223> OTHER INFORMATION: C-terminal amidation

<400> SEQUENCE: 420

Glu Arg Xaa Glu Phe Asp Val Trp Asp Leu Tyr Phe Glu Ile Val Trp
1 5 10 15

<210> SEQ ID NO 421
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa is methioninesulfoxide
<220> FEATURE:
<221> NAME/KEY: MISC_FEATURE
<222> LOCATION: (16)..(16)
<223> OTHER INFORMATION: C-terminal amidation

<400> SEQUENCE: 421

Glu Arg Xaa Glu Phe Asp Val Trp Asp Leu Tyr Phe Glu Ile Val Trp
1 5 10 15

<210> SEQ ID NO 422
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (16)..(16)
<223> OTHER INFORMATION: C-terminal amidation

<400> SEQUENCE: 422

Glu Arg Gln Glu Phe Asp Val Trp Asp Leu Tyr Phe Glu Ile Val Trp
1 5 10 15

<210> SEQ ID NO 423
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa is propargylglycine
<220> FEATURE:
<221> NAME/KEY: MISC_FEATURE
<222> LOCATION: (16)..(16)
<223> OTHER INFORMATION: C-terminal amidation

<400> SEQUENCE: 423

Glu Arg Xaa Glu Phe Asp Val Trp Asp Leu Tyr Phe Glu Ile Val Trp
1 5 10 15

<210> SEQ ID NO 424
<211> LENGTH: 15
<212> TYPE: PRT
<213> ORGANISM: Artificial Sequence
<220> FEATURE:
<223> OTHER INFORMATION: Synthetic peptide
<220> FEATURE:

<221> NAME/KEY: MISC_FEATURE
<222> LOCATION: (1)..(1)
<223> OTHER INFORMATION: N-terminal ttds
<220> FEATURE:
<221> NAME/KEY: MISC_FEATURE
<222> LOCATION: (11)..(11)
<223> OTHER INFORMATION: Xaa is 2-thienylalanine
<220> FEATURE:
<221> NAME/KEY: MISC_FEATURE
<222> LOCATION: (15)..(15)
<223> OTHER INFORMATION: Linked to ttds, which terminates in an amide

<400> SEQUENCE: 424

Arg Met Glu Phe Asp Val Trp Asp Leu Tyr Xaa Glu Ile Val Trp
1 5 10 15

<210> SEQ ID NO 425
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal ttds
<220> FEATURE:
<221> NAME/KEY: MISC_FEATURE
<222> LOCATION: (11)..(11)
<223> OTHER INFORMATION: Xaa is 1-naphthyl-alanine
<220> FEATURE:
<221> NAME/KEY: MISC_FEATURE
<222> LOCATION: (15)..(15)
<223> OTHER INFORMATION: Linked to ttds, which terminates in an amide

<400> SEQUENCE: 425

Arg Met Glu Phe Asp Val Trp Asp Leu Tyr Xaa Glu Ile Val Trp
1 5 10 15

<210> SEQ ID NO 426
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal ttds
<220> FEATURE:
<221> NAME/KEY: MISC_FEATURE
<222> LOCATION: (11)..(11)
<223> OTHER INFORMATION: Xaa is homophenylalanine
<220> FEATURE:
<221> NAME/KEY: MISC_FEATURE
<222> LOCATION: (15)..(15)
<223> OTHER INFORMATION: Linked to ttds, which terminates in an amide

<400> SEQUENCE: 426

Arg Met Glu Phe Asp Val Trp Asp Leu Tyr Xaa Glu Ile Val Trp
1 5 10 15

<210> SEQ ID NO 427
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal ttds
<220> FEATURE:

```
<221> NAME/KEY: MISC_FEATURE
<222> LOCATION: (11)..(11)
<223> OTHER INFORMATION: Xaa is s-benzyl-L-cysteine
<220> FEATURE:
<221> NAME/KEY: MISC_FEATURE
<222> LOCATION: (15)..(15)
<223> OTHER INFORMATION: Linked to ttds, which terminates in an amide

<400> SEQUENCE: 427

Arg Met Glu Phe Asp Val Trp Asp Leu Tyr Xaa Glu Ile Val Trp
1               5                   10                  15


<210> SEQ ID NO 428
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal ttds
<220> FEATURE:
<221> NAME/KEY: MISC_FEATURE
<222> LOCATION: (11)..(11)
<223> OTHER INFORMATION: Xaa is cyclohexylalanine
<220> FEATURE:
<221> NAME/KEY: MISC_FEATURE
<222> LOCATION: (15)..(15)
<223> OTHER INFORMATION: Linked to ttds, which terminates in an amide

<400> SEQUENCE: 428

Arg Met Glu Phe Asp Val Trp Asp Leu Tyr Xaa Glu Ile Val Trp
1               5                   10                  15


<210> SEQ ID NO 429
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (10)..(10)
<223> OTHER INFORMATION: C-terminal amidation

<400> SEQUENCE: 429

Lys Trp Asp Leu Tyr Phe Glu Ile Val Trp
1               5                   10


<210> SEQ ID NO 430
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(2)
<223> OTHER INFORMATION: Lys linked to Trp via ttds linker
<220> FEATURE:
<221> NAME/KEY: MISC_FEATURE
<222> LOCATION: (10)..(10)
<223> OTHER INFORMATION: C-terminal amidation

<400> SEQUENCE: 430

Lys Trp Asp Leu Tyr Phe Glu Ile Val Trp
1               5                   10


<210> SEQ ID NO 431
<211> LENGTH: 9
```

<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Ile
<220> FEATURE:
<221> NAME/KEY: MISC_FEATURE
<222> LOCATION: (2)..(2)
<223> OTHER INFORMATION: D-Met
<220> FEATURE:
<221> NAME/KEY: MISC_FEATURE
<222> LOCATION: (3)..(3)
<223> OTHER INFORMATION: D-Phe
<220> FEATURE:
<221> NAME/KEY: MISC_FEATURE
<222> LOCATION: (4)..(4)
<223> OTHER INFORMATION: D-Trp
<220> FEATURE:
<221> NAME/KEY: MISC_FEATURE
<222> LOCATION: (5)..(5)
<223> OTHER INFORMATION: D-Tyr
<220> FEATURE:
<221> NAME/KEY: MISC_FEATURE
<222> LOCATION: (6)..(6)
<223> OTHER INFORMATION: D-Asp
<220> FEATURE:
<221> NAME/KEY: MISC_FEATURE
<222> LOCATION: (7)..(7)
<223> OTHER INFORMATION: D-Cys
<220> FEATURE:
<221> NAME/KEY: MISC_FEATURE
<222> LOCATION: (8)..(8)
<223> OTHER INFORMATION: D-Tyr
<220> FEATURE:
<221> NAME/KEY: MISC_FEATURE
<222> LOCATION: (9)..(9)
<223> OTHER INFORMATION: D-Glu

<400> SEQUENCE: 431

Ile Met Phe Trp Tyr Asp Cys Tyr Glu
1               5

<210> SEQ ID NO 432
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Cys
<220> FEATURE:
<221> NAME/KEY: MISC_FEATURE
<222> LOCATION: (2)..(2)
<223> OTHER INFORMATION: D-Ile
<220> FEATURE:
<221> NAME/KEY: MISC_FEATURE
<222> LOCATION: (3)..(3)
<223> OTHER INFORMATION: D-Met
<220> FEATURE:
<221> NAME/KEY: MISC_FEATURE
<222> LOCATION: (4)..(4)
<223> OTHER INFORMATION: D-Phe
<220> FEATURE:
<221> NAME/KEY: MISC_FEATURE
<222> LOCATION: (5)..(5)
<223> OTHER INFORMATION: D-Trp
<220> FEATURE:
<221> NAME/KEY: MISC_FEATURE
<222> LOCATION: (6)..(6)
<223> OTHER INFORMATION: D-Tyr
<220> FEATURE:
<221> NAME/KEY: MISC_FEATURE
<222> LOCATION: (7)..(7)
<223> OTHER INFORMATION: D-Asp
<220> FEATURE:
<221> NAME/KEY: MISC_FEATURE
<222> LOCATION: (8)..(8)
<223> OTHER INFORMATION: D-Cys
<220> FEATURE:
<221> NAME/KEY: MISC_FEATURE
<222> LOCATION: (9)..(9)
<223> OTHER INFORMATION: D-Tyr
<220> FEATURE:
<221> NAME/KEY: MISC_FEATURE
<222> LOCATION: (10)..(10)
<223> OTHER INFORMATION: D-Glu

<400> SEQUENCE: 432

```
Cys Ile Met Phe Trp Tyr Asp Cys Tyr Glu
1               5                   10
```

<210> SEQ ID NO 433
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is D-Cys, D-Ser, D-Tyr, D-Ile, D-Pen, Cys, D-Thr, D-Nva, D-Nle, D-Lys or is absent
<220> FEATURE:
<221> NAME/KEY: MISC_FEATURE
<222> LOCATION: (2)..(2)
<223> OTHER INFORMATION: Xaa is D-Ile, D-Tyr, D-Trp or D-Asp
<220> FEATURE:
<221> NAME/KEY: MISC_FEATURE
<222> LOCATION: (3)..(3)
<223> OTHER INFORMATION: Xaa is D- Cys or D-Met
<220> FEATURE:
<221> NAME/KEY: MISC_FEATURE
<222> LOCATION: (4)..(4)
<223> OTHER INFORMATION: Xaa is D-Phe, D-Thr, D-Val or D-Cys
<220> FEATURE:
<221> NAME/KEY: MISC_FEATURE
<222> LOCATION: (5)..(5)
<223> OTHER INFORMATION: Xaa is D-Trp or D-Cys
<220> FEATURE:
<221> NAME/KEY: MISC_FEATURE
<222> LOCATION: (6)..(6)
<223> OTHER INFORMATION: Xaa is D-Tyr or D-Cys
<220> FEATURE:
<221> NAME/KEY: MISC_FEATURE
<222> LOCATION: (7)..(7)
<223> OTHER INFORMATION: Xaa is D-Asp, D-Glu or D-Phe
<220> FEATURE:
<221> NAME/KEY: MISC_FEATURE
<222> LOCATION: (8)..(8)
<223> OTHER INFORMATION: Xaa is D-Cys, D-Glu, D-Phe, D-Tyr or D-Asp
<220> FEATURE:
<221> NAME/KEY: MISC_FEATURE
<222> LOCATION: (9)..(9)
<223> OTHER INFORMATION: Xaa is D-Tyr or D-Trp
<220> FEATURE:
<221> NAME/KEY: MISC_FEATURE
<222> LOCATION: (10)..(10)
<223> OTHER INFORMATION: Xaa is D-Glu or D-Ile

<400> SEQUENCE: 433

```
Xaa Xaa Xaa Xaa Xaa Xaa Xaa Xaa Xaa Xaa
1               5                   10
```

<210> SEQ ID NO 434
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is D-Cys, Cys, D-Pen or D-Ser
<220> FEATURE:
<221> NAME/KEY: MISC_FEATURE
<222> LOCATION: (2)..(2)
<223> OTHER INFORMATION: Xaa is D-Ile, D-Tyr or D-Trp
<220> FEATURE:
<221> NAME/KEY: MISC_FEATURE
<222> LOCATION: (3)..(3)
<223> OTHER INFORMATION: Xaa is D- Cys or D-Met
<220> FEATURE:
<221> NAME/KEY: MISC_FEATURE
<222> LOCATION: (4)..(4)
<223> OTHER INFORMATION: Xaa is D-Phe, D-Thr or D-Val
<220> FEATURE:
<221> NAME/KEY: MISC_FEATURE
<222> LOCATION: (5)..(5)
<223> OTHER INFORMATION: D-Trp
<220> FEATURE:
<221> NAME/KEY: MISC_FEATURE
<222> LOCATION: (6)..(6)
<223> OTHER INFORMATION: D-Tyr
<220> FEATURE:
<221> NAME/KEY: MISC_FEATURE
<222> LOCATION: (7)..(7)
<223> OTHER INFORMATION: D-Asp
<220> FEATURE:
<221> NAME/KEY: MISC_FEATURE
<222> LOCATION: (8)..(8)
<223> OTHER INFORMATION: Xaa is D-Cys or D-Glu
<220> FEATURE:
<221> NAME/KEY: MISC_FEATURE
<222> LOCATION: (9)..(9)
<223> OTHER INFORMATION: D-Tyr
<220> FEATURE:
<221> NAME/KEY: MISC_FEATURE
<222> LOCATION: (10)..(10)
<223> OTHER INFORMATION: D-Glu

<400> SEQUENCE: 434

```
Xaa Xaa Xaa Xaa Trp Tyr Asp Xaa Tyr Glu
1               5                   10
```

<210> SEQ ID NO 435
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is D-Cys, Cys or D-Pen
<220> FEATURE:
<221> NAME/KEY: MISC_FEATURE
<222> LOCATION: (2)..(2)
<223> OTHER INFORMATION: Xaa is D-Ile or D-Tyr
<220> FEATURE:
<221> NAME/KEY: MISC_FEATURE
<222> LOCATION: (3)..(3)
<223> OTHER INFORMATION: D-Met
<220> FEATURE:
<221> NAME/KEY: MISC_FEATURE
<222> LOCATION: (4)..(4)
<223> OTHER INFORMATION: Xaa is D-Phe, D-Thr or D-Val
<220> FEATURE:
<221> NAME/KEY: MISC_FEATURE
<222> LOCATION: (5)..(5)
<223> OTHER INFORMATION: D-Trp
<220> FEATURE:
<221> NAME/KEY: MISC_FEATURE
<222> LOCATION: (6)..(6)
<223> OTHER INFORMATION: D-Tyr
<220> FEATURE:
<221> NAME/KEY: MISC_FEATURE
<222> LOCATION: (7)..(7)
<223> OTHER INFORMATION: D-Asp
<220> FEATURE:
<221> NAME/KEY: MISC_FEATURE
<222> LOCATION: (8)..(8)
<223> OTHER INFORMATION: Xaa is D-Cys or D-Glu
<220> FEATURE:
<221> NAME/KEY: MISC_FEATURE
<222> LOCATION: (9)..(9)
<223> OTHER INFORMATION: D-Tyr
<220> FEATURE:
<221> NAME/KEY: MISC_FEATURE
<222> LOCATION: (10)..(10)
<223> OTHER INFORMATION: D-Glu

<400> SEQUENCE: 435

Xaa Xaa Met Xaa Trp Tyr Asp Xaa Tyr Glu
1 5 10

<210> SEQ ID NO 436
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (1)..(1)
<223> OTHER INFORMATION: D-Cys
<220> FEATURE:
<221> NAME/KEY: MISC_FEATURE
<222> LOCATION: (2)..(2)
<223> OTHER INFORMATION: D-Ile
<220> FEATURE:
<221> NAME/KEY: MISC_FEATURE
<222> LOCATION: (3)..(3)
<223> OTHER INFORMATION: D-Met
<220> FEATURE:
<221> NAME/KEY: MISC_FEATURE
<222> LOCATION: (4)..(4)
<223> OTHER INFORMATION: D-Phe
<220> FEATURE:
<221> NAME/KEY: MISC_FEATURE
<222> LOCATION: (5)..(5)
<223> OTHER INFORMATION: D-Trp
<220> FEATURE:
<221> NAME/KEY: MISC_FEATURE
<222> LOCATION: (6)..(6)
<223> OTHER INFORMATION: D-Tyr
<220> FEATURE:
<221> NAME/KEY: MISC_FEATURE
<222> LOCATION: (7)..(7)
<223> OTHER INFORMATION: D-Asp
<220> FEATURE:
<221> NAME/KEY: MISC_FEATURE
<222> LOCATION: (8)..(8)
<223> OTHER INFORMATION: D-Glu
<220> FEATURE:
<221> NAME/KEY: MISC_FEATURE
<222> LOCATION: (9)..(9)
<223> OTHER INFORMATION: D-Tyr
<220> FEATURE:
<221> NAME/KEY: MISC_FEATURE
<222> LOCATION: (10)..(10)
<223> OTHER INFORMATION: D-Glu
<220> FEATURE:
<221> NAME/KEY: MISC_FEATURE
<222> LOCATION: (10)..(10)
<223> OTHER INFORMATION: C-terminal amidation

<400> SEQUENCE: 436

Cys Ile Met Phe Trp Tyr Asp Glu Tyr Glu
1 5 10

<210> SEQ ID NO 437
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (1)..(1)
<223> OTHER INFORMATION: D-Cys
<220> FEATURE:
<221> NAME/KEY: DISULFID
<222> LOCATION: (1)..(1)
<223> OTHER INFORMATION: D-Cys linked to identical peptide (SEQ ID NO: 436) via disulfide bond to form homodimer
<220> FEATURE:
<221> NAME/KEY: MISC_FEATURE
<222> LOCATION: (2)..(2)
<223> OTHER INFORMATION: D-Ile
<220> FEATURE:
<221> NAME/KEY: MISC_FEATURE
<222> LOCATION: (3)..(3)
<223> OTHER INFORMATION: D-Met
<220> FEATURE:
<221> NAME/KEY: MISC_FEATURE
<222> LOCATION: (4)..(4)
<223> OTHER INFORMATION: D-Phe
<220> FEATURE:
<221> NAME/KEY: MISC_FEATURE
<222> LOCATION: (5)..(5)
<223> OTHER INFORMATION: D-Trp
<220> FEATURE:
<221> NAME/KEY: MISC_FEATURE
<222> LOCATION: (6)..(6)
<223> OTHER INFORMATION: D-Tyr
<220> FEATURE:
<221> NAME/KEY: MISC_FEATURE
<222> LOCATION: (7)..(7)
<223> OTHER INFORMATION: D-Asp
<220> FEATURE:
<221> NAME/KEY: MISC_FEATURE
<222> LOCATION: (8)..(8)
<223> OTHER INFORMATION: D-Glu
<220> FEATURE:
<221> NAME/KEY: MISC_FEATURE
<222> LOCATION: (9)..(9)
<223> OTHER INFORMATION: D-Tyr
<220> FEATURE:
<221> NAME/KEY: MISC_FEATURE
<222> LOCATION: (10)..(10)
<223> OTHER INFORMATION: D-Glu
<220> FEATURE:
<221> NAME/KEY: MISC_FEATURE
<222> LOCATION: (10)..(10)
<223> OTHER INFORMATION: C-terminal amidation

<400> SEQUENCE: 437

Cys Ile Met Phe Trp Tyr Asp Glu Tyr Glu
1 5 10

<210> SEQ ID NO 438
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylated 4,7,10-trioxa-1,13-
      tridecanediamine (TTDS) linker
<220> FEATURE:
<221> NAME/KEY: MISC_FEATURE
<222> LOCATION: (1)..(1)
<223> OTHER INFORMATION: D-Cys
<220> FEATURE:
<221> NAME/KEY: DISULFID
<222> LOCATION: (1)..(8)
<223> OTHER INFORMATION: Cyclic peptide - Intramolecular disulfide bond
<220> FEATURE:
<221> NAME/KEY: MISC_FEATURE
<222> LOCATION: (2)..(2)
<223> OTHER INFORMATION: D-Tyr
<220> FEATURE:
<221> NAME/KEY: MISC_FEATURE
<222> LOCATION: (3)..(3)
<223> OTHER INFORMATION: D-Met
<220> FEATURE:
<221> NAME/KEY: MISC_FEATURE
<222> LOCATION: (4)..(4)
<223> OTHER INFORMATION: D-Phe
<220> FEATURE:
<221> NAME/KEY: MISC_FEATURE
<222> LOCATION: (5)..(5)
<223> OTHER INFORMATION: D-Trp
<220> FEATURE:
<221> NAME/KEY: MISC_FEATURE
<222> LOCATION: (6)..(6)
<223> OTHER INFORMATION: D-Tyr
<220> FEATURE:
<221> NAME/KEY: MISC_FEATURE
<222> LOCATION: (7)..(7)
<223> OTHER INFORMATION: D-Asp
<220> FEATURE:
<221> NAME/KEY: MISC_FEATURE
<222> LOCATION: (8)..(8)
<223> OTHER INFORMATION: D-Cys
<220> FEATURE:
<221> NAME/KEY: MISC_FEATURE
<222> LOCATION: (9)..(9)
<223> OTHER INFORMATION: D-Tyr
<220> FEATURE:
<221> NAME/KEY: MISC_FEATURE
<222> LOCATION: (10)..(10)
<223> OTHER INFORMATION: D-Glu
<220> FEATURE:
<221> NAME/KEY: MISC_FEATURE
<222> LOCATION: (10)..(10)
<223> OTHER INFORMATION: C-terminal amidation

<400> SEQUENCE: 438

Cys Tyr Met Phe Trp Tyr Asp Cys Tyr Glu
1               5                   10

<210> SEQ ID NO 439
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(2)
<223> OTHER INFORMATION: Lys linked to D-Cys via 4,7,10-trioxa-1,13-
      tridecanediamine (TTDS) linker
<220> FEATURE:
<221> NAME/KEY: MISC_FEATURE
<222> LOCATION: (2)..(2)
<223> OTHER INFORMATION: D-Cys
<220> FEATURE:
<221> NAME/KEY: DISULFID
<222> LOCATION: (2)..(9)
<223> OTHER INFORMATION: Cyclic peptide - Intramolecular disulfide bond
<220> FEATURE:
<221> NAME/KEY: MISC_FEATURE
<222> LOCATION: (3)..(3)
<223> OTHER INFORMATION: D-Tyr
<220> FEATURE:
<221> NAME/KEY: MISC_FEATURE
<222> LOCATION: (4)..(4)
<223> OTHER INFORMATION: D-Met
<220> FEATURE:
<221> NAME/KEY: MISC_FEATURE
<222> LOCATION: (5)..(5)
<223> OTHER INFORMATION: D-Phe
<220> FEATURE:
<221> NAME/KEY: MISC_FEATURE
<222> LOCATION: (6)..(6)
<223> OTHER INFORMATION: D-Trp
<220> FEATURE:
<221> NAME/KEY: MISC_FEATURE
<222> LOCATION: (7)..(7)
<223> OTHER INFORMATION: D-Tyr
<220> FEATURE:
<221> NAME/KEY: MISC_FEATURE
<222> LOCATION: (8)..(8)
<223> OTHER INFORMATION: D-Asp
<220> FEATURE:
<221> NAME/KEY: MISC_FEATURE
<222> LOCATION: (9)..(9)
<223> OTHER INFORMATION: D-Cys
<220> FEATURE:
<221> NAME/KEY: MISC_FEATURE
<222> LOCATION: (10)..(10)
<223> OTHER INFORMATION: D-Tyr
<220> FEATURE:
<221> NAME/KEY: MISC_FEATURE
<222> LOCATION: (11)..(11)
<223> OTHER INFORMATION: D-Glu

<400> SEQUENCE: 439

Lys Cys Tyr Met Phe Trp Tyr Asp Cys Tyr Glu
1               5                   10

<210> SEQ ID NO 440
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (1)..(1)
<223> OTHER INFORMATION: D-Cys
<220> FEATURE:
<221> NAME/KEY: MISC_FEATURE
<222> LOCATION: (2)..(2)
<223> OTHER INFORMATION: D-Ile
<220> FEATURE:
<221> NAME/KEY: MISC_FEATURE
<222> LOCATION: (3)..(3)
<223> OTHER INFORMATION: D-Met
<220> FEATURE:
<221> NAME/KEY: MISC_FEATURE
<222> LOCATION: (4)..(4)
<223> OTHER INFORMATION: D-Thr
<220> FEATURE:
<221> NAME/KEY: MISC_FEATURE
<222> LOCATION: (5)..(5)
<223> OTHER INFORMATION: D-Trp
<220> FEATURE:
<221> NAME/KEY: MISC_FEATURE
<222> LOCATION: (6)..(6)
<223> OTHER INFORMATION: D-Tyr
<220> FEATURE:
<221> NAME/KEY: MISC_FEATURE
<222> LOCATION: (7)..(7)
<223> OTHER INFORMATION: D-Asp
<220> FEATURE:
<221> NAME/KEY: MISC_FEATURE
<222> LOCATION: (8)..(8)
<223> OTHER INFORMATION: D-Cys
<220> FEATURE:
<221> NAME/KEY: MISC_FEATURE
<222> LOCATION: (9)..(9)
<223> OTHER INFORMATION: D-Tyr
<220> FEATURE:
<221> NAME/KEY: MISC_FEATURE
<222> LOCATION: (10)..(10)
<223> OTHER INFORMATION: D-Glu
<220> FEATURE:
<221> NAME/KEY: MISC_FEATURE
<222> LOCATION: (10)..(10)
<223> OTHER INFORMATION: C-terminal amidation

<400> SEQUENCE: 440

Cys Ile Met Thr Trp Tyr Asp Cys Tyr Glu
1               5                   10

<210> SEQ ID NO 441
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (1)..(1)
<223> OTHER INFORMATION: D-Cys
<220> FEATURE:
<221> NAME/KEY: MISC_FEATURE
<222> LOCATION: (2)..(2)
<223> OTHER INFORMATION: D-Ile
<220> FEATURE:
<221> NAME/KEY: MISC_FEATURE
<222> LOCATION: (3)..(3)
<223> OTHER INFORMATION: D-Met
<220> FEATURE:
<221> NAME/KEY: MISC_FEATURE
<222> LOCATION: (4)..(4)
<223> OTHER INFORMATION: D-Val
<220> FEATURE:
<221> NAME/KEY: MISC_FEATURE
<222> LOCATION: (5)..(5)
<223> OTHER INFORMATION: D-Trp
<220> FEATURE:
<221> NAME/KEY: MISC_FEATURE
<222> LOCATION: (6)..(6)
<223> OTHER INFORMATION: D-Tyr
<220> FEATURE:
<221> NAME/KEY: MISC_FEATURE
<222> LOCATION: (7)..(7)
<223> OTHER INFORMATION: D-Asp
<220> FEATURE:
<221> NAME/KEY: MISC_FEATURE
<222> LOCATION: (8)..(8)
<223> OTHER INFORMATION: D-Cys
<220> FEATURE:
<221> NAME/KEY: MISC_FEATURE
<222> LOCATION: (9)..(9)
<223> OTHER INFORMATION: D-Tyr
<220> FEATURE:
<221> NAME/KEY: MISC_FEATURE
<222> LOCATION: (10)..(10)
<223> OTHER INFORMATION: D-Glu
<220> FEATURE:
<221> NAME/KEY: MISC_FEATURE
<222> LOCATION: (10)..(10)
<223> OTHER INFORMATION: C-terminal amidation

<400> SEQUENCE: 441

Cys Ile Met Val Trp Tyr Asp Cys Tyr Glu
1 5 10

<210> SEQ ID NO 442
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Cys
<220> FEATURE:
<221> NAME/KEY: MISC_FEATURE
<222> LOCATION: (2)..(2)
<223> OTHER INFORMATION: D-Tyr
<220> FEATURE:
<221> NAME/KEY: MISC_FEATURE
<222> LOCATION: (3)..(3)
<223> OTHER INFORMATION: D-Met
<220> FEATURE:
<221> NAME/KEY: MISC_FEATURE
<222> LOCATION: (4)..(4)
<223> OTHER INFORMATION: D-Phe
<220> FEATURE:
<221> NAME/KEY: MISC_FEATURE
<222> LOCATION: (5)..(5)
<223> OTHER INFORMATION: D-Trp
<220> FEATURE:
<221> NAME/KEY: MISC_FEATURE
<222> LOCATION: (6)..(6)
<223> OTHER INFORMATION: D-Tyr
<220> FEATURE:
<221> NAME/KEY: MISC_FEATURE
<222> LOCATION: (7)..(7)
<223> OTHER INFORMATION: D-Asp
<220> FEATURE:
<221> NAME/KEY: MISC_FEATURE
<222> LOCATION: (8)..(8)
<223> OTHER INFORMATION: D-Cys
<220> FEATURE:
<221> NAME/KEY: MISC_FEATURE
<222> LOCATION: (9)..(9)
<223> OTHER INFORMATION: D-Tyr
<220> FEATURE:
<221> NAME/KEY: MISC_FEATURE
<222> LOCATION: (10)..(10)
<223> OTHER INFORMATION: D-Glu

<400> SEQUENCE: 442

Cys Tyr Met Phe Trp Tyr Asp Cys Tyr Glu
1 5 10

<210> SEQ ID NO 443
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (1)..(1)
<223> OTHER INFORMATION: D-Cys
<220> FEATURE:
<221> NAME/KEY: DISULFID
<222> LOCATION: (1)..(8)
<223> OTHER INFORMATION: Cyclic peptide - Intramolecular disulfide bond
<220> FEATURE:
<221> NAME/KEY: MISC_FEATURE
<222> LOCATION: (2)..(2)

<223> OTHER INFORMATION: D-Tyr
<220> FEATURE:
<221> NAME/KEY: MISC_FEATURE
<222> LOCATION: (3)..(3)
<223> OTHER INFORMATION: D-Met
<220> FEATURE:
<221> NAME/KEY: MISC_FEATURE
<222> LOCATION: (4)..(4)
<223> OTHER INFORMATION: D-Phe
<220> FEATURE:
<221> NAME/KEY: MISC_FEATURE
<222> LOCATION: (5)..(5)
<223> OTHER INFORMATION: D-Trp
<220> FEATURE:
<221> NAME/KEY: MISC_FEATURE
<222> LOCATION: (6)..(6)
<223> OTHER INFORMATION: D-Tyr
<220> FEATURE:
<221> NAME/KEY: MISC_FEATURE
<222> LOCATION: (7)..(7)
<223> OTHER INFORMATION: D-Asp
<220> FEATURE:
<221> NAME/KEY: MISC_FEATURE
<222> LOCATION: (8)..(8)
<223> OTHER INFORMATION: D-Cys
<220> FEATURE:
<221> NAME/KEY: MISC_FEATURE
<222> LOCATION: (9)..(9)
<223> OTHER INFORMATION: D-Tyr
<220> FEATURE:
<221> NAME/KEY: MISC_FEATURE
<222> LOCATION: (10)..(10)
<223> OTHER INFORMATION: D-Glu
<220> FEATURE:
<221> NAME/KEY: MISC_FEATURE
<222> LOCATION: (11)..(11)
<223> OTHER INFORMATION: C-terminal amidation

<400> SEQUENCE: 443

```
Cys Tyr Met Phe Trp Tyr Asp Cys Tyr Glu Gly
1               5                   10
```

<210> SEQ ID NO 444
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (1)..(1)
<223> OTHER INFORMATION: Xaa is D-penicillamine (D-Pen)
<220> FEATURE:
<221> NAME/KEY: MISC_FEATURE
<222> LOCATION: (2)..(2)
<223> OTHER INFORMATION: D-Ile
<220> FEATURE:
<221> NAME/KEY: MISC_FEATURE
<222> LOCATION: (3)..(3)
<223> OTHER INFORMATION: D-Met
<220> FEATURE:
<221> NAME/KEY: MISC_FEATURE
<222> LOCATION: (4)..(4)
<223> OTHER INFORMATION: D-Phe
<220> FEATURE:
<221> NAME/KEY: MISC_FEATURE
<222> LOCATION: (5)..(5)
<223> OTHER INFORMATION: D-Trp
<220> FEATURE:
<221> NAME/KEY: MISC_FEATURE
<222> LOCATION: (6)..(6)
<223> OTHER INFORMATION: D-Tyr
<220> FEATURE:

<221> NAME/KEY: MISC_FEATURE
<222> LOCATION: (7)..(7)
<223> OTHER INFORMATION: D-Asp
<220> FEATURE:
<221> NAME/KEY: MISC_FEATURE
<222> LOCATION: (8)..(8)
<223> OTHER INFORMATION: D-Glu
<220> FEATURE:
<221> NAME/KEY: MISC_FEATURE
<222> LOCATION: (9)..(9)
<223> OTHER INFORMATION: D-Tyr
<220> FEATURE:
<221> NAME/KEY: MISC_FEATURE
<222> LOCATION: (10)..(10)
<223> OTHER INFORMATION: D-Glu
<220> FEATURE:
<221> NAME/KEY: MISC_FEATURE
<222> LOCATION: (10)..(10)
<223> OTHER INFORMATION: C-terminal amidation

<400> SEQUENCE: 444

```
Xaa Ile Met Phe Trp Tyr Asp Glu Tyr Glu
1               5                   10
```

<210> SEQ ID NO 445
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Ile
<220> FEATURE:
<221> NAME/KEY: MISC_FEATURE
<222> LOCATION: (1)..(1)
<223> OTHER INFORMATION: D-Ile linked to identical peptide (SEQ ID NO: 476) via carboxyl of -O-CH2-CH2-O-CH2-CO- to form homodimer
<220> FEATURE:
<221> NAME/KEY: MISC_FEATURE
<222> LOCATION: (2)..(2)
<223> OTHER INFORMATION: D-Met
<220> FEATURE:
<221> NAME/KEY: MISC_FEATURE
<222> LOCATION: (3)..(3)
<223> OTHER INFORMATION: D-Phe
<220> FEATURE:
<221> NAME/KEY: MISC_FEATURE
<222> LOCATION: (4)..(4)
<223> OTHER INFORMATION: D-Trp
<220> FEATURE:
<221> NAME/KEY: MISC_FEATURE
<222> LOCATION: (5)..(5)
<223> OTHER INFORMATION: D-Tyr
<220> FEATURE:
<221> NAME/KEY: MISC_FEATURE
<222> LOCATION: (6)..(6)
<223> OTHER INFORMATION: D-Asp
<220> FEATURE:
<221> NAME/KEY: MISC_FEATURE
<222> LOCATION: (7)..(7)
<223> OTHER INFORMATION: D-Glu
<220> FEATURE:
<221> NAME/KEY: MISC_FEATURE
<222> LOCATION: (8)..(8)
<223> OTHER INFORMATION: D-Tyr
<220> FEATURE:
<221> NAME/KEY: MISC_FEATURE
<222> LOCATION: (9)..(9)
<223> OTHER INFORMATION: D-Glu
<220> FEATURE:
<221> NAME/KEY: MISC_FEATURE
<222> LOCATION: (9)..(9)
<223> OTHER INFORMATION: C-terminal amidation

<400> SEQUENCE: 445

Ile Met Phe Trp Tyr Asp Glu Tyr Glu
1 5

<210> SEQ ID NO 446
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Ile
<220> FEATURE:
<221> NAME/KEY: MISC_FEATURE
<222> LOCATION: (1)..(1)
<223> OTHER INFORMATION: D-Ile linked to identical peptide (SEQ ID NO: 476) via carboxyl of 3, 5-pyridinedicarboxylic acid to form homodimer
<220> FEATURE:
<221> NAME/KEY: MISC_FEATURE
<222> LOCATION: (2)..(2)
<223> OTHER INFORMATION: D-Met
<220> FEATURE:
<221> NAME/KEY: MISC_FEATURE
<222> LOCATION: (3)..(3)
<223> OTHER INFORMATION: D-Phe
<220> FEATURE:
<221> NAME/KEY: MISC_FEATURE
<222> LOCATION: (4)..(4)
<223> OTHER INFORMATION: D-Trp
<220> FEATURE:
<221> NAME/KEY: MISC_FEATURE
<222> LOCATION: (5)..(5)
<223> OTHER INFORMATION: D-Tyr
<220> FEATURE:
<221> NAME/KEY: MISC_FEATURE
<222> LOCATION: (6)..(6)
<223> OTHER INFORMATION: D-Asp
<220> FEATURE:
<221> NAME/KEY: MISC_FEATURE
<222> LOCATION: (7)..(7)
<223> OTHER INFORMATION: D-Glu
<220> FEATURE:
<221> NAME/KEY: MISC_FEATURE
<222> LOCATION: (8)..(8)
<223> OTHER INFORMATION: D-Tyr
<220> FEATURE:
<221> NAME/KEY: MISC_FEATURE
<222> LOCATION: (9)..(9)
<223> OTHER INFORMATION: D-Glu
<220> FEATURE:
<221> NAME/KEY: MISC_FEATURE
<222> LOCATION: (9)..(9)
<223> OTHER INFORMATION: C-terminal amidation

<400> SEQUENCE: 446

Ile Met Phe Trp Tyr Asp Glu Tyr Glu
1 5

<210> SEQ ID NO 447
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(2)
<223> OTHER INFORMATION: Glu linked to D-Cys via 4,7,10-trioxa-1,13-tridecanediamine (TTDS) linker
<220> FEATURE:
<221> NAME/KEY: MISC_FEATURE
<222> LOCATION: (2)..(2)
<223> OTHER INFORMATION: D-Cys
<220> FEATURE:
<221> NAME/KEY: DISULFID
<222> LOCATION: (2)..(9)
<223> OTHER INFORMATION: Cyclic peptide - Intramolecular disulfide bond
<220> FEATURE:
<221> NAME/KEY: MISC_FEATURE
<222> LOCATION: (3)..(3)
<223> OTHER INFORMATION: D-Tyr
<220> FEATURE:
<221> NAME/KEY: MISC_FEATURE
<222> LOCATION: (4)..(4)
<223> OTHER INFORMATION: D-Met
<220> FEATURE:
<221> NAME/KEY: MISC_FEATURE
<222> LOCATION: (5)..(5)
<223> OTHER INFORMATION: D-Phe
<220> FEATURE:
<221> NAME/KEY: MISC_FEATURE
<222> LOCATION: (6)..(6)
<223> OTHER INFORMATION: D-Trp
<220> FEATURE:
<221> NAME/KEY: MISC_FEATURE
<222> LOCATION: (7)..(7)
<223> OTHER INFORMATION: D-Tyr
<220> FEATURE:
<221> NAME/KEY: MISC_FEATURE
<222> LOCATION: (8)..(8)
<223> OTHER INFORMATION: D-Asp
<220> FEATURE:
<221> NAME/KEY: MISC_FEATURE
<222> LOCATION: (9)..(9)
<223> OTHER INFORMATION: D-Cys
<220> FEATURE:
<221> NAME/KEY: MISC_FEATURE
<222> LOCATION: (10)..(10)
<223> OTHER INFORMATION: D-Tyr
<220> FEATURE:
<221> NAME/KEY: MISC_FEATURE
<222> LOCATION: (11)..(11)
<223> OTHER INFORMATION: D-Glu

<400> SEQUENCE: 447

Glu Cys Tyr Met Phe Trp Tyr Asp Cys Tyr Glu
1               5                   10

<210> SEQ ID NO 448
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (1)..(1)
<223> OTHER INFORMATION: D-Cys
<220> FEATURE:
<221> NAME/KEY: DISULFID
<222> LOCATION: (1)..(8)
<223> OTHER INFORMATION: Cyclic peptide - Intramolecular disulfide bond
<220> FEATURE:
<221> NAME/KEY: MISC_FEATURE
<222> LOCATION: (2)..(2)
<223> OTHER INFORMATION: D-Tyr
<220> FEATURE:
<221> NAME/KEY: MISC_FEATURE
<222> LOCATION: (3)..(3)
<223> OTHER INFORMATION: D-Met
<220> FEATURE:
<221> NAME/KEY: MISC_FEATURE
<222> LOCATION: (4)..(4)
<223> OTHER INFORMATION: D-Phe
<220> FEATURE:
<221> NAME/KEY: MISC_FEATURE
<222> LOCATION: (5)..(5)
<223> OTHER INFORMATION: D-Trp
<220> FEATURE:
<221> NAME/KEY: MISC_FEATURE
<222> LOCATION: (6)..(6)
<223> OTHER INFORMATION: D-Tyr
<220> FEATURE:
<221> NAME/KEY: MISC_FEATURE
<222> LOCATION: (7)..(7)
<223> OTHER INFORMATION: D-Asp
<220> FEATURE:
<221> NAME/KEY: MISC_FEATURE
<222> LOCATION: (8)..(8)
<223> OTHER INFORMATION: D-Cys
<220> FEATURE:
<221> NAME/KEY: MISC_FEATURE
<222> LOCATION: (9)..(9)
<223> OTHER INFORMATION: D-Tyr
<220> FEATURE:
<221> NAME/KEY: MISC_FEATURE
<222> LOCATION: (10)..(10)
<223> OTHER INFORMATION: D-Glu

<400> SEQUENCE: 448

Cys Tyr Met Phe Trp Tyr Asp Cys Tyr Glu Lys
1 5 10

<210> SEQ ID NO 449
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (1)..(1)
<223> OTHER INFORMATION: D-Cys
<220> FEATURE:
<221> NAME/KEY: DISULFID
<222> LOCATION: (1)..(8)
<223> OTHER INFORMATION: Cyclic peptide - Intramolecular disulfide bond
<220> FEATURE:
<221> NAME/KEY: MISC_FEATURE
<222> LOCATION: (2)..(2)
<223> OTHER INFORMATION: D-Tyr
<220> FEATURE:
<221> NAME/KEY: MISC_FEATURE
<222> LOCATION: (3)..(3)
<223> OTHER INFORMATION: D-Met
<220> FEATURE:
<221> NAME/KEY: MISC_FEATURE
<222> LOCATION: (4)..(4)
<223> OTHER INFORMATION: D-Phe
<220> FEATURE:
<221> NAME/KEY: MISC_FEATURE
<222> LOCATION: (5)..(5)
<223> OTHER INFORMATION: D-Trp
<220> FEATURE:
<221> NAME/KEY: MISC_FEATURE
<222> LOCATION: (6)..(6)
<223> OTHER INFORMATION: D-Tyr
<220> FEATURE:
<221> NAME/KEY: MISC_FEATURE
<222> LOCATION: (7)..(7)
<223> OTHER INFORMATION: D-Asp
<220> FEATURE:
<221> NAME/KEY: MISC_FEATURE
<222> LOCATION: (8)..(8)
<223> OTHER INFORMATION: D-Cys
<220> FEATURE:
<221> NAME/KEY: MISC_FEATURE
<222> LOCATION: (9)..(9)
<223> OTHER INFORMATION: D-Tyr
<220> FEATURE:
<221> NAME/KEY: MISC_FEATURE
<222> LOCATION: (10)..(10)
<223> OTHER INFORMATION: D-Glu
<220> FEATURE:
<221> NAME/KEY: MISC_FEATURE
<222> LOCATION: (10)..(11)
<223> OTHER INFORMATION: D-Glu linked to Lys via 4,7,10-trioxa-1,13-
tridecanediamine (TTDS) linker

<400> SEQUENCE: 449

Cys Tyr Met Phe Trp Tyr Asp Cys Tyr Glu Lys
1 5 10

<210> SEQ ID NO 450
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (1)..(1)
<223> OTHER INFORMATION: D-Ser
<220> FEATURE:
<221> NAME/KEY: MISC_FEATURE
<222> LOCATION: (2)..(2)
<223> OTHER INFORMATION: D-Ile
<220> FEATURE:
<221> NAME/KEY: MISC_FEATURE
<222> LOCATION: (3)..(3)
<223> OTHER INFORMATION: D-Met
<220> FEATURE:
<221> NAME/KEY: MISC_FEATURE
<222> LOCATION: (4)..(4)
<223> OTHER INFORMATION: D-Phe
<220> FEATURE:
<221> NAME/KEY: MISC_FEATURE
<222> LOCATION: (5)..(5)
<223> OTHER INFORMATION: D-Trp
<220> FEATURE:
<221> NAME/KEY: MISC_FEATURE
<222> LOCATION: (6)..(6)
<223> OTHER INFORMATION: D-Tyr
<220> FEATURE:
<221> NAME/KEY: MISC_FEATURE
<222> LOCATION: (7)..(7)
<223> OTHER INFORMATION: D-Asp
<220> FEATURE:
<221> NAME/KEY: MISC_FEATURE
<222> LOCATION: (8)..(8)
<223> OTHER INFORMATION: D-Glu
<220> FEATURE:
<221> NAME/KEY: MISC_FEATURE
<222> LOCATION: (9)..(9)
<223> OTHER INFORMATION: D-Tyr
<220> FEATURE:
<221> NAME/KEY: MISC_FEATURE
<222> LOCATION: (10)..(10)
<223> OTHER INFORMATION: D-Glu
<220> FEATURE:
<221> NAME/KEY: MISC_FEATURE
<222> LOCATION: (10)..(10)
<223> OTHER INFORMATION: C-terminal amidation

<400> SEQUENCE: 450

Ser Ile Met Phe Trp Tyr Asp Glu Tyr Glu
1 5 10

<210> SEQ ID NO 451
<211> LENGTH: 10

<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (1)..(1)
<223> OTHER INFORMATION: D-Ser
<220> FEATURE:
<221> NAME/KEY: MISC_FEATURE
<222> LOCATION: (2)..(2)
<223> OTHER INFORMATION: D-Ile
<220> FEATURE:
<221> NAME/KEY: MISC_FEATURE
<222> LOCATION: (3)..(3)
<223> OTHER INFORMATION: D-Met
<220> FEATURE:
<221> NAME/KEY: MISC_FEATURE
<222> LOCATION: (4)..(4)
<223> OTHER INFORMATION: D-Phe
<220> FEATURE:
<221> NAME/KEY: MISC_FEATURE
<222> LOCATION: (5)..(5)
<223> OTHER INFORMATION: D-Trp
<220> FEATURE:
<221> NAME/KEY: MISC_FEATURE
<222> LOCATION: (6)..(6)
<223> OTHER INFORMATION: D-Tyr
<220> FEATURE:
<221> NAME/KEY: MISC_FEATURE
<222> LOCATION: (7)..(7)
<223> OTHER INFORMATION: D-Asp
<220> FEATURE:
<221> NAME/KEY: MISC_FEATURE
<222> LOCATION: (8)..(8)
<223> OTHER INFORMATION: D-Glu
<220> FEATURE:
<221> NAME/KEY: MISC_FEATURE
<222> LOCATION: (9)..(9)
<223> OTHER INFORMATION: D-Tyr
<220> FEATURE:
<221> NAME/KEY: MISC_FEATURE
<222> LOCATION: (10)..(10)
<223> OTHER INFORMATION: D-Glu
<220> FEATURE:
<221> NAME/KEY: MISC_FEATURE
<222> LOCATION: (10)..(10)
<223> OTHER INFORMATION: C-terminal amidation

<400> SEQUENCE: 451

```
Ser Ile Met Phe Trp Tyr Asp Glu Tyr Glu
1               5                   10
```

<210> SEQ ID NO 452
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (1)..(1)
<223> OTHER INFORMATION: D-Tyr
<220> FEATURE:
<221> NAME/KEY: MISC_FEATURE
<222> LOCATION: (2)..(2)
<223> OTHER INFORMATION: D-Asp
<220> FEATURE:
<221> NAME/KEY: MISC_FEATURE
<222> LOCATION: (3)..(3)
<223> OTHER INFORMATION: D-Met
<220> FEATURE:
<221> NAME/KEY: MISC_FEATURE
<222> LOCATION: (4)..(4)
<223> OTHER INFORMATION: D-Cys
<220> FEATURE:
<221> NAME/KEY: MISC_FEATURE
<222> LOCATION: (5)..(5)
<223> OTHER INFORMATION: D-Trp
<220> FEATURE:
<221> NAME/KEY: MISC_FEATURE
<222> LOCATION: (6)..(6)
<223> OTHER INFORMATION: D-Cys
<220> FEATURE:
<221> NAME/KEY: MISC_FEATURE
<222> LOCATION: (7)..(7)
<223> OTHER INFORMATION: D-Glu
<220> FEATURE:
<221> NAME/KEY: MISC_FEATURE
<222> LOCATION: (8)..(8)
<223> OTHER INFORMATION: D-Phe
<220> FEATURE:
<221> NAME/KEY: MISC_FEATURE
<222> LOCATION: (9)..(9)
<223> OTHER INFORMATION: D-Tyr
<220> FEATURE:
<221> NAME/KEY: MISC_FEATURE
<222> LOCATION: (10)..(10)
<223> OTHER INFORMATION: D-Ile
<220> FEATURE:
<221> NAME/KEY: MISC_FEATURE
<222> LOCATION: (10)..(10)
<223> OTHER INFORMATION: C-terminal amidation

<400> SEQUENCE: 452

```
Tyr Asp Met Cys Trp Cys Glu Phe Tyr Ile
1               5                   10
```

<210> SEQ ID NO 453
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (1)..(1)
<223> OTHER INFORMATION: D-Ile
<220> FEATURE:
<221> NAME/KEY: MISC_FEATURE
<222> LOCATION: (2)..(2)
<223> OTHER INFORMATION: D-Asp
<220> FEATURE:
<221> NAME/KEY: MISC_FEATURE
<222> LOCATION: (3)..(3)
<223> OTHER INFORMATION: D-Met
<220> FEATURE:
<221> NAME/KEY: MISC_FEATURE
<222> LOCATION: (4)..(4)
<223> OTHER INFORMATION: D-Cys
<220> FEATURE:
<221> NAME/KEY: MISC_FEATURE
<222> LOCATION: (5)..(5)
<223> OTHER INFORMATION: D-Cys
<220> FEATURE:
<221> NAME/KEY: MISC_FEATURE
<222> LOCATION: (6)..(6)
<223> OTHER INFORMATION: D-Tyr
<220> FEATURE:
<221> NAME/KEY: MISC_FEATURE
<222> LOCATION: (7)..(7)
<223> OTHER INFORMATION: D-Phe
<220> FEATURE:
<221> NAME/KEY: MISC_FEATURE
<222> LOCATION: (8)..(8)
<223> OTHER INFORMATION: D-Tyr
<220> FEATURE:
<221> NAME/KEY: MISC_FEATURE
<222> LOCATION: (9)..(9)
<223> OTHER INFORMATION: D-Trp
<220> FEATURE:
<221> NAME/KEY: MISC_FEATURE
<222> LOCATION: (10)..(10)
<223> OTHER INFORMATION: D-Glu
<220> FEATURE:
<221> NAME/KEY: MISC_FEATURE
<222> LOCATION: (10)..(10)
<223> OTHER INFORMATION: C-terminal amidation

<400> SEQUENCE: 453

Ile Asp Met Cys Cys Tyr Phe Tyr Trp Glu
1 5 10

<210> SEQ ID NO 454
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (1)..(1)
<223> OTHER INFORMATION: D-Cys
<220> FEATURE:
<221> NAME/KEY: MISC_FEATURE
<222> LOCATION: (2)..(2)
<223> OTHER INFORMATION: D-Ile
<220> FEATURE:
<221> NAME/KEY: MISC_FEATURE
<222> LOCATION: (3)..(3)
<223> OTHER INFORMATION: D-Met
<220> FEATURE:
<221> NAME/KEY: MISC_FEATURE
<222> LOCATION: (4)..(4)
<223> OTHER INFORMATION: D-Phe
<220> FEATURE:
<221> NAME/KEY: MISC_FEATURE
<222> LOCATION: (5)..(5)
<223> OTHER INFORMATION: D-Trp
<220> FEATURE:
<221> NAME/KEY: MISC_FEATURE
<222> LOCATION: (6)..(6)
<223> OTHER INFORMATION: D-Tyr
<220> FEATURE:
<221> NAME/KEY: MISC_FEATURE
<222> LOCATION: (7)..(7)
<223> OTHER INFORMATION: D-Asp
<220> FEATURE:
<221> NAME/KEY: MISC_FEATURE
<222> LOCATION: (8)..(8)
<223> OTHER INFORMATION: D-Asp
<220> FEATURE:
<221> NAME/KEY: MISC_FEATURE
<222> LOCATION: (9)..(9)
<223> OTHER INFORMATION: D-Tyr
<220> FEATURE:
<221> NAME/KEY: MISC_FEATURE
<222> LOCATION: (10)..(10)
<223> OTHER INFORMATION: D-Glu
<220> FEATURE:
<221> NAME/KEY: MISC_FEATURE
<222> LOCATION: (10)..(10)
<223> OTHER INFORMATION: C-terminal amidation

<400> SEQUENCE: 454

Cys Ile Met Phe Trp Tyr Asp Asp Tyr Glu
1 5 10

<210> SEQ ID NO 455
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (1)..(1)
<223> OTHER INFORMATION: D-Cys
<220> FEATURE:
<221> NAME/KEY: DISULFID
<222> LOCATION: (1)..(8)
<223> OTHER INFORMATION: Cyclic peptide - Intramolecular disulfide bond
<220> FEATURE:
<221> NAME/KEY: MISC_FEATURE
<222> LOCATION: (2)..(2)
<223> OTHER INFORMATION: D-Tyr
<220> FEATURE:
<221> NAME/KEY: MISC_FEATURE
<222> LOCATION: (3)..(3)
<223> OTHER INFORMATION: D-Met
<220> FEATURE:
<221> NAME/KEY: MISC_FEATURE
<222> LOCATION: (4)..(4)
<223> OTHER INFORMATION: D-Phe
<220> FEATURE:
<221> NAME/KEY: MISC_FEATURE
<222> LOCATION: (5)..(5)
<223> OTHER INFORMATION: D-Trp
<220> FEATURE:
<221> NAME/KEY: MISC_FEATURE
<222> LOCATION: (6)..(6)
<223> OTHER INFORMATION: D-Tyr
<220> FEATURE:
<221> NAME/KEY: MISC_FEATURE
<222> LOCATION: (7)..(7)
<223> OTHER INFORMATION: D-Asp
<220> FEATURE:
<221> NAME/KEY: MISC_FEATURE
<222> LOCATION: (8)..(8)
<223> OTHER INFORMATION: D-Cys
<220> FEATURE:
<221> NAME/KEY: MISC_FEATURE
<222> LOCATION: (9)..(9)
<223> OTHER INFORMATION: D-Tyr
<220> FEATURE:
<221> NAME/KEY: MISC_FEATURE
<222> LOCATION: (10)..(10)
<223> OTHER INFORMATION: D-Glu

<400> SEQUENCE: 455

Cys Tyr Met Phe Trp Tyr Asp Cys Tyr Glu
1 5 10

<210> SEQ ID NO 456
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (1)..(1)

<223> OTHER INFORMATION: D-Cys
<220> FEATURE:
<221> NAME/KEY: DISULFID
<222> LOCATION: (1)..(8)
<223> OTHER INFORMATION: Cyclic peptide - Intramolecular disulfide bond
<220> FEATURE:
<221> NAME/KEY: MISC_FEATURE
<222> LOCATION: (2)..(2)
<223> OTHER INFORMATION: D-Tyr
<220> FEATURE:
<221> NAME/KEY: MISC_FEATURE
<222> LOCATION: (3)..(3)
<223> OTHER INFORMATION: D-Met
<220> FEATURE:
<221> NAME/KEY: MISC_FEATURE
<222> LOCATION: (4)..(4)
<223> OTHER INFORMATION: D-Phe
<220> FEATURE:
<221> NAME/KEY: MISC_FEATURE
<222> LOCATION: (5)..(5)
<223> OTHER INFORMATION: D-Trp
<220> FEATURE:
<221> NAME/KEY: MISC_FEATURE
<222> LOCATION: (6)..(6)
<223> OTHER INFORMATION: D-Tyr
<220> FEATURE:
<221> NAME/KEY: MISC_FEATURE
<222> LOCATION: (7)..(7)
<223> OTHER INFORMATION: D-Asp
<220> FEATURE:
<221> NAME/KEY: MISC_FEATURE
<222> LOCATION: (8)..(8)
<223> OTHER INFORMATION: D-Cys
<220> FEATURE:
<221> NAME/KEY: MISC_FEATURE
<222> LOCATION: (9)..(9)
<223> OTHER INFORMATION: D-Tyr
<220> FEATURE:
<221> NAME/KEY: MISC_FEATURE
<222> LOCATION: (10)..(10)
<223> OTHER INFORMATION: D-Glu
<220> FEATURE:
<221> NAME/KEY: MISC_FEATURE
<222> LOCATION: (10)..(10)
<223> OTHER INFORMATION: D-Glu linked to 4,7,10-trioxa-1,13-
tridecanediamine (TTDS) which terminates in an amide

<400> SEQUENCE: 456

```
Cys Tyr Met Phe Trp Tyr Asp Cys Tyr Glu
1               5                   10
```

<210> SEQ ID NO 457
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (1)..(1)
<223> OTHER INFORMATION: D-Cys
<220> FEATURE:
<221> NAME/KEY: MISC_FEATURE
<222> LOCATION: (1)..(1)
<223> OTHER INFORMATION: D-Cys linked acetylated 4,7,10-trioxa-1,13-
tridecanediamine (TTDS) linker
<220> FEATURE:
<221> NAME/KEY: DISULFID
<222> LOCATION: (1)..(8)
<223> OTHER INFORMATION: Cyclic peptide - Intramolecular disulfide bond
<220> FEATURE:
<221> NAME/KEY: MISC_FEATURE
<222> LOCATION: (2)..(2)

<223> OTHER INFORMATION: D-Tyr
<220> FEATURE:
<221> NAME/KEY: MISC_FEATURE
<222> LOCATION: (3)..(3)
<223> OTHER INFORMATION: D-Met
<220> FEATURE:
<221> NAME/KEY: MISC_FEATURE
<222> LOCATION: (4)..(4)
<223> OTHER INFORMATION: D-Phe
<220> FEATURE:
<221> NAME/KEY: MISC_FEATURE
<222> LOCATION: (5)..(5)
<223> OTHER INFORMATION: D-Trp
<220> FEATURE:
<221> NAME/KEY: MISC_FEATURE
<222> LOCATION: (6)..(6)
<223> OTHER INFORMATION: D-Tyr
<220> FEATURE:
<221> NAME/KEY: MISC_FEATURE
<222> LOCATION: (7)..(7)
<223> OTHER INFORMATION: D-Asp
<220> FEATURE:
<221> NAME/KEY: MISC_FEATURE
<222> LOCATION: (8)..(8)
<223> OTHER INFORMATION: D-Cys
<220> FEATURE:
<221> NAME/KEY: MISC_FEATURE
<222> LOCATION: (9)..(9)
<223> OTHER INFORMATION: D-Tyr
<220> FEATURE:
<221> NAME/KEY: MISC_FEATURE
<222> LOCATION: (10)..(10)
<223> OTHER INFORMATION: D-Glu
<220> FEATURE:
<221> NAME/KEY: MISC_FEATURE
<222> LOCATION: (10)..(10)
<223> OTHER INFORMATION: D-Glu linked to 4,7,10-trioxa-1,13-
      tridecanediamine (TTDS) which terminates in an amide

<400> SEQUENCE: 457

Cys Tyr Met Phe Trp Tyr Asp Cys Tyr Glu
1               5                   10

<210> SEQ ID NO 458
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: D-Cys
<220> FEATURE:
<221> NAME/KEY: DISULFID
<222> LOCATION: (2)..(9)
<223> OTHER INFORMATION: Cyclic peptide - Intramolecular disulfide bond
<220> FEATURE:
<221> NAME/KEY: MISC_FEATURE
<222> LOCATION: (3)..(3)
<223> OTHER INFORMATION: D-Tyr
<220> FEATURE:
<221> NAME/KEY: MISC_FEATURE
<222> LOCATION: (4)..(4)
<223> OTHER INFORMATION: D-Met
<220> FEATURE:
<221> NAME/KEY: MISC_FEATURE
<222> LOCATION: (5)..(5)
<223> OTHER INFORMATION: D-Phe
<220> FEATURE:
<221> NAME/KEY: MISC_FEATURE
<222> LOCATION: (6)..(6)
<223> OTHER INFORMATION: D-Trp
<220> FEATURE:
<221> NAME/KEY: MISC_FEATURE
<222> LOCATION: (7)..(7)
<223> OTHER INFORMATION: D-Tyr
<220> FEATURE:
<221> NAME/KEY: MISC_FEATURE
<222> LOCATION: (8)..(8)
<223> OTHER INFORMATION: D-Asp
<220> FEATURE:
<221> NAME/KEY: MISC_FEATURE
<222> LOCATION: (9)..(9)
<223> OTHER INFORMATION: D-Cys
<220> FEATURE:
<221> NAME/KEY: MISC_FEATURE
<222> LOCATION: (10)..(10)
<223> OTHER INFORMATION: D-Tyr
<220> FEATURE:
<221> NAME/KEY: MISC_FEATURE
<222> LOCATION: (11)..(11)
<223> OTHER INFORMATION: D-Glu
<220> FEATURE:
<221> NAME/KEY: MISC_FEATURE
<222> LOCATION: (11)..(11)
<223> OTHER INFORMATION: C-terminal amidation

<400> SEQUENCE: 458

Lys Cys Tyr Met Phe Trp Tyr Asp Cys Tyr Glu
1               5                   10

<210> SEQ ID NO 459
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (2)..(2)
<223> OTHER INFORMATION: D-Cys
<220> FEATURE:
<221> NAME/KEY: DISULFID
<222> LOCATION: (2)..(9)
<223> OTHER INFORMATION: Cyclic peptide - Intramolecular disulfide bond
<220> FEATURE:
<221> NAME/KEY: MISC_FEATURE
<222> LOCATION: (3)..(3)
<223> OTHER INFORMATION: D-Tyr
<220> FEATURE:
<221> NAME/KEY: MISC_FEATURE
<222> LOCATION: (4)..(4)
<223> OTHER INFORMATION: D-Met
<220> FEATURE:
<221> NAME/KEY: MISC_FEATURE
<222> LOCATION: (5)..(5)
<223> OTHER INFORMATION: D-Phe
<220> FEATURE:
<221> NAME/KEY: MISC_FEATURE
<222> LOCATION: (6)..(6)
<223> OTHER INFORMATION: D-Trp
<220> FEATURE:
<221> NAME/KEY: MISC_FEATURE
<222> LOCATION: (7)..(7)
<223> OTHER INFORMATION: D-Tyr
<220> FEATURE:
<221> NAME/KEY: MISC_FEATURE
<222> LOCATION: (8)..(8)
<223> OTHER INFORMATION: D-Asp
<220> FEATURE:
<221> NAME/KEY: MISC_FEATURE
<222> LOCATION: (9)..(9)
<223> OTHER INFORMATION: D-Cys
<220> FEATURE:
<221> NAME/KEY: MISC_FEATURE
<222> LOCATION: (10)..(10)
<223> OTHER INFORMATION: D-Tyr
<220> FEATURE:
<221> NAME/KEY: MISC_FEATURE
<222> LOCATION: (11)..(11)
<223> OTHER INFORMATION: D-Glu
<220> FEATURE:
<221> NAME/KEY: MISC_FEATURE
<222> LOCATION: (11)..(11)
<223> OTHER INFORMATION: C-terminal amidation

<400> SEQUENCE: 459

Lys Cys Tyr Met Phe Trp Tyr Asp Cys Tyr Glu
1 5 10

<210> SEQ ID NO 460
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: D-Cys
<220> FEATURE:
<221> NAME/KEY: DISULFID
<222> LOCATION: (2)..(9)
<223> OTHER INFORMATION: Cyclic peptide - Intramolecular disulfide bond
<220> FEATURE:
<221> NAME/KEY: MISC_FEATURE
<222> LOCATION: (3)..(3)
<223> OTHER INFORMATION: D-Tyr
<220> FEATURE:
<221> NAME/KEY: MISC_FEATURE
<222> LOCATION: (4)..(4)
<223> OTHER INFORMATION: D-Met
<220> FEATURE:
<221> NAME/KEY: MISC_FEATURE
<222> LOCATION: (5)..(5)
<223> OTHER INFORMATION: D-Phe
<220> FEATURE:
<221> NAME/KEY: MISC_FEATURE
<222> LOCATION: (6)..(6)
<223> OTHER INFORMATION: D-Trp
<220> FEATURE:
<221> NAME/KEY: MISC_FEATURE
<222> LOCATION: (7)..(7)
<223> OTHER INFORMATION: D-Tyr
<220> FEATURE:
<221> NAME/KEY: MISC_FEATURE
<222> LOCATION: (8)..(8)
<223> OTHER INFORMATION: D-Asp
<220> FEATURE:
<221> NAME/KEY: MISC_FEATURE
<222> LOCATION: (9)..(9)
<223> OTHER INFORMATION: D-Cys
<220> FEATURE:
<221> NAME/KEY: MISC_FEATURE
<222> LOCATION: (10)..(10)
<223> OTHER INFORMATION: D-Tyr
<220> FEATURE:
<221> NAME/KEY: MISC_FEATURE
<222> LOCATION: (11)..(11)
<223> OTHER INFORMATION: D-Glu
<220> FEATURE:
<221> NAME/KEY: MISC_FEATURE
<222> LOCATION: (11)..(11)
<223> OTHER INFORMATION: C-terminal amidation

<400> SEQUENCE: 460

Glu Cys Tyr Met Phe Trp Tyr Asp Cys Tyr Glu
1 5 10

<210> SEQ ID NO 461
<211> LENGTH: 11
<212> TYPE: PRT
<213> ORGANISM: Artificial Sequence
<220> FEATURE:

<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (1)..(2)
<223> OTHER INFORMATION: Lys linked to D-Cys via 4,7,10-trioxa-1,13-
tridecanediamine (TTDS) linker
<220> FEATURE:
<221> NAME/KEY: MISC_FEATURE
<222> LOCATION: (2)..(2)
<223> OTHER INFORMATION: D-Cys
<220> FEATURE:
<221> NAME/KEY: DISULFID
<222> LOCATION: (2)..(9)
<223> OTHER INFORMATION: Cyclic peptide - Intramolecular disulfide bond
<220> FEATURE:
<221> NAME/KEY: MISC_FEATURE
<222> LOCATION: (3)..(3)
<223> OTHER INFORMATION: D-Tyr
<220> FEATURE:
<221> NAME/KEY: MISC_FEATURE
<222> LOCATION: (4)..(4)
<223> OTHER INFORMATION: D-Met
<220> FEATURE:
<221> NAME/KEY: MISC_FEATURE
<222> LOCATION: (5)..(5)
<223> OTHER INFORMATION: D-Phe
<220> FEATURE:
<221> NAME/KEY: MISC_FEATURE
<222> LOCATION: (6)..(6)
<223> OTHER INFORMATION: D-Trp
<220> FEATURE:
<221> NAME/KEY: MISC_FEATURE
<222> LOCATION: (7)..(7)
<223> OTHER INFORMATION: D-Tyr
<220> FEATURE:
<221> NAME/KEY: MISC_FEATURE
<222> LOCATION: (8)..(8)
<223> OTHER INFORMATION: D-Asp
<220> FEATURE:
<221> NAME/KEY: MISC_FEATURE
<222> LOCATION: (9)..(9)
<223> OTHER INFORMATION: D-Cys
<220> FEATURE:
<221> NAME/KEY: MISC_FEATURE
<222> LOCATION: (10)..(10)
<223> OTHER INFORMATION: D-Tyr
<220> FEATURE:
<221> NAME/KEY: MISC_FEATURE
<222> LOCATION: (11)..(11)
<223> OTHER INFORMATION: D-Glu
<220> FEATURE:
<221> NAME/KEY: MISC_FEATURE
<222> LOCATION: (11)..(11)
<223> OTHER INFORMATION: C-terminal amidation

<400> SEQUENCE: 461

```
Lys Cys Tyr Met Phe Trp Tyr Asp Cys Tyr Glu
1               5                   10
```

<210> SEQ ID NO 462
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (1)..(1)
<223> OTHER INFORMATION: D-Cys
<220> FEATURE:
<221> NAME/KEY: DISULFID
<222> LOCATION: (1)..(8)
<223> OTHER INFORMATION: Cyclic peptide - Intramolecular disulfide bond
<220> FEATURE:
<221> NAME/KEY: MISC_FEATURE
<222> LOCATION: (2)..(2)
<223> OTHER INFORMATION: D-Tyr
<220> FEATURE:
<221> NAME/KEY: MISC_FEATURE
<222> LOCATION: (3)..(3)
<223> OTHER INFORMATION: D-Met
<220> FEATURE:
<221> NAME/KEY: MISC_FEATURE
<222> LOCATION: (4)..(4)
<223> OTHER INFORMATION: D-Phe
<220> FEATURE:
<221> NAME/KEY: MISC_FEATURE
<222> LOCATION: (5)..(5)
<223> OTHER INFORMATION: D-Trp
<220> FEATURE:
<221> NAME/KEY: MISC_FEATURE
<222> LOCATION: (6)..(6)
<223> OTHER INFORMATION: D-Tyr
<220> FEATURE:
<221> NAME/KEY: MISC_FEATURE
<222> LOCATION: (7)..(7)
<223> OTHER INFORMATION: D-Asp
<220> FEATURE:
<221> NAME/KEY: MISC_FEATURE
<222> LOCATION: (8)..(8)
<223> OTHER INFORMATION: D-Cys
<220> FEATURE:
<221> NAME/KEY: MISC_FEATURE
<222> LOCATION: (9)..(9)
<223> OTHER INFORMATION: D-Tyr
<220> FEATURE:
<221> NAME/KEY: MISC_FEATURE
<222> LOCATION: (10)..(10)
<223> OTHER INFORMATION: D-Glu
<220> FEATURE:
<221> NAME/KEY: MISC_FEATURE
<222> LOCATION: (11)..(11)
<223> OTHER INFORMATION: C-terminal amidation

<400> SEQUENCE: 462

Cys Tyr Met Phe Trp Tyr Asp Cys Tyr Glu Lys
1               5                   10

<210> SEQ ID NO 463
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (1)..(1)
<223> OTHER INFORMATION: D-Cys
<220> FEATURE:
<221> NAME/KEY: DISULFID
<222> LOCATION: (1)..(8)
<223> OTHER INFORMATION: Cyclic peptide - Intramolecular disulfide bond
<220> FEATURE:
<221> NAME/KEY: MISC_FEATURE
<222> LOCATION: (2)..(2)
<223> OTHER INFORMATION: D-Tyr
<220> FEATURE:
<221> NAME/KEY: MISC_FEATURE
<222> LOCATION: (3)..(3)
<223> OTHER INFORMATION: D-Met
<220> FEATURE:
<221> NAME/KEY: MISC_FEATURE
<222> LOCATION: (4)..(4)
<223> OTHER INFORMATION: D-Phe
<220> FEATURE:
<221> NAME/KEY: MISC_FEATURE
<222> LOCATION: (5)..(5)
<223> OTHER INFORMATION: D-Trp
<220> FEATURE:
<221> NAME/KEY: MISC_FEATURE
<222> LOCATION: (6)..(6)
<223> OTHER INFORMATION: D-Tyr
<220> FEATURE:
<221> NAME/KEY: MISC_FEATURE
<222> LOCATION: (7)..(7)
<223> OTHER INFORMATION: D-Asp
<220> FEATURE:
<221> NAME/KEY: MISC_FEATURE
<222> LOCATION: (8)..(8)
<223> OTHER INFORMATION: D-Cys
<220> FEATURE:
<221> NAME/KEY: MISC_FEATURE
<222> LOCATION: (9)..(9)
<223> OTHER INFORMATION: D-Tyr
<220> FEATURE:
<221> NAME/KEY: MISC_FEATURE
<222> LOCATION: (10)..(10)
<223> OTHER INFORMATION: D-Glu
<220> FEATURE:
<221> NAME/KEY: MISC_FEATURE
<222> LOCATION: (10)..(11)
<223> OTHER INFORMATION: D-Glu linked to Lys via 4,7,10-trioxa-1,13-
      tridecanediamine (TTDS) linker
<220> FEATURE:
<221> NAME/KEY: MISC_FEATURE
<222> LOCATION: (11)..(11)
<223> OTHER INFORMATION: C-terminal amidation

<400> SEQUENCE: 463

Cys Tyr Met Phe Trp Tyr Asp Cys Tyr Glu Lys
1               5                   10

<210> SEQ ID NO 464
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (1)..(1)
<223> OTHER INFORMATION: D-Cys
<220> FEATURE:
<221> NAME/KEY: DISULFID
<222> LOCATION: (1)..(8)
<223> OTHER INFORMATION: Cyclic peptide - Intramolecular disulfide bond
<220> FEATURE:
<221> NAME/KEY: MISC_FEATURE
<222> LOCATION: (2)..(2)
<223> OTHER INFORMATION: D-Tyr
<220> FEATURE:
<221> NAME/KEY: MISC_FEATURE
<222> LOCATION: (3)..(3)
<223> OTHER INFORMATION: D-Met
<220> FEATURE:
<221> NAME/KEY: MISC_FEATURE
<222> LOCATION: (4)..(4)
<223> OTHER INFORMATION: D-Phe
<220> FEATURE:
<221> NAME/KEY: MISC_FEATURE
<222> LOCATION: (5)..(5)
<223> OTHER INFORMATION: D-Trp
<220> FEATURE:
<221> NAME/KEY: MISC_FEATURE
<222> LOCATION: (6)..(6)

<223> OTHER INFORMATION: D-Tyr
<220> FEATURE:
<221> NAME/KEY: MISC_FEATURE
<222> LOCATION: (7)..(7)
<223> OTHER INFORMATION: D-Asp
<220> FEATURE:
<221> NAME/KEY: MISC_FEATURE
<222> LOCATION: (8)..(8)
<223> OTHER INFORMATION: D-Cys
<220> FEATURE:
<221> NAME/KEY: MISC_FEATURE
<222> LOCATION: (9)..(9)
<223> OTHER INFORMATION: D-Tyr
<220> FEATURE:
<221> NAME/KEY: MISC_FEATURE
<222> LOCATION: (10)..(10)
<223> OTHER INFORMATION: D-Glu
<220> FEATURE:
<221> NAME/KEY: MISC_FEATURE
<222> LOCATION: (10)..(11)
<223> OTHER INFORMATION: D-Glu linked to Glu via 4,7,10-trioxa-1,13-
tridecanediamine (TTDS) linker
<220> FEATURE:
<221> NAME/KEY: MISC_FEATURE
<222> LOCATION: (11)..(11)
<223> OTHER INFORMATION: C-terminal amidation

<400> SEQUENCE: 464

Cys Tyr Met Phe Trp Tyr Asp Cys Tyr Glu Glu
1               5                   10

<210> SEQ ID NO 465
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal Acylation
<220> FEATURE:
<221> NAME/KEY: MISC_FEATURE
<222> LOCATION: (1)..(1)
<223> OTHER INFORMATION: D-Tyr
<220> FEATURE:
<221> NAME/KEY: MISC_FEATURE
<222> LOCATION: (2)..(2)
<223> OTHER INFORMATION: D-Ile
<220> FEATURE:
<221> NAME/KEY: MISC_FEATURE
<222> LOCATION: (3)..(3)
<223> OTHER INFORMATION: D-Met
<220> FEATURE:
<221> NAME/KEY: MISC_FEATURE
<222> LOCATION: (4)..(4)
<223> OTHER INFORMATION: D-Phe
<220> FEATURE:
<221> NAME/KEY: MISC_FEATURE
<222> LOCATION: (5)..(5)
<223> OTHER INFORMATION: D-Trp
<220> FEATURE:
<221> NAME/KEY: MISC_FEATURE
<222> LOCATION: (6)..(6)
<223> OTHER INFORMATION: D-Tyr
<220> FEATURE:
<221> NAME/KEY: MISC_FEATURE
<222> LOCATION: (7)..(7)
<223> OTHER INFORMATION: D-Asp
<220> FEATURE:
<221> NAME/KEY: MISC_FEATURE
<222> LOCATION: (8)..(8)
<223> OTHER INFORMATION: D-Glu
<220> FEATURE:
<221> NAME/KEY: MISC_FEATURE
<222> LOCATION: (9)..(9)
<223> OTHER INFORMATION: D-Tyr
<220> FEATURE:
<221> NAME/KEY: MISC_FEATURE
<222> LOCATION: (10)..(10)
<223> OTHER INFORMATION: D-Glu
<220> FEATURE:
<221> NAME/KEY: MISC_FEATURE
<222> LOCATION: (10)..(10)
<223> OTHER INFORMATION: C-terminal amidation

<400> SEQUENCE: 465

Thr Ile Met Phe Trp Tyr Asp Glu Tyr Glu
1 5 10

<210> SEQ ID NO 466
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (1)..(1)
<223> OTHER INFORMATION: D-Cys
<220> FEATURE:
<221> NAME/KEY: DISULFID
<222> LOCATION: (1)..(8)
<223> OTHER INFORMATION: Cyclic peptide - Intramolecular disulfide bond
<220> FEATURE:
<221> NAME/KEY: MISC_FEATURE
<222> LOCATION: (2)..(2)
<223> OTHER INFORMATION: D-Ile
<220> FEATURE:
<221> NAME/KEY: MISC_FEATURE
<222> LOCATION: (3)..(3)
<223> OTHER INFORMATION: D-Met
<220> FEATURE:
<221> NAME/KEY: MISC_FEATURE
<222> LOCATION: (4)..(4)
<223> OTHER INFORMATION: D-Phe
<220> FEATURE:
<221> NAME/KEY: MISC_FEATURE
<222> LOCATION: (5)..(5)
<223> OTHER INFORMATION: D-Trp
<220> FEATURE:
<221> NAME/KEY: MISC_FEATURE
<222> LOCATION: (6)..(6)
<223> OTHER INFORMATION: D-Tyr
<220> FEATURE:
<221> NAME/KEY: MISC_FEATURE
<222> LOCATION: (7)..(7)
<223> OTHER INFORMATION: D-Asp
<220> FEATURE:
<221> NAME/KEY: MISC_FEATURE
<222> LOCATION: (8)..(8)
<223> OTHER INFORMATION: D-Cys
<220> FEATURE:
<221> NAME/KEY: MISC_FEATURE
<222> LOCATION: (9)..(9)
<223> OTHER INFORMATION: D-Tyr
<220> FEATURE:
<221> NAME/KEY: MISC_FEATURE
<222> LOCATION: (10)..(10)
<223> OTHER INFORMATION: D-Glu
<220> FEATURE:
<221> NAME/KEY: MISC_FEATURE
<222> LOCATION: (10)..(10)
<223> OTHER INFORMATION: C-terminal amidation

<400> SEQUENCE: 466

Cys Ile Met Phe Trp Tyr Asp Cys Tyr Glu
1 5 10

<210> SEQ ID NO 467
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (1)..(1)
<223> OTHER INFORMATION: D-Cys
<220> FEATURE:
<221> NAME/KEY: DISULFID
<222> LOCATION: (1)..(8)
<223> OTHER INFORMATION: Cyclic peptide - Intramolecular disulfide bond
<220> FEATURE:
<221> NAME/KEY: MISC_FEATURE
<222> LOCATION: (2)..(2)
<223> OTHER INFORMATION: D-Tyr
<220> FEATURE:
<221> NAME/KEY: MISC_FEATURE
<222> LOCATION: (3)..(3)
<223> OTHER INFORMATION: D-Met
<220> FEATURE:
<221> NAME/KEY: MISC_FEATURE
<222> LOCATION: (4)..(4)
<223> OTHER INFORMATION: D-Phe
<220> FEATURE:
<221> NAME/KEY: MISC_FEATURE
<222> LOCATION: (5)..(5)
<223> OTHER INFORMATION: D-Trp
<220> FEATURE:
<221> NAME/KEY: MISC_FEATURE
<222> LOCATION: (6)..(6)
<223> OTHER INFORMATION: D-Tyr
<220> FEATURE:
<221> NAME/KEY: MISC_FEATURE
<222> LOCATION: (7)..(7)
<223> OTHER INFORMATION: D-Asp
<220> FEATURE:
<221> NAME/KEY: MISC_FEATURE
<222> LOCATION: (8)..(8)
<223> OTHER INFORMATION: D-Cys
<220> FEATURE:
<221> NAME/KEY: MISC_FEATURE
<222> LOCATION: (9)..(9)
<223> OTHER INFORMATION: D-Tyr
<220> FEATURE:
<221> NAME/KEY: MISC_FEATURE
<222> LOCATION: (10)..(10)
<223> OTHER INFORMATION: D-Glu
<220> FEATURE:
<221> NAME/KEY: MISC_FEATURE
<222> LOCATION: (10)..(10)
<223> OTHER INFORMATION: C-terminal amidation

<400> SEQUENCE: 467

```
Cys Tyr Met Phe Trp Tyr Asp Cys Tyr Glu
1               5                   10
```

<210> SEQ ID NO 468
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (1)..(1)

<223> OTHER INFORMATION: D-Cys
<220> FEATURE:
<221> NAME/KEY: DISULFID
<222> LOCATION: (1)..(8)
<223> OTHER INFORMATION: Cyclic peptide - Intramolecular disulfide bond
<220> FEATURE:
<221> NAME/KEY: MISC_FEATURE
<222> LOCATION: (2)..(2)
<223> OTHER INFORMATION: D-Trp
<220> FEATURE:
<221> NAME/KEY: MISC_FEATURE
<222> LOCATION: (3)..(3)
<223> OTHER INFORMATION: D-Met
<220> FEATURE:
<221> NAME/KEY: MISC_FEATURE
<222> LOCATION: (4)..(4)
<223> OTHER INFORMATION: D-Phe
<220> FEATURE:
<221> NAME/KEY: MISC_FEATURE
<222> LOCATION: (5)..(5)
<223> OTHER INFORMATION: D-Trp
<220> FEATURE:
<221> NAME/KEY: MISC_FEATURE
<222> LOCATION: (6)..(6)
<223> OTHER INFORMATION: D-Tyr
<220> FEATURE:
<221> NAME/KEY: MISC_FEATURE
<222> LOCATION: (7)..(7)
<223> OTHER INFORMATION: D-Asp
<220> FEATURE:
<221> NAME/KEY: MISC_FEATURE
<222> LOCATION: (8)..(8)
<223> OTHER INFORMATION: D-Cys
<220> FEATURE:
<221> NAME/KEY: MISC_FEATURE
<222> LOCATION: (9)..(9)
<223> OTHER INFORMATION: D-Tyr
<220> FEATURE:
<221> NAME/KEY: MISC_FEATURE
<222> LOCATION: (10)..(10)
<223> OTHER INFORMATION: D-Glu
<220> FEATURE:
<221> NAME/KEY: MISC_FEATURE
<222> LOCATION: (10)..(10)
<223> OTHER INFORMATION: C-terminal amidation

<400> SEQUENCE: 468

Cys Trp Met Phe Trp Tyr Asp Cys Tyr Glu
1               5                   10

<210> SEQ ID NO 469
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (1)..(1)
<223> OTHER INFORMATION: D-Cys
<220> FEATURE:
<221> NAME/KEY: MISC_FEATURE
<222> LOCATION: (2)..(2)
<223> OTHER INFORMATION: D-Ile
<220> FEATURE:
<221> NAME/KEY: MISC_FEATURE
<222> LOCATION: (3)..(3)
<223> OTHER INFORMATION: D-Cys
<220> FEATURE:
<221> NAME/KEY: MISC_FEATURE
<222> LOCATION: (4)..(4)
<223> OTHER INFORMATION: D-Phe
<220> FEATURE:

<221> NAME/KEY: MISC_FEATURE
<222> LOCATION: (5)..(5)
<223> OTHER INFORMATION: D-Trp
<220> FEATURE:
<221> NAME/KEY: MISC_FEATURE
<222> LOCATION: (6)..(6)
<223> OTHER INFORMATION: D-Tyr
<220> FEATURE:
<221> NAME/KEY: MISC_FEATURE
<222> LOCATION: (7)..(7)
<223> OTHER INFORMATION: D-Asp
<220> FEATURE:
<221> NAME/KEY: MISC_FEATURE
<222> LOCATION: (8)..(8)
<223> OTHER INFORMATION: D-Cys
<220> FEATURE:
<221> NAME/KEY: MISC_FEATURE
<222> LOCATION: (9)..(9)
<223> OTHER INFORMATION: D-Tyr
<220> FEATURE:
<221> NAME/KEY: MISC_FEATURE
<222> LOCATION: (10)..(10)
<223> OTHER INFORMATION: D-Glu
<220> FEATURE:
<221> NAME/KEY: MISC_FEATURE
<222> LOCATION: (10)..(10)
<223> OTHER INFORMATION: C-terminal amidation

<400> SEQUENCE: 469

Cys Ile Cys Phe Trp Tyr Asp Cys Tyr Glu
1               5                   10

<210> SEQ ID NO 470
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (1)..(1)
<223> OTHER INFORMATION: Xaa is D-norvaline (D-Nva)
<220> FEATURE:
<221> NAME/KEY: MISC_FEATURE
<222> LOCATION: (2)..(2)
<223> OTHER INFORMATION: D-Ile
<220> FEATURE:
<221> NAME/KEY: MISC_FEATURE
<222> LOCATION: (3)..(3)
<223> OTHER INFORMATION: D-Met
<220> FEATURE:
<221> NAME/KEY: MISC_FEATURE
<222> LOCATION: (4)..(4)
<223> OTHER INFORMATION: D-Phe
<220> FEATURE:
<221> NAME/KEY: MISC_FEATURE
<222> LOCATION: (5)..(5)
<223> OTHER INFORMATION: D-Trp
<220> FEATURE:
<221> NAME/KEY: MISC_FEATURE
<222> LOCATION: (6)..(6)
<223> OTHER INFORMATION: D-Tyr
<220> FEATURE:
<221> NAME/KEY: MISC_FEATURE
<222> LOCATION: (7)..(7)
<223> OTHER INFORMATION: D-Asp
<220> FEATURE:
<221> NAME/KEY: MISC_FEATURE
<222> LOCATION: (8)..(8)
<223> OTHER INFORMATION: D-Glu
<220> FEATURE:
<221> NAME/KEY: MISC_FEATURE
<222> LOCATION: (9)..(9)

<223> OTHER INFORMATION: D-Tyr
<220> FEATURE:
<221> NAME/KEY: MISC_FEATURE
<222> LOCATION: (10)..(10)
<223> OTHER INFORMATION: D-Glu
<220> FEATURE:
<221> NAME/KEY: MISC_FEATURE
<222> LOCATION: (10)..(10)
<223> OTHER INFORMATION: C-terminal amidation

<400> SEQUENCE: 470

Xaa Ile Met Phe Trp Tyr Asp Glu Tyr Glu
1 5 10

<210> SEQ ID NO 471
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (1)..(1)
<223> OTHER INFORMATION: Xaa is D-norleucine (D-Nle)
<220> FEATURE:
<221> NAME/KEY: MISC_FEATURE
<222> LOCATION: (2)..(2)
<223> OTHER INFORMATION: D-Ile
<220> FEATURE:
<221> NAME/KEY: MISC_FEATURE
<222> LOCATION: (3)..(3)
<223> OTHER INFORMATION: D-Met
<220> FEATURE:
<221> NAME/KEY: MISC_FEATURE
<222> LOCATION: (4)..(4)
<223> OTHER INFORMATION: D-Phe
<220> FEATURE:
<221> NAME/KEY: MISC_FEATURE
<222> LOCATION: (5)..(5)
<223> OTHER INFORMATION: D-Trp
<220> FEATURE:
<221> NAME/KEY: MISC_FEATURE
<222> LOCATION: (6)..(6)
<223> OTHER INFORMATION: D-Tyr
<220> FEATURE:
<221> NAME/KEY: MISC_FEATURE
<222> LOCATION: (7)..(7)
<223> OTHER INFORMATION: D-Asp
<220> FEATURE:
<221> NAME/KEY: MISC_FEATURE
<222> LOCATION: (8)..(8)
<223> OTHER INFORMATION: D-Glu
<220> FEATURE:
<221> NAME/KEY: MISC_FEATURE
<222> LOCATION: (9)..(9)
<223> OTHER INFORMATION: D-Tyr
<220> FEATURE:
<221> NAME/KEY: MISC_FEATURE
<222> LOCATION: (10)..(10)
<223> OTHER INFORMATION: D-Glu
<220> FEATURE:
<221> NAME/KEY: MISC_FEATURE
<222> LOCATION: (10)..(10)
<223> OTHER INFORMATION: C-terminal amidation

<400> SEQUENCE: 471

Xaa Ile Met Phe Trp Tyr Asp Glu Tyr Glu
1 5 10

<210> SEQ ID NO 472
<211> LENGTH: 10

<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (2)..(2)
<223> OTHER INFORMATION: D-Ile
<220> FEATURE:
<221> NAME/KEY: MISC_FEATURE
<222> LOCATION: (3)..(3)
<223> OTHER INFORMATION: D-Met
<220> FEATURE:
<221> NAME/KEY: MISC_FEATURE
<222> LOCATION: (4)..(4)
<223> OTHER INFORMATION: D-Phe
<220> FEATURE:
<221> NAME/KEY: MISC_FEATURE
<222> LOCATION: (5)..(5)
<223> OTHER INFORMATION: D-Trp
<220> FEATURE:
<221> NAME/KEY: MISC_FEATURE
<222> LOCATION: (6)..(6)
<223> OTHER INFORMATION: D-Tyr
<220> FEATURE:
<221> NAME/KEY: MISC_FEATURE
<222> LOCATION: (7)..(7)
<223> OTHER INFORMATION: D-Asp
<220> FEATURE:
<221> NAME/KEY: MISC_FEATURE
<222> LOCATION: (8)..(8)
<223> OTHER INFORMATION: D-Glu
<220> FEATURE:
<221> NAME/KEY: MISC_FEATURE
<222> LOCATION: (9)..(9)
<223> OTHER INFORMATION: D-Tyr
<220> FEATURE:
<221> NAME/KEY: MISC_FEATURE
<222> LOCATION: (10)..(10)
<223> OTHER INFORMATION: D-Glu
<220> FEATURE:
<221> NAME/KEY: MISC_FEATURE
<222> LOCATION: (10)..(10)
<223> OTHER INFORMATION: C-terminal amidation

<400> SEQUENCE: 472

```
Cys Ile Met Phe Trp Tyr Asp Glu Tyr Glu
1               5                   10
```

<210> SEQ ID NO 473
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Cys
<220> FEATURE:
<221> NAME/KEY: DISULFID
<222> LOCATION: (1)..(8)
<223> OTHER INFORMATION: Cyclic peptide - Intramolecular disulfide bond
<220> FEATURE:
<221> NAME/KEY: MISC_FEATURE
<222> LOCATION: (2)..(2)
<223> OTHER INFORMATION: D-Tyr
<220> FEATURE:
<221> NAME/KEY: MISC_FEATURE
<222> LOCATION: (3)..(3)
<223> OTHER INFORMATION: D-Met
<220> FEATURE:
<221> NAME/KEY: MISC_FEATURE
<222> LOCATION: (4)..(4)
<223> OTHER INFORMATION: D-Phe
<220> FEATURE:
<221> NAME/KEY: MISC_FEATURE
<222> LOCATION: (5)..(5)
<223> OTHER INFORMATION: D-Trp
<220> FEATURE:
<221> NAME/KEY: MISC_FEATURE
<222> LOCATION: (6)..(6)
<223> OTHER INFORMATION: D-Tyr
<220> FEATURE:
<221> NAME/KEY: MISC_FEATURE
<222> LOCATION: (7)..(7)
<223> OTHER INFORMATION: D-Asp
<220> FEATURE:
<221> NAME/KEY: MISC_FEATURE
<222> LOCATION: (8)..(8)
<223> OTHER INFORMATION: D-Cys
<220> FEATURE:
<221> NAME/KEY: MISC_FEATURE
<222> LOCATION: (9)..(9)
<223> OTHER INFORMATION: D-Tyr
<220> FEATURE:
<221> NAME/KEY: MISC_FEATURE
<222> LOCATION: (10)..(10)
<223> OTHER INFORMATION: D-Glu
<220> FEATURE:
<221> NAME/KEY: MISC_FEATURE
<222> LOCATION: (10)..(10)
<223> OTHER INFORMATION: C-terminal amidation

<400> SEQUENCE: 473

Cys Tyr Met Phe Trp Tyr Asp Cys Tyr Glu
1 5 10

<210> SEQ ID NO 474
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (1)..(1)
<223> OTHER INFORMATION: D-Cys
<220> FEATURE:
<221> NAME/KEY: MISC_FEATURE
<222> LOCATION: (1)..(1)
<223> OTHER INFORMATION: D-Cys linked to 4,7,10-trioxa-1,13-
tridecanediamine (TTDS) linker
<220> FEATURE:
<221> NAME/KEY: DISULFID
<222> LOCATION: (1)..(8)
<223> OTHER INFORMATION: Cyclic peptide - Intramolecular disulfide bond
<220> FEATURE:
<221> NAME/KEY: MISC_FEATURE
<222> LOCATION: (2)..(2)
<223> OTHER INFORMATION: D-Tyr
<220> FEATURE:
<221> NAME/KEY: MISC_FEATURE
<222> LOCATION: (3)..(3)
<223> OTHER INFORMATION: D-Met
<220> FEATURE:
<221> NAME/KEY: MISC_FEATURE
<222> LOCATION: (4)..(4)
<223> OTHER INFORMATION: D-Phe
<220> FEATURE:
<221> NAME/KEY: MISC_FEATURE
<222> LOCATION: (5)..(5)
<223> OTHER INFORMATION: D-Trp
<220> FEATURE:
<221> NAME/KEY: MISC_FEATURE
<222> LOCATION: (6)..(6)

<223> OTHER INFORMATION: D-Tyr
<220> FEATURE:
<221> NAME/KEY: MISC_FEATURE
<222> LOCATION: (7)..(7)
<223> OTHER INFORMATION: D-Asp
<220> FEATURE:
<221> NAME/KEY: MISC_FEATURE
<222> LOCATION: (8)..(8)
<223> OTHER INFORMATION: D-Cys
<220> FEATURE:
<221> NAME/KEY: MISC_FEATURE
<222> LOCATION: (9)..(9)
<223> OTHER INFORMATION: D-Tyr
<220> FEATURE:
<221> NAME/KEY: MISC_FEATURE
<222> LOCATION: (10)..(10)
<223> OTHER INFORMATION: D-Glu
<220> FEATURE:
<221> NAME/KEY: MISC_FEATURE
<222> LOCATION: (10)..(10)
<223> OTHER INFORMATION: D-Glu linked to 4,7,10-trioxa-1,13-
tridecanediamine (TTDS) which terminates in an amide

<400> SEQUENCE: 474

Cys Tyr Met Phe Trp Tyr Asp Cys Tyr Glu
1 5 10

<210> SEQ ID NO 475
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (1)..(1)
<223> OTHER INFORMATION: D-Lys
<220> FEATURE:
<221> NAME/KEY: MISC_FEATURE
<222> LOCATION: (2)..(2)
<223> OTHER INFORMATION: D-Ile
<220> FEATURE:
<221> NAME/KEY: MISC_FEATURE
<222> LOCATION: (3)..(3)
<223> OTHER INFORMATION: D-Met
<220> FEATURE:
<221> NAME/KEY: MISC_FEATURE
<222> LOCATION: (4)..(4)
<223> OTHER INFORMATION: D-Phe
<220> FEATURE:
<221> NAME/KEY: MISC_FEATURE
<222> LOCATION: (5)..(5)
<223> OTHER INFORMATION: D-Trp
<220> FEATURE:
<221> NAME/KEY: MISC_FEATURE
<222> LOCATION: (6)..(6)
<223> OTHER INFORMATION: D-Tyr
<220> FEATURE:
<221> NAME/KEY: MISC_FEATURE
<222> LOCATION: (7)..(7)
<223> OTHER INFORMATION: D-Asp
<220> FEATURE:
<221> NAME/KEY: MISC_FEATURE
<222> LOCATION: (8)..(8)
<223> OTHER INFORMATION: D-Glu
<220> FEATURE:
<221> NAME/KEY: MISC_FEATURE
<222> LOCATION: (9)..(9)
<223> OTHER INFORMATION: D-Tyr
<220> FEATURE:
<221> NAME/KEY: MISC_FEATURE
<222> LOCATION: (10)..(10)
<223> OTHER INFORMATION: D-Glu
<220> FEATURE:
<221> NAME/KEY: MISC_FEATURE
<222> LOCATION: (10)..(10)
<223> OTHER INFORMATION: C-terminal amidation

<400> SEQUENCE: 475

Lys Ile Met Phe Trp Tyr Asp Glu Tyr Glu
1               5                   10

<210> SEQ ID NO 476
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Ile
<220> FEATURE:
<221> NAME/KEY: MISC_FEATURE
<222> LOCATION: (2)..(2)
<223> OTHER INFORMATION: D-Met
<220> FEATURE:
<221> NAME/KEY: MISC_FEATURE
<222> LOCATION: (3)..(3)
<223> OTHER INFORMATION: D-Phe
<220> FEATURE:
<221> NAME/KEY: MISC_FEATURE
<222> LOCATION: (4)..(4)
<223> OTHER INFORMATION: D-Trp
<220> FEATURE:
<221> NAME/KEY: MISC_FEATURE
<222> LOCATION: (5)..(5)
<223> OTHER INFORMATION: D-Tyr
<220> FEATURE:
<221> NAME/KEY: MISC_FEATURE
<222> LOCATION: (6)..(6)
<223> OTHER INFORMATION: D-Asp
<220> FEATURE:
<221> NAME/KEY: MISC_FEATURE
<222> LOCATION: (7)..(7)
<223> OTHER INFORMATION: D-Glu
<220> FEATURE:
<221> NAME/KEY: MISC_FEATURE
<222> LOCATION: (8)..(8)
<223> OTHER INFORMATION: D-Tyr
<220> FEATURE:
<221> NAME/KEY: MISC_FEATURE
<222> LOCATION: (9)..(9)
<223> OTHER INFORMATION: D-Glu
<220> FEATURE:
<221> NAME/KEY: MISC_FEATURE
<222> LOCATION: (9)..(9)
<223> OTHER INFORMATION: C-terminal amidation

<400> SEQUENCE: 476

Ile Met Phe Trp Tyr Asp Glu Tyr Glu
1               5

<210> SEQ ID NO 477
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Trp
<220> FEATURE:
<221> NAME/KEY: MISC_FEATURE
<222> LOCATION: (2)..(2)
<223> OTHER INFORMATION: D-Asp
<220> FEATURE:

<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: D-Tyr
<220> FEATURE:
<221> NAME/KEY: MISC_FEATURE
<222> LOCATION: (5)..(5)
<223> OTHER INFORMATION: D-Phe
<220> FEATURE:
<221> NAME/KEY: MISC_FEATURE
<222> LOCATION: (6)..(6)
<223> OTHER INFORMATION: D-Glu
<220> FEATURE:
<221> NAME/KEY: MISC_FEATURE
<222> LOCATION: (7)..(7)
<223> OTHER INFORMATION: D-Ile
<220> FEATURE:
<221> NAME/KEY: MISC_FEATURE
<222> LOCATION: (8)..(8)
<223> OTHER INFORMATION: D-Val
<220> FEATURE:
<221> NAME/KEY: MISC_FEATURE
<222> LOCATION: (9)..(9)
<223> OTHER INFORMATION: D-Trp

<400> SEQUENCE: 477

Trp Val Ile Glu Phe Tyr Leu Asp Trp
1               5

<210> SEQ ID NO 478
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (1)..(1)
<223> OTHER INFORMATION: D-Cys
<220> FEATURE:
<221> NAME/KEY: DISULFID
<222> LOCATION: (1)..(8)
<223> OTHER INFORMATION: Cyclic peptide - Intramolecular disulfide bond
<220> FEATURE:
<221> NAME/KEY: MISC_FEATURE
<222> LOCATION: (2)..(2)
<223> OTHER INFORMATION: D-Ile
<220> FEATURE:
<221> NAME/KEY: MISC_FEATURE
<222> LOCATION: (3)..(3)
<223> OTHER INFORMATION: D-Met
<220> FEATURE:
<221> NAME/KEY: MISC_FEATURE
<222> LOCATION: (4)..(4)
<223> OTHER INFORMATION: D-Thr
<220> FEATURE:
<221> NAME/KEY: MISC_FEATURE
<222> LOCATION: (5)..(5)
<223> OTHER INFORMATION: D-Trp
<220> FEATURE:
<221> NAME/KEY: MISC_FEATURE
<222> LOCATION: (6)..(6)
<223> OTHER INFORMATION: D-Tyr
<220> FEATURE:
<221> NAME/KEY: MISC_FEATURE
<222> LOCATION: (7)..(7)
<223> OTHER INFORMATION: D-Asp
<220> FEATURE:
<221> NAME/KEY: MISC_FEATURE
<222> LOCATION: (8)..(8)

<223> OTHER INFORMATION: D-Cys
<220> FEATURE:
<221> NAME/KEY: MISC_FEATURE
<222> LOCATION: (9)..(9)
<223> OTHER INFORMATION: D-Tyr
<220> FEATURE:
<221> NAME/KEY: MISC_FEATURE
<222> LOCATION: (10)..(10)
<223> OTHER INFORMATION: D-Glu
<220> FEATURE:
<221> NAME/KEY: MISC_FEATURE
<222> LOCATION: (10)..(10)
<223> OTHER INFORMATION: C-terminal amidation

<400> SEQUENCE: 478

Cys Ile Met Thr Trp Tyr Asp Cys Tyr Glu
1               5                   10

<210> SEQ ID NO 479
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (1)..(1)
<223> OTHER INFORMATION: D-Cys
<220> FEATURE:
<221> NAME/KEY: DISULFID
<222> LOCATION: (1)..(8)
<223> OTHER INFORMATION: Cyclic peptide - Intramolecular disulfide bond
<220> FEATURE:
<221> NAME/KEY: MISC_FEATURE
<222> LOCATION: (2)..(2)
<223> OTHER INFORMATION: D-Ile
<220> FEATURE:
<221> NAME/KEY: MISC_FEATURE
<222> LOCATION: (3)..(3)
<223> OTHER INFORMATION: D-Met
<220> FEATURE:
<221> NAME/KEY: MISC_FEATURE
<222> LOCATION: (4)..(4)
<223> OTHER INFORMATION: D-Val
<220> FEATURE:
<221> NAME/KEY: MISC_FEATURE
<222> LOCATION: (5)..(5)
<223> OTHER INFORMATION: D-Trp
<220> FEATURE:
<221> NAME/KEY: MISC_FEATURE
<222> LOCATION: (6)..(6)
<223> OTHER INFORMATION: D-Tyr
<220> FEATURE:
<221> NAME/KEY: MISC_FEATURE
<222> LOCATION: (7)..(7)
<223> OTHER INFORMATION: D-Asp
<220> FEATURE:
<221> NAME/KEY: MISC_FEATURE
<222> LOCATION: (8)..(8)
<223> OTHER INFORMATION: D-Cys
<220> FEATURE:
<221> NAME/KEY: MISC_FEATURE
<222> LOCATION: (9)..(9)
<223> OTHER INFORMATION: D-Tyr
<220> FEATURE:
<221> NAME/KEY: MISC_FEATURE
<222> LOCATION: (10)..(10)
<223> OTHER INFORMATION: D-Glu
<220> FEATURE:
<221> NAME/KEY: MISC_FEATURE
<222> LOCATION: (10)..(10)
<223> OTHER INFORMATION: C-terminal amidation

<400> SEQUENCE: 479

Cys Ile Met Val Trp Tyr Asp Cys Tyr Glu
1 5 10

<210> SEQ ID NO 480
<211> LENGTH: 10
<212> TYPE: PRT
<213> ORGANISM: Artificial Sequence
<220> FEATURE:
<223> OTHER INFORMATION: Synthetic peptide

<400> SEQUENCE: 480

Phe Glu Ile Tyr Cys Trp Asp Cys Tyr Met
1 5 10

<210> SEQ ID NO 481
<211> LENGTH: 10
<212> TYPE: PRT
<213> ORGANISM: Artificial Sequence
<220> FEATURE:
<223> OTHER INFORMATION: Synthetic peptide

<400> SEQUENCE: 481

Tyr Trp Cys Phe Ile Tyr Met Cys Glu Asp
1 5 10

<210> SEQ ID NO 482
<211> LENGTH: 10
<212> TYPE: PRT
<213> ORGANISM: Artificial Sequence
<220> FEATURE:
<223> OTHER INFORMATION: Synthetic peptide

<400> SEQUENCE: 482

Asp Met Trp Cys Glu Tyr Phe Cys Tyr Ile
1 5 10

<210> SEQ ID NO 483
<211> LENGTH: 10
<212> TYPE: PRT
<213> ORGANISM: Artificial Sequence
<220> FEATURE:
<223> OTHER INFORMATION: Synthetic peptide

<400> SEQUENCE: 483

Cys Glu Ile Cys Trp Tyr Phe Asp Tyr Met
1 5 10

<210> SEQ ID NO 484
<211> LENGTH: 10
<212> TYPE: PRT
<213> ORGANISM: Artificial Sequence
<220> FEATURE:
<223> OTHER INFORMATION: Synthetic peptide

<400> SEQUENCE: 484

Cys Cys Trp Phe Ile Glu Met Asp Tyr Tyr
1 5 10

<210> SEQ ID NO 485
<211> LENGTH: 10
<212> TYPE: PRT
<213> ORGANISM: Artificial Sequence
<220> FEATURE:
<223> OTHER INFORMATION: Synthetic peptide

<400> SEQUENCE: 485

Cys Glu Met Asp Trp Tyr Cys Tyr Phe Ile
1 5 10

<210> SEQ ID NO 486
<211> LENGTH: 10
<212> TYPE: PRT
<213> ORGANISM: Artificial Sequence
<220> FEATURE:
<223> OTHER INFORMATION: Synthetic peptide

<400> SEQUENCE: 486

Ala Ile Met Phe Trp Tyr Asp Cys Tyr Glu
1 5 10

<210> SEQ ID NO 487
<211> LENGTH: 10
<212> TYPE: PRT
<213> ORGANISM: Artificial Sequence
<220> FEATURE:
<223> OTHER INFORMATION: Synthetic peptide

<400> SEQUENCE: 487

Asp Ile Met Phe Trp Tyr Asp Cys Tyr Glu
1 5 10

<210> SEQ ID NO 488
<211> LENGTH: 10
<212> TYPE: PRT
<213> ORGANISM: Artificial Sequence
<220> FEATURE:
<223> OTHER INFORMATION: Synthetic peptide

<400> SEQUENCE: 488

Glu Ile Met Phe Trp Tyr Asp Cys Tyr Glu
1 5 10

<210> SEQ ID NO 489
<211> LENGTH: 10
<212> TYPE: PRT
<213> ORGANISM: Artificial Sequence
<220> FEATURE:
<223> OTHER INFORMATION: Synthetic peptide

<400> SEQUENCE: 489

Phe Ile Met Phe Trp Tyr Asp Cys Tyr Glu
1 5 10

<210> SEQ ID NO 490
<211> LENGTH: 10
<212> TYPE: PRT
<213> ORGANISM: Artificial Sequence
<220> FEATURE:
<223> OTHER INFORMATION: Synthetic peptide

<400> SEQUENCE: 490

His Ile Met Phe Trp Tyr Asp Cys Tyr Glu
1 5 10

<210> SEQ ID NO 491
<211> LENGTH: 10
<212> TYPE: PRT
<213> ORGANISM: Artificial Sequence
<220> FEATURE:
<223> OTHER INFORMATION: Synthetic peptide

<400> SEQUENCE: 491

Ile Ile Met Phe Trp Tyr Asp Cys Tyr Glu
1               5                   10

<210> SEQ ID NO 492
<211> LENGTH: 10
<212> TYPE: PRT
<213> ORGANISM: Artificial Sequence
<220> FEATURE:
<223> OTHER INFORMATION: Synthetic peptide

<400> SEQUENCE: 492

Lys Ile Met Phe Trp Tyr Asp Cys Tyr Glu
1               5                   10

<210> SEQ ID NO 493
<211> LENGTH: 10
<212> TYPE: PRT
<213> ORGANISM: Artificial Sequence
<220> FEATURE:
<223> OTHER INFORMATION: Synthetic peptide

<400> SEQUENCE: 493

Leu Ile Met Phe Trp Tyr Asp Cys Tyr Glu
1               5                   10

<210> SEQ ID NO 494
<211> LENGTH: 10
<212> TYPE: PRT
<213> ORGANISM: Artificial Sequence
<220> FEATURE:
<223> OTHER INFORMATION: Synthetic peptide

<400> SEQUENCE: 494

Met Ile Met Phe Trp Tyr Asp Cys Tyr Glu
1               5                   10

<210> SEQ ID NO 495
<211> LENGTH: 10
<212> TYPE: PRT
<213> ORGANISM: Artificial Sequence
<220> FEATURE:
<223> OTHER INFORMATION: Synthetic peptide

<400> SEQUENCE: 495

Asn Ile Met Phe Trp Tyr Asp Cys Tyr Glu
1               5                   10

<210> SEQ ID NO 496
<211> LENGTH: 10
<212> TYPE: PRT
<213> ORGANISM: Artificial Sequence
<220> FEATURE:
<223> OTHER INFORMATION: Synthetic peptide

<400> SEQUENCE: 496

Pro Ile Met Phe Trp Tyr Asp Cys Tyr Glu
1               5                   10

<210> SEQ ID NO 497
<211> LENGTH: 10
<212> TYPE: PRT
<213> ORGANISM: Artificial Sequence
<220> FEATURE:
<223> OTHER INFORMATION: Synthetic peptide

<400> SEQUENCE: 497

Gln Ile Met Phe Trp Tyr Asp Cys Tyr Glu 1 5 10

<210> SEQ ID NO 498
<211> LENGTH: 10
<212> TYPE: PRT
<213> ORGANISM: Artificial Sequence
<220> FEATURE:
<223> OTHER INFORMATION: Synthetic peptide

<400> SEQUENCE: 498

Arg Ile Met Phe Trp Tyr Asp Cys Tyr Glu
1 5 10

<210> SEQ ID NO 499
<211> LENGTH: 10
<212> TYPE: PRT
<213> ORGANISM: Artificial Sequence
<220> FEATURE:
<223> OTHER INFORMATION: Synthetic peptide

<400> SEQUENCE: 499

Ser Ile Met Phe Trp Tyr Asp Cys Tyr Glu
1 5 10

<210> SEQ ID NO 500
<211> LENGTH: 10
<212> TYPE: PRT
<213> ORGANISM: Artificial Sequence
<220> FEATURE:
<223> OTHER INFORMATION: Synthetic peptide

<400> SEQUENCE: 500

Thr Ile Met Phe Trp Tyr Asp Cys Tyr Glu
1 5 10

<210> SEQ ID NO 501
<211> LENGTH: 10
<212> TYPE: PRT
<213> ORGANISM: Artificial Sequence
<220> FEATURE:
<223> OTHER INFORMATION: Synthetic peptide

<400> SEQUENCE: 501

Val Ile Met Phe Trp Tyr Asp Cys Tyr Glu
1 5 10

<210> SEQ ID NO 502
<211> LENGTH: 10
<212> TYPE: PRT
<213> ORGANISM: Artificial Sequence
<220> FEATURE:
<223> OTHER INFORMATION: Synthetic peptide

<400> SEQUENCE: 502

Trp Ile Met Phe Trp Tyr Asp Cys Tyr Glu
1 5 10

<210> SEQ ID NO 503
<211> LENGTH: 10
<212> TYPE: PRT
<213> ORGANISM: Artificial Sequence
<220> FEATURE:
<223> OTHER INFORMATION: Synthetic peptide

<400> SEQUENCE: 503

Tyr Ile Met Phe Trp Tyr Asp Cys Tyr Glu
1 5 10

<210> SEQ ID NO 504
<211> LENGTH: 10
<212> TYPE: PRT
<213> ORGANISM: Artificial Sequence
<220> FEATURE:
<223> OTHER INFORMATION: Synthetic peptide

<400> SEQUENCE: 504

Cys Ala Met Phe Trp Tyr Asp Cys Tyr Glu
1 5 10

<210> SEQ ID NO 505
<211> LENGTH: 10
<212> TYPE: PRT
<213> ORGANISM: Artificial Sequence
<220> FEATURE:
<223> OTHER INFORMATION: Synthetic peptide

<400> SEQUENCE: 505

Cys Cys Met Phe Trp Tyr Asp Ser Tyr Glu
1 5 10

<210> SEQ ID NO 506
<211> LENGTH: 10
<212> TYPE: PRT
<213> ORGANISM: Artificial Sequence
<220> FEATURE:
<223> OTHER INFORMATION: Synthetic peptide

<400> SEQUENCE: 506

Cys Asp Met Phe Trp Tyr Asp Cys Tyr Glu
1 5 10

<210> SEQ ID NO 507
<211> LENGTH: 10
<212> TYPE: PRT
<213> ORGANISM: Artificial Sequence
<220> FEATURE:
<223> OTHER INFORMATION: Synthetic peptide

<400> SEQUENCE: 507

Cys Glu Met Phe Trp Tyr Asp Cys Tyr Glu
1 5 10

<210> SEQ ID NO 508
<211> LENGTH: 10
<212> TYPE: PRT
<213> ORGANISM: Artificial Sequence
<220> FEATURE:
<223> OTHER INFORMATION: Synthetic peptide

<400> SEQUENCE: 508

Cys Phe Met Phe Trp Tyr Asp Cys Tyr Glu
1 5 10

<210> SEQ ID NO 509
<211> LENGTH: 10
<212> TYPE: PRT
<213> ORGANISM: Artificial Sequence
<220> FEATURE:
<223> OTHER INFORMATION: Synthetic peptide

<400> SEQUENCE: 509

Cys His Met Phe Trp Tyr Asp Cys Tyr Glu
1 5 10

<210> SEQ ID NO 510
<211> LENGTH: 10
<212> TYPE: PRT
<213> ORGANISM: Artificial Sequence
<220> FEATURE:
<223> OTHER INFORMATION: Synthetic peptide

<400> SEQUENCE: 510

Cys Lys Met Phe Trp Tyr Asp Cys Tyr Glu
1 5 10

<210> SEQ ID NO 511
<211> LENGTH: 10
<212> TYPE: PRT
<213> ORGANISM: Artificial Sequence
<220> FEATURE:
<223> OTHER INFORMATION: Synthetic peptide

<400> SEQUENCE: 511

Cys Leu Met Phe Trp Tyr Asp Cys Tyr Glu
1 5 10

<210> SEQ ID NO 512
<211> LENGTH: 10
<212> TYPE: PRT
<213> ORGANISM: Artificial Sequence
<220> FEATURE:
<223> OTHER INFORMATION: Synthetic peptide

<400> SEQUENCE: 512

Cys Met Met Phe Trp Tyr Asp Cys Tyr Glu
1 5 10

<210> SEQ ID NO 513
<211> LENGTH: 10
<212> TYPE: PRT
<213> ORGANISM: Artificial Sequence
<220> FEATURE:
<223> OTHER INFORMATION: Synthetic peptide

<400> SEQUENCE: 513

Cys Asn Met Phe Trp Tyr Asp Cys Tyr Glu
1 5 10

<210> SEQ ID NO 514
<211> LENGTH: 10
<212> TYPE: PRT
<213> ORGANISM: Artificial Sequence
<220> FEATURE:
<223> OTHER INFORMATION: Synthetic peptide

<400> SEQUENCE: 514

Cys Pro Met Phe Trp Tyr Asp Cys Tyr Glu
1 5 10

<210> SEQ ID NO 515
<211> LENGTH: 10
<212> TYPE: PRT
<213> ORGANISM: Artificial Sequence
<220> FEATURE:
<223> OTHER INFORMATION: Synthetic peptide

<400> SEQUENCE: 515

Cys Gln Met Phe Trp Tyr Asp Cys Tyr Glu
1 5 10

<210> SEQ ID NO 516
<211> LENGTH: 10
<212> TYPE: PRT
<213> ORGANISM: Artificial Sequence
<220> FEATURE:
<223> OTHER INFORMATION: Synthetic peptide

<400> SEQUENCE: 516

Cys Arg Met Phe Trp Tyr Asp Cys Tyr Glu
1               5                   10

<210> SEQ ID NO 517
<211> LENGTH: 10
<212> TYPE: PRT
<213> ORGANISM: Artificial Sequence
<220> FEATURE:
<223> OTHER INFORMATION: Synthetic peptide

<400> SEQUENCE: 517

Cys Ser Met Phe Trp Tyr Asp Cys Tyr Glu
1               5                   10

<210> SEQ ID NO 518
<211> LENGTH: 10
<212> TYPE: PRT
<213> ORGANISM: Artificial Sequence
<220> FEATURE:
<223> OTHER INFORMATION: Synthetic peptide

<400> SEQUENCE: 518

Cys Thr Met Phe Trp Tyr Asp Cys Tyr Glu
1               5                   10

<210> SEQ ID NO 519
<211> LENGTH: 10
<212> TYPE: PRT
<213> ORGANISM: Artificial Sequence
<220> FEATURE:
<223> OTHER INFORMATION: Synthetic peptide

<400> SEQUENCE: 519

Cys Val Met Phe Trp Tyr Asp Cys Tyr Glu
1               5                   10

<210> SEQ ID NO 520
<211> LENGTH: 10
<212> TYPE: PRT
<213> ORGANISM: Artificial Sequence
<220> FEATURE:
<223> OTHER INFORMATION: Synthetic peptide

<400> SEQUENCE: 520

Cys Ile Ala Phe Trp Tyr Asp Cys Tyr Glu
1               5                   10

<210> SEQ ID NO 521
<211> LENGTH: 10
<212> TYPE: PRT
<213> ORGANISM: Artificial Sequence
<220> FEATURE:
<223> OTHER INFORMATION: Synthetic peptide

<400> SEQUENCE: 521

Cys Ile Asp Phe Trp Tyr Asp Cys Tyr Glu
1               5                   10

<210> SEQ ID NO 522

<211> LENGTH: 10
<212> TYPE: PRT
<213> ORGANISM: Artificial Sequence
<220> FEATURE:
<223> OTHER INFORMATION: Synthetic peptide

<400> SEQUENCE: 522

Cys Ile Glu Phe Trp Tyr Asp Cys Tyr Glu
1 5 10

<210> SEQ ID NO 523
<211> LENGTH: 10
<212> TYPE: PRT
<213> ORGANISM: Artificial Sequence
<220> FEATURE:
<223> OTHER INFORMATION: Synthetic peptide

<400> SEQUENCE: 523

Cys Ile Phe Phe Trp Tyr Asp Cys Tyr Glu
1 5 10

<210> SEQ ID NO 524
<211> LENGTH: 10
<212> TYPE: PRT
<213> ORGANISM: Artificial Sequence
<220> FEATURE:
<223> OTHER INFORMATION: Synthetic peptide

<400> SEQUENCE: 524

Cys Ile His Phe Trp Tyr Asp Cys Tyr Glu
1 5 10

<210> SEQ ID NO 525
<211> LENGTH: 10
<212> TYPE: PRT
<213> ORGANISM: Artificial Sequence
<220> FEATURE:
<223> OTHER INFORMATION: Synthetic peptide

<400> SEQUENCE: 525

Cys Ile Ile Phe Trp Tyr Asp Cys Tyr Glu
1 5 10

<210> SEQ ID NO 526
<211> LENGTH: 10
<212> TYPE: PRT
<213> ORGANISM: Artificial Sequence
<220> FEATURE:
<223> OTHER INFORMATION: Synthetic peptide

<400> SEQUENCE: 526

Cys Ile Lys Phe Trp Tyr Asp Cys Tyr Glu
1 5 10

<210> SEQ ID NO 527
<211> LENGTH: 10
<212> TYPE: PRT
<213> ORGANISM: Artificial Sequence
<220> FEATURE:
<223> OTHER INFORMATION: Synthetic peptide

<400> SEQUENCE: 527

Cys Ile Leu Phe Trp Tyr Asp Cys Tyr Glu
1 5 10

<210> SEQ ID NO 528
<211> LENGTH: 10

```
<212> TYPE: PRT
<213> ORGANISM: Artificial Sequence
<220> FEATURE:
<223> OTHER INFORMATION: Synthetic peptide

<400> SEQUENCE: 528

Cys Ile Asn Phe Trp Tyr Asp Cys Tyr Glu
1               5                   10


<210> SEQ ID NO 529
<211> LENGTH: 10
<212> TYPE: PRT
<213> ORGANISM: Artificial Sequence
<220> FEATURE:
<223> OTHER INFORMATION: Synthetic peptide

<400> SEQUENCE: 529

Cys Ile Pro Phe Trp Tyr Asp Cys Tyr Glu
1               5                   10


<210> SEQ ID NO 530
<211> LENGTH: 10
<212> TYPE: PRT
<213> ORGANISM: Artificial Sequence
<220> FEATURE:
<223> OTHER INFORMATION: Synthetic peptide

<400> SEQUENCE: 530

Cys Ile Gln Phe Trp Tyr Asp Cys Tyr Glu
1               5                   10


<210> SEQ ID NO 531
<211> LENGTH: 10
<212> TYPE: PRT
<213> ORGANISM: Artificial Sequence
<220> FEATURE:
<223> OTHER INFORMATION: Synthetic peptide

<400> SEQUENCE: 531

Cys Ile Arg Phe Trp Tyr Asp Cys Tyr Glu
1               5                   10


<210> SEQ ID NO 532
<211> LENGTH: 10
<212> TYPE: PRT
<213> ORGANISM: Artificial Sequence
<220> FEATURE:
<223> OTHER INFORMATION: Synthetic peptide

<400> SEQUENCE: 532

Cys Ile Ser Phe Trp Tyr Asp Cys Tyr Glu
1               5                   10


<210> SEQ ID NO 533
<211> LENGTH: 10
<212> TYPE: PRT
<213> ORGANISM: Artificial Sequence
<220> FEATURE:
<223> OTHER INFORMATION: Synthetic peptide

<400> SEQUENCE: 533

Cys Ile Thr Phe Trp Tyr Asp Cys Tyr Glu
1               5                   10


<210> SEQ ID NO 534
<211> LENGTH: 10
<212> TYPE: PRT
```

<213> ORGANISM: Artificial Sequence
<220> FEATURE:
<223> OTHER INFORMATION: Synthetic peptide

<400> SEQUENCE: 534

Cys Ile Val Phe Trp Tyr Asp Cys Tyr Glu
1               5                   10

<210> SEQ ID NO 535
<211> LENGTH: 10
<212> TYPE: PRT
<213> ORGANISM: Artificial Sequence
<220> FEATURE:
<223> OTHER INFORMATION: Synthetic peptide

<400> SEQUENCE: 535

Cys Ile Trp Phe Trp Tyr Asp Cys Tyr Glu
1               5                   10

<210> SEQ ID NO 536
<211> LENGTH: 10
<212> TYPE: PRT
<213> ORGANISM: Artificial Sequence
<220> FEATURE:
<223> OTHER INFORMATION: Synthetic peptide

<400> SEQUENCE: 536

Cys Ile Tyr Phe Trp Tyr Asp Cys Tyr Glu
1               5                   10

<210> SEQ ID NO 537
<211> LENGTH: 10
<212> TYPE: PRT
<213> ORGANISM: Artificial Sequence
<220> FEATURE:
<223> OTHER INFORMATION: Synthetic peptide

<400> SEQUENCE: 537

Cys Ile Met Ala Trp Tyr Asp Cys Tyr Glu
1               5                   10

<210> SEQ ID NO 538
<211> LENGTH: 10
<212> TYPE: PRT
<213> ORGANISM: Artificial Sequence
<220> FEATURE:
<223> OTHER INFORMATION: Synthetic peptide

<400> SEQUENCE: 538

Cys Ile Met Cys Trp Tyr Asp Ser Tyr Glu
1               5                   10

<210> SEQ ID NO 539
<211> LENGTH: 10
<212> TYPE: PRT
<213> ORGANISM: Artificial Sequence
<220> FEATURE:
<223> OTHER INFORMATION: Synthetic peptide

<400> SEQUENCE: 539

Cys Ile Met Asp Trp Tyr Asp Cys Tyr Glu
1               5                   10

<210> SEQ ID NO 540
<211> LENGTH: 10
<212> TYPE: PRT
<213> ORGANISM: Artificial Sequence -continued
<220> FEATURE:
<223> OTHER INFORMATION: Synthetic peptide

<400> SEQUENCE: 540

Cys Ile Met Glu Trp Tyr Asp Cys Tyr Glu
1               5                   10

<210> SEQ ID NO 541
<211> LENGTH: 10
<212> TYPE: PRT
<213> ORGANISM: Artificial Sequence
<220> FEATURE:
<223> OTHER INFORMATION: Synthetic peptide

<400> SEQUENCE: 541

Cys Ile Met His Trp Tyr Asp Cys Tyr Glu
1               5                   10

<210> SEQ ID NO 542
<211> LENGTH: 10
<212> TYPE: PRT
<213> ORGANISM: Artificial Sequence
<220> FEATURE:
<223> OTHER INFORMATION: Synthetic peptide

<400> SEQUENCE: 542

Cys Ile Met Ile Trp Tyr Asp Cys Tyr Glu
1               5                   10

<210> SEQ ID NO 543
<211> LENGTH: 10
<212> TYPE: PRT
<213> ORGANISM: Artificial Sequence
<220> FEATURE:
<223> OTHER INFORMATION: Synthetic peptide

<400> SEQUENCE: 543

Cys Ile Met Lys Trp Tyr Asp Cys Tyr Glu
1               5                   10

<210> SEQ ID NO 544
<211> LENGTH: 10
<212> TYPE: PRT
<213> ORGANISM: Artificial Sequence
<220> FEATURE:
<223> OTHER INFORMATION: Synthetic peptide

<400> SEQUENCE: 544

Cys Ile Met Leu Trp Tyr Asp Cys Tyr Glu
1               5                   10

<210> SEQ ID NO 545
<211> LENGTH: 10
<212> TYPE: PRT
<213> ORGANISM: Artificial Sequence
<220> FEATURE:
<223> OTHER INFORMATION: Synthetic peptide

<400> SEQUENCE: 545

Cys Ile Met Met Trp Tyr Asp Cys Tyr Glu
1               5                   10

<210> SEQ ID NO 546
<211> LENGTH: 10
<212> TYPE: PRT
<213> ORGANISM: Artificial Sequence
<220> FEATURE:

<223> OTHER INFORMATION: Synthetic peptide

<400> SEQUENCE: 546

Cys Ile Met Asn Trp Tyr Asp Cys Tyr Glu
1 5 10

<210> SEQ ID NO 547
<211> LENGTH: 10
<212> TYPE: PRT
<213> ORGANISM: Artificial Sequence
<220> FEATURE:
<223> OTHER INFORMATION: Synthetic peptide

<400> SEQUENCE: 547

Cys Ile Met Pro Trp Tyr Asp Cys Tyr Glu
1 5 10

<210> SEQ ID NO 548
<211> LENGTH: 10
<212> TYPE: PRT
<213> ORGANISM: Artificial Sequence
<220> FEATURE:
<223> OTHER INFORMATION: Synthetic peptide

<400> SEQUENCE: 548

Cys Ile Met Gln Trp Tyr Asp Cys Tyr Glu
1 5 10

<210> SEQ ID NO 549
<211> LENGTH: 10
<212> TYPE: PRT
<213> ORGANISM: Artificial Sequence
<220> FEATURE:
<223> OTHER INFORMATION: Synthetic peptide

<400> SEQUENCE: 549

Cys Ile Met Arg Trp Tyr Asp Cys Tyr Glu
1 5 10

<210> SEQ ID NO 550
<211> LENGTH: 10
<212> TYPE: PRT
<213> ORGANISM: Artificial Sequence
<220> FEATURE:
<223> OTHER INFORMATION: Synthetic peptide

<400> SEQUENCE: 550

Cys Ile Met Ser Trp Tyr Asp Cys Tyr Glu
1 5 10

<210> SEQ ID NO 551
<211> LENGTH: 10
<212> TYPE: PRT
<213> ORGANISM: Artificial Sequence
<220> FEATURE:
<223> OTHER INFORMATION: Synthetic peptide

<400> SEQUENCE: 551

Cys Ile Met Trp Trp Tyr Asp Cys Tyr Glu
1 5 10

<210> SEQ ID NO 552
<211> LENGTH: 10
<212> TYPE: PRT
<213> ORGANISM: Artificial Sequence
<220> FEATURE:
<223> OTHER INFORMATION: Synthetic peptide

<400> SEQUENCE: 552

Cys Ile Met Tyr Trp Tyr Asp Cys Tyr Glu
1 5 10

<210> SEQ ID NO 553
<211> LENGTH: 10
<212> TYPE: PRT
<213> ORGANISM: Artificial Sequence
<220> FEATURE:
<223> OTHER INFORMATION: Synthetic peptide

<400> SEQUENCE: 553

Cys Ile Met Phe Ala Tyr Asp Cys Tyr Glu
1 5 10

<210> SEQ ID NO 554
<211> LENGTH: 10
<212> TYPE: PRT
<213> ORGANISM: Artificial Sequence
<220> FEATURE:
<223> OTHER INFORMATION: Synthetic peptide

<400> SEQUENCE: 554

Cys Ile Met Phe Cys Tyr Asp Ser Tyr Glu
1 5 10

<210> SEQ ID NO 555
<211> LENGTH: 10
<212> TYPE: PRT
<213> ORGANISM: Artificial Sequence
<220> FEATURE:
<223> OTHER INFORMATION: Synthetic peptide

<400> SEQUENCE: 555

Cys Ile Met Phe Asp Tyr Asp Cys Tyr Glu
1 5 10

<210> SEQ ID NO 556
<211> LENGTH: 10
<212> TYPE: PRT
<213> ORGANISM: Artificial Sequence
<220> FEATURE:
<223> OTHER INFORMATION: Synthetic peptide

<400> SEQUENCE: 556

Cys Ile Met Phe Glu Tyr Asp Cys Tyr Glu
1 5 10

<210> SEQ ID NO 557
<211> LENGTH: 10
<212> TYPE: PRT
<213> ORGANISM: Artificial Sequence
<220> FEATURE:
<223> OTHER INFORMATION: Synthetic peptide

<400> SEQUENCE: 557

Cys Ile Met Phe Phe Tyr Asp Cys Tyr Glu
1 5 10

<210> SEQ ID NO 558
<211> LENGTH: 10
<212> TYPE: PRT
<213> ORGANISM: Artificial Sequence
<220> FEATURE:
<223> OTHER INFORMATION: Synthetic peptide -continued

<400> SEQUENCE: 558

Cys Ile Met Phe His Tyr Asp Cys Tyr Glu
1               5                   10

<210> SEQ ID NO 559
<211> LENGTH: 10
<212> TYPE: PRT
<213> ORGANISM: Artificial Sequence
<220> FEATURE:
<223> OTHER INFORMATION: Synthetic peptide

<400> SEQUENCE: 559

Cys Ile Met Phe Ile Tyr Asp Cys Tyr Glu
1               5                   10

<210> SEQ ID NO 560
<211> LENGTH: 10
<212> TYPE: PRT
<213> ORGANISM: Artificial Sequence
<220> FEATURE:
<223> OTHER INFORMATION: Synthetic peptide

<400> SEQUENCE: 560

Cys Ile Met Phe Lys Tyr Asp Cys Tyr Glu
1               5                   10

<210> SEQ ID NO 561
<211> LENGTH: 10
<212> TYPE: PRT
<213> ORGANISM: Artificial Sequence
<220> FEATURE:
<223> OTHER INFORMATION: Synthetic peptide

<400> SEQUENCE: 561

Cys Ile Met Phe Leu Tyr Asp Cys Tyr Glu
1               5                   10

<210> SEQ ID NO 562
<211> LENGTH: 10
<212> TYPE: PRT
<213> ORGANISM: Artificial Sequence
<220> FEATURE:
<223> OTHER INFORMATION: Synthetic peptide

<400> SEQUENCE: 562

Cys Ile Met Phe Met Tyr Asp Cys Tyr Glu
1               5                   10

<210> SEQ ID NO 563
<211> LENGTH: 10
<212> TYPE: PRT
<213> ORGANISM: Artificial Sequence
<220> FEATURE:
<223> OTHER INFORMATION: Synthetic peptide

<400> SEQUENCE: 563

Cys Ile Met Phe Asn Tyr Asp Cys Tyr Glu
1               5                   10

<210> SEQ ID NO 564
<211> LENGTH: 10
<212> TYPE: PRT
<213> ORGANISM: Artificial Sequence
<220> FEATURE:
<223> OTHER INFORMATION: Synthetic peptide

<400> SEQUENCE: 564

Cys Ile Met Phe Pro Tyr Asp Cys Tyr Glu
1 5 10

<210> SEQ ID NO 565
<211> LENGTH: 10
<212> TYPE: PRT
<213> ORGANISM: Artificial Sequence
<220> FEATURE:
<223> OTHER INFORMATION: Synthetic peptide

<400> SEQUENCE: 565

Cys Ile Met Phe Gln Tyr Asp Cys Tyr Glu
1 5 10

<210> SEQ ID NO 566
<211> LENGTH: 10
<212> TYPE: PRT
<213> ORGANISM: Artificial Sequence
<220> FEATURE:
<223> OTHER INFORMATION: Synthetic peptide

<400> SEQUENCE: 566

Cys Ile Met Phe Arg Tyr Asp Cys Tyr Glu
1 5 10

<210> SEQ ID NO 567
<211> LENGTH: 10
<212> TYPE: PRT
<213> ORGANISM: Artificial Sequence
<220> FEATURE:
<223> OTHER INFORMATION: Synthetic peptide

<400> SEQUENCE: 567

Cys Ile Met Phe Ser Tyr Asp Cys Tyr Glu
1 5 10

<210> SEQ ID NO 568
<211> LENGTH: 10
<212> TYPE: PRT
<213> ORGANISM: Artificial Sequence
<220> FEATURE:
<223> OTHER INFORMATION: Synthetic peptide

<400> SEQUENCE: 568

Cys Ile Met Phe Thr Tyr Asp Cys Tyr Glu
1 5 10

<210> SEQ ID NO 569
<211> LENGTH: 10
<212> TYPE: PRT
<213> ORGANISM: Artificial Sequence
<220> FEATURE:
<223> OTHER INFORMATION: Synthetic peptide

<400> SEQUENCE: 569

Cys Ile Met Phe Val Tyr Asp Cys Tyr Glu
1 5 10

<210> SEQ ID NO 570
<211> LENGTH: 10
<212> TYPE: PRT
<213> ORGANISM: Artificial Sequence
<220> FEATURE:
<223> OTHER INFORMATION: Synthetic peptide

<400> SEQUENCE: 570

-continued

Cys Ile Met Phe Tyr Tyr Asp Cys Tyr Glu
1 5 10

<210> SEQ ID NO 571
<211> LENGTH: 10
<212> TYPE: PRT
<213> ORGANISM: Artificial Sequence
<220> FEATURE:
<223> OTHER INFORMATION: Synthetic peptide

<400> SEQUENCE: 571

Cys Ile Met Phe Trp Ala Asp Cys Tyr Glu
1 5 10

<210> SEQ ID NO 572
<211> LENGTH: 10
<212> TYPE: PRT
<213> ORGANISM: Artificial Sequence
<220> FEATURE:
<223> OTHER INFORMATION: Synthetic peptide

<400> SEQUENCE: 572

Cys Ile Met Phe Trp Cys Asp Ser Tyr Glu
1 5 10

<210> SEQ ID NO 573
<211> LENGTH: 10
<212> TYPE: PRT
<213> ORGANISM: Artificial Sequence
<220> FEATURE:
<223> OTHER INFORMATION: Synthetic peptide

<400> SEQUENCE: 573

Cys Ile Met Phe Trp Asp Asp Cys Tyr Glu
1 5 10

<210> SEQ ID NO 574
<211> LENGTH: 10
<212> TYPE: PRT
<213> ORGANISM: Artificial Sequence
<220> FEATURE:
<223> OTHER INFORMATION: Synthetic peptide

<400> SEQUENCE: 574

Cys Ile Met Phe Trp Glu Asp Cys Tyr Glu
1 5 10

<210> SEQ ID NO 575
<211> LENGTH: 10
<212> TYPE: PRT
<213> ORGANISM: Artificial Sequence
<220> FEATURE:
<223> OTHER INFORMATION: Synthetic peptide

<400> SEQUENCE: 575

Cys Ile Met Phe Trp Phe Asp Cys Tyr Glu
1 5 10

<210> SEQ ID NO 576
<211> LENGTH: 10
<212> TYPE: PRT
<213> ORGANISM: Artificial Sequence
<220> FEATURE:
<223> OTHER INFORMATION: Synthetic peptide

<400> SEQUENCE: 576

Cys Ile Met Phe Trp His Asp Cys Tyr Glu 1 5 10

<210> SEQ ID NO 577
<211> LENGTH: 10
<212> TYPE: PRT
<213> ORGANISM: Artificial Sequence
<220> FEATURE:
<223> OTHER INFORMATION: Synthetic peptide

<400> SEQUENCE: 577

Cys Ile Met Phe Trp Ile Asp Cys Tyr Glu
1 5 10

<210> SEQ ID NO 578
<211> LENGTH: 10
<212> TYPE: PRT
<213> ORGANISM: Artificial Sequence
<220> FEATURE:
<223> OTHER INFORMATION: Synthetic peptide

<400> SEQUENCE: 578

Cys Ile Met Phe Trp Lys Asp Cys Tyr Glu
1 5 10

<210> SEQ ID NO 579
<211> LENGTH: 10
<212> TYPE: PRT
<213> ORGANISM: Artificial Sequence
<220> FEATURE:
<223> OTHER INFORMATION: Synthetic peptide

<400> SEQUENCE: 579

Cys Ile Met Phe Trp Leu Asp Cys Tyr Glu
1 5 10

<210> SEQ ID NO 580
<211> LENGTH: 10
<212> TYPE: PRT
<213> ORGANISM: Artificial Sequence
<220> FEATURE:
<223> OTHER INFORMATION: Synthetic peptide

<400> SEQUENCE: 580

Cys Ile Met Phe Trp Met Asp Cys Tyr Glu
1 5 10

<210> SEQ ID NO 581
<211> LENGTH: 10
<212> TYPE: PRT
<213> ORGANISM: Artificial Sequence
<220> FEATURE:
<223> OTHER INFORMATION: Synthetic peptide

<400> SEQUENCE: 581

Cys Ile Met Phe Trp Asn Asp Cys Tyr Glu
1 5 10

<210> SEQ ID NO 582
<211> LENGTH: 10
<212> TYPE: PRT
<213> ORGANISM: Artificial Sequence
<220> FEATURE:
<223> OTHER INFORMATION: Synthetic peptide

<400> SEQUENCE: 582

Cys Ile Met Phe Trp Pro Asp Cys Tyr Glu
1 5 10

<210> SEQ ID NO 583
<211> LENGTH: 10
<212> TYPE: PRT
<213> ORGANISM: Artificial Sequence
<220> FEATURE:
<223> OTHER INFORMATION: Synthetic peptide

<400> SEQUENCE: 583

Cys Ile Met Phe Trp Gln Asp Cys Tyr Glu
1 5 10

<210> SEQ ID NO 584
<211> LENGTH: 10
<212> TYPE: PRT
<213> ORGANISM: Artificial Sequence
<220> FEATURE:
<223> OTHER INFORMATION: Synthetic peptide

<400> SEQUENCE: 584

Cys Ile Met Phe Trp Arg Asp Cys Tyr Glu
1 5 10

<210> SEQ ID NO 585
<211> LENGTH: 10
<212> TYPE: PRT
<213> ORGANISM: Artificial Sequence
<220> FEATURE:
<223> OTHER INFORMATION: Synthetic peptide

<400> SEQUENCE: 585

Cys Ile Met Phe Trp Ser Asp Cys Tyr Glu
1 5 10

<210> SEQ ID NO 586
<211> LENGTH: 10
<212> TYPE: PRT
<213> ORGANISM: Artificial Sequence
<220> FEATURE:
<223> OTHER INFORMATION: Synthetic peptide

<400> SEQUENCE: 586

Cys Ile Met Phe Trp Thr Asp Cys Tyr Glu
1 5 10

<210> SEQ ID NO 587
<211> LENGTH: 10
<212> TYPE: PRT
<213> ORGANISM: Artificial Sequence
<220> FEATURE:
<223> OTHER INFORMATION: Synthetic peptide

<400> SEQUENCE: 587

Cys Ile Met Phe Trp Val Asp Cys Tyr Glu
1 5 10

<210> SEQ ID NO 588
<211> LENGTH: 10
<212> TYPE: PRT
<213> ORGANISM: Artificial Sequence
<220> FEATURE:
<223> OTHER INFORMATION: Synthetic peptide

<400> SEQUENCE: 588

Cys Ile Met Phe Trp Trp Asp Cys Tyr Glu
1 5 10

<210> SEQ ID NO 589
<211> LENGTH: 10
<212> TYPE: PRT
<213> ORGANISM: Artificial Sequence
<220> FEATURE:
<223> OTHER INFORMATION: Synthetic peptide

<400> SEQUENCE: 589

Cys Ile Met Phe Trp Tyr Ala Cys Tyr Glu
1 5 10

<210> SEQ ID NO 590
<211> LENGTH: 10
<212> TYPE: PRT
<213> ORGANISM: Artificial Sequence
<220> FEATURE:
<223> OTHER INFORMATION: Synthetic peptide

<400> SEQUENCE: 590

Cys Ile Met Phe Trp Tyr Cys Ser Tyr Glu
1 5 10

<210> SEQ ID NO 591
<211> LENGTH: 10
<212> TYPE: PRT
<213> ORGANISM: Artificial Sequence
<220> FEATURE:
<223> OTHER INFORMATION: Synthetic peptide

<400> SEQUENCE: 591

Cys Ile Met Phe Trp Tyr Glu Cys Tyr Glu
1 5 10

<210> SEQ ID NO 592
<211> LENGTH: 10
<212> TYPE: PRT
<213> ORGANISM: Artificial Sequence
<220> FEATURE:
<223> OTHER INFORMATION: Synthetic peptide

<400> SEQUENCE: 592

Cys Ile Met Phe Trp Tyr Phe Cys Tyr Glu
1 5 10

<210> SEQ ID NO 593
<211> LENGTH: 10
<212> TYPE: PRT
<213> ORGANISM: Artificial Sequence
<220> FEATURE:
<223> OTHER INFORMATION: Synthetic peptide

<400> SEQUENCE: 593

Cys Ile Met Phe Trp Tyr His Cys Tyr Glu
1 5 10

<210> SEQ ID NO 594
<211> LENGTH: 10
<212> TYPE: PRT
<213> ORGANISM: Artificial Sequence
<220> FEATURE:
<223> OTHER INFORMATION: Synthetic peptide

<400> SEQUENCE: 594

Cys Ile Met Phe Trp Tyr Ile Cys Tyr Glu
1 5 10

<210> SEQ ID NO 595
<211> LENGTH: 10
<212> TYPE: PRT
<213> ORGANISM: Artificial Sequence
<220> FEATURE:
<223> OTHER INFORMATION: Synthetic peptide

<400> SEQUENCE: 595

Cys Ile Met Phe Trp Tyr Lys Cys Tyr Glu
1               5                   10

<210> SEQ ID NO 596
<211> LENGTH: 10
<212> TYPE: PRT
<213> ORGANISM: Artificial Sequence
<220> FEATURE:
<223> OTHER INFORMATION: Synthetic peptide

<400> SEQUENCE: 596

Cys Ile Met Phe Trp Tyr Leu Cys Tyr Glu
1               5                   10

<210> SEQ ID NO 597
<211> LENGTH: 10
<212> TYPE: PRT
<213> ORGANISM: Artificial Sequence
<220> FEATURE:
<223> OTHER INFORMATION: Synthetic peptide

<400> SEQUENCE: 597

Cys Ile Met Phe Trp Tyr Met Cys Tyr Glu
1               5                   10

<210> SEQ ID NO 598
<211> LENGTH: 10
<212> TYPE: PRT
<213> ORGANISM: Artificial Sequence
<220> FEATURE:
<223> OTHER INFORMATION: Synthetic peptide

<400> SEQUENCE: 598

Cys Ile Met Phe Trp Tyr Asn Cys Tyr Glu
1               5                   10

<210> SEQ ID NO 599
<211> LENGTH: 10
<212> TYPE: PRT
<213> ORGANISM: Artificial Sequence
<220> FEATURE:
<223> OTHER INFORMATION: Synthetic peptide

<400> SEQUENCE: 599

Cys Ile Met Phe Trp Tyr Pro Cys Tyr Glu
1               5                   10

<210> SEQ ID NO 600
<211> LENGTH: 10
<212> TYPE: PRT
<213> ORGANISM: Artificial Sequence
<220> FEATURE:
<223> OTHER INFORMATION: Synthetic peptide

<400> SEQUENCE: 600

Cys Ile Met Phe Trp Tyr Gln Cys Tyr Glu
1               5                   10

<210> SEQ ID NO 601

<211> LENGTH: 10
<212> TYPE: PRT
<213> ORGANISM: Artificial Sequence
<220> FEATURE:
<223> OTHER INFORMATION: Synthetic peptide

<400> SEQUENCE: 601

Cys Ile Met Phe Trp Tyr Arg Cys Tyr Glu
1 5 10

<210> SEQ ID NO 602
<211> LENGTH: 10
<212> TYPE: PRT
<213> ORGANISM: Artificial Sequence
<220> FEATURE:
<223> OTHER INFORMATION: Synthetic peptide

<400> SEQUENCE: 602

Cys Ile Met Phe Trp Tyr Ser Cys Tyr Glu
1 5 10

<210> SEQ ID NO 603
<211> LENGTH: 10
<212> TYPE: PRT
<213> ORGANISM: Artificial Sequence
<220> FEATURE:
<223> OTHER INFORMATION: Synthetic peptide

<400> SEQUENCE: 603

Cys Ile Met Phe Trp Tyr Thr Cys Tyr Glu
1 5 10

<210> SEQ ID NO 604
<211> LENGTH: 10
<212> TYPE: PRT
<213> ORGANISM: Artificial Sequence
<220> FEATURE:
<223> OTHER INFORMATION: Synthetic peptide

<400> SEQUENCE: 604

Cys Ile Met Phe Trp Tyr Val Cys Tyr Glu
1 5 10

<210> SEQ ID NO 605
<211> LENGTH: 10
<212> TYPE: PRT
<213> ORGANISM: Artificial Sequence
<220> FEATURE:
<223> OTHER INFORMATION: Synthetic peptide

<400> SEQUENCE: 605

Cys Ile Met Phe Trp Tyr Trp Cys Tyr Glu
1 5 10

<210> SEQ ID NO 606
<211> LENGTH: 10
<212> TYPE: PRT
<213> ORGANISM: Artificial Sequence
<220> FEATURE:
<223> OTHER INFORMATION: Synthetic peptide

<400> SEQUENCE: 606

Cys Ile Met Phe Trp Tyr Tyr Cys Tyr Glu
1 5 10

<210> SEQ ID NO 607
<211> LENGTH: 10

<212> TYPE: PRT
<213> ORGANISM: Artificial Sequence
<220> FEATURE:
<223> OTHER INFORMATION: Synthetic peptide

<400> SEQUENCE: 607

Cys Ile Met Phe Trp Tyr Asp Ala Tyr Glu
1 5 10

<210> SEQ ID NO 608
<211> LENGTH: 10
<212> TYPE: PRT
<213> ORGANISM: Artificial Sequence
<220> FEATURE:
<223> OTHER INFORMATION: Synthetic peptide

<400> SEQUENCE: 608

Cys Ile Met Phe Trp Tyr Asp Phe Tyr Glu
1 5 10

<210> SEQ ID NO 609
<211> LENGTH: 10
<212> TYPE: PRT
<213> ORGANISM: Artificial Sequence
<220> FEATURE:
<223> OTHER INFORMATION: Synthetic peptide

<400> SEQUENCE: 609

Cys Ile Met Phe Trp Tyr Asp His Tyr Glu
1 5 10

<210> SEQ ID NO 610
<211> LENGTH: 10
<212> TYPE: PRT
<213> ORGANISM: Artificial Sequence
<220> FEATURE:
<223> OTHER INFORMATION: Synthetic peptide

<400> SEQUENCE: 610

Cys Ile Met Phe Trp Tyr Asp Ile Tyr Glu
1 5 10

<210> SEQ ID NO 611
<211> LENGTH: 10
<212> TYPE: PRT
<213> ORGANISM: Artificial Sequence
<220> FEATURE:
<223> OTHER INFORMATION: Synthetic peptide

<400> SEQUENCE: 611

Cys Ile Met Phe Trp Tyr Asp Lys Tyr Glu
1 5 10

<210> SEQ ID NO 612
<211> LENGTH: 10
<212> TYPE: PRT
<213> ORGANISM: Artificial Sequence
<220> FEATURE:
<223> OTHER INFORMATION: Synthetic peptide

<400> SEQUENCE: 612

Cys Ile Met Phe Trp Tyr Asp Leu Tyr Glu
1 5 10

<210> SEQ ID NO 613
<211> LENGTH: 10
<212> TYPE: PRT

<213> ORGANISM: Artificial Sequence
<220> FEATURE:
<223> OTHER INFORMATION: Synthetic peptide

<400> SEQUENCE: 613

Cys Ile Met Phe Trp Tyr Asp Met Tyr Glu
1 5 10

<210> SEQ ID NO 614
<211> LENGTH: 10
<212> TYPE: PRT
<213> ORGANISM: Artificial Sequence
<220> FEATURE:
<223> OTHER INFORMATION: Synthetic peptide

<400> SEQUENCE: 614

Cys Ile Met Phe Trp Tyr Asp Asn Tyr Glu
1 5 10

<210> SEQ ID NO 615
<211> LENGTH: 10
<212> TYPE: PRT
<213> ORGANISM: Artificial Sequence
<220> FEATURE:
<223> OTHER INFORMATION: Synthetic peptide

<400> SEQUENCE: 615

Cys Ile Met Phe Trp Tyr Asp Pro Tyr Glu
1 5 10

<210> SEQ ID NO 616
<211> LENGTH: 10
<212> TYPE: PRT
<213> ORGANISM: Artificial Sequence
<220> FEATURE:
<223> OTHER INFORMATION: Synthetic peptide

<400> SEQUENCE: 616

Cys Ile Met Phe Trp Tyr Asp Gln Tyr Glu
1 5 10

<210> SEQ ID NO 617
<211> LENGTH: 10
<212> TYPE: PRT
<213> ORGANISM: Artificial Sequence
<220> FEATURE:
<223> OTHER INFORMATION: Synthetic peptide

<400> SEQUENCE: 617

Cys Ile Met Phe Trp Tyr Asp Arg Tyr Glu
1 5 10

<210> SEQ ID NO 618
<211> LENGTH: 10
<212> TYPE: PRT
<213> ORGANISM: Artificial Sequence
<220> FEATURE:
<223> OTHER INFORMATION: Synthetic peptide

<400> SEQUENCE: 618

Cys Ile Met Phe Trp Tyr Asp Ser Tyr Glu
1 5 10

<210> SEQ ID NO 619
<211> LENGTH: 10
<212> TYPE: PRT
<213> ORGANISM: Artificial Sequence
<220> FEATURE:
<223> OTHER INFORMATION: Synthetic peptide

<400> SEQUENCE: 619

Cys Ile Met Phe Trp Tyr Asp Thr Tyr Glu
1 5 10

<210> SEQ ID NO 620
<211> LENGTH: 10
<212> TYPE: PRT
<213> ORGANISM: Artificial Sequence
<220> FEATURE:
<223> OTHER INFORMATION: Synthetic peptide

<400> SEQUENCE: 620

Cys Ile Met Phe Trp Tyr Asp Val Tyr Glu
1 5 10

<210> SEQ ID NO 621
<211> LENGTH: 10
<212> TYPE: PRT
<213> ORGANISM: Artificial Sequence
<220> FEATURE:
<223> OTHER INFORMATION: Synthetic peptide

<400> SEQUENCE: 621

Cys Ile Met Phe Trp Tyr Asp Trp Tyr Glu
1 5 10

<210> SEQ ID NO 622
<211> LENGTH: 10
<212> TYPE: PRT
<213> ORGANISM: Artificial Sequence
<220> FEATURE:
<223> OTHER INFORMATION: Synthetic peptide

<400> SEQUENCE: 622

Cys Ile Met Phe Trp Tyr Asp Tyr Tyr Glu
1 5 10

<210> SEQ ID NO 623
<211> LENGTH: 10
<212> TYPE: PRT
<213> ORGANISM: Artificial Sequence
<220> FEATURE:
<223> OTHER INFORMATION: Synthetic peptide

<400> SEQUENCE: 623

Cys Ile Met Phe Trp Tyr Asp Cys Ala Glu
1 5 10

<210> SEQ ID NO 624
<211> LENGTH: 10
<212> TYPE: PRT
<213> ORGANISM: Artificial Sequence
<220> FEATURE:
<223> OTHER INFORMATION: Synthetic peptide

<400> SEQUENCE: 624

Cys Ile Met Phe Trp Tyr Asp Ser Cys Glu
1 5 10

<210> SEQ ID NO 625
<211> LENGTH: 10
<212> TYPE: PRT
<213> ORGANISM: Artificial Sequence
<220> FEATURE:

<223> OTHER INFORMATION: Synthetic peptide

<400> SEQUENCE: 625

Cys Ile Met Phe Trp Tyr Asp Cys Asp Glu
1 5 10

<210> SEQ ID NO 626
<211> LENGTH: 10
<212> TYPE: PRT
<213> ORGANISM: Artificial Sequence
<220> FEATURE:
<223> OTHER INFORMATION: Synthetic peptide

<400> SEQUENCE: 626

Cys Ile Met Phe Trp Tyr Asp Cys Glu Glu
1 5 10

<210> SEQ ID NO 627
<211> LENGTH: 10
<212> TYPE: PRT
<213> ORGANISM: Artificial Sequence
<220> FEATURE:
<223> OTHER INFORMATION: Synthetic peptide

<400> SEQUENCE: 627

Cys Ile Met Phe Trp Tyr Asp Cys Phe Glu
1 5 10

<210> SEQ ID NO 628
<211> LENGTH: 10
<212> TYPE: PRT
<213> ORGANISM: Artificial Sequence
<220> FEATURE:
<223> OTHER INFORMATION: Synthetic peptide

<400> SEQUENCE: 628

Cys Ile Met Phe Trp Tyr Asp Cys His Glu
1 5 10

<210> SEQ ID NO 629
<211> LENGTH: 10
<212> TYPE: PRT
<213> ORGANISM: Artificial Sequence
<220> FEATURE:
<223> OTHER INFORMATION: Synthetic peptide

<400> SEQUENCE: 629

Cys Ile Met Phe Trp Tyr Asp Cys Ile Glu
1 5 10

<210> SEQ ID NO 630
<211> LENGTH: 10
<212> TYPE: PRT
<213> ORGANISM: Artificial Sequence
<220> FEATURE:
<223> OTHER INFORMATION: Synthetic peptide

<400> SEQUENCE: 630

Cys Ile Met Phe Trp Tyr Asp Cys Lys Glu
1 5 10

<210> SEQ ID NO 631
<211> LENGTH: 10
<212> TYPE: PRT
<213> ORGANISM: Artificial Sequence
<220> FEATURE:
<223> OTHER INFORMATION: Synthetic peptide

<400> SEQUENCE: 631

Cys Ile Met Phe Trp Tyr Asp Cys Leu Glu
1 5 10

<210> SEQ ID NO 632
<211> LENGTH: 10
<212> TYPE: PRT
<213> ORGANISM: Artificial Sequence
<220> FEATURE:
<223> OTHER INFORMATION: Synthetic peptide

<400> SEQUENCE: 632

Cys Ile Met Phe Trp Tyr Asp Cys Met Glu
1 5 10

<210> SEQ ID NO 633
<211> LENGTH: 10
<212> TYPE: PRT
<213> ORGANISM: Artificial Sequence
<220> FEATURE:
<223> OTHER INFORMATION: Synthetic peptide

<400> SEQUENCE: 633

Cys Ile Met Phe Trp Tyr Asp Cys Asn Glu
1 5 10

<210> SEQ ID NO 634
<211> LENGTH: 10
<212> TYPE: PRT
<213> ORGANISM: Artificial Sequence
<220> FEATURE:
<223> OTHER INFORMATION: Synthetic peptide

<400> SEQUENCE: 634

Cys Ile Met Phe Trp Tyr Asp Cys Pro Glu
1 5 10

<210> SEQ ID NO 635
<211> LENGTH: 10
<212> TYPE: PRT
<213> ORGANISM: Artificial Sequence
<220> FEATURE:
<223> OTHER INFORMATION: Synthetic peptide

<400> SEQUENCE: 635

Cys Ile Met Phe Trp Tyr Asp Cys Gln Glu
1 5 10

<210> SEQ ID NO 636
<211> LENGTH: 10
<212> TYPE: PRT
<213> ORGANISM: Artificial Sequence
<220> FEATURE:
<223> OTHER INFORMATION: Synthetic peptide

<400> SEQUENCE: 636

Cys Ile Met Phe Trp Tyr Asp Cys Arg Glu
1 5 10

<210> SEQ ID NO 637
<211> LENGTH: 10
<212> TYPE: PRT
<213> ORGANISM: Artificial Sequence
<220> FEATURE:
<223> OTHER INFORMATION: Synthetic peptide

<400> SEQUENCE: 637

Cys Ile Met Phe Trp Tyr Asp Cys Ser Glu
1 5 10

<210> SEQ ID NO 638
<211> LENGTH: 10
<212> TYPE: PRT
<213> ORGANISM: Artificial Sequence
<220> FEATURE:
<223> OTHER INFORMATION: Synthetic peptide

<400> SEQUENCE: 638

Cys Ile Met Phe Trp Tyr Asp Cys Thr Glu
1 5 10

<210> SEQ ID NO 639
<211> LENGTH: 10
<212> TYPE: PRT
<213> ORGANISM: Artificial Sequence
<220> FEATURE:
<223> OTHER INFORMATION: Synthetic peptide

<400> SEQUENCE: 639

Cys Ile Met Phe Trp Tyr Asp Cys Val Glu
1 5 10

<210> SEQ ID NO 640
<211> LENGTH: 10
<212> TYPE: PRT
<213> ORGANISM: Artificial Sequence
<220> FEATURE:
<223> OTHER INFORMATION: Synthetic peptide

<400> SEQUENCE: 640

Cys Ile Met Phe Trp Tyr Asp Cys Trp Glu
1 5 10

<210> SEQ ID NO 641
<211> LENGTH: 10
<212> TYPE: PRT
<213> ORGANISM: Artificial Sequence
<220> FEATURE:
<223> OTHER INFORMATION: Synthetic peptide

<400> SEQUENCE: 641

Cys Ile Met Phe Trp Tyr Asp Cys Tyr Ala
1 5 10

<210> SEQ ID NO 642
<211> LENGTH: 10
<212> TYPE: PRT
<213> ORGANISM: Artificial Sequence
<220> FEATURE:
<223> OTHER INFORMATION: Synthetic peptide

<400> SEQUENCE: 642

Cys Ile Met Phe Trp Tyr Asp Ser Tyr Cys
1 5 10

<210> SEQ ID NO 643
<211> LENGTH: 10
<212> TYPE: PRT
<213> ORGANISM: Artificial Sequence
<220> FEATURE:
<223> OTHER INFORMATION: Synthetic peptide

<400> SEQUENCE: 643

Cys Ile Met Phe Trp Tyr Asp Cys Tyr Asp
1 5 10

<210> SEQ ID NO 644
<211> LENGTH: 10
<212> TYPE: PRT
<213> ORGANISM: Artificial Sequence
<220> FEATURE:
<223> OTHER INFORMATION: Synthetic peptide

<400> SEQUENCE: 644

Cys Ile Met Phe Trp Tyr Asp Cys Tyr Phe
1 5 10

<210> SEQ ID NO 645
<211> LENGTH: 10
<212> TYPE: PRT
<213> ORGANISM: Artificial Sequence
<220> FEATURE:
<223> OTHER INFORMATION: Synthetic peptide

<400> SEQUENCE: 645

Cys Ile Met Phe Trp Tyr Asp Cys Tyr His
1 5 10

<210> SEQ ID NO 646
<211> LENGTH: 10
<212> TYPE: PRT
<213> ORGANISM: Artificial Sequence
<220> FEATURE:
<223> OTHER INFORMATION: Synthetic peptide

<400> SEQUENCE: 646

Cys Ile Met Phe Trp Tyr Asp Cys Tyr Ile
1 5 10

<210> SEQ ID NO 647
<211> LENGTH: 10
<212> TYPE: PRT
<213> ORGANISM: Artificial Sequence
<220> FEATURE:
<223> OTHER INFORMATION: Synthetic peptide

<400> SEQUENCE: 647

Cys Ile Met Phe Trp Tyr Asp Cys Tyr Lys
1 5 10

<210> SEQ ID NO 648
<211> LENGTH: 10
<212> TYPE: PRT
<213> ORGANISM: Artificial Sequence
<220> FEATURE:
<223> OTHER INFORMATION: Synthetic peptide

<400> SEQUENCE: 648

Cys Ile Met Phe Trp Tyr Asp Cys Tyr Leu
1 5 10

<210> SEQ ID NO 649
<211> LENGTH: 10
<212> TYPE: PRT
<213> ORGANISM: Artificial Sequence
<220> FEATURE:
<223> OTHER INFORMATION: Synthetic peptide

<400> SEQUENCE: 649

Cys Ile Met Phe Trp Tyr Asp Cys Tyr Met
1 5 10

<210> SEQ ID NO 650
<211> LENGTH: 10
<212> TYPE: PRT
<213> ORGANISM: Artificial Sequence
<220> FEATURE:
<223> OTHER INFORMATION: Synthetic peptide

<400> SEQUENCE: 650

Cys Ile Met Phe Trp Tyr Asp Cys Tyr Asn
1 5 10

<210> SEQ ID NO 651
<211> LENGTH: 10
<212> TYPE: PRT
<213> ORGANISM: Artificial Sequence
<220> FEATURE:
<223> OTHER INFORMATION: Synthetic peptide

<400> SEQUENCE: 651

Cys Ile Met Phe Trp Tyr Asp Cys Tyr Pro
1 5 10

<210> SEQ ID NO 652
<211> LENGTH: 10
<212> TYPE: PRT
<213> ORGANISM: Artificial Sequence
<220> FEATURE:
<223> OTHER INFORMATION: Synthetic peptide

<400> SEQUENCE: 652

Cys Ile Met Phe Trp Tyr Asp Cys Tyr Gln
1 5 10

<210> SEQ ID NO 653
<211> LENGTH: 10
<212> TYPE: PRT
<213> ORGANISM: Artificial Sequence
<220> FEATURE:
<223> OTHER INFORMATION: Synthetic peptide

<400> SEQUENCE: 653

Cys Ile Met Phe Trp Tyr Asp Cys Tyr Arg
1 5 10

<210> SEQ ID NO 654
<211> LENGTH: 10
<212> TYPE: PRT
<213> ORGANISM: Artificial Sequence
<220> FEATURE:
<223> OTHER INFORMATION: Synthetic peptide

<400> SEQUENCE: 654

Cys Ile Met Phe Trp Tyr Asp Cys Tyr Ser
1 5 10

<210> SEQ ID NO 655
<211> LENGTH: 10
<212> TYPE: PRT
<213> ORGANISM: Artificial Sequence
<220> FEATURE:
<223> OTHER INFORMATION: Synthetic peptide

<400> SEQUENCE: 655

Cys Ile Met Phe Trp Tyr Asp Cys Tyr Thr

-continued

```
1               5                   10


<210> SEQ ID NO 656
<211> LENGTH: 10
<212> TYPE: PRT
<213> ORGANISM: Artificial Sequence
<220> FEATURE:
<223> OTHER INFORMATION: Synthetic peptide

<400> SEQUENCE: 656

Cys Ile Met Phe Trp Tyr Asp Cys Tyr Val
1               5                   10


<210> SEQ ID NO 657
<211> LENGTH: 10
<212> TYPE: PRT
<213> ORGANISM: Artificial Sequence
<220> FEATURE:
<223> OTHER INFORMATION: Synthetic peptide

<400> SEQUENCE: 657

Cys Ile Met Phe Trp Tyr Asp Cys Tyr Trp
1               5                   10


<210> SEQ ID NO 658
<211> LENGTH: 10
<212> TYPE: PRT
<213> ORGANISM: Artificial Sequence
<220> FEATURE:
<223> OTHER INFORMATION: Synthetic peptide

<400> SEQUENCE: 658

Cys Ile Met Phe Trp Tyr Asp Cys Tyr Tyr
1               5                   10
```